US012691165B2

(12) United States Patent
Fredriksen et al.

(10) Patent No.: US 12,691,165 B2
(45) Date of Patent: Jul. 28, 2026

(54) INDIVIDUALIZED THERAPEUTIC ANTICANCER VACCINE

(71) Applicant: Nykode Therapeutics ASA, Oslo (NO)

(72) Inventors: Agnete Brunsvik Fredriksen, Rælingen (NO); Monika Sekelja, Oslo (NO); Karoline Schjetne, Lommedalen (NO); Stine Granum, Oslo (NO)

(73) Assignee: Nykode Therapeutics ASA, Oslo (NO)

( * ) Notice: Subject to any disclaimer, the term of this patent is extended or adjusted under 35 U.S.C. 154(b) by 753 days.

(21) Appl. No.: 17/995,780

(22) PCT Filed: Apr. 9, 2021

(86) PCT No.: PCT/EP2021/059353
§ 371 (c)(1),
(2) Date: Oct. 7, 2022

(87) PCT Pub. No.: WO2021/205027
PCT Pub. Date: Oct. 14, 2021

(65) Prior Publication Data
US 2023/0293650 A1 Sep. 21, 2023

(30) Foreign Application Priority Data

Apr. 9, 2020 (DK) ........................... PA 2020 70221
May 26, 2020 (DK) ........................... PA 2020 70338

(51) Int. Cl.
A61K 39/00 (2006.01)
A61P 35/00 (2006.01)

(52) U.S. Cl.
CPC .. *A61K 39/0011* (2013.01); *A61K 39/001156* (2018.08); *A61K 39/001188* (2018.08); *A61P 35/00* (2018.01); *A61K 2039/53* (2013.01); *A61K 2039/6031* (2013.01); *A61K 2039/70* (2013.01)

(58) Field of Classification Search
CPC .. A61K 39/0011; A61K 2039/53; A61P 35/00
See application file for complete search history.

(56) References Cited

U.S. PATENT DOCUMENTS

| | | | |
|---|---|---|---|
| 5,580,859 | A | 12/1996 | Felgner et al. |
| 5,646,016 | A | 7/1997 | McCoy et al. |
| 6,099,846 | A | 8/2000 | Levy et al. |
| 6,306,397 | B1 | 10/2001 | Edwards et al. |
| 7,223,408 | B2 | 5/2007 | Cassetti |
| 8,932,603 | B2 | 1/2015 | Bogen et al. |
| 9,169,322 | B2 | 10/2015 | Bogen et al. |
| 2003/0100497 | A1 | 5/2003 | Baker et al. |
| 2004/0253238 | A1 | 12/2004 | Bogen et al. |
| 2005/0069549 | A1 | 3/2005 | Herman |
| 2006/0165713 | A1 | 7/2006 | Gough et al. |
| 2007/0065444 | A1 | 3/2007 | North et al. |
| 2007/0298051 | A1 | 12/2007 | Barouch et al. |

| | | | |
|---|---|---|---|
| 2008/0102084 | A1 | 5/2008 | Wu et al. |
| 2009/0010948 | A1 | 1/2009 | Huang et al. |
| 2009/0092578 | A1 | 4/2009 | Su et al. |
| 2011/0263835 | A1 | 10/2011 | Ting et al. |
| 2013/0336971 | A9 | 12/2013 | Ruffini et al. |
| 2016/0331821 | A1 | 11/2016 | Bill et al. |
| 2017/0016075 | A1 | 1/2017 | Velculescu et al. |

FOREIGN PATENT DOCUMENTS

| | | |
|---|---|---|
| EP | 920522 | 2/1998 |
| EP | 3 053 592 A1 | 8/2016 |
| JP | 2013-532971 | 8/2013 |
| JP | 2014523406 | 9/2014 |
| WO | WO 92/13955 | 8/1992 |
| WO | WO 92/16636 | 10/1992 |
| WO | WO 95/32731 | 12/1995 |
| WO | WO 99/58552 | 11/1999 |
| WO | WO 00/15663 | 3/2000 |
| WO | WO 2002/060919 | 8/2002 |
| WO | WO 2002/04664 | 6/2003 |
| WO | WO 03/059952 | 7/2003 |
| WO | WO 2003/059951 | 7/2003 |
| WO | WO 2003/084467 | 10/2003 |
| WO | WO 2003/087162 | 10/2003 |
| WO | WO 2003/096017 | 11/2003 |
| WO | WO 2003/106692 | 12/2003 |
| WO | WO 2004/030636 | 4/2004 |
| WO | WO 2004/076489 A1 | 9/2004 |
| WO | WO 2004/111075 | 12/2004 |
| WO | WO 2005/089792 | 9/2005 |
| WO | WO 2006/002114 | 1/2006 |
| WO | WO 2006/138567 | 12/2006 |
| WO | WO 2007/031222 | 3/2007 |

(Continued)

OTHER PUBLICATIONS

Grodeland et al.: "Targeting of HA to chemokine receptors induces strong and cross-reactive T cell responses after DNA vaccination in pigs," *Vaccine*, 38, 1280-1285 (Feb. 2020).
A. A. Yarilin, Immunology: Manual, Moscow: GEOTAR-Media Publishing Group, 2010, pp. 263-267.
Andersen et al. Enhanced germinal center reaction by targeting vaccine antigen to major histocompatibility complex class II molecules. NPJ Vaccines. 2019;4:9. Published Feb. 11, 2019. doi:10.1038/s41541-019-0101-0.
Andreatta, Massimo et al., "Accurate pan-specific prediction of peptide-MHC class II binding affinity with improved binding core identification", Immunogenetics, Nov. 2015; 67(0);641-650.
Ballhausen et al.: "The shared frameshift mutation landscape of microsatellite-unstable cancers suggests immunoediting during tumor evolution", Nature communication, 2020, 11:4740, https://doi.org/10.1038/s41467-020-18514-5.
Beckman et al. Antibody constructs in cancer therapy: protein engineering strategies to improve exposure in solid tumors. Cancer. 2007;109(2):170-179. doi:10.1002/cncr.22402.

(Continued)

*Primary Examiner* — Elly-Gerald Stoica
(74) *Attorney, Agent, or Firm* — Womble Bond Dickinson (US) LLP

(57) ABSTRACT

The present invention relates to an individualized therapeutic anticancer vaccine, methods of treatment of cancer wherein such an anticancer vaccine is used as well as methods for producing the vaccine.

19 Claims, 13 Drawing Sheets
Specification includes a Sequence Listing.

(56)        References Cited

FOREIGN PATENT DOCUMENTS

| WO | WO 2007/101227 | 9/2007 | | |
| WO | WO 2008/014521 | 1/2008 | | |
| WO | WO 2008/138648 | 11/2008 | | |
| WO | WO 2009/003623 | 1/2009 | | |
| WO | WO 2009/039341 | 3/2009 | | |
| WO | WO 2009/053041 | 4/2009 | | |
| WO | WO 2011/143656 | 11/2011 | | |
| WO | WO 2012/159643 A1 | 11/2012 | | |
| WO | WO 2012/159754 | 11/2012 | | |
| WO | WO 2013/112549 | 8/2013 | | |
| WO | WO 2014/052707 | 4/2014 | | |
| WO | WO 2014/082729 | 6/2014 | | |
| WO | WO 2014/165291 | 10/2014 | | |
| WO | WO 2014/168874 | 10/2014 | | |
| WO | WO 2014/180490 | 11/2014 | | |
| WO | WO 2015/085233 A1 | 6/2015 | | |
| WO | WO 2016/015095 | 2/2016 | | |
| WO | WO 2016/040900 | 3/2016 | | |
| WO | WO 2016/081947 | 5/2016 | | |
| WO | WO 2016/090177 | 6/2016 | | |
| WO | WO 2016/128060 | 8/2016 | | |
| WO | WO 2016/128376 A1 | 8/2016 | | |
| WO | WO 2016/191545 | 12/2016 | | |
| WO | WO 2017/011660 | 1/2017 | | |
| WO | WO 2017/066256 | 4/2017 | | |
| WO | WO 2017/066290 | 4/2017 | | |
| WO | WO2017/066339 | 4/2017 | | |
| WO | WO 2017/106638 | 6/2017 | | |
| WO | WO 2017/118702 | 7/2017 | | |
| WO | WO2017118695 | * 7/2017 | .............. | A61P 39/00 |
| WO | WO 2017/165464 | 9/2017 | | |
| WO | WO 2017/173321 | 10/2017 | | |
| WO | WO 2017/194170 | 11/2017 | | |
| WO | WO 2017/194610 | 11/2017 | | |
| WO | WO 2017/205810 | 11/2017 | | |
| WO | WO 2017/222619 | 12/2017 | | |
| WO | WO 2018/015433 | 1/2018 | | |
| WO | WO 2018/102613 | 6/2018 | | |
| WO | WO 2018/106699 | 6/2018 | | |
| WO | WO 2018/112449 | 6/2018 | | |
| WO | WO 2018/136664 A1 | 7/2018 | | |
| WO | WO 2018/148381 | 8/2018 | | |
| WO | WO 2018/148671 | 8/2018 | | |
| WO | WO2019/048936 | 3/2019 | | |

OTHER PUBLICATIONS

Borysiewicz, L.K., et al., "A recombinant vaccinia virus encoding human papillomavirus types 16 and 18, E6 and E7 proteins as immunotherapy for cervical cancer" The Lancet, vol. 347, Jun. 1, 1996.

Brown et al., 2014, Genome research 24(5): 743-750.

Castle, John C., et al., "Exploiting the Mutanome for Tumor Vaccination", American Association for Cancer research, 2012, downloaded from www.aacrjournals.org.

Cespdes et al. (Clin. Trans!. Oncol. 8(5):318-329 (2006)).

Dobin, Alexander et al., "STAR: ultrafast universal RNA-seq aligner", Bioinformatics, vol. 29, No. 1, 2013, p. 15-21.

Duan Fei et al., "Genomic and bioinformatic profiling of mutational neoepitopes reveals new rules to predict anticancer immunogenicity", The Journal of Experimental Medicine, Rockfeller University Press, US, vol. 211, No. 11, Oct. 20, 2014, p. 2231-2248, XP002757114.

Dutton, G. (2016) "From DNA to Diagnosis without Delay. Purpose-Built for Genomics, Dragen Processor Could Form Core of Clinic-Ready Data Systems." Genet Eng Biotechn N. 36 (5): 8-9.

Fredriksen, Agnete B. et al., "Chemokine-idiotype fusion DNA vaccines are potentiated by bivalency and xenogeneic sequesnces", Blood, vol. 110, No. 6, Sep. 15, 2007.

Fritsch, Edward F. et al., "HLA-Binding Properties of Tumor Neoepitopes in Humans", Cancer Immunology Research, 2(6) Jun. 2014, American Association for Cancer Research.

Fujimori et al. (J. Nuc. Med. 31:1191-1198 (1990)).

Genbank: AAP36497.1 *Homo sapiens* chemokine (C—C motif) ligand 3, partial [synthetic construct]. Dated May 13, 2003.

Georgetta Cannon and Drew Weissman: "RNA Based Vacines", DNA and Cell Biology, vol. 21, No. 12, 2002, © Mary Ann Liebert, Inc., pp. 953-961.

Grødeland, G., et al., "DNA Vaccine that Targets Hemagglutinin to MHC Class II Molecules Rapidly Induces Antibody-Mediated Protection against Influenza," The Journal of Immunology, 2013, vol. 191(6), pp. 3221-3231.

Grødeland, G., et al., "The Specificity of Targeted Vaccines for APC Surface Molecules Influences the Immune Response Phenotype," PLOS One, 2013, vol. 8(11), pp. 1-11.

Gubin, Matthew M. et al., "Tumor neoantigens: building a framework for personalized cancer immunotherapy", The Journal of Clinical Investigation, vol. 125, No. 9, Sep. 2015.

Guettinger et al: "A Recombinant Bispecific Single-Chain Fragment Variable Specific for HLA Class II and Fc Rl (CD89) Recruits Polymorphonuclear Neutrophils for Efficient Lysis of Malignant B Lymphoid Cells", J. Immunol., vol. 184, No. 3, Dec. 30, 2009, pp. 1210-1217.

Henikoff, S; Henikoff, JG (1992). "Amino acid substitution matrices from protein blocks". Proceedings of the National Academy of Sciences of the United States of America. 89 (22): 10915-9.

Hillemanns Peter: Abstract CT209: Safety, efficacy and immunogenicity of VB10.16, a therapeutic DNA vaccine targeting human papillomavirus (HPV) 16 E6 and E7 proteins for high grade cervical intraepithelial neoplasia ( CIN 2/3): 6-month data from an exploratoryopen-label . . . Proceedings of the American Association for Cancer Research Annual Meeting 2019, Apr. 3, 2019 (Apr. 3, 2019) pp. 1-4.

Huang et al. (Appl Microbiol Biotechnol (2010) 87:401-410).

Jurtz, Vanessa et al., "NetMHCpan-4.0: Improved Peptide-MHC Class I Interaction Predictions Integrating Eluted Ligand and Peptide Binding Affinity Data", The Journal of Immunology, 2017.

Kreiter et al—Correction and Amendment to "Mutant MHC class II epitopes drive therapeutic immune responses to cancer" Nature. Apr. 30, 2015;520(7549):692-6.

Kreiter, Sebastian et al., "Mutant MHC class II epitopes drive therapeutic immune responses to cancer", Nature, Apr. 30, 2015; 520(7549).

Miller, Neil A. et al., "A 26-hour system of highly sensitive whole genome sequencing for emergency management of genetic diseases", Genome Medicine (2015) 7:100.

Nielsen, Morten and Andreatta, Massimo, "NetMHCpan-3.0; improved prediction of biinding to MHC class I molecules integrating information from multiple receptor and peptide length datasets", Genome Medicine, 2016, 8:33.

Nielsen, Morten et al., "The role of the proteasome in generating cytotoxic T-cell epitopes: insights obtained from improved predictions of proteasomal cleavage", Immunogenetics, 2005, 57; 33-41.

NP_41325.1 transforming protein E6 [Human papillomavirus type 16] Oct. 27, 2010.

NP_41326.1 transforming protein E7 [Human papillomavirus type 16] Oct. 27, 2010.

Ott, Patrick A., "An immunogenic personal neoantigen vaccine for patients with melanoma", Nature, Nature publishing group, United Kingdom, vol. 547, No. 7662, Jul. 13, 2017, p. 217, XP002785348, ISSN: 1476-4687.

Pearson, W. P., "Flexible Sequence Similarity Searching with the FASTA3 Program Package", Methods in Molecular Biology, vol. 132: Bioinformatics Methods and Protocols, 2000.

Rasmussen, Michael et al., Pan-Specific Prediction of peptide-MHC Class I Complex Stability, a Correlate of T Cell Immunogenicity, J. Immunol, 2016, 197:1517-1524.

Ristriani T. et al., A single-codon mutation converts HPV 16 E6 oncoprotein into a potential tumor suppressor, which induces p53-dependent senescence of HPV-positive HeLa cervical cancer cells, Oncogene 28, p. 762-772, 2009.

Rubinsteyn, Alex et al.:"Computational Pipeline for the PGV-001 Neoantigen Vaccine Trial", Frontiers in Immunology, vol. 8, Jan. 18, 2018, XP55519329.

(56) References Cited

OTHER PUBLICATIONS

Ruffini et al. (Journal of Translational Medicine 2014, vol. 12207, pp. 1-12).

Schiavo et al. Blood, 107: 4597-4605, 2006.

Schmidt J et al. J Biol Chem. Jul. 14, 2017;292(28):11840-11849. doi: 10.1074/jbc.M117.789511. Epub May 23, 2017. In silico and cell-based analyses reveal strong divergence between prediction and observation of T-cell-recognized tumor antigen T-cell epitopes.

Talmadge et al. (Am. J. Pathol 170(3):793-804 (2007)).

Uhlén, M. et al. (2015) "Proteomics. Tissue-based map of the human proteome." Science;347(6220).

Ulmer, jeffrey B. et al.: "RNA-based vaccines", Elsevier, Vaccine 30, Feb. 2012, p. 4414-4418.

Van der Auwera G.A. et al. (2013) "From FastQ data to high confidence variant calls: the Genome Analysis Toolkit best practices pipeline." Curr Protoc Bioinformatics. 43.

Vuzman et al: "Utility of comprehensive 1-4 genomic profiling ( CGP) for personal cancer vaccine development via neoantigen analysis.", Journal of Clinical Oncology, Jun. 1, 2018 (Jun. 1, 2018).

WIKI Gene therapy—https://en.wikipedia.org/wiki/Gene_therapy—Retrieved on Feb. 4, 2020.

Zhang X et al. Cancer Immunol Res. Jul. 2017;5(7):516-523. doi: 10.1158/2326-6066.CIR-16-0264. Epub Jun. 15, 2017. Breast Cancer Neoantigens Can Induce CD8+ T-Cell Responses and Antitumor Immunity.

Zimmerer et al. CD8+ T cells negatively regulate IL-4-dependent, IgG1-dominant posttransplant alloantibody production. J Immunol. 2010; 185(12):7285-7292. doi:10.4049/jimmunol.1001655.

Bendandi, M., C. D. Gocke, et al. (1999). "Complete molecular remissions induced by patient-specific vaccination plus granulocyte-monocyte colony-stimulating factor against lymphoma." Nat Med 5(10): 1171-7.

Biragyn et al., Genetic Fusion of Chemokines to a Self Tumor Antigen Induces Protective, T-cell Dependent Antitumor Immunity; Nature Biotechnology; V 17; Mar. 1999; pp. 253-258.

Biragyn et al., Tool-Like Receptor 4-Dependent Activation of Dendritic Cells by Beta-Detensin 2; Science, V 298; Nov. 2002; pp. 1025-1029.

Bogen, B. (1989). "Monoclonal antibodies specific for variable and constant domains of murine lambda chains." Scand J Immuno129(3): 273-9.

Bogen, B. and J. D. Lambris (1989). "Minimum length of an idiotypic peptide and a model for its binding to a major histocompatibility complex class II molecule." Embo J 8(7): 1947-52.

Bogen, B., B. Malissen, et al. (1986). "Idiotope-specific T cell clones that recognize syngeneic immunoglobulin fragments in the context of class II molecules." Eur J Immunol 16(11): 1373-8.

Bogen, B., L. Gleditsch, et al. (1992). "Weak positive selection of transgenic T cell receptor-bearing thymocytes: importance of major histocompatibility complex class II, T cell receptor and CD4 surface molecule densities." European Journey of Immunology 22(3): 703-9.

Bronte, "Genetic vaccination for the active immunotherapy of cancer." Curr. Gene Therapy 1:53-100, 2001.

Brunsvik, A. et al., "Vaccibodies: Future Vaccines for B Cell Lymphoma and Myeloma?" Institute of Immunology, Univ. of Oslo, Oslo National Hospital; Oslo, NO, Abstract, 2003.

Brunsvik, A. et al; Construction of Tetrabodies for Cancer Vaccines; Institute of Immunology, University of Oslo; Oslo National Hospital, Oslo, Norway, abstract.

Brunsvik, A. et al; Construction of Tetrabodies for Cancer Vaccines; The National Hospital, University of Oslo; abstract, 2002.

Casten, L. A. and S. K. Pierce (1988). "Receptor-mediated B cell antigen processing. Increased antigenicity of a globular protein covalently coupled to antibodies specific for B cell surface structures." J Immunol 140(2): 404-10.

Chen et al., Linkage of CD40L to a Self-Tumor Antigen Enhances the Anti-Tumor Immune Response to Dendritic Cell-Based Treatment; Cancer Immunoll Immunother; V. 51, 2002; pp. 341-348.

Cheung et al. "Plasmid encoding papillomavirus Type 16 (HPV16) DNA constructed with codon optimization improved the immunogenicity against HPV infection", Vaccine. Dec. 16, 2004;23(5):629-38.

Chudley et al., DNA Fusion-Gene Vaccination in patients with prostate cancer induces high-frequency CD8 T-cell responses and increases PSA doubling time; Cancer Immunoll Immunother, 2012 61:2161-2170.

Crook et al., "Degradation of P53 Can Be Targeted by HPV E6 Sequences Distinct from Those Required for p53 Binding and Trans-Activation", Cell, 1991, vol. 67, pp. 547-556, Cell Press.

Dalal et al., "Mutational Analysis of Human Papillomavirus Type 14 E6 Demonstrates that p53 Degradation Is Necessary for Immortalization of Mammary Epithelial Cells," Journal of Virology, 1996, pp. 683-688, American Society for Microbiology.

Dennis, "Off by a whisker", Nature Pub. 442: 739-741, 2006.

Dong et al. "Determination of the binding affinity of different human papillomavirus E7 proteins for the tumor suppressor pRb by a plate-binding assay" J Virol Methods. Oct. 2001; 98(1): 91-8.

Drew et al. "The human IgG3 hinge mediates the formation of antigen dimers that enhance humoral immune responses to DNA immunisation.", Vaccine. Jul. 20, 2001;19(30):4115-20.

Eisen et al., "Lambda Chains and Genes in Inbred Mice," Ann. Rev. Immunol. 3: 337-365; 1985.

Eisen et al., "Mouse Myeloma Proteins with Antihapten Antibody Activity. The Protein Produced by Plasma Cell Tumor MOPC-315," Biochem 7(11): 4126-4134; 1968.

Fredriksen, Agnete Brunsvik et al., "DNA Vaccines Increase Immunogenicity of Idiotypic Tumor Antigen by Targeting Novel Fusion Proteins to Antigen-Presenting Cells" Molecular Therapy, 2006, pp. 776-785, vol. 13.

Frøyland et al., "Targeted idiotype-fusion DNA vaccines for human multiple myeloma: preclinical testing," European Journal of Haematology, vol. 86, pp. 385-395.

Glick, Defending Pharma Companies: Innovation is Alive and Well in the Therapeutic Drug Industry, Gen. Engineer, News 28(7), pp. 6 and 9, Apr. 1, 2008.

Grodeland et al., Antigen Targeting to Human HLA Class II Molecules Increases Efficacy of DNA Vaccination, J. Immunol 2016; 197:3375-3585.

Gulliver, G., et al., "Both Conserved Region 1 (CR1) and CR2 of the Human Papillomavirus Type 16 E7 Oncogene Are Required for Induction of Epidermal Hyperplasia and Tumor Formation in Transgenic Mice," Journal of Virology, 1997, vol. 71(8), pp. 5905-5914.

Hakim, I., S. Levy, et al. (1996). "A nine-amino acid peptide from IL-1beta augments antitumor immune responses induced by protein and DNA vaccines." J Immunol 157(12): 5503-11.

Haupt et al., "The Potential of DNA Vaccination against Tumor-Associated Antigens for Antitumor Therapy," Exp Biol Med 227, v: 227-237, 2002.

Hoogenboom., Mix and Match: Building Manifold Binding Sites; Nature Biotechnology; V 15, Feb. 1997; pp. 125-226.

Horwell, D. C., "The 'peptoid' approach to the design of non-peptide, small molecule agonists and antagonists of neuropeptides," Trends in Biotechnology, 1995, pp. 132-134, vol. 13(4).

Hough, D. W., R. P. Eady, et al. (1976). "Anti-idiotype sera raised against surface immunoglobulin of human neoplastic lymphocytes." J Exp Med 144(4): 960-9.

Hu, Shi-zhen et al., "Minibody: A Novel Engineered Anti-Carcinoembryotic Antigen Antibody Fragment Single-Chain Fv-CH3), Which Exhibits Rapid, High-Level Targeting of Xenografts" Cancer Research, 1996, pp. 3055-3061, vol. 56.

Huang et al. "DNA vaccine encoding heat shock protein 60 co-linked to HPV16 E6 and E7 tumor antigens generates more potent immunotherapeutic effects than respective E6 or E7 tumor antigens." Gynecol Oncol. Dec. 2007;107(3):404-12. Epub Oct. 1, 2007.

Huang, Hsing-I et al., "Improved immonugenicity of a self tumor antigen by covalent linkage to CD40 ligand" International Journal of Cancer, 2004, pp. 696-703, vol. 108.

Huang, Tzu-Hsuan et al., "Enhanced antitumor immunity by fusion of CTLA-4 to a self tumor antigen" Blood, 2000, pp. 3663-3670, vol. 96, No. 12.

(56) References Cited

OTHER PUBLICATIONS

International Searching Authority, International Search Report and Written Opinion for International Application No. PCT/EP2012/076404, Mar. 25, 2013, 15 pages, European Patent Office, The Netherlands.

Kim et al., "Enhanced immunogenicity of human papillomavirus 16 L1 genetic vaccines fused to an ER-targeting secretory signal peptide and RANTES." Gene Therapy (2003), vol. 10, pp. 1268-1273.

King, C. A., M. B. Spellerberg, et al. (1998). "DNA vaccines with single-chain Fv fused to fragment C of tetanus toxin induce protective immunity against lymphoma and myeloma." Nat Med 4(11): 1281-6.

Knappscog, S., et al., "The level of synthesis and secretion of Gaussia princeps luciferase in transfected CHO cells is heavily dependent on the choice of signal peptide," Journal of Biotechnology, 2007, vol. 128, pp. 705-715.

Kriangkum et al., Bispecific and Bifunctional Single Chain Recombinant Antibodies; Biomolecular Engineering; v 18:2, 2001; pp. 31-40.

Kristoffersen, G., K. Hannestad, et al. (1987). "Two M315 idiotopes defined by isologous monoclonal antibodies: one depends on germline and the other on mutated murine lambda 2 light chain sequences." Scand J Immunol 26(5): 535-46.

Kutzler, M et al.; DNA Vaccines; Ready for Prime Time?; Nature Reviews Genetics, V 9, 2008, pp. 776-788.

Lambert et al., DNA Vaccines Encoding Antigen Targeted to MHC Class II Induce Influenza-Specific CD8+ T Cell Responses, Enabling Faster Resolution of Influenza Disease. Frontiers in Immunology Aug. 2016. v7, article 321, pp. 1-11.

Lauritzsen, G. F., S. Weiss, et al. (1993). "Anti-tumour activity of idiotype-specific, MHC-restricted Th1 and Th2 clones in vitro and in vivo." Scand J Immunol 37(1): 77-85.

Lauritzsen, G. F., S. Weiss, et al. (1994). "Naive idiotype-specific CD4+ T cells and immunosurveillance of B-cell tumors." Proe Natl Acad Sci U S A 91(12): 5700-4.

Lewis, A.D., et al., Generation of Neutralizing Activity against Human Immunodeficiency Virus Type 1 in Serum by Antibody Gene Transfer, J. Virol., 76(17), pp. 8769-8775, 2002.

Lewis, Anne D. et al., "Generation of Neutralizing Activity against Human Immunodeficiency Virus Type 1 in Serum by Antibody Gene Transfer" Journal of Virology, 2002, pp. 8769-8775, vol. 76, No. 17.

Lunde et al., Troybodies and Pepbodies; Biochemical Society Transactions, V 30; part 4, 2002; pp. 500-506.

Lunde et al., Troy-bodies: Recombinant Antibodies that Target T cell Epitopes to Antigen Presenting Cells; Intern. REv. Immunol. V 20, 2001; pp. 647-673.

Lunde, E., K. H. Western, et al. (2002). "Efficient delivery of T cell epitopes to APC by use of MHC class II-specific Troybodies." J Immuno 1168(5): 2154-62.

Lunde, E., L. A. Munthe, et al. (1999). "Antibodies engineered with IgD specificity efficiently deliver integrated T-cell epitopes for antigen presentation by B cells." Nat Biotechnol 17(7): 670-5.

Lunde, E., I. B. Rasmussen, et al. (2001). "Troy-bodies': antibodies as vector proteins for T cell epitopes." Biomol Eng 8(3): 109-16.

Macgregor et al; T-cell Responses Induced in Normal Volunteers Immunized with a DNA-based Vaccine Containing HIV-1 env and rev; AIDS 2002; V 16, pp. 2137-2143.

Martoglio, B., et al., "Signal sequences: more than just greasy peptides," trends in Cell Biology, 1998, vol. 8, pp. 410-415.

Menten, P., et al., "The LD78B insoform of MIP-1a is the most potent CCr5 agonist and HIV-1-inhibiting chemokine," The Journal of Clinical Investigation, 1999, pp. R1-R5, vol. 104(4).

Mesplede et al., "p53 Degradation Activity, Expression, and Subcellular Localization of E6 Proteins from 29 Human Papillomavirus Genotypes," Journal of Virology, 2011, vol. 86, No. 1, pp. 94-107.

Moody et al., "Human papillomavirus oncoproteins: pathways to transformation," Nature Reviews Cancer, 2010, vol. 10, pp. 550-560.

Münger et al., "Complex formation of human papillomavirus E7 proteins with the retinoblastoma tumor suppressor gene product," The EMBO Journal, 1989, vol. 8, No. 13, pp. 4099-4105.

Münger et al., "E6 Alignments HPV Compendium," 1997, 24 pp.

Münger et al., "E7 Alignments HPV Compendium," 1997, 22 pp.

Nagakawa et al., "Mutational Analysis of Human Papillomavirus Type 16 E6 Protein: Transforming Function for Human Cells and Degradation of p53 in vitro," Virology, 2002, vol. 76, No. 24, pp. 13039-13048.

Neuberger, M. S. (1983). "Expression and regulation of immunoglobulin heavy chain gene transfected into lymphoid cells." Embo J 2(8): 1373-8.

Nguyen et al. A mutant of human papillomavirus type 16 e6 deficient in binding alpha-helix partners displays reduced oncogenic potential in vivo. J Virol. Dec. 2002; 76(24): 13039-48.

Noel, D., et al; High in vivo Production of Model Monoclonal Antibody on Adenoviral Gene Transfer, Hum. Gene Ther., 13(12), pp. 1483-1493, 2002.

Nomine' et al., "Structural and Functional Analysis of E6 Oncoprotein: Insights in the Molecular Pathways of Human Papillomavirus-Mediated Pathogenesis," Molecular Cell, 2006, vol. 21, pp. 665-678.

Norderhaug, L., T. Olafsen, et al. (1997). "Versatile vectors for transient and stable expression of recombinant antibody molecules in mammalian cells." J Immunol Methods 204(1): 77-87.

Olafsen, T., I. B. Rasmussen, et al. (1998). "IgM secretory tailpiece drives multimerisation of bivalent scFv fragments in eukaryotic cells." Immunotechnology 4(2): 141-53.

Oynebraten et al., Generation of Antibody-Producing Hybridomas Following One Single Immunization with a Targeted DNA Vaccine, Scandinavian Journal of Immunology 2011; v75, pp. 379-488.

Oynebraten et al., Increased Generation of HIV-1 gp120-Reactive CD8+ T Cells by a DNA Vaccine Construct Encoding the Chemokine CCL3, PLOS One, Aug. 2014, v9, issue 8, pp. 1-11.

Ozato, K., N. Mayer, et al. (1980). "Hybridoma cell lines secreting monoclonal antibodies to mouse H-2 and la antigens." J Immunol 124(2): 533-40.

Phelps, W., et al., "Structure-Function Analysis of the Human Papillomavirus Type 16 E7 Oncoprotein," Journal of Virology, 1992, vol. 66(4), pp. 2418-2427.

Pluckthun et al., New Protein Engineering Approaches to Multivalent and Bispecific Antibody Fragments; Immunotechnology, V. 3, 1997; pp. 83-105.

Poláková et al., "DNA vaccine against human papillomavirus type 16: Modifications of E6 oncogene," Vaccine, 2010, vol. 28, pp. 1506-1513.

Proost et al., "Cleavage by CD26/dipeptidyl peptidase IV converts the chemokine LD78beta into a Most Efficient Monocyte Attractant and CCR1 Agonist," Blood, 2000.

Ravetch, J. V. and S. Bolland (2001). "IgG Fe receptors." Annu Rev Immunol 19: 275-90.

Rochlitz C.F., "Gene Therapy of Cancer," Swiss Medicine Weekly, 131:4-9, 2001.

Ruffini et al., "Human chemokine MIP1alpha increases efficiency of targeted DNA fusion vaccines," Vaccine, 2010, pp. 191-199, vol. 29.

Ruffini et al., Idiotypic Vaccination for B-cell Malignancies as a Model for Therapeutic Cancer Vaccines: From Prototype Protein to Second Generation Vaccines; Haematologica; V 871 2002, Pier, pp. 989-1001.

Schall, T., et al., "Human Macrophage Inflammatory Protein a (MIP-1a) and MIP-1B Chemokines Attract Distinct Populations of Lymphocytes," J. Exp. Med., 1993, vol. 177, pp. 1821-1825.

Schjetne et al., "Delivery of Antigen to CD40 Induces Protective Immune Response against Tumors," J. Immunol. 178:4169-4176; 2007.

Schulenburg et al., Amino Acid Sequence of the Light Chain from a Mouse Myeloma Protein with Anti-Hapten Activity: Evicence for a Third Type of Light Chain, ONAS 68:2623-2626, 1971.

Simon, R. J., et al., "Peptoids: A modular approach to drug discovery," Proceedings of the National Academy of Sciences of the United States of America, 1992, pp. 9367-9371, vol. 89(20).

(56)        References Cited

OTHER PUBLICATIONS

Sirisinha, S. and H. N. Eisen (1971). "Autoimmune-like antibodies to the ligand-binding sites of myeloma proteins." Proc Natl Acad Sci U S A 68(12): 3130-5.

Slavin-Chiorini et al, "Biologic Properties of a CH2 Domain-Deleted Recombinant Immunoglobin," Int. J. Can. 53:97-103, 1993.

Snider, D. P. and D. M. Segal (1987). "Targeted antigen presentation using crosslinked antibody heteroaggregates." J Immunol 139(5): 1609-16.

Snodgrass, H. R., et al, "Restricted a/B receptor gene usage of idiotype-specific major histocompatibility complex-restricted T cells: selection for CDR3-related sequences," European Journal of Immunology, 1992, pp. 2169-2172.

Stevenson et al., "DNA vaccines to attack cancer" PNAS, 2004, pp. 14646-14652 vol. 101.

Tang et al; Genetic Immunization is a Simple Method for Eliciting an Immune Response; Nature, 1992, V 356; abstract.

Tao, et al. (1993). "Idiotype/granulocyte-macrophage colony-stimulating factor fusion protein as a vaccine or B-cell lymphoma." Nature 362(6422): 755-8.

The Norwegian Biotechnology Advisory Board—Discussion Paper, Regulation of DNA Vaccines and Gene Therapy on Animals, 2003.

Tjelle, et al. (2004). "Monoclonal antibodies produced by muscle after plasmid injection and electroporation. " J Mol Ther.

Tollefsen, S., T. Tjelle, et al. (2002). "Improved cellular and humoral immune responses against *Mycobacterium tuberculosis* antigens after intramuscular DNA immunisation combined with muscle electroporation." Vaccine 20 (27-28):3370-8.

Tunheim, G., et al., Human receptors of innate immunity (CD14, TLR2) are promising targets for novel recombinant immunoglobulin-based vaccine candidates, Vaccine, 2007, pp. 4723-4734, vol. 25(24).

Van Spriel et al., Immunothera Peutic Perspective for Bispecific Antibodies; Immunology Today; V 21; No. 8, Aug. 2000; pp. 391-396.

Van Spriel, Annemiek B. et al., "Immunotherapeutic perspective for bispecific antibodies" Immunology Today, 2000, pp. 391-396, vol. 21, No. 8.

Verma, et al., "Gene Therapy-Promises, Problems, and Prospects," Nature, vol. 389, p. 239-242, 1997.

Vile et al., "Cancer Gene Therapy: Hard Lessons and New Courses," Gene Therapy, V7; pp. 2-8; 2000.

Vile, RG et al., "Cancer Gene Therapy: Hard Lessons and New Courses" Gene Therapy, 2000, pp. 2-8, vol. 7, Macmilan Publishers Ltd.

Voskoglou-Nomikos, "Clinical Predictive Value of the in Vitro Cell Line, Human Xenograft, and Mouse Allograft Preclinical Cancer Models," Clin.Can.Res.; 9:4227-4239; 2003.

Wang, R., et al., "Induction of Antigen-Specific Cytotoxic T Lymphocytes in Humans by a Malaria DNA Vaccine," Science, 1998, pp. 476-480, vol. 282.

Wolff et al., The Mechanism of Naked DNA Uptake and Expression; Adv Genet. 2005, 54:3-20, pp. 1-3.

Xie et al., "Transforming Activity of a Novel Mutant of HPV16 E6E7 Fusion Gene," Virologica Sinica, 2011, vol. 26, No. 3, pp. 206-213.

Øynebråten, I et al., "P19-39. Vaccibodies: a Novel Vaccine Strategy for HIV that Target Viral Antigens to APC (Poster Presentation)," Retrovirology, 2009, vol. 6, Suppl. 3, p. 359, BioMed Central Ltd.

Bansal A, Singh MP, Rai B. Human papillomavirus-associated cancers: A growing global problem. Int J Appl Basic Med Res. Apr.-Jun 2016;6(2):84-9. doi: 10.4103/2229-516X.179027. PMID: 27127735; PMCID: PMC4830161.

Duperret, Elizabeth K et al. "A Synthetic DNA, Multi-Neoantigen Vaccine Drives Predominately MHC Class I CD8+ T-cell Responses, Impacting Tumor Challenge." Cancer immunology research vol. 7,2 (2019): 174-182. doi:10.1158/2326-6066.CIR-18-0283.

Holmström, M O et al. "The calreticulin (CALR) exon 9 mutations are promising targets for cancer immune therapy." Leukemia vol. 32, 2 (2018) : 429-437. doi:10.1038/leu.2017.214.

Jäger, E et al. "Induction of primary NY-ESO-1 immunity: CD8+ T lymphocyte and antibody responses in peptide-vaccinated patients with NY-ESO-1+ cancers." Proceedings of the National Academy of Sciences of the United States of America vol. 97,22 (2000): 12198-203. doi:10.1073/pnas.220413497.

Liu, Xiuli et al. "KRAS gene mutation in colorectal cancer is correlated with increased proliferation and spontaneous apoptosis." American journal of clinical pathology vol. 135,2 (2011): 245-52. doi:10.1309/AJCP7F02VAXIVSTP.

Thomas, Remy et al. "NY-ESO-1 Based Immunotherapy of Cancer: Current Perspectives." Frontiers in immunology vol. 9 947. May 1, 2018, doi:10.3389/fimmu.2018.00947.

Tsao, Sai Wah et al. "Epstein-Barr virus infection and nasopharyngeal carcinoma." Philosophical transactions of the Royal Society of London. Series B, Biological sciences vol. 372,1732 (2017): 20160270. doi:10.1098/rstb.2016.0270.

Wang, R F et al. "Identification of TRP-2 as a human tumor antigen recognized by cytotoxic T lymphocytes." The Journal of experimental medicine vol. 184, 6 (1996): 2207-16. doi:10.1084/jem.184.6.2207.

Xie, Youhua. "Hepatitis B Virus-Associated Hepatocellular Carcinoma." Advances in experimental medicine and biology vol. 1018 (2017): 11-21. doi:10.1007/978-981-10-5765-6_2.

Zhu, Xiao-li et al. Zhonghua bing li xue za zhi = Chinese journal of pathology vol. 41,9 (2012): 584-9. doi:10.3760/cma.j.issn.0529-5807.2012.09.003.

U.S. Appl. No. 13/805,709, filed Jul. 4, 2013, Vaccibody AS.

Bak et al., "Neoantigen-based cancer immunotherapy: One step closer to the promise of personalized medicine", Back Bay Life Science Advisors, Jun. 2018, 24 pages.

* cited by examiner

HPV16 E6 for patient 1: all epitopes predicted to bind to this patient's HLA class I alleles

FIG. 1

HPV16 E6 for patient 1: all epitopes predicted to bind to this patient's HLA class I and II alleles

FIG. 2

HPV16 E7 for patient 1: all epitopes predicted to bind to this patient's HLA class I alleles

FIG. 3

HPV16 E7 for patient 1: all epitopes predicted to bind to this patient's HLA class I and II alleles

FIG. 4

HPV16 E6 for patient 2: all epitopes predicted to bind to this patient's HLA class I alleles

FIG. 5

HPV16 E6 for patient 2: all epitopes predicted to bind to this patient's HLA class I and II alleles

MFQDPQERPRKLPQLCTELQTTIHDIILECVYCKQQLLRREVYDFAFRDLCIVYRDGNPYAVRDKCLKFYSKI

CTELQTTIH

VYDFAFRDL

FAFRDLCIV

IVYRDGNPY

YRDGNPYAV

KFYSKI

I

ELQTTIHDIILECVYI

DLCIVYRDGNPYAVR

LCIVYRDGNPYAVRD

CIVYRDGNPYAVRDK

FIG. 6

HPV16 E7 for patient 2: all epitopes predicted to bind to this patient's HLA class I alleles

```
MHGDTPTLHEYMLDLQPETTDLYGYGQLNDSSEEEDEIDGPAGQAEPDRAHYNIVTFCCKCDSTLRLCVQSTHVDIRTLEDLLMGTLGIVCPICSQKP
--GDTPTLHEY
-----TLHEYMLDL
-------HEYMLDLQP
---------LQPETTDLY
--------------TTDLYGYGQ
----------------TDLYGYGQL
-------------------------------------QAEPDRAHY
----------------------------------------RAHYNIVTF
------------------------------------------------STHVDIRTL
---------------------------------------------------------LEDLLMGTL
```

FIG. 7

INDIVIDUALIZED THERAPEUTIC ANTICANCER VACCINE

RELATED APPLICATIONS

This application is a national stage filing under 35 U.S.C. 371 of PCT/EP2021/059353, filed Apr. 9, 2021, which International Application was published by the International Bureau in English on Oct. 14, 2021, and application claims priority from Danish Application No. PA 2020 70221, filed Apr. 9, 2020, and Danish Application No. PA 2020 70338, filed May 26, 2020 which applications are hereby incorporated in their entirety by reference in this application.

FIELD OF INVENTION

The present invention relates to an individualized therapeutic anticancer vaccine, methods of treatment of cancer wherein such an anticancer vaccine is used as well as methods for producing the vaccine.

BACKGROUND OF INVENTION

Although treatment of cancer has been improved over the past few decades in particularly due to early detection and diagnosis, which has significantly increased the survival, only about 60% of patients diagnosed with cancer are alive 5 years after the diagnosis. Most of the cancer treatments in use are surgical procedures, radiation and cytotoxic chemotherapeutics, however they all have serious side effects. Within the last few years cancer immune therapies targeting cancer cells with the help of the patient's own immune system, i.e. anticancer vaccines, have attracted interest because such therapies may reduce or even eliminate some of the side effects seen in traditional cancer treatment.

The foundation of immunology is based on self-non-self-discrimination. Most of the pathogens inducing infectious diseases contain molecular signatures that can be recognized by the host and trigger immune responses. However, tumor cells are derived from normal cells, and do not generally express any molecular signatures, making them more difficult to be distinguished from normal cells. Nevertheless, most tumor cells express different types of tumor antigens. These can be shared tumor antigens, i.e. antigens that are expressed by tumors of the same kind in multiple individuals or expressed by a variety of tumors in multiple individuals or patient-specific antigens that are found in a particular patient.

Shared tumor antigens include overexpressed or aberrantly expressed cellular proteins, mutations in oncogenes or tumor suppressor genes and viral antigens. Patient-specific tumor antigens may arise due to one or more mutations in the tumor genome leading to a change in the amino acid sequence of the protein in question. These include non-synonymous mutations, frameshift mutations, fusion antigens and intron-retention antigens.

SUMMARY OF INVENTION

The present inventors have realized that an individualized anticancer vaccine raising immune response against shared tumor antigens that are present in the patient for whom the vaccine is designed and manufactured, and optionally in addition thereto against patient-specific tumor antigens, improves the anticancer immune response necessary to control or inhibit growth of the tumor cells.

Definitions

Tumor is used in the present context for both a solid tumor as well as for tumor cells found in a bodily fluid, such as blood.

Patient-specific tumor antigen, patient-specific cancer antigen and patient-specific antigen are used interchangeably herein for a tumor antigen found in a specific individual/patient, wherein said tumor antigen comprises one or more mutations found in the tumor cell as compared to the patient's normal cells.

Patient-specific tumor epitope, patient-specific cancer epitope, patient-specific epitope and neoepitope are used interchangeably herein for a peptide comprised in a patient-specific tumor antigen, which peptide comprises one or more immunogenic mutations.

Patient-specific tumor epitope sequence, patient-specific cancer epitope sequence, patient-specific epitope sequence and neoepitope sequence are used interchangeably herein to describe a nucleic acid sequence encoding the epitope/neoepitope or an amino acid sequence comprising the epitope/neoepitope.

Shared tumor antigen, shared cancer antigen and shared antigen are used interchangeably herein to describe a tumor antigen expressed by tumors of the same kind in multiple individuals or expressed by a variety of tumors in multiple individuals.

Shared tumor antigen sequence, shared cancer antigen sequence and shared antigen sequence are used interchangeably herein to describe a nucleic acid sequence encoding or an amino acid sequence comprising a part of or the whole of a shared antigen.

Patient-present shared tumor antigen, patient-present shared cancer antigen and patient-present shared antigen are used interchangeably herein to describe a shared tumor antigen that is or has been identified to be present in said patient.

Patient-present shared tumor antigen sequence, patient-present shared cancer antigen sequence and patient-present shared antigen sequence are used interchangeably herein to describe a nucleic acid sequence encoding or an amino acid sequence comprising a part of or the whole of a patient-present shared antigen.

Individualized therapeutic anticancer vaccine is used to describe a vaccine which is designed and manufactured for a specific individual/patient with the aim to stimulate an immune response that can recognize tumor cells already present in the individual and control or inhibit growth of such tumor cells.

Individual and patient are used interchangeably herein and denote a specific human being having cancer or suspected to have cancer.

DETAILED DESCRIPTION OF THE INVENTION

Cancers develop from the patient's normal tissue by one or a few cells starting an abnormal, uncontrolled proliferation of the cells due to mutations. Although the cancer cells are mutated, most of the genome is intact and identical to the remaining cells in the patient. One approach of attacking a tumor is based on the knowledge that any tumor in an individual/patient is unique: patient-specific mutations lead to expression of patient-specific mutated proteins (tumor-specific antigens), that are unique for the particular patient. These tumor specific and patient-specific antigens are not identical to any proteins in the normal cells of the patient.

Therefore, such patient-specific antigens should be suitable targets for a therapeutic anticancer vaccine which is manufactured specifically for the patient in question, i.e. an individualized therapeutic anticancer vaccine. The challenge with this type of anticancer vaccine is that, although patient-specific antigens are selected for inclusion into the vaccine according to their predicted therapeutic efficacy, some but not all show the expected therapeutic efficacy in the clinical setting. There is a need for improvement.

Shared tumor antigens have been found to be expressed by many tumors, either across patients with the same cancer type, or across patients and cancer types. An example is the HPV16 antigen, a viral antigen that is expressed in about 50% of all squamous cell carcinoma of the head and neck (SCCHN) patients, but also in patients with different cancers such as cervical cancer and vulvar squamous cell carcinoma (vSCC). Many of these shared antigens have previously been characterized as immunogenic and/or to be presented on specific HLA class I or class II alleles. Shared antigens may be included in an off-the-shelf therapeutic anticancer vaccine to be use in many patients (see for instance WO 2013/092875). However, while this type of anticancer vaccine shows clinical efficacy in some patients, no or little therapeutic efficacy is seen in others.

T cell responses are dependent on processing and presentation of cancer epitopes on each patient's HLA molecules. Due to the diversity of HLA class I and HLA class II molecules, off-the-shelf vaccines used in multiple patients normally include large full-length antigens to optimize the chance that the antigen includes epitopes that are present on a wide range of HLA molecules. However, a patient will only need shorter sequences of the antigen that include those epitopes that match that particular patient's HLA molecules. Hence, it is not possible to design and produce an off-the-shelf anticancer vaccine that covers all tumor antigens in every patient.

Further, off-the-shelf therapeutic anticancer vaccines that only target one tumor antigen do disregard tumor heterogeneity commonly found in a tumor and immune pressure against the one antigen may result tumor clones with different mutations.

The present invention presents an individualized therapeutic anticancer vaccine that targets patient-present shared antigens, optionally in addition thereto patient-specific antigens. This will increase the therapeutic effect compared to an anticancer vaccine comprising only patient-specific antigens or compared to an off-the-self anticancer vaccine including shared antigens.

Patient-present shared antigens to be included in the vaccine of the invention can have known immunogenicity, known expression patterns and known binding to specific HLA class I and/or class II molecules. T cells specific to patient-present shared antigens can travel to the tumor and affect the tumor microenvironment, thus increasing the likelihood that additional tumor-specific T cells are to able attack the tumor cells. Tumors are to various degrees heterogenic and thus may be composed of tumor cells expressing different subsets of the patient-present shared antigens included in the vaccine. Including patient-present shared antigens and optionally patient-specific antigens in the individualized vaccine according to the invention increases the chance of recognition and killing of multiple or all tumor cells due to shift in the immune microenvironment when reaching a threshold of activated T cells trafficking to the tumor.

The vaccines according to the present invention use the normal adaptive immune system to provide immunity against the tumor cells. The adaptive immune system is specific in that every antigen evokes an immune response specifically towards said antigen by the recognition of specific antigens during a process called antigen presentation. The cells of the adaptive immune system are lymphocytes, in particularly B cells and T cells. B cells are involved in the humoral immune response, whereas T cells are involved in cell-mediated immune response.

In particular, the vaccine according to the present invention is designed for evoking a cell-mediated immune response through activation of T cells against the tumor antigens. T cells recognize epitopes when they have been processed and presented complexed to an MHC molecule as discussed below.

The patient-present shared antigens sequences and optionally patient-specific antigens sequences of shared antigens and optionally patient-specific antigens included in the vaccine according to the invention are designed to be presented in the peptide-binding groove of MHC molecules as MHC-peptide complexes. There are two primary classes of major histocompatibility complex (MHC) molecules, MHC I and MHC II. The terms MHC (class) I and MHC (class) II are interchangeably used herein with HLA (class) I and HLA (class) II. Human leukocyte antigen (HLA) is a major histocompatibility complex in humans.

MHC I is found on the cell surface of all nucleated cells in the body. One function of MHC I is to display peptides of non-self-proteins from within the cell to cytotoxic T cells. The MHC I peptide complex is inserted into the plasma membrane of the cell presenting the peptide to the cytotoxic T cells, whereby an activation of cytotoxic T cells against the particular MHC-peptide complex is triggered. The peptide is positioned in a groove in the MHC I molecule, allowing the peptide to be about 8-10 amino acids long.

MHC II molecules are a family of molecules normally found only on antigen-presenting cells such as dendritic cells, mononuclear phagocytes, some endothelial cells, thymic epithelial cells, and B cells.

As opposed to MHC I, the antigens presented by MHC class II molecules are derived from extracellular proteins. Extracellular proteins are endocytosed, digested in lysosomes, and the resulting peptides are loaded onto MHC class II molecules and then presented at the cell surface. The antigen-binding groove of MHC class II molecules is open at both ends and is able to present longer peptides, generally between 15 and 24 amino acid residues long.

MHC class I molecules are recognized by CD8 and co-receptors on the T cells, normally called CD8+ T cells (or CD8+ cells), whereas MHC class II molecules are recognized by CD4 and co-receptors on the T cells, normally called CD4+ T cells (or CD4+ cells).

The individualized anticancer vaccines of the present invention comprise a polynucleotide encoding a polypeptide comprising three units, i.e. a targeting unit, a dimerization unit and an antigenic unit. Due to the dimerization unit, the polypeptide forms a dimeric protein, a so-called vaccibody.

The genes encoding the three units are genetically engineered to be expressed as one gene. When expressed in vivo, the polypeptides/dimeric proteins target antigen presenting cells (APCs), which results in enhanced vaccine potency compared to identical non-targeted antigens.

In a first aspect the invention relates to a polynucleotide comprising a nucleotide sequence encoding a targeting unit, a dimerization unit and an antigenic unit, wherein said antigenic unit comprises at least one patient-present shared antigen sequence or one or more parts thereof, and optionally one or more patient-specific antigen sequences or one or more parts thereof.

In a second aspect the invention relates to a polypeptide encoded by a polynucleotide comprising a nucleotide sequence encoding a targeting unit, a dimerization unit and an antigenic unit, wherein said antigenic unit comprises at least one patient-present shared antigen sequence or one or more parts thereof, and optionally one or more patient-specific antigen sequences or one or more parts thereof.

In a third aspect the invention relates to a dimeric protein consisting of two polypeptides encoded by a polynucleotide comprising a nucleotide sequence encoding a targeting unit, a dimerization unit and an antigenic unit, wherein said antigenic unit comprises at least one patient-present shared antigen sequence or one or more parts thereof, and optionally one or more patient-specific antigen sequences or one or more parts thereof.

In a fourth aspect the invention relates to an individualized therapeutic anticancer vaccine comprising an immunologically effective amount of:

(i) a polynucleotide comprising a nucleotide sequence encoding a targeting unit, a dimerization unit and an antigenic unit, wherein said antigenic unit comprises at least one patient-present shared antigen sequence or one or more parts thereof, and optionally one or more patient-specific antigen sequences or one or more parts thereof; or (ii) a polypeptide encoded by the polynucleotide as defined in (i), or (iii) a dimeric protein consisting of two polypeptides encoded by the polynucleotide as defined in (i); and a pharmaceutically acceptable carrier.

In one embodiment, the invention relates to an individualized therapeutic anticancer vaccine comprising an immunologically effective amount of:

(a) a polynucleotide comprising a nucleotide sequence encoding a targeting unit, a dimerization unit and an antigenic unit, wherein said antigenic unit comprises at least one patient-present shared antigen sequence or one or more parts thereof, and optionally one or more patient-specific antigen sequences or one or more parts thereof; and (b) a pharmaceutically acceptable carrier.

In another embodiment, the invention relates to an individualized therapeutic anticancer vaccine comprising an immunologically effective amount of (a) a dimeric protein or polypeptide encoded by a polynucleotide comprising a nucleotide sequence encoding a targeting unit, a dimerization unit and an antigenic unit, wherein said antigenic unit comprises at least one patient-present shared antigen sequence or one or more parts thereof, and optionally one or more patient-specific antigen sequences or one or more parts thereof; and (b) a pharmaceutically acceptable carrier.

The antigenic unit comprised in the polynucleotide, polypeptide, dimeric protein and individualized therapeutic anticancer vaccine according to the invention comprises at least one patient-present shared antigen sequence or one or more parts thereof. In one embodiment, the patient-present shared antigen is a shared antigen selected from the group consisting of overexpressed cellular proteins, aberrantly expressed cellular proteins, cancer testis antigens, viral antigens, differentiation antigens, mutated oncogenes, mutated tumor suppressor genes, oncofetal antigens, shared fusion antigens, shared intron retention antigens, dark matter antigens, shared antigens caused by spliceosome mutations and shared antigens caused by frameshift mutations.

In one embodiment, the patient-present shared antigen is an overexpressed or aberrantly expressed human cellular protein, i.e. a cellular protein found at increased levels in tumors compared with normal healthy cells and tissues. Examples of such overexpressed or aberrantly expressed cellular proteins include tumor protein D52, Her-2/neu, hTERT (telomerase) and survivin. In another embodiment, the patient-present shared antigen is a cancer testis antigen whose expression occurs in human malignancies as well as in normal testicular tissue. Examples of cancer testis antigens include MAGE-A, MAGE-B, GAGE, PAGE-1, SSX, HOM-MEL-40 (SSX2), NY-ESO-1, LAGE-1 and SCP-1. In yet another embodiment, the patient-present shared antigen is a differentiation antigen, for example tyrosinase and TRP-2. In yet another embodiment, the patient-present shared antigen is a viral antigen. Examples of viral antigens include human papilloma virus (HPV), hepatitis B virus (HBV), Epstein-Barr virus (EBV), Kaposi's sarcoma-associated herpesvirus (KSHV), Merkel cell polyomavirus (MCV or MCPyV), human cytomegalovirus (HCMV) and human T-lymphotropic virus (HTLV). In yet another embodiment, the patient-present shared antigen is a mutated oncogene. Examples of mutated oncogenes include RAS mutations, including KRAS, PIK3CA mutations and EGFR mutations. In yet another embodiment, the patient-present shared antigen is a mutated tumor suppressor gene. Examples include mutated p53, mutated pRB, mutated BCL2 and mutated SWI/SNF. In yet another embodiment, the patient-present shared antigen is an oncofetal antigen, for example alpha-fetoprotein or carcinoembryonic antigen. In yet another embodiment, the patient-present shared antigen is a shared intron retention antigen or shared antigen caused by frameshift mutation, for example CDX2 or CALR. In yet another embodiment, the patient-present shared antigen is a shared antigen caused by spliceosome mutations. An example is an antigen caused by mutations like SF3B1 mut.

For any cancer antigen, immune tolerance has likely occurred when a patient presents with cancer. An anticancer vaccine should specifically trigger immune response to the antigens incorporated in the vaccine. The peripheral immune tolerance to the selected antigens may be weak or strong. A patient is more likely to establish central immune tolerance against a shared antigen that is also expressed in normal tissue, i.e. a human cellular protein, such as overexpressed antigens and differentiation antigens. By incorporating such shared antigen sequences or parts thereof in the antigenic unit (either alone or together with other patient-present shared antigen sequences and optionally patient-specific antigen sequences), the vaccine according to the invention comprising the antigenic unit could elicit an immune response which is strong and broad enough to affect the tumor microenvironment and change the patient's immune response against the tumor from a suppressive/tolerated type to a pro-inflammatory type of immune response. This may help to break tolerance to several other antigens, thus representing a considerable clinical benefit for the patient. The afore-described concept may be referred to as tipping the cancer immunity set-point, Thus, in one embodiment the at least one patient-present shared antigen sequence is a shared antigen that is a human cellular protein, preferably an overexpressed or aberrantly expressed human cellular protein or a differentiation antigen.

The at least one patient-present shared antigen may be detected in the tissue or body fluid of the patient by methods known in the art, including:

sequencing the patient's genome or exome and optionally searching by tailor-made software in whole genome/exome-seq data to e.g. identify mutated oncogenes or mutated tumor suppressor genes;

immunohistochemistry of the patient's tumor tissue to detect the presence of mutated proteins;

RT-PCR to detect the presence of viral antigens or known mutations in oncogenes;

ELISA using antibodies against mutated tumor proteins in serum samples;

RNA-seq of tumor tissue and comparison to healthy tissue to detect expression/over-expression of shared antigens;

searching by tailor-made software in raw RNA sequence data to identify intron retention antigens;

searching by tailor-made software in whole genome-seq data to identify transposable elements which are elements of dark matter antigens;

detection of short repeats in raw whole exome/RNA sequence data to identify dark matter antigens;

RNA-seq data to identify shared viral antigens; and comparing RNA-seq of the patient's tumor samples with either patient's own healthy tissue or a cohort/database (e.g. TCGA) versus GTEX/HPA gene expression data.

In a preferred embodiment, the antigenic unit comprises at least one patient-present shared antigen sequence or part(s) of such antigen sequence that is known to be immunogenic, e.g. has previously shown an immunogenic response in other patients, has been described to elicit an immune response in other patients, or is predicted to bind to the particular patient's HLA class I and/or HLA class II alleles. In another preferred embodiment, the antigenic unit comprises one or more parts of at least one patient-present shared antigen sequence, e.g. one or more epitopes that are known to be immunogenic or are predicted to bind to the particular patient's HLA class I and/or HLA class II alleles. In a further preferred embodiment, the antigenic unit comprises one or more parts of at least one patient-present shared antigen sequence, e.g. one or more epitopes that are known to be immunogenic or are predicted to bind to the particular patient's HLA class I alleles.

In one embodiment, the antigenic unit comprises a patient-present shared antigen sequence or one or more parts thereof that have a length suitable for presentation by the particular patient's HLA alleles. Thus, in one embodiment the patient-present shared antigen sequence or the part thereof is from 7 to 30 amino acids long. In another embodiment, the patient-present shared antigen sequence or the part thereof has a length of from 7 to 10 amino acids or a length of from 13 to 30 amino acids, such as 7, 8, 9, 10, 11, 12, 13, 14 or 15 amino acids e.g. 9 amino acids.

The antigenic unit can comprise the at least one patient-present shared antigen sequence either in full length or can comprise one or more parts thereof. In one embodiment, the antigenic unit comprises one part of a patient-present shared antigen sequence. In another embodiment, the antigenic unit comprises several parts of a patient-present shared antigen sequence. The antigenic unit can comprise more than one patient-present shared antigen sequence, i.e. sequences of several patient-shared antigens, either each in full length or one or more parts of each such antigen. In one embodiment, the antigenic unit comprises one patient-present shared antigen sequence in full length and one or more parts of sequences of one or several other patient-present shared antigens, e.g. one part of a sequence of one other patient-present shared antigen or several parts of a sequence of one other patient-present shared antigen or one part of a sequence of each of the several other patient-present shared antigens or several parts of sequences of some or each of the several other patient-present shared antigens. In a preferred embodiment, the antigenic unit comprises sequences of several patient-present shared antigens, e.g. several parts of sequences of several patient-present shared antigens, more preferably several epitopes of several patient-present shared antigen, which epitopes are known to be immunogenic or are predicted to bind to the particular patient's HLA class I and/or HLA class II alleles, preferably to the particular patient's HLA class I alleles.

In yet another embodiment, the antigenic unit comprises one or more patient-present shared antigens in full length and one or more parts of one or more patient-present shared cancer antigens. Examples include:

antigenic units comprising one patient-present shared antigen in full length and one or more epitopes of one patient-present shared cancer antigen; and antigenic units comprising several patient-present shared cancer antigens, each of them in full length and one or more epitopes of one patient-present shared cancer antigen; and antigenic units comprising one patient-present shared antigen in full length and one or more epitopes of several patient-present shared cancer antigens; and antigenic units comprising several patient-present shared cancer antigens, each of them in full length and one or more epitopes of several patient-present shared cancer antigens.

In yet another embodiment, the antigenic unit comprises at least one patient-present shared antigen sequence in full length or more than one patient-present shared antigen sequences in full length. In one embodiment, the antigenic unit comprises 1 to 10 patient-present shared antigen sequences in full length. In another embodiment, the antigenic unit comprises 1 to 30 parts of patient-present shared antigen sequences in the form of long peptide sequences, e.g. from about 28 to 100 amino acids long, or nucleic acid sequences encoding such long peptide sequences, wherein the long peptide sequences include multiple epitopes that are predicted to bind to the patient's HLA class I and/or HLA class II alleles. In yet another embodiment, the antigenic unit comprises 1 to 50 parts of patient-present shared antigen sequences in the form of short peptide sequences/epitopes or nucleic acid sequences encoding such short peptide sequences/epitopes that are predicted to bind to the patient's HLA class I and/or HLA class II alleles.

In one embodiment from 3 to 50 patient-present shared antigen sequences are included in the antigenic unit, such as from 3 to 30 sequences, such as from 3 to 20 sequences, such as from 3 to 15 sequences, or such as from 3 to 10 sequences.

In another embodiment 5 to 50 patient-present shared antigen sequences are included in the antigenic unit, such as from 5 to 30 sequences, such as for example from 5 to 25 sequences, such as from 5 to 20 sequences, such as from 5 to 15 sequences or such as from 5 to 10 sequences.

In a further embodiment 10 to 50 patient-present shared antigen sequences are included in the antigenic unit, such as from 10 to 40 sequences, such as from 10 to 30 sequences, such as from 10 to 25 sequences, such as from 10 to 20 sequences or such as from 10 to 15 sequences.

In order to avoid that tumors escape the immune system by e.g. shutting down expression of an antigen that is the target of the anticancer vaccine, it is preferred to include sequences of a plurality of different patient-present shared antigens and optionally sequences of a plurality of different patient-specific antigens into the antigenic unit. Generally, the more genes the tumor needs to shut down in order to escape the immune system the less likely is it that the tumor is actually capable of shutting down all of them while still be able to proliferate or even survive. Furthermore, the tumor may be heterogeneous in that not each and every patient-present shared antigen or patient-specific antigen is expressed by all of the tumor cells.

Accordingly, in a preferred embodiment, the approach is to include as many patient-present shared antigen sequences and optionally patient-specific antigen sequences as possible into the antigenic unit of the vaccine of the invention in order to attack the tumor efficiently by activating T-cells able to recognize more tumor antigens expressed by the tumor cells. Also, in order to secure that all patient-present shared antigen sequences and optionally patient-specific antigen sequences are taken up efficiently into the same antigen presenting cell they are arranged such that they are one amino acid chain or encode for one amino acid chain (i.e. antigenic unit) instead of discrete peptides. However, as described above, the object of the vaccine of the invention is to activate the patient's T cells against the patient-present shared antigen sequences and optionally patient-specific antigen sequences comprised in the antigenic unit, and including too many of such sequences into the antigenic unit may result in the dilution of T-cells. Therefore, it is important to select the optimal patient-present shared antigen sequences and optionally patient-specific antigen sequences for inclusion into the antigenic unit.

The optimal patient-present shared antigen sequences are those that are known to be immunogenic. In a preferred embodiment, the antigenic unit comprises one or more parts of at least one patient-present shared antigen sequence, e.g. one or more epitopes that are known to be immunogenic or are predicted to bind the particular patient's HLA alleles, preferably to the patient's HLA class I alleles.

It is preferred to make "best use" of the antigenic unit, i.e. the antigenic unit comprises the least possible number of amino acids/sequences which do not contribute to the immunogenicity of the antigenic unit. As an example, it is less preferred to include a full-length patient-present shared antigen sequence into the antigenic unit, if such sequence only contains a few epitopes that are known to be immunogenic or are predicted to bind the particular patient's HLA alleles and the remainder of the sequence does not contribute to the immunogenicity of the antigenic unit. On the other hand, if such sequence contains several or many such epitopes which are close together, it may make sense to include the full length of the patient-present shared antigen sequence.

The antigenic unit may further comprise one or more patient-specific antigen sequences. Patient-specific antigens may be identified by sequencing the genome or exome of a patient's tumor. Compared to the patient's normal tissue exome, such sequences comprise one or more mutations. The mutation may be any mutation leading to a change in at least one amino acid. Accordingly, the mutation may be one of the following:

a non-synonymous mutation leading to a change in the amino acid a mutation leading to a frame shift and thereby a completely different open reading frame in the direction after the mutation a read-through mutation in which a stop codon is modified or deleted leading to a longer protein with a tumor-specific epitope splice mutations that lead to a unique tumor-specific protein sequence chromosomal rearrangements that give rise to a chimeric protein with a tumor-specific epitope at the junction of the two proteins.

The antigenic unit may comprise one or more patient-specific antigen sequences or one or more parts thereof. In one embodiment, the antigenic unit comprises one or more (several) patient-specific antigen sequences. In another embodiment, the antigenic unit comprises one or more parts of such one or more patient-specific antigen sequences, preferably one or more patient-specific epitopes.

The epitopes preferably have a length suitable for presentation by the MHC molecules discussed above. Thus, in a preferred embodiment the epitope is from 7 to 30 amino acids long. More preferred are epitope sequences having a length of from 7 to 10 amino acids or epitope sequences having a length of from 13 to 30 amino acids, such as 7, 8, 9, 10, 11, 12, 13, 14 or 15 amino acids.

In a preferred embodiment, the antigenic unit comprises at least one patient-specific epitope or at least 5 patent specific epitopes or at least 10 patient-specific epitopes. In another preferred embodiment, the antigenic unit comprises at least 15 patient-specific epitopes, such as at least 20 patient-specific epitopes.

In one embodiment from 3 to 50 patient-specific antigen sequences are included in the antigenic unit, such as from 3 to 30 sequences, such as from 3 to 20 sequences, such as from 3 to 15 sequences or such as from 3 to 10 sequences. In a preferred embodiment, such sequences are epitopes.

In another embodiment 5 to 50 patient-specific antigen sequences are included in the antigenic unit, such as from 5 to 30 sequences, such as for example from 5 to 25 sequences, such as from 5 to 20 sequences, such as from 5 to 15 sequences or such as from 5 to 10 sequences. In a preferred embodiment, such sequences are epitopes.

In a further embodiment 10 to 50 patient-specific antigen sequences may be included in the antigenic unit, such as from 10 to 40 sequences, such as from 10 to 30 sequences, such as from 10 to 25 sequences, such as from 10 to 20 sequences or such as from 10 to 15 sequences. In a preferred embodiment, such sequences are epitopes.

Particularly when the patient specific antigen sequences to be included in the antigenic unit is a short epitope, e.g. only a few amino acids long, the short epitope is included in the antigenic unit such that it is flanked at both sides by an amino acid sequence. Preferably, the short epitope is positioned essentially in the middle of two flanking sequences, in order to ensure that the epitope is presented by the antigen presenting cells after it has been processed. The flanking sequences are preferably the amino acid sequences flanking the epitope in the antigen.

The following applies to the patient-present shared antigen sequences and parts thereof and, if present, also to the patient-specific antigen sequences and parts thereof. Thus, in the following the term antigen sequence is used and intended to cover both patient-present shared antigen sequences and parts thereof and patient-specific antigen sequences and parts thereof.

In one embodiment, the antigenic unit comprises one copy of each antigen sequence, so that when e.g. 10 different of such sequences are comprised in the antigenic unit, a vaccine comprising said antigenic unit elicits a cell mediated immune response against all 10 different antigen sequences.

However, if only a few antigen sequences are included in the antigenic unit—either because only a few antigens have been identified or because only a few of the identified antigens are sufficiently immunogenic/known to or predicted to bind to the patient's HLA alleles—then the antigenic unit may comprise at least two copies of a particular antigen sequence in order to strengthen the immune response to the antigen.

The length of the antigenic unit is primarily determined by the length of the antigen sequences comprised therein as well as their number. In one embodiment, the antigenic unit comprises from 7 to 2000 amino acids, e.g. from 21 to 2000 amino acids, preferably from about 30 amino acids to about a 1500 amino acids, more preferably from about 50 to about 1000 amino acids, such as from about 100 to about 500 amino acids or from about 100 to about 400 amino acids or from about 100 to about 300 amino acids.

Although it is possible to obtain a relevant immune response towards the tumor if the antigen sequences are randomly arranged in the antigenic subunit, it is preferred to follow at least one of the following methods for arranging them in the antigenic unit in order to enhance the immune response:

The antigenic unit can be described as a polypeptide having an N-terminal start and a C-terminal end. The antigenic unit is connected to the dimerization unit, preferably via a unit linker. The antigenic unit is either located at the COOH-terminal end or the NH2-terminal end of the polypeptide/dimeric protein. It is preferred that the antigenic unit is in the COOH-terminal end of the polypeptide/dimeric protein.

The antigen sequences are preferably separated by a linker. In one embodiment, all but the terminal antigen sequence, i.e. the antigen sequence located at the end of the antigenic unit that is not connected to the dimerization unit, are arranged in antigenic subunits, each subunit consist of an antigen sequence and a subunit linker. Due to the separation of the antigen sequences by the linkers, each antigen is presented in an optimal way to the immune system.

In one embodiment, the antigen sequences are arranged from most antigenic to least antigenic in the direction from the N-terminal start of the antigenic unit to the C-terminal end of the antigenic unit, preferably in the direction of the dimerization unit towards the C-terminal end of the antigenic unit.

In another embodiment, in particular if the hydrophilicity/hydrophobicity varies greatly among the antigen sequences, it is preferred that the most hydrophobic antigenic sequence(s) is/are positioned substantially in the middle of the antigenic unit and the most hydrophilic antigen sequence(s) is/are positioned at the beginning and/or end of the antigenic unit.

Since a true positioning in the middle of the antigenic unit is only possible if the antigenic unit comprises an odd number of antigen sequences, the term "substantially" in this context refers to antigenic units comprising an even number of antigen sequences, wherein the most hydrophobic antigen sequence is positioned as close to the middle as possible.

By way of example, an antigenic unit comprises 5 antigenic subunits, each comprising a different antigen sequence, which are arranged as follows: 1-2-3*-4-5; with 1, 2, 3*,4 and 5 each being a different antigen sequence and—being a linker and * indicates the most hydrophobic antigen sequence, which is positioned in the middle of the antigenic unit.

In another example, an antigenic unit comprises 6 antigenic subunits, each comprising a different antigen sequence, which are arranged as follows: 1-2-3*-4-5-6 or, alternatively, as follows: 1-2-4-3*-5-6, with 1, 2, 3*, 4, 5 and 6 each being a different antigen sequence and—being a linker and * indicates the most hydrophobic antigen sequence, which is positioned substantially in the middle of the antigenic unit.

Alternatively, the antigen sequences may be arranged alternating between a hydrophilic and a hydrophobic antigen sequence.

Furthermore, GC rich antigen sequences should not be arranged adjacent to each other to avoid GC clusters. In a preferred embodiment, one GC rich antigen sequence is followed by at least one non-GC rich antigen sequence before a second GC rich antigen sequence follows.

In one embodiment the antigenic unit comprises antigen sequences in the following order: E7|linker|NY-ESO-1|linker|E6. In a preferred embodiment the antigenic unit comprises SEQ ID NO: 14.

In another preferred embodiment the antigenic unit comprises SEQ ID NO: 14 and SEQ ID NO: 15. SEQ ID NO: 15 comprises antigen sequences in the following order: T1D320|linker|T1D814|linker|T1D182|linker|T1D689| linker|E7|linker|T1D339|linker ST1D428|linker|NY-ESO-1|linker|T1D572|linker|T1D359|linker|T1D488|linker| T1D554|linker|T1D272|linker|T1D210|linker|T1D849| linker|T1D4|linker|T1D77|linker|T1D717|linker| T1D586|linker|E6.

In one embodiment the antigenic unit comprises antigen sequences in the following order: E6|linker|NY-ESO-1|linker|E7. In a preferred embodiment the antigenic unit comprises SEQ ID NO: 16.

In another preferred embodiment the antigenic unit comprises SEQ ID NO: 16 and SEQ ID NO: 17. SEQ ID NO: 17 comprises antigen sequences in the following order: E6|linker|T1D323|linker|T1D506|linker|T1D12|linker| T1D315|linker|T1D302|linker|T1D700|linker|NY-ESO-1|linker|T1D535|linker|T1D358|linker|T1D670|linker| T1D294|linker|T1D336|linker|T1D499|linker|T1D425| linker|T1D491|linker|T1D314|linker|T1D430|linker|E7| linker|T1D582.

In one embodiment the antigenic unit comprises antigen sequences in the following order: NY-ESO-1|linker|E7|linker|E6. In a preferred embodiment the antigenic unit comprises SEQ ID NO: 18.

In another preferred embodiment the antigenic unit comprises SEQ ID NO: 18 and SEQ ID NO: 19. SEQ ID NO: 19 comprises antigen sequences in the following order: T1D223 |linker|T1D164|linker|T1D56| linker|T1D36|linker|T1D129|linker|T1D274|linker| T1D62|linker|T1D5|linker|T1D144|linker|T1D441| linker|T1D368|linker|NY-ESO-1|linker|T1D234|linker|T1D162|linker|T1D39|linker| T1D272|linker|E7|linker|T1D328|linker|T1D188|linker|E6.

The antigenic unit may further comprise one or more linkers, which separate one antigen sequence from the other and a linker which connects the antigenic unit to the dimerization unit (hereinafter also called the unit linker). The one or more linkers ensure that each antigen sequence is presented in an optimal way to the immune system, which, if the antigenic units are included in the vaccine of the invention, increases the vaccine's efficacy.

The one or more linkers are preferably designed to be non-immunogenic and are preferably also flexible, which allows for the antigen sequences to be presented in an optimal manner to the T cells, even if the antigenic unit comprises a high number of antigen sequences.

Preferably, the length of the one or more linkers is from 4 to 20 amino acids to secure flexibility. In another preferred embodiment, the length of the one or more linkers is from 8 to 20 amino acids, such as from 8 to 15 amino acids, for example 8 to 12 amino acids or such as for example from 10 to 15 amino acids. In a particular embodiment, the length of the one or more linkers is 10 amino acids.

In a specific embodiment, the antigenic unit comprises 10 antigen sequences, wherein the linkers between these sequences have a length of from 8 to 20 amino acids, such as from 8 to 15 amino acids, for example 8 to 12 amino acids or such as for example from 10 to 15 amino acids. In a particular embodiment, the antigenic unit comprises 10 antigen sequences and the linkers between these sequences have a length of 10 amino acids.

The one or more linkers have preferably all the same nucleotide or amino acid sequence. If, however, one or more of the antigen sequences comprise an amino acid motif similar to the linker, it may be an advantage to substitute the neighboring linkers of that antigen sequence with linker of a different sequence. Further, if an antigen sequence/linker junction is predicted to constitute an immunogenic epitope in itself, then a linker of a different sequence might be used.

The one or more linkers are preferably serine (S)-glycine (G) linkers or comprise or consist of nucleotides that encode a serine-glycine amino acid sequence, such as GGGGS, GGGSS, GGGSG, GGGGS or multiple variants thereof such as GGGGSGGGGS or $(GGGGS)_m$, $(GGGSS)_m$, $(GGGSG)_m$, where m is an integer from 1 to 5, from 1 to 4 or from 1 to 3. In a preferred embodiment, m is 2.

In a preferred embodiment, the serine-glycine linker further comprises at least one leucine (L), such as at least 2 or at least 3 leucines. The serine-glycine linker may for example comprise 1, 2, 3 or 4 leucine. Preferably, the serine-glycine linker comprises 1 leucine or 2 leucines.

In one embodiment, the one or more linkers comprise or consist of the sequence LGGGS, GLGGS, GGLGS, GGGLS or GGGGL. In another embodiment, the one or more linkers comprise or consist of the sequence LGGSG, GLGSG, GGLSG, GGGLG or GGGSL. In yet another embodiment, the one or more linkers comprise or consist of the sequence LGGSS, GLGSS, GGLSS, GGGLS or GGGSL.

In yet another embodiment, the one or more linkers comprise or consist of the sequence LGLGS, GLGLS, GLLGS, LGGLS or GLGGL. In yet another embodiment, one or more linkers comprise or consist of the sequence LGLSG, GLLSG, GGLSL, GGLLG or GLGSL. In yet another embodiment, the one or more linkers comprise or consist of the sequence LGLSS, GLGLS, GGLLS, GLGSL or GLGSL.

In another embodiment, the one or more linkers are serine-glycine linkers that have a length of 10 amino acids and comprise 1 leucine or 2 leucines.

In one embodiment, the one or more linkers comprise or consist of the sequence LGGGSGGGGS, GLGGSGGGGS, GGLGSGGGGS, GGGLSGGGGS or GGGGLGGGGS. In another embodiment, the one or more linkers comprise or consist of the sequence LGGSG GGGSG, GLGSGGGGSG, GGLSGGGGSG, GGGLGGGGSG or GGGSLGGGSG. In yet another embodiment, the one or more linkers comprise or consist of the sequence LGGSSGGGSS, GLGSSGGGSS, GGLSSGGGSS, GGGLSGGGSS or GGGSLGGGSS.

In a further embodiment, the one or more linkers comprise or consist of the sequence LGGGSLGGGS, GLGGSGLGGS, GGLGSGGLGS, GGGLSGGGLS or GGGGLGGGGL. In another embodiment, the one or more linkers comprise or consist of the sequence LGGSGLGGSG, GLGSGGLGSG, GGLSGGGLSG, GGGLGGGGLG or GGGSLGGGSL. In yet another embodiment, the one or more linkers comprise or consist of the sequence LGGSSLGGSS, GLGSSGLGSS, GGLSSG-GLSS, GGGLSGGGLS or GGGSLGGGSL.

In one embodiment, the antigenic unit comprises 10 antigen sequences that are separated by 9 linkers, i.e. the terminal sequence is an antigen sequence, not a linker. In another embodiment, the antigenic unit comprises 15 antigen sequences that are separated by 14 linkers or 20 antigen sequences that are separated by 19 linkers.

In another embodiment, the antigenic unit comprises from 10 to 20 or from 10 to 25 antigen sequences that are separated by linkers. Preferably, said linkers have a length of 10 amino acids. The linkers may also have any length as defined herein above, such as for example from 5 to 12 amino acids.

Alternatively, the one or more linkers may be selected from the group consisting of GSAT linkers, i.e. a linkers comprising one or more glycine, serine, alanine and threonine residues and SEG linkers, i.e. linkers comprising one or more serine, glutamic acid and glycine residues or multiple variants thereof.

The antigenic unit and the dimerization unit are preferably connected by a unit linker. The unit linker may comprise a restriction site in order to facilitate the construction of the polynucleotide. It is preferred that the unit linker is a GLGGL linker or a GLSGL linker.

The vaccine of the invention comprises a targeting unit that targets antigen-presenting cells. Due to the targeting unit, the polypeptide/dimeric protein/vaccine of the invention leads to attraction of dendritic cells (DCs), neutrophils and other immune cells. Thus, the polypeptide/dimeric protein/vaccine comprising the targeting unit will not only target the antigenic unit to specific cells, but in addition facilitate a response-amplifying effect (adjuvant effect) by recruiting specific immune cells to the administration site of the polynucleotide/polypeptide/dimeric protein/vaccine. This unique mechanism is of great importance in a clinical setting where patients can receive the vaccine of the invention without any additional adjuvants since the vaccine itself provides the adjuvant effect.

The term "targeting unit" as used herein refers to a unit that delivers the polypeptide/dimeric protein/vaccine with its antigenic unit to an antigen presenting cell for MHC class II-restricted presentation to CD4+ T cells or for providing cross presentation to CD8+ T cells by MHC class I restriction.

The targeting unit is connected through the dimerization unit to the antigenic unit, wherein the latter is in either the COOH-terminal or the $NH_2$-terminal end of the polypeptide/dimeric protein. It is preferred that the antigenic unit is in the COOH-terminal end of the polypeptide/dimeric protein.

The targeting unit is designed to target the polypeptide/dimeric protein/vaccine of the invention to surface molecules expressed on the relevant antigen presenting cells, such as molecules expressed exclusively on subsets of dendritic cells (DC).

Examples of such target surface molecules on APC are HLA, cluster of differentiation 14 (CD14), cluster of differentiation 40 (CD40), chemokine receptors and Toll-like receptors (TLRs). Chemokine receptors include C-C motif chemokine receptor 1 (CCR1), C-C motif chemokine receptor 3 (CCR3) and C-C motif chemokine receptor 5 (CCR5) and XCR1. The Toll-like receptors may for example include TLR-2, TLR-4 and/or TLR-5.

The polypeptide/dimeric protein/vaccine of the invention can be targeted to said surface molecules by means of the targeting unit which comprises or consists, for example, of one or more antibody binding regions with specificity for HLA, CD14, CD40, or Toll-like receptor; ligands, e.g. soluble CD40 ligand; natural ligands like chemokines, e.g. chemokine ligand 5, also called C-C motif ligand 5 (CCL5 or RANTES) or macrophage inflammatory protein alpha (CCL3 or MIP-1a/MIP1-α); chemokine motif ligand 1 or 2 (XCL1 or XCL2) or bacterial antigens like for example flagellin.

In one embodiment, the targeting unit has affinity for an MHC class II protein. Thus, in one embodiment the nucleotide sequence encoding the targeting unit encodes the antibody variable domains (VL and VH) with specificity for MHC class II proteins, selected from the group consisting of anti-HLA-DP, anti-HLA-DR and anti-pan HLA class II.

In another embodiment, the targeting unit has affinity for a surface molecule selected from the group consisting of CD40, TLR-2, TLR-4 and TLR-5. Thus, in one embodiment the nucleotide sequence encoding the targeting unit encodes the antibody variable domains (VL and VH) with specificity for anti-CD40, anti-TLR-2, anti-TLR-4 and anti-TLR-5. In one embodiment, the nucleotide sequence encoding the targeting unit encodes Flagellin. Flagellin has affinity for TLR-5.

Preferably, the targeting unit has affinity for a chemokine receptor selected from CCR1, CCR3 and CCR5. More preferably, the nucleotide sequence encoding the targeting unit encodes the chemokine human macrophage inflammatory protein alpha (hMIP-1alpha, also called LD78beta, and hereinafter also denoted (h)MIP1α and LD78β), which binds to its cognate receptors, CCR1 and CCR5 expressed on the cell surface of APCs.

The binding of the polypeptide/dimeric protein/vaccine of the invention to its cognate receptors leads to internalization in the APC and degradation of the proteins into small peptides that are loaded onto MHC molecules and presented to CD4+ and CD8+ T cells to induce tumor specific immune responses. Once stimulated and with help from activated CD4+ T cells, CD8+ T cells will target and kill tumor cells expressing the same antigens.

In one embodiment of the present invention, the targeting unit comprises an amino acid sequence having at least 80% sequence identity to the amino acid sequence 24-93 of SEQ ID NO: 1. In a preferred embodiment, the targeting unit comprises an amino acid sequence having at least 85% sequence identity to the amino acid sequence 24-93 of SEQ ID NO:1, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% sequence identity. In one embodiment, the targeting unit comprises the amino acid sequence 24-93 of SEQ ID NO: 1.

In a more preferred embodiment the targeting unit consists of an amino acid sequence having at least 80% sequence identity to the amino acid sequence 24-93 of SEQ ID NO:1, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as at least 100% sequence identity to the amino acid sequence 24-93 of SEQ ID NO:1.

The term "dimerization unit" as used herein, refers to a sequence of nucleotides or amino acids between the antigenic unit and the targeting unit. Thus, the dimerization unit serves to connect the antigenic unit and the targeting unit and facilitates dimerization of two monomeric polypeptides into a dimeric protein. Furthermore, the dimerization unit also provides the flexibility in the polypeptide/dimeric protein to allow optimal binding of the targeting unit to the surface molecules on the APCs, even if they are located at variable distances. The dimerization unit may be any unit that fulfils these requirements.

Accordingly, in one embodiment the dimerization unit may comprise a hinge region. In another embodiment, the dimerization unit comprises another domain that facilitates dimerization. In yet another embodiment, the dimerization unit comprises a hinge region and another domain that facilitates dimerization. In one embodiment, the hinge region and the other domain may be connected through a linker (dimerization unit linker). In yet another embodiment, the dimerization unit comprises a hinge region, a dimerization unit linker and another domain that facilitates dimerization, wherein the dimerization unit linker is located between the hinge region and the other domain that facilitates dimerization.

The term "hinge region" refers to a peptide sequence of the dimeric protein that facilitates the dimerization. In other words, the term "hinge region" refers to an amino acid sequence comprised in the dimerization unit that contributes to joining two of the polypeptides, i.e. contributes to the formation of a dimeric protein.

Moreover, the hinge region functions as a flexible spacer between the units allowing the two targeting units of the dimeric protein to bind simultaneously to two target molecules on APCs, even if they are expressed with variable distances. The hinge region may be Ig derived, such as derived from IgG3. The hinge region may comprise of one or more parts of an Ig-derived hinge region. The hinge region may contribute to the dimerization through the formation of covalent bond(s), e.g. disulfide bridge(s) between cysteines. Thus, in one embodiment the hinge region has the ability to form one or more covalent bonds. The covalent bond can for example be a disulfide bridge.

In one embodiment, the dimerization unit comprises a hinge exon h1 and hinge exon h4 (human hinge region 1 and human hinge region 4) having an amino acid sequence having at least 80% sequence identity to the amino acid sequence 94-120 of SEQ ID NO: 2.

In a preferred embodiment, the dimerization unit comprises a hinge exon h1 and hinge exon h4 with an amino acid sequence having at least 85% sequence identity to the amino acid sequence 94-120 of SEQ ID NO: 2, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98% or such as at least 99% sequence identity. In a preferred embodiment, the dimerization unit comprises a hinge exon h1 and hinge exon h4 with the amino acid sequence 94-120 of SEQ ID NO: 2.

In one embodiment, the other domain that facilitates dimerization is an immunoglobulin domain, such as a carboxyterminal C domain (C domain), such as a CH1 domain, a CH2 domain or a carboxyterminal C domain (i.e. a CH3 domain), or a sequence that is substantially identical to the C domain or a variant thereof. Preferably, the other domain that facilitates dimerization is a carboxyterminal C domain derived from IgG. More preferably, the other domain that facilitates dimerization is a carboxyterminal C domain derived from IgG3.

In one embodiment, the dimerization unit comprises a carboxyterminal C domain derived from IgG3 with an amino acid sequence having at least 80% sequence identity to the amino acid sequence 131-237 of SEQ ID NO: 2.

In a preferred embodiment, the dimerization unit comprises a carboxyterminal C domain derived from IgG3 with an amino acid sequence having at least 85% sequence identity to the amino acid sequence 131-237 of SEQ ID NO: 2, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98% or such as at least 99% sequence identity. In a preferred embodiment, the dimerization unit comprises a carboxyterminal C domain derived from IgG3 with the amino acid sequence 131-237 of SEQ ID NO: 2.

The immunoglobulin domain contributes to dimerization through non-covalent interactions, e.g. hydrophobic interactions. Thus, in one embodiment, the immunoglobulin domain has the ability to form dimers via noncovalent interactions. Preferably, the noncovalent interactions are hydrophobic interactions.

It is preferred that if the dimerization unit comprises a CH3 domain, it does not comprise a CH2 domain. Further, it is preferred that if the dimerization unit comprises a CH2 domain, it does not comprise a CH3 domain.

In a preferred embodiment, the dimerization unit consists of a polypeptide consisting of hinge exon h1 and hinge exon h4, a third linker (or dimerization unit linker) and a CH3 domain of human IgG3.

In one embodiment of the present invention, the dimerization unit comprises an amino acid sequence having at least 80% sequence identity to the amino acid sequence 94-237 of SEQ ID NO: 2. In a preferred embodiment, the dimerization unit comprises an amino acid sequence having at least 85% sequence identity to the amino acid sequence 94-237 of SEQ ID NO: 2, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, or such as at least 99% sequence identity.

In a more preferred embodiment the dimerization unit consists of an amino acid sequence having at least 80% sequence identity to the amino acid sequence 94-237 of SEQ ID NO: 2, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% sequence identity to the amino acid sequence 94-237 of SEQ ID NO: 2.

In an even more preferred embodiment, the dimerization unit consists of the amino acid sequence 94-237 of SEQ ID NO: 2.

In one embodiment the linker connecting the hinge region to the other domain (the dimerization unit linker) is present in the dimerization unit. In another embodiment, the linker is present and is a G3S2G3SG linker. In an alternative embodiment, the dimerization unit linker is a glycine-serine rich linker, preferably GGGSSGGGSG, i.e. the dimerization unit comprises a glycine-serine rich dimerization unit linker and preferably the dimerization unit linker is GGGSSGGGSG. It is to be understood that the dimerization unit may have any orientation with respect to antigenic unit and targeting unit. In one embodiment, the antigenic unit is in the COOH— terminal end of the dimerization unit (e.g. via a unit linker) with the targeting unit in the N-terminal end of the dimerization unit. In another embodiment, the antigenic unit is in the N-terminal end of the dimerization unit with the targeting unit in the COOH-terminal end of the dimerization unit. It is preferred that the antigenic unit is in the COOH end of the dimerization unit.

In a preferred embodiment, the polynucleotide of the invention further comprises a nucleotide sequence encoding a signal peptide. The signal peptide is either located at the N-terminal end of the targeting unit or the C-terminal end of the targeting unit, depending on the orientation of the targeting unit in the polypeptide. The signal peptide is constructed to allow secretion of the polypeptide encoded by the polynucleotide in the cells transfected with said polynucleotide.

Any suitable signal peptide may be used. Examples of suitable peptides are an Ig VH signal peptide, such as SEQ ID NO: 9 a human TPA signal peptide, such as SEQ ID NO: 10 and a signal peptide comprising an amino acid sequence having at least 80% sequence identity to the amino acid sequence 1-23 of SEQ ID NO:1. In an alternative embodiment, the signal peptide is a human MIP1-a signal peptide.

In a preferred embodiment, the signal peptide comprises an amino acid sequence having at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% sequence identity to the amino acid sequence 1-23 of SEQ ID NO:1. In an alternative embodiment, the signal peptides comprises the amino acid sequence 1-23 of SEQ ID NO:1.

In a more preferred embodiment, the signal peptide consists of an amino acid sequence having at least 80%, preferably at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% sequence identity to the amino acid sequence 1-23 of SEQ ID NO:1. In an alternative embodiment, the signal peptides consists of the amino acid sequence 1-23 of SEQ ID NO:1.

Sequence identity may be determined as follows: A high level of sequence identity indicates likelihood that a second sequence is derived from a first sequence. Amino acid sequence identity requires identical amino acid sequences between two aligned sequences. Thus, a candidate sequence sharing 70% amino acid identity with a reference sequence requires that, following alignment, 70% of the amino acids in the candidate sequence are identical to the corresponding amino acids in the reference sequence. Identity may be determined by aid of computer analysis, such as, without limitations, the ClustalW computer alignment program (Higgins D., Thompson J., Gibson T., Thompson J. D., Higgins D. G., Gibson T. J., 1994. CLUSTAL W: improving the sensitivity of progressive multiple sequence alignment through sequence weighting, position-specific gap penalties and weight matrix choice. Nucleic Acids Res. 22:4673-4680), and the default parameters suggested therein. Using this program with its default settings, the mature (bioactive) part of a query and a reference polypeptide are aligned. The number of fully conserved residues is counted and divided by the length of the reference polypeptide. In doing so, any tags or fusion protein sequences, which form part of the query sequence, are disregarded in the alignment and subsequent determination of sequence identity.

The ClustalW algorithm may similarly be used to align nucleotide sequences. Sequence identities may be calculated in a similar way as indicated for amino acid sequences.

Another preferred mathematical algorithm utilized for the comparison of sequences is the algorithm of Myers and Miller, CABIOS (1989). Such an algorithm is incorporated into the ALIGN program (version 2.0) which is part of the FASTA sequence alignment software package (Pearson WR, Methods Mol Biol, 2000, 132:185-219). Align calculates sequence identities based on a global alignment. Align0 does not penalize to gaps in the end of the sequences. When utilizing the ALIGN and Align0 program for comparing amino acid sequences, a BLOSUM50 substitution matrix with gap opening/extension penalties of −12/−2 is preferably used.

The vaccine of the invention may comprise a polynucleotide as described above. The polynucleotide may comprise a DNA nucleotide sequence or an RNA nucleotide sequence, such as genomic DNA, cDNA, and RNA sequences, either double stranded or single stranded.

It is preferred that the polynucleotide is optimized to the species to express the polypeptide according to the invention, i.e. it is preferred that the polynucleotide sequence is human codon optimized.

The vaccine of the invention may further comprise a polypeptide encoded by the polynucleotide sequence as defined above. The polypeptide may be expressed in vitro for production of the vaccine according to the invention, or the polypeptide may be expressed in vivo as a result of administration of the polynucleotide as defined above to an individual/patient.

Due to the presence of the dimerization unit, dimeric proteins are formed when the polypeptide is expressed. The dimeric protein may be a homodimer, i.e. wherein the two polypeptide chains are identical and consequently comprise identical antigen sequences, or the dimeric protein may be a heterodimer comprising two different monomeric polypeptides encoded in the antigenic units. The latter may be relevant if the amount of antigen sequences exceeds an upper size limit for the antigenic unit. It is however preferred that the dimeric protein is a homodimeric protein.

In a fifth aspect, the invention relates to a vector comprising a polynucleotide comprising a nucleotide sequence encoding a targeting unit, a dimerization unit and an antigenic unit, wherein said antigenic unit comprises at least one patient-present shared antigen sequence or one or more parts thereof, and optionally one or more patient-specific antigen sequences or one or more parts thereof.

The vector is for transfecting a host cell and expression of a polypeptide/dimeric protein encoded by the polynucleotide described above, i.e. an expression vector, e.g. a DNA plasmid.

It is preferred that the vector allows for easy exchange of the various units described above, particularly the antigenic unit. In one embodiment, the vector may be a pUMVC4a vector or a vector comprising NTC9385R vector backbones. The antigenic unit may be exchanged with an antigenic unit cassette restricted by the SfiI restriction enzyme cassette where the 5' site is incorporated in the GLGGL/GLSGL linker and the 3' site is included after the stop codon in the vector.

In a sixth aspect, the invention relates to a host cell comprising a polynucleotide comprising a nucleotide sequence encoding a targeting unit, a dimerization unit and an antigenic unit, wherein said antigenic unit comprises at least one patient-present shared antigen sequence or one or more parts thereof, and optionally one or more patient-specific antigen sequences or one or more parts thereof.

In a seventh aspect, the invention relates to a host cell comprising a vector comprising a polynucleotide comprising a nucleotide sequence encoding a targeting unit, a dimerization unit and an antigenic unit, wherein said antigenic unit comprises at least one patient-present shared antigen sequence or one or more parts thereof, and optionally one or more patient-specific antigen sequences or one or more parts thereof.

Suitable host cells include prokaryotes, yeast, insect or higher eukaryotic cells. In a preferred embodiment, the host cell is a human cell, preferably the cell of a cancer patient, more preferably the same cancer patient whose at least one patient-present shared antigen sequence or one or more parts thereof, and optionally whose one or more patient-specific antigen sequences or one or more parts thereof is derived from.

The vaccine according to the invention is an individualized therapeutic anticancer vaccine in the sense that the at least one patient-present shared antigen sequence and optionally one or more patient-specific antigen sequences are identified in the patient who will be vaccinated with said vaccine, in e.g. the patient's tumor tissue or body fluids such as blood.

Accordingly, in an eighth aspect the invention relates to a method for preparing an individualized therapeutic anticancer vaccine comprising an immunologically effective amount of the dimeric protein, or the polypeptide as defined above by producing the polypeptide in vitro.

The in vitro synthesis of the polypeptides and proteins may be carried out by any suitable method known to the person skilled in the art, such as by peptide synthesis or expression of the polypeptide in any of the suitable expressions systems known in the art, followed by purification.

Accordingly, in one embodiment the invention provides a method for preparing an individualized therapeutic anticancer vaccine comprising an immunologically effective amount of (i) a dimeric protein consisting of two polypeptides encoded by a polynucleotide comprising a nucleotide sequence encoding a targeting unit, a dimerization unit and an antigenic unit, wherein said antigenic unit comprises at least one patient-present shared antigen sequence or one or more parts thereof, and optionally one or more patient-specific antigen sequences or one or more parts thereof; or (ii) (ii) a polypeptide encoded by a polynucleotide comprising a nucleotide sequence encoding a targeting unit, a dimerization unit and an antigenic unit, wherein said antigenic unit comprises at least one patient-present shared antigen sequence or one or more parts thereof, and optionally one or more patient-specific antigen sequences or one or more parts thereof by producing the dimeric protein or polypeptide in vitro, the method comprises a) transfecting cells with the polynucleotide;

b) culturing the cells;

c) collecting and purifying the dimeric protein or the polypeptide expressed from the cells, and d) mixing the dimeric protein or polypeptide obtained from step c) with a pharmaceutically acceptable carrier.

In a preferred embodiment, the dimeric protein or polypeptide from step c) is dissolved in said pharmaceutically acceptable carrier.

The pharmaceutically acceptable carrier is preferably an aqueous pharmaceutically acceptable carrier, such as water or a buffer. In one embodiment, the vaccine comprises further an adjuvant.

Purification may be carried out according to any suitable method, such as chromatography, centrifugation, or differential solubility.

In a ninth aspect the invention relates to a method for preparing an individualized therapeutic anticancer vaccine comprising an immunologically effective amount of polynucleotide as defined above in vitro.

Thus, in one embodiment, the invention provides a method for preparing an individualized therapeutic anticancer vaccine comprising an immunologically effective amount of a polynucleotide comprising a nucleotide sequence encoding a targeting unit, a dimerization unit and an antigenic unit, wherein said antigenic unit comprises at least one patient-present shared antigen sequence or one or more parts thereof, and optionally one or more patient-specific antigen sequences or one or more parts thereof, the method comprises a. preparing the polynucleotide;

b. optionally cloning the polynucleotide into an expression vector and c. mixing the polynucleotide from step a) or the vector form step b) with a pharmaceutically acceptable carrier.

The polynucleotide may be prepared by any suitable method known to the skilled person. For example, the polynucleotide may be prepared by chemical synthesis using an oligonucleotide synthesizer.

In particularly, smaller nucleotide sequences, such as for example nucleotide sequences encoding the targeting unit, the dimerization unit and/or parts of the antigenic unit may be synthesized individually and then ligated to produce the final polynucleotide for inclusion into the vector backbone.

For the design of the antigenic unit comprised in the individualized therapeutic anticancer vaccine, the method of preparing the vaccine is preceded by a method of identifying the antigen sequences (i.e. patient-present shared antigen sequences and optionally patient-specific antigen sequences) to be included into the antigenic unit.

The patient-present shared antigens may be identified in the (tumor) tissue or body fluid of the patient (obtained by methods known in the art) by methods known in the art, including:

sequencing the patient's genome or exome and optionally searching by tailor-made software in whole genome/exome-seq data to e.g. identify mutated oncogenes or mutated tumor suppressor genes;

immunohistochemistry of the patient's tumor tissue to detect the presence of mutated proteins;

RT-PCR to detect the presence of viral antigens or known mutations in oncogenes;

ELISA using antibodies against mutated tumor proteins in serum samples;

RNA-seq of tumor tissue and comparison to healthy tissue to detect expression/over-expression of shared antigens;

searching by tailor-made software in raw RNA sequence data to identify intron retention antigens;

searching by tailor-made software in whole genome-seq data to identify transposable elements which are elements of dark matter antigens;

detection of short repeats in raw whole exome/RNA sequence data to identify dark matter antigens;

RNA-seq data to identify shared viral antigens; and comparing RNA-seq of the patient's tumor samples with either patient's own healthy tissue or a cohort/database (e.g. TCGA) versus GTEX/HPA gene expression data In a preferred embodiment, the antigenic unit comprises at least one patient-present shared antigen sequence that is known to be immunogenic. In another preferred embodiment, the antigenic unit comprises one or more parts of at least one patient-present shared antigen sequence, e.g. one or multiple epitopes that are known to be immunogenic or are predicted to bind the particular patient's HLA alleles. If patient-specific antigen sequences are included in the antigenic unit, the antigenic unit preferably comprises patient-specific antigen sequences with predicted immunogenicity.

Thus, the identified patient-present shared antigens and patient-specific antigens may be further processed to find those sequences which renders the vaccine of the invention most effective, when such sequences are included into the antigenic unit. The way and sequence such processing is done depends on how said antigens were identified, i.e. the data that form the basis for such processing. In one embodiment, the processing and selecting of the antigen sequences to be included in the vaccine of the invention is carried out as follows:

1) A search in the literature and/or in one or more databases is carried out to retrieve information about and sequences of shared antigens and preferably information about their expression pattern, immunogenicity, epitopes and HLA presentation. Such search is carried out to determine whether the identified antigen is a patient-present shared antigen or a patient-specific antigen.

2) If it was determined that the identified antigen is a patient-present shared antigen, the sequence thereof is studied to identify epitopes, preferably all epitopes, that are predicted to bind to patient-specific HLA class I and/or class II alleles. The patient's HLA class I and/or II alleles are determined, e.g. by sequencing normal tissue such as blood cells. The prediction may be carried out by prediction tools known in the art, i.e. prediction software known in the art, e.g. NetMHCpan and similar tools.

3) The most promising, i.e. the most immunogenic sequences showing predicted binding to one or more of the patient's HLA class I/II alleles, of the patient-present shared antigen are selected for inclusion into the antigenic unit. In one embodiment, a number of minimal epitopes is selected, e.g. if only a few promising epitopes were identified in step 2 or if longer stretches of non-immunogenic sequences are present between the epitopes. In another embodiment, a longer sequence is selected which comprises several epitopes that bind to patient's specific HLA alleles. In yet another embodiment, the full-length sequence is selected for inclusion into the antigenic unit.

4) Optionally, the most promising patient-specific antigen sequences, e.g. epitopes, are selected for inclusion into the antigenic unit based on predicted immunogenicity and binding to the patient's HLA class I and/or class II alleles of such sequences.

If patient-specific antigen sequences are to be included in the antigenic unit, once such antigens are identified and the patient's HLA class I and/or II alleles are determined, the next step is to select the most promising sequences thereof, e.g. epitopes, based on predicted immunogenicity and binding to the patient's HLA class I and/or class II alleles of such sequences.

Tumor mutations are discovered by sequencing of tumor and normal tissue and make a comparison of the obtained sequences. A variety of methods are available for detecting the presence of a particular mutation or allele in an individual's DNA or RNA. For example, techniques including dynamic allele- specific hybridization (DASH), microplate array diagonal gel electrophoresis (MADGE), pyrosequencing, oligonucleotide- specific ligation, the TaqMan system as well as various DNA "chip" technologies such as the Affymetrix SNP chips may be applied. Alternatively, a method for identifying mutations by direct protein sequencing may be carried out.

Out of the maybe hundreds or thousands of mutations in the tumor exome, the most promising sequences are selected in silico on the basis of predictive HLA-binding algorithms. The intention is to identify all relevant epitopes and after a ranking or scoring, determine the sequences to be included in the antigenic unit.

Any suitable algorithm may be used, such as one of the following: Available free software analysis of peptide-MHC binding (IEDB and NetMHCpan) may be downloaded from the following websites:

http://www.iedb.org/ http://www.cbs.dtu.dk/services/NetMHC/

Commercially available advanced software to predict optimal sequences for vaccine design are found here:

http://www.oncoimmunity.com/ https://omictools.com/t-cell-epitopes-category https://github.com/griffithlab/pVAC-Seq http://crdd.osdd.net/raghava/cancertope/help.php http://www.epivax.com/tag/neoantigen/

Each mutation is scored with respect to its antigenicity, and the most antigenic epitopes are selected and optimally arranged in the antigenic unit.

Thus, in one embodiment, the invention provides a method for preparing an individualized therapeutic anticancer vaccine comprising the steps of:

a) identifying at least one patient-present shared antigen in the tumor tissue or body fluid of a patient b) determining the patient's HLA class I and/or class II alleles c) predicting the immunogenicity of the identified at least one antigen or one or more parts thereof by their predicted binding to the patient's HLA class I and/or II alleles d) selecting at least one antigen or one or more parts thereof based on their immunogenicity predicted in step c); and e) preparing a polynucleotide sequence comprising an antigenic unit comprising a nucleotide sequence encoding the at least one antigen or one or more parts thereof selected in step d).

In another embodiment, the invention provides a method for preparing an individualized therapeutic anticancer vaccine comprising the steps of:

a) identifying at least one patient-present shared antigens in the tumor tissue or body fluid of a patient and identifying one or more patient-specific antigens in the tumor tissue of said patient;

b) determining the patient's HLA class I and/or class II alleles;

c) predicting the immunogenicity of the identified at least one patient-present shared antigens or parts thereof and the identified one or more patient-specific antigens or one or more parts thereof by their predicted binding to the patient's HLA class I and/or II alleles;

d) selecting at least one patient-specific shared antigens or one or more parts thereof and one or more patient-specific antigens or one or more parts thereof based on their immunogenicity predicted in step c); and e) preparing a polynucleotide sequence comprising an antigenic unit comprising a nucleotide sequence encoding the at least one patient-specific shared antigens or one or more parts thereof and one or more patient-specific antigens or one or more parts thereof selected in step d).

In one embodiment, the polynucleotide sequence prepared in step e) further comprises nucleotide sequences encoding a targeting unit as described herein and a dimerization unit as described herein.

In a preferred embodiment, the prepared polynucleotide sequence is cloned into an expression vector. In yet another preferred embodiment, the polynucleotide sequence of step e) is cloned into an expression vector comprising nucleotide sequences encoding the dimerization unit and the targeting unit.

In yet another embodiment, the polynucleotide or the vector is mixed with a pharmaceutically acceptable carrier.

The final vaccine is then produced to comprise one of the following:

the polynucleotide as defined above the polypeptide encoded by the polynucleotide as defined above the dimeric protein comprising to polypeptide chains encoded by the polynucleotide as defined above The vaccine further comprises a pharmaceutically acceptable carrier and may further comprise other pharmaceutically acceptable excipients, e.g. stabilizers, adjuvants, buffers and the like.

Pharmaceutically acceptable carriers include, but are not limited to, saline, buffered saline, such as PBS, dextrose, water, glycerol, ethanol, sterile isotonic aqueous buffer(s), and combinations thereof.

In particularly for vaccines comprising polypeptides/proteins, pharmaceutically acceptable excipients include, but are not limited to poly-ICLC, 1018 ISS, aluminum salts, Amplivax, AS 15, BCG, CP-870,893, CpG7909, CyaA, dSLIM, GM-CSF, IC30, IC31, Imiquimod, ImuFact EV1 P321, IS Patch, ISS, ISCOMATRIX, Juvlmmune, LipoVac, MF59, monophosphoryl lipid A, Montanide IMS 1312, Montanide ISA 206, Montanide ISA 50V, Montanide ISA-51, OK-432, OM-174, OM-197-MP-EC, ONTAK, PepTel.RTM, vector system, PLGA microparticles, resiquimod, SRL172, virosomes and other virus-like particles, YF-17D, VEGF trap, R848, beta-glucan, Pam3Cys, Aquila's QS21 stimulon, vadimezan, and/or AsA404 (DMXAA).

Particularly for vaccines comprising polynucleotides comprised in an expression vector, the vaccine may comprise molecules that ease the transfection of cells and/or adjuvants in the form of plasmids comprising nucleotide sequences encoding chemokines or cytokines in order to enhance the immune response.

The vaccine is formulated into any suitable formulation for administration to the patient, such as a liquid formulation for intradermal or intramuscular injection.

The vaccine may be administered in any way suitable for either a polypeptide/protein vaccine or a polynucleotide vaccine, such as administered by injection intradermally, intramuscularly, subcutaneously, or by mucosal or epithelial application, such as intranasally, orally, enterally or to the bladder.

In particularly the vaccine is preferably administered intramuscularly or intradermally when the vaccine is a polynucleotide vaccine.

In one embodiment the vaccine is administered by intranodal injection. As used herein, the term "intranodal injection" means that the vaccine is injected into the lymph nodes.

The individualized therapeutic anticancer vaccine of the invention prepared by the methods described above may be obtained within less than 12 weeks, e.g. within less than 9 weeks or less than 8 weeks or less than 6 weeks or within 4 weeks.

The cancer treated may be any cancer, e.g. a cancer wherein the cancer cells comprise alterations resulting in a shared cancer antigen and optionally a patient-specific cancer antigen.

The cancer may be a primary tumor, metastasis or both. The tumor examined for alterations may be a primary tumor or a metastasis. In one embodiment, the cancers to be treated are cancers known to have a high antigen load, such as melanomas, lung cancer, renal, head and neck or bladder cancer. In another embodiment, the cancer treated is a solid cancer or liquid cancer. Examples of solid cancers are cancers forming a solid mass, e.g. a tumor. Examples of liquid cancers are cancers present in body fluid, such as lymphomas or blood cancers. Examples of cancers that can be treated with vaccine of the invention are breast cancer, ovarian cancer, colon cancer, prostate cancer, bone cancer, colorectal cancer, gastric cancer, lymphoma, malignant melanoma, liver cancer, small cell lung cancer, non-small cell lung cancer, pancreatic cancer, thyroid cancers, kidney cancer, cancer of the bile duct, brain cancer, cervical cancer, bladder cancer, esophageal cancer, Hodgkin's disease and adrenocortical cancer.

In a preferred embodiment the treatment is performed with a vaccine comprising the polynucleotide as described above, for example wherein the polynucleotide is DNA or RNA, preferably comprised in a vector.

It is preferred to inject the polynucleotide vaccine of the invention intramuscularly, such as in the big muscles, for example in the shoulder, buttock or thigh. It has been found that the polypeptide/dimeric protein of the invention is produced locally, and relevant immune cells internalize the polypeptide/dimeric protein essentially at the site of their production, i.e. substantially no polypeptide/dimeric protein reaches the blood stream.

Any suitable method for injecting the polynucleotide vaccine may be used, such as by the use of a jet injector or assisted by electroporation.

The vaccine may be administered as a single dosage, or administration may be repeated. When the vaccine administration is repeated, it is preferred that it is administered with at least 3 weeks intervals, to avoid exhaustion of the T cells.

Accordingly, in one embodiment the dosage regimen is vaccination in week 0, 3 and 6 and then every 4 weeks as long as the patient has a clinical benefit. The vaccine may be administered for as long as a year.

The vaccine comprises an immunologically effective amount of the polynucleotide/polypeptide/dimeric protein. By "immunologically effective amount" is meant the amount of the aforementioned compounds required to elicit an immune response in the patient being vaccinated with such compounds. Non-limiting parameters that indicate such an immune response include one or more of the following: stop the growth of a tumor and/or stop its spreading and/or reduce the size of a tumor, reduction in disease progression or stable disease, i.e. the cancer does progress at a slower rate or does not progress. This includes that a tumor does grow at a slower rate or does not grow and/or does spread slower or does not spread, e.g. to lymph nodes or forming metastases and/or does not become more aggressive. Other non-limiting parameters that indicate such an immune response are tumor shrinkage (in terms of weight and/or volume); a decrease in the number of individual tumor colonies; tumor elimination; and progression-free survival. Ultimately, the physician determines the dosage which may vary and depend on the age, weight, and general condition of the patient being treated, the severity of the cancer being treated, the judgment of the physician and the particular nature and properties the individualized vaccine of the invention. In one embodiment, the dosage typically is in the range of 0.3-6 mg for DNA vaccines, and in the range of 5 pg-5 mg for polypeptide/protein vaccines.

In a tenth aspect, the invention provides a method of treating cancer in a patient, the method comprising administering to the patient an individualized therapeutic anticancer vaccine comprising an immunologically effective amount of:

(i) a polynucleotide comprising a nucleotide sequence encoding a targeting unit, a dimerization unit and an antigenic unit, wherein said antigenic unit comprises at least one shared antigen sequence present in said patient or one or more parts thereof and optionally one or more antigen sequences specific for said patient or one or more parts thereof; or (ii) a polypeptide encoded by the polynucleotide as defined in (i); or (iii) a dimeric protein consisting of two polypeptides encoded by the polynucleotide as defined in (i); and a pharmaceutically acceptable carrier.

Thus, the invention provides a method of treating cancer in a patient, the method comprising administering to the patient an individualized therapeutic anticancer vaccine according to the invention, which has been prepared specifically for the patient.

Alternatively, the invention provides an individualized therapeutic anticancer vaccine comprising an immunologically effective amount of:

(i) a polynucleotide comprising a nucleotide sequence encoding a targeting unit, a dimerization unit and an antigenic unit, wherein said antigenic unit comprises at least one patient-present shared antigen sequence or one or more parts thereof and optionally one or more patient-specific antigen sequences or one or more parts thereof; or (ii) a polypeptide encoded by the polynucleotide as defined in (i); or (iii) a dimeric protein consisting of two polypeptides encoded by the polynucleotide as defined in (i); and a pharmaceutically acceptable carrier for use in a method of treating cancer in a patient, wherein the vaccine has been specifically prepared for the patient.

Further, the invention provides the use of (i) a polynucleotide comprising a nucleotide sequence encoding a targeting unit, a dimerization unit and an antigenic unit, wherein said antigenic unit comprises at least one patient-present shared antigen sequence or one or more parts thereof and optionally one or more patient-specific antigen sequences or one or more parts thereof; or (ii) a polypeptide encoded by the polynucleotide as defined in (i); or (iii) a dimeric protein consisting of two polypeptides encoded by the polynucleotide as defined in (i); for the manufacture of a medicament for the treatment of cancer in a patient, wherein the polynucleotide, polypeptide or dimeric protein has been specifically prepared for the patient.

The vaccine treatment according to the present invention may be combined with any other anticancer treatment, such as radiation therapy, chemotherapy, and surgical treatment.

The vaccine treatment according to the invention may also be combined with checkpoint-blockade inhibitor treatment.

DESCRIPTION OF THE DRAWINGS

FIG. 1 shows the amino acid sequence of HPV16 E6 and all epitopes predicted to bind to the HLA class I alleles of patient 1. The two underlined sequences constitute HLA class I optimized sequences for inclusion into the antigenic unit of a therapeutic anticancer vaccine individualized for patient 1.

FIG. 3 shows the amino acid sequence of HPV16 E7 and all epitopes predicted to bind to the HLA class I alleles of patient 1. The underlined sequence constitutes an HLA class I optimized sequence for inclusion into the antigenic unit of a therapeutic anticancer vaccine individualized for patient 1.

Figure 4:
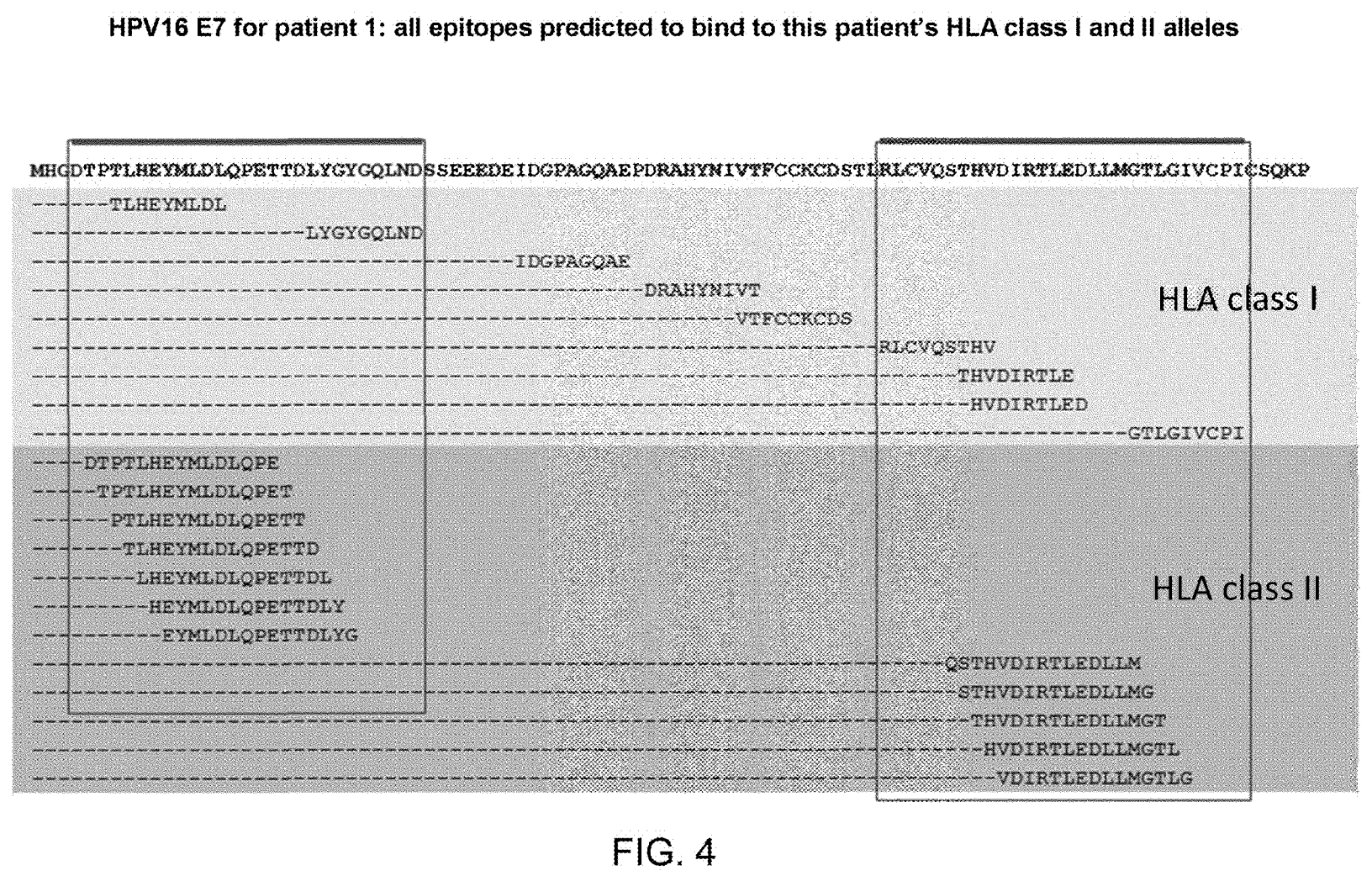

FIG. 4 shows the amino acid sequence of HPV16 E7 and all epitopes predicted to bind to the HLA class I and HLA class II alleles of patient 1. The sequences in the two boxes constitute HLA class I/HLA class II optimized sequences for inclusion into the antigenic unit of a therapeutic anticancer vaccine individualized for patient 1.

FIG. 5 shows the amino acid sequence of HPV16 E6 and all epitopes predicted to bind to the HLA class I alleles of patient 2. The underlined sequence constitutes an HLA class I optimized sequence for inclusion into the antigenic unit of a therapeutic anticancer vaccine individualized for patient 2.

FIG. 7 shows the amino acid sequence of HPV16 E7 and all epitopes predicted to bind to the HLA class I alleles of patient 2. The underlined sequence constitutes an HLA class I optimized sequence for inclusion into the antigenic unit of a therapeutic anticancer vaccine individualized for patient 2.

EXAMPLES

Figure 2:
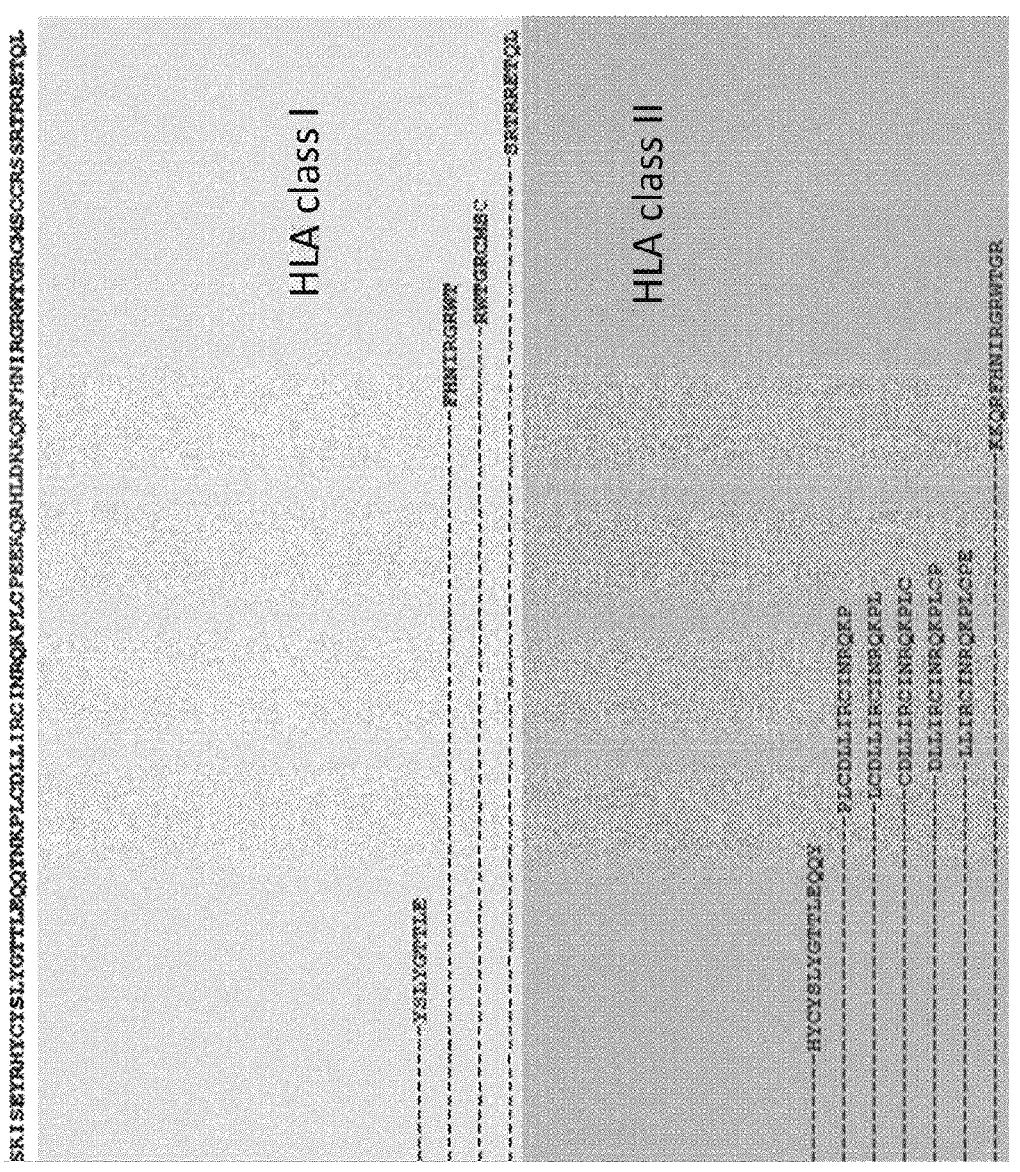
FIG. 2 shows the amino acid sequence of HPV16 E6 and all epitopes predicted to bind to the HLA class I and HLA class II alleles of patient 1. The sequence in the box constitutes an HLA class I/HLA class II optimized sequence for inclusion into the antigenic unit of a therapeutic anticancer vaccine individualized for patient 1.

Example 1: Design of the Antigenic Unit Comprised in the Polynucleotide/Polypeptide/Dimeric Protein and Vaccine of the Invention The antigenic unit may be designed with the following variations in the patient-present shared antigen sequence:

A. Full-length sequence

B. HLA-optimized sequences. The selected sequence for inclusion into the antigenic unit is optimized to cover the most immunogenic epitopes, i.e. those having a high binding affinity to the patient's HLA I and/or HLA II molecules C. Epitopes with predicted binding to the patient's HLA I and/or HLA II molecules.

D. Combination of A+C

E. Combination of B+C

F. Combination of A+B

The patient-present shared antigen sequence above may for instance be HPV16. In cases D and F, which include a full-length sequence, case D may for instance be the combination of HPV16 E7 as a full-length sequence (A) and epitopes from HPV E6 (C) while case F may for instance be the combination of HPV16 E7 as a full-length sequence (A) and HLA-optimized sequences (B). The aforementioned example includes one single patient-present shared antigen but two different regions thereof. In another embodiment, cases D and F relate to the combination of the full-length sequence (A) of a first patient-present shared antigen, e.g. HPV16 E7 and epitopes (C) or HLA-optimized sequences (B) of a second patient-shared antigen, e.g. KRAS.

Thus, the antigenic unit may comprise A-F from one patient-present shared antigen or comprise A-F from several patient-present shared antigens.

Sequences A-F are arranged in the antigenic unit according to the methods provided herein. Different antigenic unit designs may be evaluated in animal models, e.g. as described in Example 3 to determine the optimal antigenic unit design. Breadth, strength and kinetics for the antigen-specific immunogenicity can be determined by IFN-gamma ELISPOT analysis.

Anti-tumor efficacy can be tested in a tumor challenge experiment.

Example 2: Construction of a Polynucleotide According to the Invention

A polynucleotide according to the invention is designed and comprises the following units and components:

TABLE 1

| 1: Native leader sequence for human LD78b | Signal peptide |
|---|---|
| 2: Full-length LD78b sequence | Targeting unit |
| 3: Human hinge-region 1 from IgG3 | Dimerization unit |
| 4: Human hinge region 4 from IgG3 | |
| 5: Glycine-Serine linker | |
| 6: Human CH3 domain from IgG3 | |
| 7: Glycine-Leucine linker | Unit linker |
| 8: Patient-present shared antigen sequence(s) | Antigenic unit |
| 9: Optionally: patient-specific antigen sequence(s) | |

Example 3: Selecting Sequences of Patient-Present Shared Antigens for Inclusion into the Antigenic Unit Comprised in the Polynucleotides/Polypeptides/Dimeric Peptides and Vaccines According to the Invention Blood samples and tumor tissue samples of two patients—patient 1 and 2—presenting with squamous cell carcinoma of the head and neck were obtained. The blood sample was analyzed for exome sequencing to characterize the exons in the healthy cells. The tumor tissue sample was analyzed for exome sequencing to characterize the exons in the tumor tissue and RNA-seq to evaluate RNA expression level of each gene. The presence of HPV16 shared antigen was identified using anti-HPV16 antibodies in an ELISA.

To find the most immunogenic sequences, each patients HLA class I and II alleles were determined by sequencing normal tissue (blood cells). The following HLA class I and II alleles were found:

TABLE 2

| Patient 1 - HLA class I alleles | Patient 1 - HLA class II alleles |
|---|---|
| HLA-A01:01 | DRB1_0701 |
| HLA-A24:02 | DRB1_1301 |
| HLA-B08:01 | DRB3_0202 |
| HLA-B40:01 | DRB4_0101 |
| HLA-C03:04 | HLA-DQA10103-DQB10202 |
| HLA-C07:01 | HLA-DQA10103-DQB10603 |
| | HLA-DQA10201-DQB10202 |
| | HLA-DQA10201-DQB10603 |

| Patient 2 - HLA class I alleles | Patient 2 - HLA class II alleles |
|---|---|
| HLA-A01:01 | DRB1_0101 |
| HLA-A24:02 | DRB1_1301 |
| HLA-B40:01 | DRB3_0202 |
| HLA-C03:04 | HLA-DPA10103-DPB10401 |
| | HLA-DQA10101-DQB10501 |
| | HLA-DQA10101-DQB10603 |
| | HLA-DQA10103-DQB10501 |
| | HLA-DQA10103-DQB10603 |

HPVs have circular, double-stranded DNA genomes that are approximately 8 kb in size and encode eight genes, of which E6 and E7 have transforming properties. The viral E6 and E7 proteins are known to be involved in conversion of healthy cells into malignant cells. The abilities of HPV16 E6 and E7 proteins to associate with the tumor suppressors p53 and pRB, respectively, have been suggested as a mechanism by which these viral proteins induce tumors. Thus, the E6 and E7 sequences of HPV16 are known shared tumor antigens and were selected for finding sequences therein for inclusion into the antigenic unit. Prediction of binding to the patients' HLA class I and HLA class II alleles was carried out using the NetMHCpan 4.0 software.

Patient 1:

HPV 16 E6:

A total of 16 epitopes, each 9 amino acids long, were predicted to bind to HLA class I alleles of patient 1 and a total of 16 epitopes, each 9 amino acids long, were predicted to bind to HLA class II alleles of patient 1 (FIG. 2 and table 3)

Thus, an antigenic unit for inclusion into an individualized therapeutic anticancer vaccine for patient 1 is designed, which may comprise:

A. The full-length HPV16 E6 sequence (151 amino acids)

Figure 1:
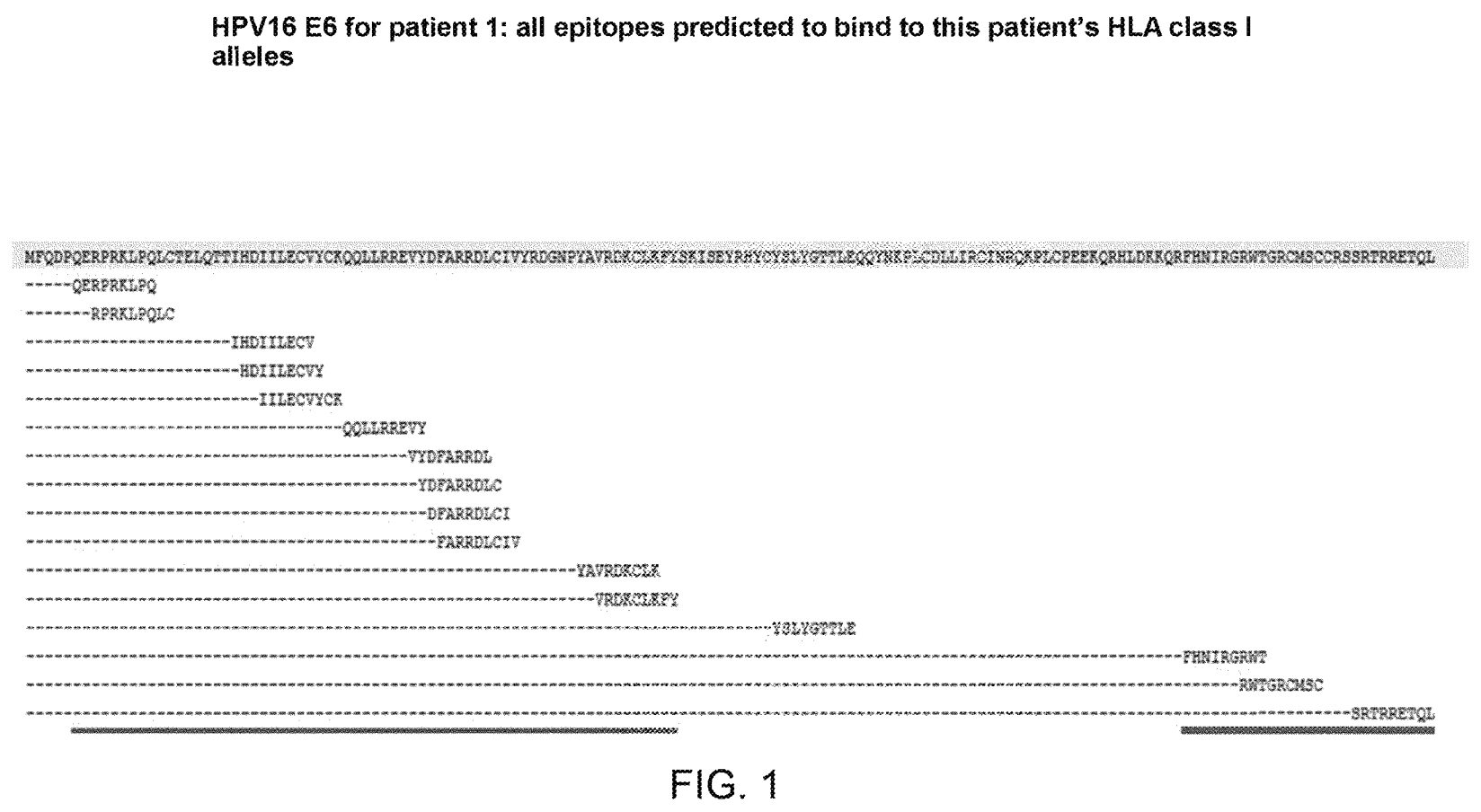

B. An HLA class I optimized sequence comprising some of the 16 epitopes, e.g. the 12 underlined epitopes shown on the left side of FIG. 1. This sequence contains 65 amino acids, i.e. 43% of the full-length sequence.

C. Two HLA class I optimized sequences, wherein the first sequence comprises 12 of the 16 epitopes and the second sequence comprises 3 of the epitopes (FIG. 1). Thus, the two sequences combined include 15 of the 16 epitopes and contain 92 amino acids, i.e. 61% of the full-length sequence.

D. An HLA class I/HLA class II optimized sequence, comprising 12 of the 16 HLA class I epitopes and 9 of the 16 HLA class II epitopes, thus including 21 of the 32 HLA class I/class 11 epitopes (FIG. 2, box). This sequence contains 65 amino acids, i.e. 43% of the full-length sequence.

Inclusion of C or D into the antigenic unit is preferred.

TABLE 3

HPV E6:
MFQDPQERPRKLPQLCTELQTTIHDIILECVYCKQQLLRREVYDFARRD
LCIVYRDGNPYAVRDKCLKFYSKISEYRHYCYSLYGTTLEQQYNKPLCD
LLIRCINRQKPLCPEEKQRHLDKKQRFHNIRGRWTGRCMSCCRSSRTRR
ETQL

| Epitope corresponding to amino acids in full length sequence | Sequence of epitope |
|---|---|
| 6-15 | QERPRKLPQ |
| 8-17 | RPRKLPQLC |
| 23-32 | IHDIILECV |
| 24-33 | HDIILECVY |
| 26-35 | IILECVYCK |
| 35-44 | QQLLRREVY |
| 42-51 | VYDFARRDL |
| 43-52 | YDFARRDLC |
| 44-53 | DFARRDLCI |
| 45-54 | FARRDLCIV |
| 60-69 | YAVRDKCLK |
| 62-71 | VRDKCLKFY |
| 81-90 | YSLYGTTLE |
| 125-134 | FHNIRGRWT |
| 131-140 | RWTGRCMSC |
| 143-152 | SRTRRETQL |
| 16-31 | CTELQTTIHDIILEC |

TABLE 3-continued

| 17-32 | TELQTTIHDIILECV |
| 18-33 | ELQTTIHDIILECVY |
| 19-34 | LQTTIHDIILECVYC |
| 20-35 | QTTIHDIILECVYCK |
| 34-49 | KQQLLRREVYDFARR |
| 49-64 | DLCIVYRDGNPYAVR |
| 50-65 | LCIVYRDGNPYAVRD |
| 51-66 | CIVYRDGNPYAVRDK |
| 78-93 | HYCYSLYGTTLEQQY |
| 95-110 | PLCDLLIRCINRQKP |
| 96-111 | LCDLLIRCINRQKPL |
| 97-112 | CDLLIRCINRQKPLC |
| 98-113 | DLLIRCINRQKPLCP |
| 99-114 | LLIRCINRQKPLCPE |
| 121-136 | KKQRFHNIRGRWTGR |

HPV16 E7:

A total of 9 epitopes, each 9 amino acids long, were predicted to bind to HLA class I alleles of patient 1 and a total of 12 epitopes, each 9 amino acids long, were predicted to bind to HLA class II alleles of patient 1 (FIG. 4 and table 4)

Thus, an antigenic unit for inclusion into an individualized therapeutic anticancer vaccine for patient 1 is designed, which may comprise:

E. The full length HPV16 E7 sequence (98 amino acids)

Figure 3:
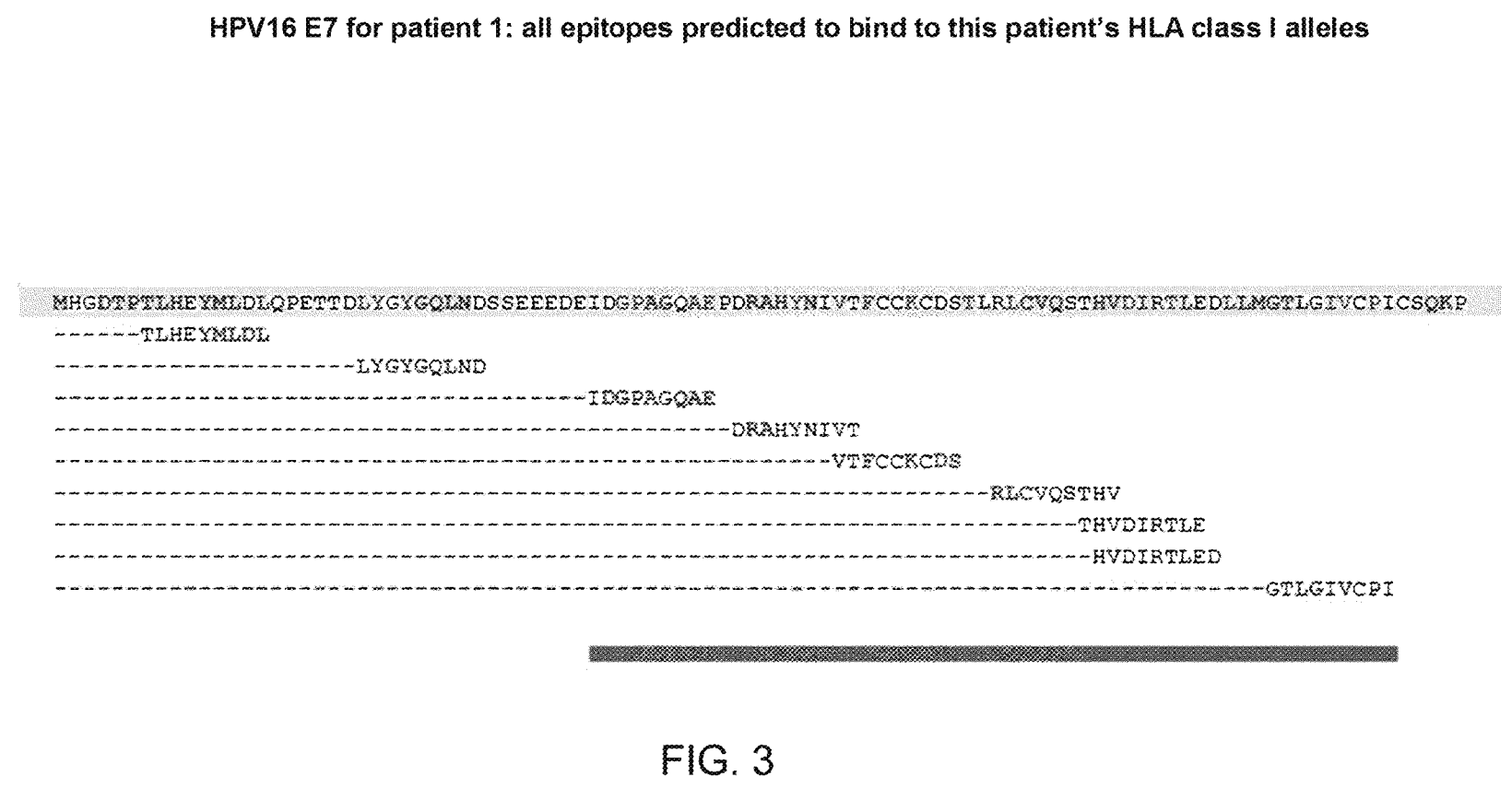

F. An HLA class I optimized sequence comprising some of the 9 epitopes, e.g. the underlined epitopes shown in FIG. 3. This sequence contains 56 amino acids, i.e. 57% of the full-length sequence G. Two HLA class I/HLA class II optimized sequences, wherein the first sequence comprises 2 of the 9 HLA class I epitopes and 7 of the 16 HLA class II epitopes and the second sequence comprises 4 of the 9 HLA class I epitopes and 5 of the 16 HLA class II epitopes (FIG. 4, boxes). Thus, the two sequences combined include 6 of the 9 HLA class I epitopes and all of the HLA class II epitopes. The two sequences combined contain 54 amino acids, i.e. 55% of the full-length sequence.

Inclusion of F or G into the antigenic unit is preferred.

Based on the above, an antigenic unit for inclusion into an individualized therapeutic anticancer vaccine for patient 1 is designed, which comprises at least one of C, D, F and G or all of C, D, F and G or an combination thereof between these two described extrema.

TABLE 4

HPV E7:
MHGDTPTLHEYMLDLQPETTDLYGYGQLNDSSEEEDEIDGPAGQAEPDR
AHYNIVTFCCKCDSTLRLCVQSTHVDIRTLEDLLMGTLGIVCPICSQKP

| Epitope corresponding to amino acids in full length sequence | Sequence of epitope |
|---|---|
| 7-16 | TLHEYMLDL |
| 22-31 | LYGYGQLND |
| 38-47 | IDGPAGQAE |
| 48-57 | DRAHYNIVT |
| 55-64 | VTFCCKCDS |
| 66-75 | RLCVQSTHV |
| 72-81 | THVDIRTLE |
| 73-82 | HVDIRTLED |
| 85-94 | GTLGIVCPI |
| 4-19 | DTPTLHEYMLDLQPE |
| 5-20 | TPTLHEYMLDLQPET |
| 6-21 | PTLHEYMLDLQPETT |
| 7-22 | TLHEYMLDLQPETTD |
| 8-23 | LHEYMLDLQPETTDL |
| 9-24 | HEYMLDLQPETTDLY |
| 10-25 | EYMLDLQPETTDLYG |
| 70-85 | QSTHVDIRTLEDLLM |
| 71-86 | STHVDIRTLEDLLMG |
| 72-87 | THVDIRTLEDLLMGT |
| 73-88 | HVDIRTLEDLLMGTL |
| 74-89 | VDIRTLEDLLMGTLG |

Patient 2:

HPV16 E6

Figure 6:
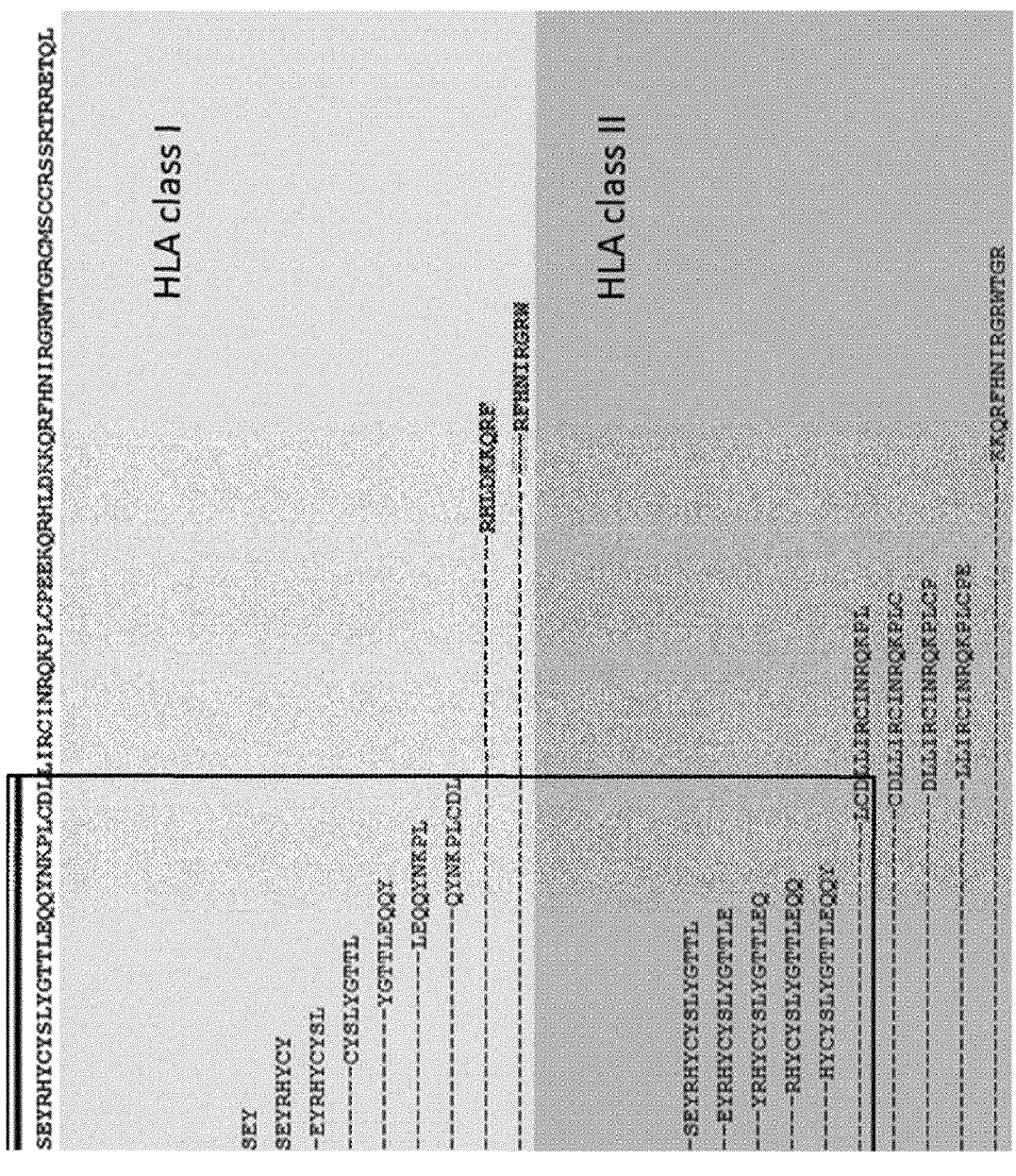
FIG. 6 shows the amino acid sequence of HPV16 E6 and all epitopes predicted to bind to the HLA class I and HLA class II alleles of patient 2. The sequence in the box constitutes an HLA class I/HLA class II optimized sequence for inclusion into the antigenic unit of a therapeutic anticancer vaccine individualized for patient 2.

A total of 14 epitopes, each 9 amino acids long, were predicted to bind to HLA class I alleles of patient 2 and a total of 14 epitopes, each 9 amino acids long, were predicted to bind to HLA class II alleles of patient 2 (FIG. 6 and table 5)

Thus, an antigenic unit for inclusion into an individualized therapeutic anticancer vaccine for patient 2 is designed, which may comprise;

H. The full-length HPV16 E6 sequence (151 amino acids)

Figure 5:
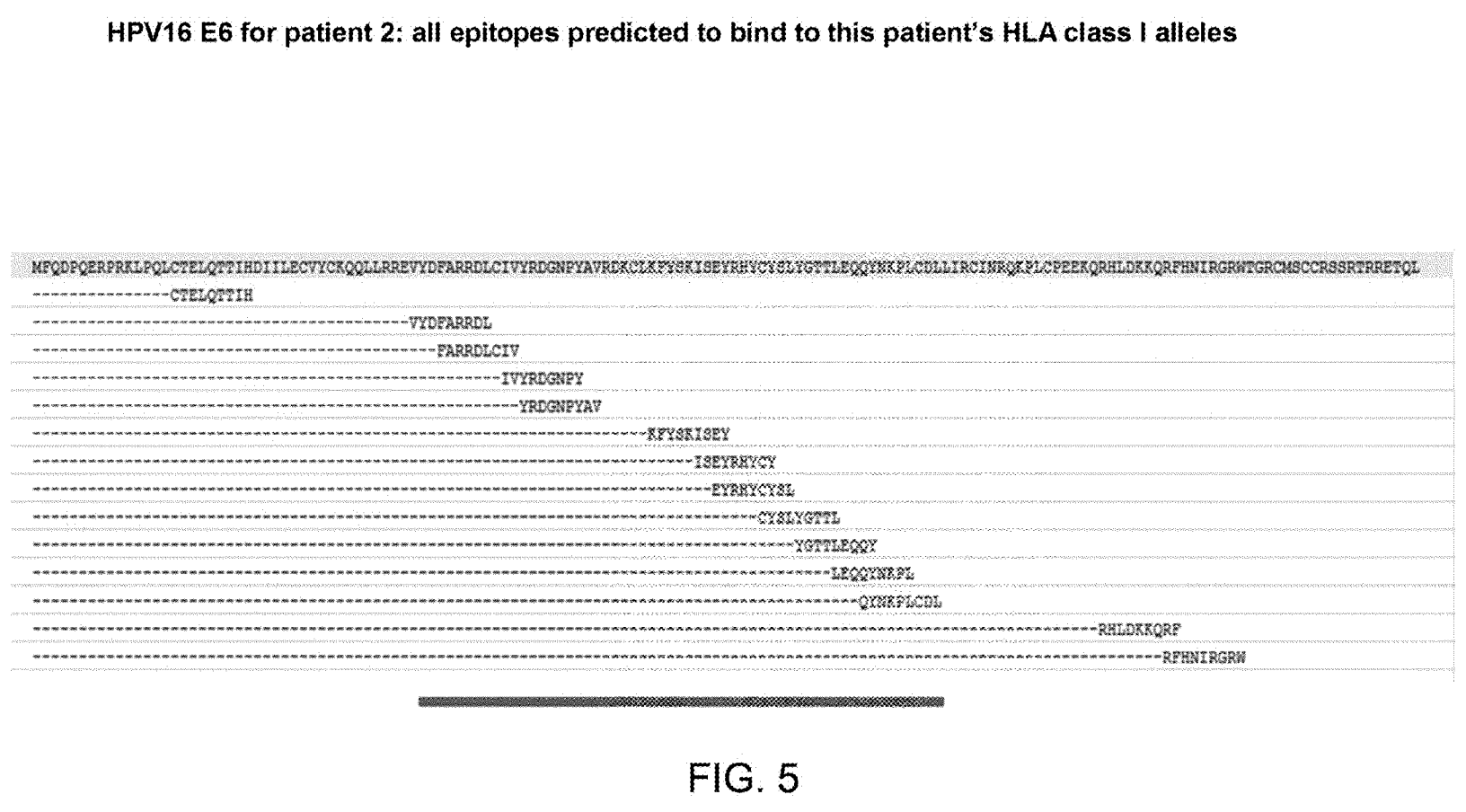

I. An HLA class I optimized sequence comprising some of the 14 epitopes, e.g. the 11 underlined epitopes shown in FIG. 5. This sequence contains 57 amino acids, i.e. 38% of the full-length sequence.

J. An HLA class I/HLA class II optimized sequence, comprising 11 of the 14 HLA class I epitopes and 8 of the 14 HLA class II epitopes, thus including 19 of the 28 HLA class I/class II epitopes (FIG. 6, box). This sequence contains 59 amino acids, i.e. 39% of the full-length sequence.

Inclusion of J into the antigenic unit is referred.

TABLE 5

HPV E6:
MFQDPQERPRKLPQLCTELQTTIHDIILECVYCKQQLLRREVYDFARRD
LCIVYRDGNPYAVRDKCLKFYSKISEYRHYCYSLYGTTLEQQYNKPLCD
LLIRCINRQKPLCPEEKQRHLDKKQRFHNIRGRWTGRCMSCCRSSRTRR
ETQL

| Epitope corresponding to amino acids in full length sequence | Sequence of epitope |
|---|---|
| 16-25 | CTELQTTIH |
| 42-51 | VYDFARRDL |
| 45-54 | FARRDLCIV |
| 52-61 | IVYRDGNPY |
| 54-63 | YRDGNPYAV |
| 68-77 | KFYSKISEY |
| 73-82 | ISEYRHYCY |
| 75-84 | EYRHYCYSL |
| 80-89 | CYSLYGTTL |
| 84-93 | YGTTLEQQY |
| 88-97 | LEQQYNKPL |
| 91-100 | QYNKPLCDL |
| 11-20 | RHLDKKQRF |
| 12-21 | RFHNIRGRW |
| 18-33 | ELQTTIHDIILECVY |
| 49-64 | DLCIVYRDGNPYAVR |
| 50-65 | LCIVYRDGNPYAVRD |
| 51-66 | CIVYRDGNPYAVRDK |
| 74-89 | SEYRHYCYSLYGTTL |
| 75-90 | EYRHYCYSLYGTTLE |
| 76-91 | YRHYCYSLYGTTLEQ |
| 77-92 | RHYCYSLYGTTLEQQ |
| 78-93 | HYCYSLYGTTLEQQY |
| 96-111 | LCDLLIRCINRQKPL |
| 97-112 | CDLLIRCINRQKPLC |
| 98-113 | DLLIRCINRQKPLCP |
| 99-114 | LLIRCINRQKPLCPE |
| 121-136 | KKQRFHNIRGRWTGR |

HPV16 E7

Figure 8:
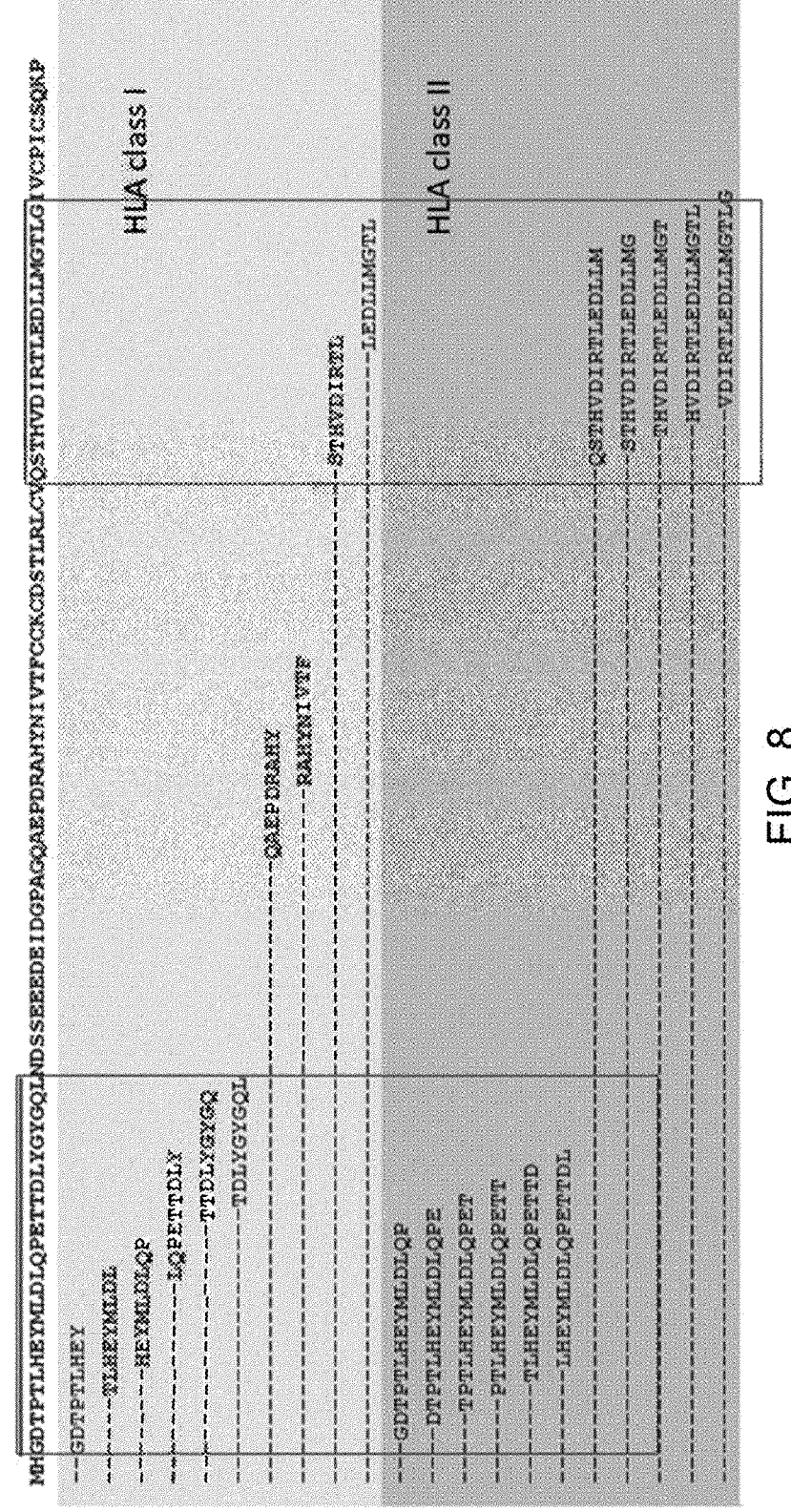
FIG. 8 shows the amino acid sequence of HPV16 E7 and all epitopes predicted to bind to the HLA class I and HLA class II alleles of patient 2. The sequences in the two boxes constitute HLA class I/HLA class II optimized sequences for inclusion into the antigenic unit of a therapeutic anticancer vaccine individualized for patient 2.

A total of 10 epitopes, each 9 amino acids long, were predicted to bind to HLA class I alleles of patient 2 and a total of 11 epitopes, each 9 amino acids long, were predicted to bind to HLA class II alleles of patient 2 (FIG. 8 and table 6)

Thus, an antigenic unit for inclusion into an individual-ized therapeutic anticancer vaccine for patient 2 may be designed which comprises:

A. The full length HPV16 E7 sequence (98 amino acids)

B. An HLA class I optimized sequence comprising some of the 10 epitopes, e.g. the 6 underlined epitopes shown in FIG. 7. This sequence contains 26 amino acids, i.e. 27% of the full-length sequence.

C. Two HLA class I/HLA class II optimized sequences, wherein the first sequence comprises 6 of the 10 HLA class I epitopes and 6 of the 11 HLA class II epitopes and the second sequence comprises 2 of the 10 HLA class I epitopes and 5 of the 11 HLA class II epitopes (FIG. 8, boxes). Thus, the two sequences combined include 8 of the 11 HLA class I epitopes and all of the HLA class II epitopes. The two sequences combined contain 45 amino acids, i.e. 45% of the full-length sequence.

Inclusion of L or M into the antigenic unit is preferred.

Based on the above, an antigenic unit for inclusion into an individualized therapeutic anticancer vaccine for patient 2 is designed, which comprises at least one of J, L and M or all of J, L and M or any combination thereof between these two described extrema.

TABLE 6

HPV E7:
MHGDTPTLHEYMLDLQPETTDLYGYGQLNDSSEEEDEIDGPAGQAEPDR
AHYNIVTFCCKCDSTLRLCVQSTHVDIRTLEDLLMGTLGIVCPICSQKP

| Epitope corresponding to amino acids in full length sequence | Sequence of epitope |
|---|---|
| 3-12 | GDTPTLHEY |
| 7-16 | TLHEYMLDL |
| 9-18 | HEYMLDLQP |
| 15-24 | LQPETTDLY |
| 19-28 | TTDLYGYGQ |
| 20-29 | TDLYGYGQL |
| 44-53 | QAEPDRAHY |
| 49-58 | RAHYNIVTF |
| 71-80 | STHVDIRTL |
| 79-88 | LEDLLMGTL |
| 3-18 | GDTPTLHEYMLDLQP |
| 4-19 | DTPTLHEYMLDLQPE |
| 5-20 | TPTLHEYMLDLQPET |
| 6-21 | PTLHEYMLDLQPETT |
| 7-22 | TLHEYMLDLQPETTD |
| 8-23 | LHEYMLDLQPETTDL |
| 70-85 | QSTHVDIRTLEDLLM |
| 71-86 | STHVDIRTLEDLLMG |
| 72-87 | THVDIRTLEDLLMGT |

TABLE 6-continued

| 73-88 | HVDIRTLEDLLMGTL |
| 74-89 | VDIRTLEDLLMGTLG |

Comparing patient 1 and 2, i.e. FIGS. 2 and 6 and FIGS. 4 and 8, it is apparent that the optimal sequences for inclusion into a vaccine according to the invention differ considerably between the two patients.

Example 4: Comparing Vaccines Comprising Patient-Specific Antigens and Patient-Present Shared Antigens To compare the efficacy of vaccines comprising only patient-specific antigen sequences with vaccines according to the invention comprising patient-present shared antigen sequences and optionally patient-specific antigen sequences, a mouse TC-2 tumor model is used.

Shared antigens and specific antigens present in the TC-2 tumor cell line are identified, processed and selected as described herein, i.e. shared antigen sequences for inclusion into the antigenic unit are selected based on their binding to MHC molecules while specific antigen sequences are selected based on additional parameters in an in silico predicted immunogenicity method. The shared antigen which is selected for inclusion into the antigenic unit is the viral antigen HPV16 and sequences encoding parts of the E6 and E7 proteins thereof were selected.

All selected antigen sequences are ordered from a commercial supplier, e.g. from Genscript (New Jersey, US) and cloned into the expression vector pUMVC4a, which comprises sequences encoding the LD78beta targeting unit and the hIgG3 dimerization unit.

The antigenic unit of vector 1 only comprises shared antigen sequences while the antigenic unit of vector 2 comprises both shared antigen sequences and specific antigen sequences.

To verify correct vaccibody formation, HEK293 cells are transfected with the vectors and vaccibody proteins in the supernatant are identified by Western blot and/or sandwich ELISA. The empty pUMVC4a vector is included as a negative control. Intact homodimeric protein formation is confirmed as follows: the proteins in the supernatant from transfected cells are detected in a Western blot by an anti-hMIP-1alpha antibody, in either the presence of reducing agents, which result in dimeric proteins being reduced to monomers, or absence of reducing agents.

A vaccine is prepared by mixing 20 μg of the vector 1 and 2, respectively, with an aqueous buffer. The vaccine is injected intramuscularly in the tibial anterior muscle of the mouse followed by electroporation using TriGrid, Ichor, (US). At day 13, the mice are euthanized, and spleens are harvested.

The T cell responses are evaluated by IFN-gamma ELISpot. We observe that vaccines according to the present invention induce broader T cell responses that are higher compared to vaccines comprising only specific antigen sequences.

Example 5: Individual Therapeutic Anticancer DNA Vaccine According to the Invention An individual therapeutic anticancer DNA vaccine according to the invention may be prepared by GMP manufacturing of the vector comprising the polynucleotide according to the invention according to regulatory authorities' guidelines, and Fill & Finish of the DNA vaccine. The vector may be formulated by dissolving it in a sterile saline solution, such as PBS, at a concentration of 2-6 mg/ml. The vaccine may be administered either intradermally or intramuscularly with or without following electroporation or may alternatively be administered with a jet injector.

Example 6: Selecting Sequences of Patient-Present Shared Antigens (and Patient-Specific Antigens) for Inclusion into the Antigenic Unit Comprised in the Polynucleotides/Polypeptides/Dimeric Peptides and Vaccines According to the Invention Blood samples and tumor tissue samples of three patients (patient 1, 2 and 3) presenting with squamous cell carcinoma of the head and neck were obtained. The blood sample was analyzed for exome sequencing to characterize the exons in the healthy cells. The tumor tissue sample was analyzed for exome sequencing to characterize the exons in the tumor tissue and RNA-seq to evaluate RNA expression level of each gene.

The presence of HPV16 shared antigen was identified using PCR. The ectopic expression of NY-ESO-1 was determined by anti-NY-ESO-1 antibodies in an ELISA. Patient-specific antigen sequences for each patient were identified as previously described in this application and in WO 2017/118695, which is included herein by reference.

NY-ESO-1 (also known as cancer/testis antigen 1 B) is a protein belonging to the family of cancer-testis antigens (CTAs) that have been found to be re-expressed in a variety of malignant tumors at the mRNA and protein levels, while its normal expression in adult tissue is restricted to germ cells and placental cells. NY-ESO-1 expression has been reported in a wide range of tumor types.

For HPV, the E6 and E7 sequences of HPV16 are known shared tumor antigens and were selected for finding sequences therein for inclusion into the antigenic unit.

To find the most immunogenic sequences, each patients HLA class I and II alleles were determined by sequencing normal tissue (blood cells). Prediction of binding of HPV16 E6/E7 sequences and NY-ESO-1 sequences to the patients' HLA class I and HLA class II alleles was carried out using the NetMHCpan 4.0 software. Included in the analysis were sequences from the IEDB database which are known from the literature to have elicited a positive T cell response (not matched to patients' HLA alleles).

The HLA class I and II alleles which were found for patients 1, 2 and 3 are listed in the table below:

TABLE 7

| Patient 1 - HLA class I alleles | Patient 1 - HLA class II alleles |
|---|---|
| HLA-A02:01 | DRB1_0701 |
| HLA-A31:01 | DRB1_1301 |
| HLA-B37:01 | DRB3_0202 |
| HLA-B51:01 | DRB4_0101 |
| HLA-C06:02 | HLA-DQA10103-DQB10202 |
| HLA-C15:02 | HLA-DQA10103-DQB10603 |
| | HLA-DQA10201-DQB10202 |
| | HLA-DQA10201-DQB10603 |

TABLE 7-continued

| Patient 2 - HLA class I alleles | Patient 2 - HLA class II alleles |
|---|---|
| HLA-A01:01 | DRB1_0101 |
| HLA-A24:02 | DRB1_1301 |
| HLA-B08:01 | DRB3_0202 |
| HLA-B40:01 | HLA-DPA10103-DPB10401 |
| HLA-C03:04 | HLA-DQA10101-DQB10501 |
| HLA-C07:01 | HLA-DQA10101-DQB10603 |
| | HLA-DQA10103-DQB10501 |
| | HLA-DQA10103-DQB10603 |

| Patient 3 - HLA class I alleles | Patient 3 - HLA class II alleles |
|---|---|
| HLA-A02:01 | DRB1_0112 |
| HLA-B44:02 | DRB1_0480 |
| HLA-B57:01 | DRB5_0202 |
| HLA-C05:01 | HLA-DPA10201-DPB10402 |
| HLA-C06:02 | HLA-DQA10102-DQB10301 |
| | HLA-DQA10101-DQB10603 |
| | HLA-DQA10201-DQB10501 |
| | HLA-DQA10103-DQB10603 |

TABLE 8

Patient 1:

| Protein/Alleles/ IEDB epitopes | Total number of epitopes | Epitopes selected for inclusion into antigenic unit | Remarks |
|---|---|---|---|
| HPV16 E6 | | | Full length E6 sequence selected, i.e. SEQ ID NO: 11 |
| HLA I | 25* | 25 | |
| HLA II | 16 | 16 | |
| IEDB HLA I | 26 | 26 | |
| IEDB HLA II | 18 | 18 | |
| HPV 16 E7 | | | Amino acid 69-98 of SEQ ID NO: 12 selected |
| HLA I | 16* | 9 | |
| HLA II | 12 | 5 | |
| IEDB HLA I | 20 | 7 | |
| IEDB HLA II | 22 | 7 | |
| NY-ESO-1 | | | Amino acid 80-101 of SEQ ID NO: 13 selected |
| HLA I | 26* | | |
| HLA II | 43* | | |
| IEDB HLA I | 7 | | |
| IEDB HLA II | 6 | | |

*total number of epitopes, each 9 amino acids long, predicted to bind to HLA class I and II alleles of patient 1, respectively.

An antigenic unit for inclusion into an individualized therapeutic anticancer vaccine for patient 1 was designed, which comprises SEQ ID NO: 14, comprising the sequences set forth in the right hand column of the table above in the following order: E7|linker|NY-ESO-1|linker|E6.

A second antigenic unit for inclusion into an individualized therapeutic anticancer vaccine for patient 1 was designed, which comprises SEQ ID NO: 15, comprising the sequences set forth in the right hand column of the table above and in addition 17 patient-specific antigen sequences. The most hydrophobic sequences were positioned substantially in the middle of the antigenic unit and the most hydrophilic sequence were positioned at the beginning and at end of the antigenic unit. Glycine-serine linkers were inserted between the sequences. The antigenic unit comprises the sequences in the following order, with T1D denoting the patient-specific antigen sequences:

T1D320|linker|T1D814|linker|T1D182|linker| T1D689|linker|E7|linker|T1D339|linker|T1D428|linker| NY-ESO-1|linker|T1D572|linker|T1D359|linker|T1D488| linker|T1D554|linker|T1D272|linker|T1D210|linker| T1D849|linker|T1D4|linker|T1D77|linker|T1D717| linker|T1D586|linker|E6.

TABLE 9

| T1D320 | HNEGDDQQGSRYSLIPQIQKVCEVVDG |
|---|---|
| T1D814 | SEQERMKSSLLKEHMLRKQAELESAQC |
| T1D182 | ELRENLLTYLPDSVTQLRRLEELDLGN |
| T1D689 | QEVFSSYKFNHLVRRLVLQREKHFHYL |
| T1D339 | IEKNADLCYLSTVHWSLILDAVSNNYI |
| T1D428 | LATAGEPYHDIRFKLMAVVPDRRIKYE |
| T1D572 | MLRLPTVFRQIRPVSRVLAPHLTR |
| T1D359 | IQIMENPFVQSMLWNPDLMRQLIMANP |
| T1D488 | LLRFLFLGLSALALPSRAQLQLHLPAN |
| T1D554 | MGKNPVRPPRAFPPVPSIDDIPLSR |
| T1D272 | GHVDFTIEVERALTVLDGAVLVLCAVG |
| T1D210 | EYKLMYGMLFSIRLFVSKMSPLDMKDG |
| T1D849 | SQGAGVESLDFRLYLRYEFLMLGIQPV |
| T1D4 | AAKTLVLCVSDIILLSANISETSSNKT |
| T1D77 | CKDLQLYLSNLANHIDRETGIGDVPLV |
| T1D717 | QSKHTEARELMYSAALLFFSHGQQNSA |
| T1D586 | MTLAESYAQYVYNLCNSLSIKVEES |

TABLE 10

Patient 2:

| Protein/Alleles/ IEDB epitopes | Total number of epitopes | Epitopes selected for inclusion into antigenic unit | Remarks |
|---|---|---|---|
| HPV16 E6 | | | Amino acid 62-151 of SEQ ID NO: 11 selected |
| HLA I | 25* | 15 | |
| HLA II | 14* | 10 | |
| IEDB HLA I | 26 | 15 | |
| IEDB HLA II | 18 | 13 | |
| HPV 16 E7 | | | Amino acid 42-87 of SEQ ID NO: 12 selected |
| HLA I | 13* | 5 | |
| HLA II | 11* | 5 | |
| IEDB HLA I | 20 | 6 | |
| IEDB HLA II | 22 | 11 | |
| NY-ESO-1 | | | Amino acid 79-149 of SEQ ID NO: 13 selected |
| HLA I | 19* | 19 | |
| HLA II | 11* | 11 | |
| IEDB HLA I | 7 | 4 | |
| IEDB HLA II | 6 | 3 | |

*total number of epitopes, each 9 amino acids long, predicted to bind to HLA class I and II alleles of patient 2, respectively.

An antigenic unit for inclusion into an individualized therapeutic anticancer vaccine for patient 2 was designed, which comprises SEQ ID NO: 16, comprising the sequences set forth in the right hand column of the table above in the following order: E6|linker|NY-ESO-1|linker|E7.

A second antigenic unit for inclusion into an individualized therapeutic anticancer vaccine for patient 2 was designed, which comprises SEQ ID NO: 17, comprising the sequences set forth in the right hand column of the table above and in addition 17 patient-specific antigen sequences. The most hydrophobic sequences were positioned substantially in the middle of the antigenic unit and the most hydrophilic sequence were positioned at the beginning and at end of the antigenic unit. Glycine-serine linkers were inserted between the sequences. The antigenic unit comprises the sequences in the following order, with T1D denoting the patient-specific antigen sequences:

E6|linker|T1D323|linker|T1D506|linker|T1D12|
linker|T1D315|linker|T1D302|linker|T1D700|
linker|NY-ESO-1|linker|T1D535|linker|
T1D358|linker|T1D670|linker|T1D294
|linker|T1D336|linker|T1D499|linker|T1D425|
linker|T1D491|linker|T1D314|linker|T1D430|
linker|E7|linker|T1D582.

TABLE 11

| | |
|---|---|
| T11D323 | KKVSKTRHTRETVFRRAKRRWAPIPCS |
| T11D506 | NLKHENILQFLTAQERKTELGKQYWLI |
| T11D12 | VQVFGLYFGEEFHETFDCPIK |
| T11D315 | GQAAASQAGGARGYARGAQLWPPGSDP |
| T11D302 | SIMQTWFTLFTPTDATSIVATTVMSNS |
| T11D700 | QENVRFVLVRSEALLPNAGPRSAEARV |
| T11D535 | DAFPNLKDFISRFQVMPPSSFLFDAPC |
| T11D358 | PSSLQVKPETPASEAVAVAAAAAPTTT |
| T11D670 | RFFHLADLFLSSSQLPAYLVAAFAKRL |
| T11D294 | LVFLWLHSLRRLFGCLYVSVFSNVMIH |
| T11D336 | WENAIAALFRRHIAVSWLIRATLSESE |
| T11D499 | RYIFVKSAGSRIEEGVLQFLVLLVAGR |
| T11D425 | QEIEWLPFRCIKCLKLSFSTAELLCMH |
| T11D491 | LVARCPPCLRLLRQARDFQAARYDRHD |
| T11D314 | ALGTPEDLDSYIDLSLESLNQMILELD |
| T11D430 | SQDMLSIMEKLEFLDFSYDLNLCGLTE |
| T11D582 | RREQYIPNEEFLHFDLLEDSKYRKIYS |

TABLE 12

| | | | |
|---|---|---|---|
| | | Patient 3: | |
| Protein/Alleles/ IEDB epitopes | Total number of epitopes | Epitopes selected for inclusion into antigenic unit | Remarks |
| HPV16 E6 | | | Amino acid 68-138 of SEQ ID NO: 11 selected |
| HLA I | 18* | 6 | |
| HLA II | 17* | 8 | |
| IEDB HLA I | 26 | 11 | |
| IEDB HLA II | 18 | 6 | |

TABLE 12-continued

| | | | |
|---|---|---|---|
| | | Patient 3: | |
| Protein/Alleles/ IEDB epitopes | Total number of epitopes | Epitopes selected for inclusion into antigenic unit | Remarks |
| HPV 16 E7 | | | Amino acid 42-79 of SEQ ID NO: 12 selected |
| HLA I | 11* | 3 | |
| HLA II | 0* | 0 | |
| IEDB HLA I | 20 | 5 | |
| IEDB HLA II | 22 | 8 | |
| NY-ESO-1 | | | Amino acid 79-170 of SEQ ID NO: 13 selected |
| HLA I | 20* | 20 | |
| HLA II | 58* | 42 | |
| IEDB HLA I | 7 | 6 | |
| IEDB HLA II | 6 | 6 | |

*total number of epitopes, each 9 amino acids long, predicted to bind to HLA class and II alleles of patient 3, respectively.

An antigenic unit for inclusion into an individualized therapeutic anticancer vaccine for patient 3 was designed, which comprises SEQ ID NO: 18, comprising the sequences set forth in the right hand column of the table above in the following order: NY-ESO-1|linker|E7|linker|E6.

A second antigenic unit for inclusion into an individualized therapeutic anticancer vaccine for patient 3 was designed, which comprises SEQ ID NO: 19, comprising the sequences set forth in the right hand column of the table above and in addition 17 patient-specific antigen sequences. The most hydrophobic sequences were positioned substantially in the middle of the antigenic unit and the most hydrophilic sequence were positioned at the beginning and at end of the antigenic unit. Glycine-serine linkers were inserted between the sequences. The antigenic unit comprises the sequences in the following order, with T1D denoting the patient-specific antigen sequences:

T1D223|linker|T1D164|linker|T1D56|linker|
T1D36|linker|T1D129|linker|T1D274|linker|T1D62|
linker|T1D5|linker|T1D144|linker|T1D441|linker|
T1D368|linker|NY-ESO-1|linker|T1D234|linker|T1D162|
linker|T1D39|linker|T1D272|linker|E7|linker|
T1D328|linker|T1D188|linker|E6.

TABLE 13.

| | |
|---|---|
| T1D223 | GPSYRSNSVSSLDLEGE |
| T1D164 | LKEEKENLQGLVTHQTYIIQELEKQLN |
| T1D56 | QRQKTAGKIFRAEVSTGQDAPRQAQAR |
| T1D36 | ILRPSTVNELESGEISYDEVGERIKDF |
| T1D129 | DTCINEDVESLRKMVQDLLAKLQEAKR |
| T1D274 | LREEGTKYKSFVQRARLVFREEGYLAF |
| T1D62 | HEGARPMRAIFLANGNVFTTGFSRMSE |
| T1D5 | IPDAAFIQAARRKCELARAQDDYISLD |
| T1D144 | MEIAKMRAGRRLWVHLIEKMFQPKNSK |
| T1D441 | MELVSFRDVAIEFSPEEW |
| T1D368 | TCVHEIPFHFDLMELLPQCQQLQMFFL |

TABLE 13.-continued

| T1D234 | VRRVFITDDFHDMIPKYLNFVKGVVDS |
|--------|------------------------------|
| T1D162 | NFHAHREKAPSLFCSRILNKAVYLFYG |
| T1D39 | DANKEGMFLFRAAHKLRQFLKMNSTGD |
| T1D272 | LLSLGWSVDVGRHSGWTGHVSTSWSIN |
| T1D328 | NTIFSLRKDLRQGKARRLRCMEEKEMF |
| T1D188 | NHFNDFEGDPAMTQFLEEFEKNLEDTK |

Example 7: Immunogenicity of DNA Vaccines According to the Invention

Design of DNA Vaccines Comprising Shared Antigen Sequences and/or Neoepitopes:

Five DNA vaccines (constructs) were designed comprising nucleotide sequences encoding the units/parts shown in table 14:

TABLE 14

| Unit/Part | Function |
|-----------|----------|
| 1: Native leader sequence for human MIP1α (LD78β) | Signal peptide |
| 2: Full-length human MIP1α (LD78β) sequence | Targeting unit |
| 3: Human hinge-region 1 from IgG3 | Dimerization unit |
| 4: Human hinge region 4 from IgG3 | |

TABLE 14-continued

| Unit/Part | Function |
|-----------|----------|
| 5: Glycine-Serine linker | |
| 6: Human CH3 domain from IgG3 | |
| 7: Glycine-Leucine linker | Unit linker |
| 8: Patient-present shared antigen sequences: VB4100, VB4101, VB4102 | Antigenic unit |
| 9: Patient-specific antigen sequences (neoepitopes) VB4097 | |
| 10: Patient-present shared antigen sequences and patient-specific antigen sequences (neoepitopes): VB4105 | |

DNA Vaccine VB4097 Comprising 10 CT26 Neoepitopes:

This construct was chosen as a model of an individualized DNA vaccine comprising patient-specific antigen sequences, i.e., neoepitopes.

Previously described exome sequencing and RNA sequencing of the mouse colon cancer cell line CT26 revealed hundreds to thousands of tumor-specific non-synonymous mutations. In silico methods were used to identify potential immunogenic sequences, i.e., neoepitopes, and 10 of them (table 15) were chosen for inclusion into the antigenic unit of VB4097. Each of the identified 10 neoepitopes is a peptide consisting of 27 amino acids. All but the terminal neoepitope were arranged in subunits, each subunit consisting of one neoepitope and one flexible glycine-serine linker (GGGGSGGGGS).

VB4097 consists of a DNA sequence encoding the polypeptide with amino acid sequence of SEQ ID NO: 20.

TABLE 15

| Neoantigen | Gene | Sequence | Reactive T cell subtype |
|------------|------|----------|-------------------------|
| C-pepM1 | E2f8 | VILPQAPSGPSYATYLQPAQAQMLTPP | CD8+/CD4+ |
| C-pepM6 | Ubqln1 | DTLSAMSNPRAMQVLLQIQQGLQTLAT | CD4+ |
| C-pepM8 | Dhx35 | EVIQTSKYYMRDVIAIESAWLLELAPH | CD4+ |
| C-pepM29 | Anapc1 | GSLFGSSRVQYVVNPAVKIVFLNIDPS | ND |
| C-pepM31 | Ptpn13 | AEYGDYQPEVHGVPYFRLEHYLPARVM | CD4+ |
| C-pepM43 | Mtch1 | KSWIHCWKYLSVQSQLFRGSSLLFRRV | CD8+/CD4+ |
| C-pepM89 | Mmachc | TLAFLVLSTPAMFNRALKPFLKSCHFQ | CD4+ |
| C-pep149 | 3110057O12Rik | FVSPMAHYVPGIMAIESVVARFQFIVP | CD8+ |
| C-pepM171 | Gdf11 | LWVYLRPVPRPATIYLQILRLKPLTGE | CD8+ |
| C-pepM173 | Top3a | KIYEFDYHLYGQNITMIMTSVSGHLLA | CD4+ |

DNA Vaccines VB4100, VB4101 and VB4102 Comprising NY-ESO-1 Sequences or Parts Thereof.

These constructs were chosen as models of individualized DNA vaccines comprising patient-present shared antigen sequences.

Human New York esophageal squamous cell carcinoma 1 (NY-ESO-1) has been shown to be a highly immunogenic cancer testis antigen aberrantly expressed in several cancer-types. NY-ESO-1 is not endogenously expressed in the CT26 cancer cell line, but using in silico methods, several immunogenic sequences were predicted to bind mouse MHC class I and II in BALB/c mice. The above-mentioned constructs were chosen as a model of an individualized DNA vaccine comprising patient-present shared antigen sequences.

Three NY-ESO-1 constructs were thus designed:

VB4100 having an antigenic unit that comprises NY-ESO-1 in full length. VB4100 consists of a DNA sequence encoding the polypeptide with amino acid sequence of SEQ ID NO: 21.

VB4101 having an antigenic unit that comprises amino acids 81-88 of the NY-ESO-1 sequence which is predicted to be an MHC class I antigen. VB4101 consists of a DNA sequence encoding the polypeptide with amino acid sequence of SEQ ID NO: 22.

VB4102 having an antigenic unit that comprises amino acids 81-126 of the NY-ESO-1 sequence which contains several antigens that are predicted to be MHC class and class II antigens. VB4102 consists of a DNA sequence encoding the polypeptide with amino acid sequence of SEQ ID NO: 23.

The various NY-ESO-1 sequences comprised in the constructs are shown in table 16.

Negative Control VB1026:

This construct is identical to the aforementioned constructs, but comprises neither a unit linker, nor an antigenic unit. It serves as a negative control. VB1026 consists of a DNA sequence encoding the polypeptide with amino acid sequence of SEQ ID NO: 25.

Construction of Expression Vectors Comprising the Constructs and Confirmation of Expression and Secretion of Intact Dimeric Proteins Encoded by the Constructs:

The sequences of the antigenic units of all aforementioned constructs were ordered from Genscript (New Jersey, USA) and cloned into the expression vector pUMVC4a; a master plasmid comprising a nucleotide sequence encoding the signal peptide, targeting unit and dimerization unit described in table 14 above.

HEK293 cells (ATCC) were transiently transfected with the above-mentioned constructs. Briefly, $2 \times 10^5$ cells/well were plated in 24-well tissue culture plates with 10% FBS growth medium and transfected with 1 µg of respective DNA plasmid using Lipofectamine® 2000 reagent under the conditions suggested by the manufacturer (Invitrogen, Thermo Fischer Scientific). The transfected cells were then maintained for up to 5 days at 37° C. with 5% $CO_2$. Later the cell supernatants were harvested for characterization of the expression of the proteins encoded by the constructs by sandwich ELISA of the supernatant using antibodies specific for anti hIgG (CH3 domain), hMIP-1α and the respective antigenic units.

Assessment of Immunogenicity of the Constructs:

Immunogenicity of the constructs was determined by way of measuring the T cell immune response elicited in vivo in mice vaccinated with the constructs.

TABLE 16

| Construct | NY-ESO-1 | Sequence | Length | Reactive T cell subtype |
|---|---|---|---|---|
| VB4100 | Full length | MQAEGRGTGGSTGDADGPGGPG IPDGPGGNAGGPGEAGATGGRG PRGAGAARASGPGGGAPRGPHG GAASGLNGCCRCGARGPESRLLE FYLAMPFATPMEAELARRSLAQD APPLPVPGVLLKEFTVSGNILTIRL TAADHRQLQLSISSCLQQLSLLMW ITQCFLPVFLAQPPSGQRR (SEQ ID NO: 13) | 180 amino acids | Both CD4+ and CD8+ |
| VB4101 | Amino acids 81-88 | RGPESRLL | 8 amino acids | CD8+ |
| VB4102 | Amino Acids 81-126 | RGPESRLLEFYLAMPFATPMEAEL ARRSLAQDAPPLPVPGVLLKEF | 46 amino acids | Both CD4+ and CD8+ |

DNA Vaccine VB4105 Comprising 10 CT26 Neoepitopes and the Full-Length Sequence of NY-ESO-1 Sequence This construct was chosen as a model of an individualized DNA vaccine comprising patient-present shared antigen sequences and patient-specific antigen sequences (neoepitopes). It comprises an antigenic unit comprising the full-length sequence of NY-ESO-1 and the 10 CT26 neoepitopes shown in table 1, each of them separated from the following neoepitope or the NY-ESO-1 sequence by a flexible glycine-serine linker (GGGGSGGGGS). VB4105 consists of a DNA sequence encoding the polypeptide with amino acid sequence of SEQ ID NO: 24.

Female, 6-week-old BALB/c mice were obtained from Janvier Labs (France). All animals were housed in the animal facility at the Radium Hospital (Oslo, Norway). All animal protocols were approved by the Norwegian Food Safety Authority (Oslo, Norway). 5 mice/group were used for the testing of the constructs comprising an antigenic unit, whereas 3 mice/group were used for the negative control.

20 µg of the construct was administered intramuscularly twice, i.e., on day 0 and on day 21, followed by electroporation. Spleens were collected on day 28.

Spleens were mashed in cell strainer to obtain a single cell suspension. For each construct tested, a portion of the single cell suspension was used to purify CD4+ and CD8+ T cells using Dynabeads™ depletion. Total splenocytes, CD4 depleted splenocytes and CD8 depleted splenocytes were then tested for production of INF-y in ELISpot assays. The 10 neoepitopes shown in table 15 were used to re-stimulate the splenocytes harvested from mice vaccinated with constructs VB4097 and VB4105, while the NY-ESO-1 peptides shown in table 17 below were used to re-stimulate the splenocytes harvested from mice vaccinated with the construct indicated in said table.

TABLE 17

| NY-ESO-1 peptides used for stimulation of splenocytes. | | | |
|---|---|---|---|
| NY-ESO-1 peptide ID | Sequence | Length (amino acids) | Used for constructs |
| NY-ESO_Pep-1 | MQAEGRGTGGSTGDA | 15 | VB4100, VB4105 |
| NY-ESO_Pep-2 | TGGSTGDADGPGGPG | 15 | VB4100, VB4105 |
| NY-ESO_Pep-3 | ADGPGGPGIPDGPGG | 15 | VB4100, VB4105 |
| NY-ESO_Pep-4 | GIPDGPGGNAGGPGE | 15 | VB4100, VB4105 |
| NY-ESO_Pep-5 | GNAGGPGEAGATGGR | 15 | VB4100, VB4105 |
| NY-ESO_Pep-6 | EAGATGGRGPRGAGA | 15 | VB4100, VB4105 |
| NY-ESO_Pep-7 | RGPRGAGAARASGPG | 15 | VB4100, VB4105 |
| NY-ESO_Pep-8 | AARASGPGGGAPRGP | 15 | VB4100, VB4105 |
| NY-ESO_Pep-9 | GGGAPRGPHGGAASG | 15 | VB4100, VB4105 |
| NY-ESO_Pep-10 | PHGGAASGLNGCCRC | 15 | VB4100, VB4105 |
| NY-ESO_Pep-11 | GLNGCCRCGARGPES | 15 | VB4100, VB4105 |
| NY-ESO_Pep-12 | CGARGPESRLLEFYL | 15 | VB4100, VB4102, VB4105 |
| NY-ESO_Pep-13 | RGPESRLLEFYLAMP | 15 | VB4100, VB4102, VB4105 |
| NY-ESO_Pep-14 | SRLLEFYLAMPFATP | 15 | VB4100, VB4102, VB4105 |
| NY-ESO_Pep-15 | LAMPFATPMEAELAR | 15 | VB4100, VB4102, VB4105 |
| NY-ESO_Pep-16 | PMEAELARRSLAQDA | 15 | VB4100, VB4102, VB4105 |
| NY-ESO_Pep-17 | RRSLAQDAPPLPVPG | 15 | VB4100, VB4102, VB4105 |
| NY-ESO_Pep-18 | DAPPLPVPGVLLKEF | 15 | VB4100, VB4102, VB4105 |
| NY-ESO_Pep-19 | APPLPVPGVLLKEFT | 15 | VB4100, VB4102, VB4105 |
| NY-ESO_Pep-20 | GVLLKEFTVSGNILT | 15 | VB4100, VB4105 |
| NY-ESO_Pep-21 | TVSGNILTIRLTAAD | 15 | VB4100, VB4105 |
| NY-ESO_Pep-22 | TIRLTAADHRQLQLS | 15 | VB4100, VB4105 |
| NY-ESO_Pep-23 | DHRQLQLSISSCLQQ | 15 | VB4100, VB4105 |
| NY-ESO_Pep-24 | SISSCLQQLSLLMWI | 15 | VB4100, VB4105 |
| NY-ESO_Pep-25 | QLSLLMWITQCFLPV | 15 | VB4100, VB4105 |
| NY-ESO_Pep-26 | ITQCFLPVFLAQPPS | 15 | VB4100, VB4105 |
| NY-ESO_Pep-27 | VFLAQPPSGQRR | 12 | VB4100, VB4105 |
| NY-ESO_Pep-28 | RGPESRLL | 8 | VB4100, VB4101, VB4102, VB4105 |

Comparison of Immunogenicity of Constructs VB4097, VB4100 and VB4105

Constructs VB4097 (10 neoepitopes), VB4100 (NY-ESO-1 full length), and VB4105 (10 neoepitopes and NY-ESO-1 full length) were compared for their ability to elicit T cell immune response against the peptides in tables 15 (VB4097 and VB4105) and 17 (VB4100 and VB4105).

Figure 9:
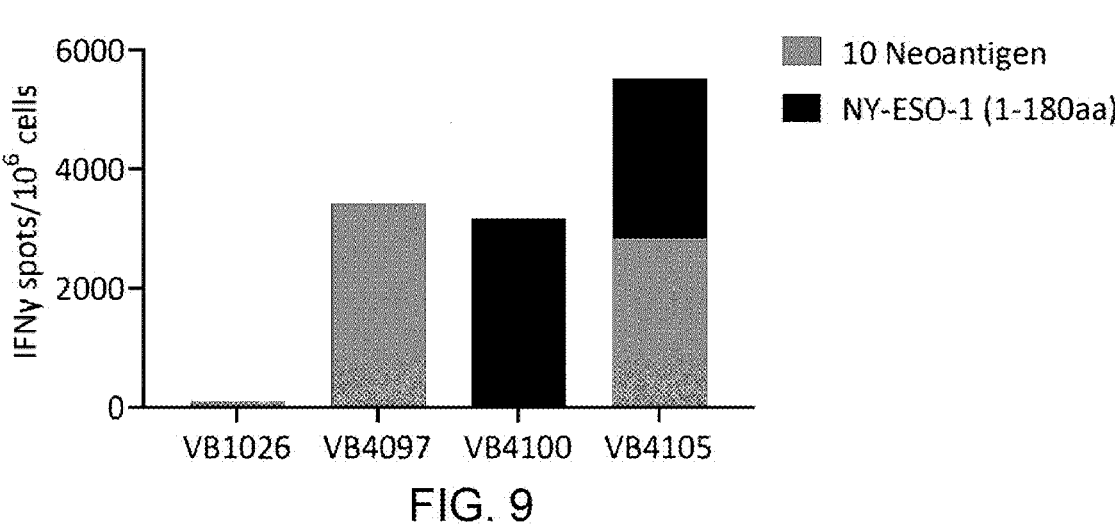
FIG. 9 shows the immunogenicity of DNA vaccines (constructs) VB4097, VB4100 and VB4105 in mice vaccinated with these constructs by way of measuring the IFN-γ immune responses from T cells (total T cell response), compared to the negative control VB1026.

As shown in FIG. 9, mice vaccinated with the negative control VB1026 showed low basal immunogenicity against both the neoepitopes and the NY-ESO-peptide sequences.

VB4097 and VB4105, both comprising the same 10 CT26 neoepitopes, induce a similar a total T cell response (INF-γ response) against the 10 neoepitopes (FIG. 9, grey bars), independent of whether the antigenic unit only comprises the 10 neoepitopes (VB4097) or comprises in addition the full-length sequence of NY-ESO-1 (VB4105).

Also, VB4100 and VB4105, both comprising the full-length sequence of NY-ESO-1 induce a similar a total T cell response (INF-γ response) against the peptides used for re-stimulation as shown in table 17 (FIG. 9, black bars), independent of whether the antigenic unit only comprises the full-length sequence of NY-ESO-1 (VB4100) or comprises in addition the 10 neoepitopes (VB4105).

For VB4105, the addition of the NY-ESO-1 full length sequence to the antigenic unit of VB4097 comprising the 10 neoepitopes did elicit a higher total T cell response compared to that elicited by vaccination with VB4097, due to the added immunogenicity against NY-ESO-1.

These results indicate that a vaccine according to the invention comprising a patient-present shared antigen is able to elicit an immune response which is similar to that of a vaccine comprising patient-specific antigens (neoepitopes). Moreover, these results indicate that there is a benefit in including both a patient-present shared antigen and patients-specific antigens (neoepitopes) into the antigenic unit.

Comparison of Immunogenicity of Constructs VB4100, VB4101 and VB4102

Using in silico methods, the epitope consisting of amino acids 81-88 of NY-ESO-1 was predicted to strongly bind to MHC class I to active CD8+ T cells, whereas the peptide consisting of amino acids 81 to 126 of NY-ESO-1 was predicted to contain several MHC class I and class II antigens. Therefore, constructs VB4100 (NY-ESO-1 full length), VB4101 (NY-ESO-1 amino acids 81-88) and VB4102 (NY-ESO-1 amino acids 81-126) were constructed and compared for their ability to elicit T cells immune response.

Figure 10:
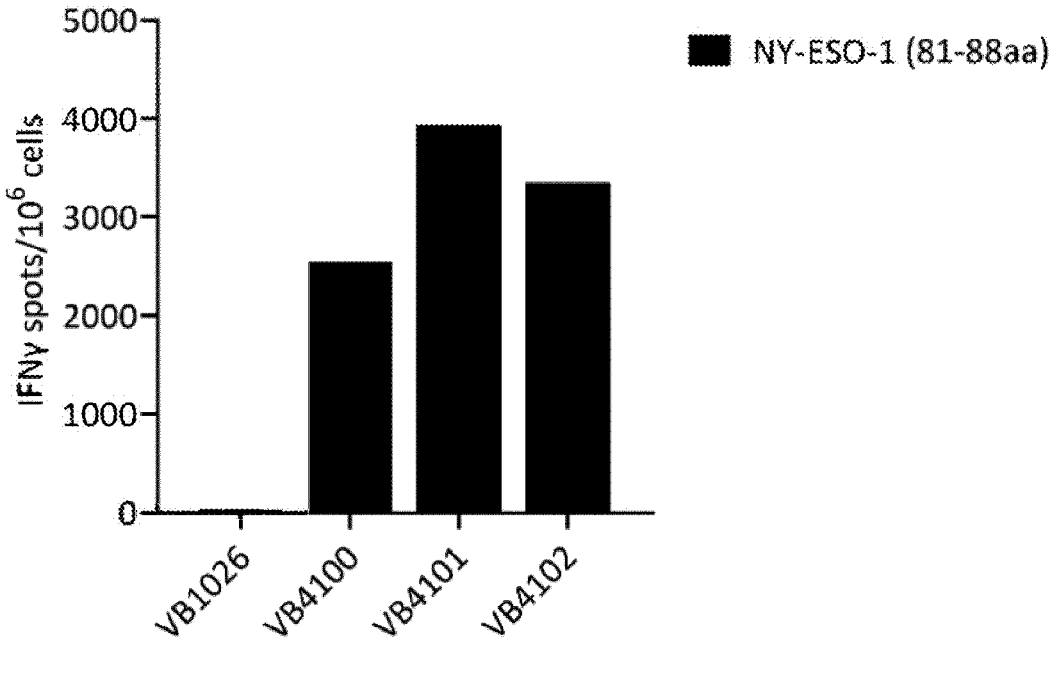
FIG. 10 shows the immunogenicity of DNA vaccines (constructs) VB4100, VB4101 and VB4102 in mice vaccinated with these constructs by way of measuring the IFN-γ immune responses from CD8+ T cells, compared to the negative control VB1026.

First, the three constructs were compared for their ability to elicit CD8+ T cell immune response against the predicted amino acid 81-88 region. The CD8+ T cells isolated from splenocytes of mice vaccinated with the constructs were re-stimulated with the amino acid 81-88 minimal epitope shown in table 16. As shown in FIG. 10, the experiments confirmed that the epitope consisting of amino acids 81-88 of NY-ESO-1 is indeed a strong CD8+ T cell epitope. Moreover, the immunogenicity for this region is independent of whether the epitope is the only sequence in the antigenic unit (VB4101) or the antigenic unit comprising a longer NY-ESO-1 sequence or the full NY-ESO-1 sequence.

Figure 11A:
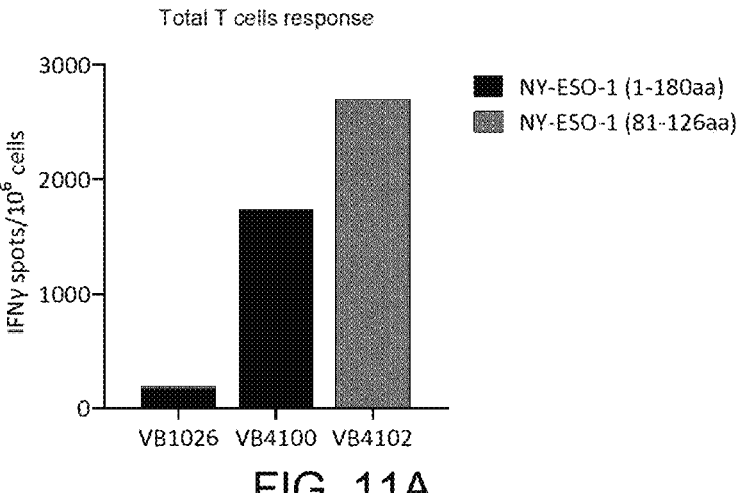
FIG. 11 shows the immunogenicity of DNA vaccines (constructs) VB4100 and VB4102 in mice vaccinated with these constructs by way of measuring the IFN-γ immune responses from A) T cells (total T cell response), B) CD8+ T cells and C) CD4+ T cells, compared to the negative control VB1026.
Figure 11B:
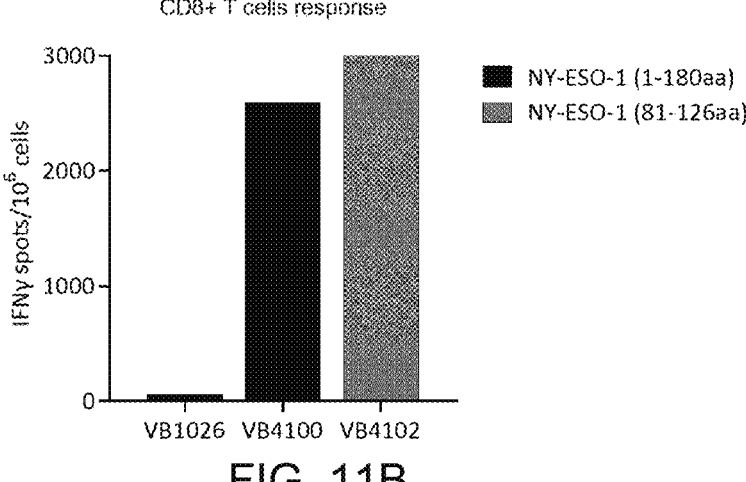
Figure 11C:
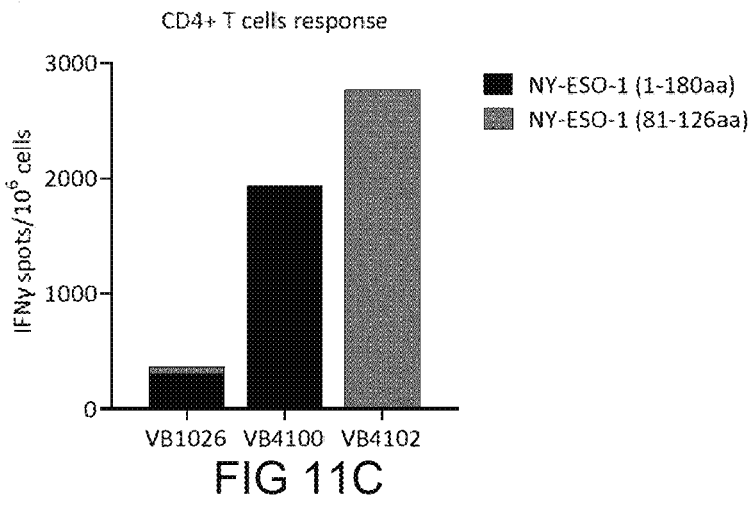

Next, VB4102 was compared to VB4100 to assess whether the several predicted MHC class I and class II antigens in the amino acid sequence 81-126 of NY-ESO-1 elicit a similar response as the full-length NY-ESO-1 sequence. The CD4+ T cells and CD8+ T cells isolated from splenocytes of mice vaccinated with the constructs were re-stimulated with the peptides shown in table 17. As shown in FIG. 11, the amino acid sequence 81-126 of NY-ESO-1 elicits a stronger response than the NY-ESO-1 full length sequence, both from isolated CD8+(FIG. 11B) and CD4+ T cells (FIG. 11C) and in terms of total T cell response (FIG. 11A).

These results suggest that by using in silico methods, short(er) sequences/epitopes of patient-present shared antigens can be identified that are predicted to elicit strong immune responses. By including such sequences/epitopes into the antigenic unit of the vaccine of the invention instead of longer sequences or the full-length sequence of a patient-present shared antigen, there is space left in the antigenic unit for including sequences of other patient-present shared antigens and/or patient-specific antigens/neoepitopes. This will enhance the chance that the patient receiving such an individual anticancer vaccine will show a strong immune response to the vaccine.

Example 8: Immunogenicity of DNA Vaccines According to the Invention Design of DNA Vaccines Comprising Shared Antigen Sequences and/or Neoepitopes Six DNA vaccines (constructs) were designed comprising nucleotide sequences encoding the units/parts shown in table 18:

TABLE 18

| Unit/Part | Function |
|---|---|
| 1: Native leader sequence for human MIP1α (LD78β) | Signal peptide |
| 2: Full-length human MIP1α (LD78β) sequence | Targeting unit |
| 3: Human hinge-region 1 from IgG3 | Dimerization unit |
| 4: Human hinge region 4 from IgG3 | |
| 5: Glycine-Serine linker | |
| 6: Human CH3 domain from IgG3 | |
| 7: Glycine-Leucine linker | Unit linker |
| 8: Patient-present shared antigen sequences: VB4119, VB4127 | Antigenic unit |
| 9: Patient-specific antigen sequences (neoepitopes) VB4118 | |
| 10: Patient-present shared antigen sequences and patient-specific antigen sequences (neoepitopes): VB4121, VB4128, VB4130 | |

DNA Vaccine VB4118 Comprising 10 B16 Neoepitopes:

This construct was chosen as a model of an individualized DNA vaccine comprising patient-specific antigen sequences, i.e. neoepitopes.

Previously described exome sequencing and RNA sequencing of the mouse melanoma cell line B16.F10 revealed hundreds to thousands of tumor-specific non-synonymous mutations. In silico methods were used to identify potential immunogenic sequences, i.e. neoepitopes, and 10 of them (table 19) were chosen for inclusion into the antigenic unit of VB4118. Each of the identified 10 neoepitopes is a peptide consisting of 27 amino acids. All but the terminal neoepitope were arranged in subunits, each subunit consisting of one neoepitope and one flexible glycine-serine linker (GGGGSGGGGS).

VB4118 consists of a DNA sequence encoding the polypeptide with amino acid sequence of SEQ ID NO: 26.

TABLE 19

| Neo-antigen | Gene | Sequence | Reactive T cell subtype |
|---|---|---|---|
| B-pepM2 | Obsl1 | REGVELCPGNKYEMRR HGTTHSLVIHD | CD8+ |

TABLE 19-continued

| Neo-antigen | Gene | Sequence | Reactive T cell subtype |
|---|---|---|---|
| B-pepM7 | Atp11a | SSPDEVALVEGVQSLG FTYLRLKDNYM | CD8+ |
| B-pepM36 | Pcmtd1 | KNILAVSFAPLVQLSK NDNGTPDSVGL | CD4+ |
| B-pepM78 | Klhl26 | PAADRWEPRAPMRAPR VLHAMLGAAGR | CD4+ |
| B-pepM79 | B3galt6 | VLSADLVHYLRLSLEY LRAWHSEDVSL | CD4+ |
| B-pepM82 | Mta1 | LEAVLRYLETHPRLPK PDPVKSSSSVL | CD4+ |
| B-pepM83 | Ddit41 | LKDFFFSRGRFSSALK RTLILSSGFRL | CD4+ |
| B-pepM84 | Wdr3 | AGKDHKIKQWDADTFE HIQTLEGHHQE | CD8+ |
| B-pepM85 | Rfx3 | PATIEMAIETLQKFDG LSTHRSSLLNS | ND |
| B-pepM86 | Map1s | YLPGGGAGHLDQNVFL RVRALCYVISG | CD8+ |

DNA Vaccines VB4119 Comprising a TRP-2 Sequence and VB4127 Comprising Frameshift Antigens These constructs were chosen as models of individualized DNA vaccine comprising patient-present shared antigen sequences.

Tyrosinase related protein 2 (TRP-2) is a melanocyte lineage normal differentiation protein. This shared antigen (differentiation antigen) is known to induce tumor rejection of B16 melanoma cells in C57BL/6 mice in vivo. In the literature, the 9 amino acid long MHC class I epitope shown in table 20 (amino acids 180-188 of TRP-2) has been identified as the immunogenic sequence responsible for the anti-tumor effect of TRP-2.

VB4119 consists of a DNA sequence encoding the polypeptide with amino acid sequence of SEQ ID NO: 27

TABLE 20

| Construct | TRP-2 epitope | Sequence | Length | Reactive T cell subtype |
|---|---|---|---|---|
| VB4119 | Amino acids 180-188 | SVYDFFVWL | 9 amino acids | CD8+ |

Frameshift mutations are DNA mutations that arise when indels (insertions or deletions) of nucleotides lead to a shift in the DNA reading frame. Consequently, the entire DNA sequence following the indel will be read incorrectly and the resulting protein will be altered. Frameshift mutations arising in tumor cells generate novel peptide sequences that could be highly immunogenic, and, moreover, identical frameshift antigens could arise across different patients, and thus represent promising targets for shared antigen cancer vaccines (see for instance Ballhausen et al., Nat. Commun. 11, 2020, 1-13). The three frameshift antigens shown in table 21 were identified as immunogenic by in silico methods and are encoded in the VB4127 construct. In the antigenic unit, they are separated from each other by a flexible glycine-serine linker (GGGGSGGGGS).

VB4127 consists of a DNA sequence encoding the polypeptide with amino acid sequence of SEQ ID NO: 28.

TABLE 21

| Frameshift antigen | Gene | Sequence | Reactive T cell subtype |
|---|---|---|---|
| B-pepM108 | Maz | YISDHMKVHSPSPCL | CD4+ |
| B-pepM115-M122 | Dync1h1 | EGWQTCWGRSRKHWGSTWN GSARLSPGSTLWVMRICLRSL GIARTWLSCRSTSRKCSPAFP ASS | CD4+/CD8+ |
| B-pepM141-M142 | Prtg | LFRLLPSGPKVNDGHRSRRW HSLDLYPHLCSHLDLPKQSQE VIRL | CD8+ |

DNA Vaccines Comprising 10 B16 Neoepitopes and the TRP-2 Epitope (VB4121) or 10 B16 Neoepitopes and the 3 Frameshift Antigens (VB4128) or 10 B16 Neoepitopes, the TRP-2 Epitope and the 3 Frameshift Antigens (VB4130)

These constructs were chosen as models of individualized DNA vaccines comprising patient-present shared antigen sequences and patient-specific antigen sequences (neoepitopes). Each construct comprises an antigenic unit comprising the 10 B16 neoepitopes shown in table 19, each of them separated from the following neoepitope or the shared antigen sequence by a flexible glycine-serine linker (GGGGSGGGGS).The same linker was used to separate the shared antigens sequences in constructs comprising several of such sequences. VB4121 consists of a DNA sequence encoding the polypeptide with amino acid sequence of SEQ ID NO: 29; VB4128 consists of a DNA sequence encoding the polypeptide with amino acid sequence of SEQ ID NO: 30 and VB4130 consists of a DNA sequence encoding the polypeptide with amino acid sequence of SEQ ID NO: 31.

The construct VB1026, described in Example 7, was used as a negative control.

Construction of Expression Vectors Comprising the Constructs and Confirmation of Expression and Secretion of Intact Dimeric Proteins Encoded by the Constructs The expression vectors comprising the aforementioned constructs were constructed as described in Example 7. Expression and secretion of intact dimeric proteins encoded by the constructs was confirmed as described in Example 7.

Assessment of Immunogenicity of the Constructs

Immunogenicity of the constructs was determined by way of measuring the T cell immune response elicited in vivo in mice vaccinated with the constructs.

Female, 6-week-old C57BL/6 mice were obtained from Janvier Labs (France). All animals were housed in the animal facility at the Radium Hospital (Oslo, Norway). All animal protocols were approved by the Norwegian Food Safety Authority (Oslo, Norway). 5 mice/group were used for the testing of the constructs comprising an antigenic unit, whereas 3 mice/group were used for the negative control.

20 µg of the construct was administered intramuscularly on day 0 followed by electroporation. The spleens from the vaccinated mice were collected on day 14. The collected spleens were processed and ELISpot assays were carried out as described in Example 7.

The 10 neoepitopes shown in table 19 were used to re-stimulate the splenocytes harvested from mice vaccinated with the constructs VB4118, VB4121, VB4128, and VB4130. The TRP-2 peptide in table 20 was used to re-stimulate the splenocytes harvested from mice vaccinated with the constructs VB4119, VB4121, and VB4130. The frameshift peptides shown in table 22 below were used to re-stimulate the splenocytes harvested from mice vaccinated with the constructs VB4127, VB4128, and VB4130.

TABLE 22

| Gene | Frameshift peptide ID | Sequence | Length |
|------|----------------------|----------|--------|
| Maz | B-pepM108 | YISDHMKVHSPSPCL | |
| Dync1h1 | B-pepM115 | EGWQTCWGRSRKHWG | 15 amino acids |
| Dync1h1 | B-pepM116 | GRSRKHWGSTWNGSA | 15 amino acids |
| Dync1h1 | B-pepM117 | GSTWNGSARLSPGST | 15 amino acids |
| Dync1h1 | B-pepM118 | ARLSPGSTLWVMRIC | 15 amino acids |
| Dync1h1 | B-pepM119 | TLWVMRICLRSLGIA | 15 amino acids |
| Dync1h1 | B-pepM120 | CLRSLGIARTWLSCR | 15 amino acids |
| Dync1h1 | B-pepM121 | ARTWLSCRSTSRKCS | 15 amino acids |
| Dync1h1 | B-pepM122 | RSTSRKCSPAFPASS | 15 amino acids |
| Prtg | B-pepM141 | LFRLLPSGPKVNDGHRSRRWHSLDLYP | 27 amino acids |
| Prtg | B-pepM142 | SRRWHSLDLYPHLCSHLDLPKQSQEVIRL | 29 amino acids |

Comparison of Immunogenicity of Constructs VB4118, VB4119, VB4121, VB4127, VB4128, and VB4130

Constructs VB4118 (10 neoepitopes), VB4119 (TRP-2), VB4121 (10 neoepitopes and TRP-2), VB4127 (3 frameshift antigens), VB4128 (10 neoantigens and 3 frameshift antigens), and VB4130 (10 neoepitopes, 3 frameshift antigens and TRP-2) were compared for their ability to elicit T cell immune response against the peptides in tables 19, 20, and 22, as applicable.

Figure 12:
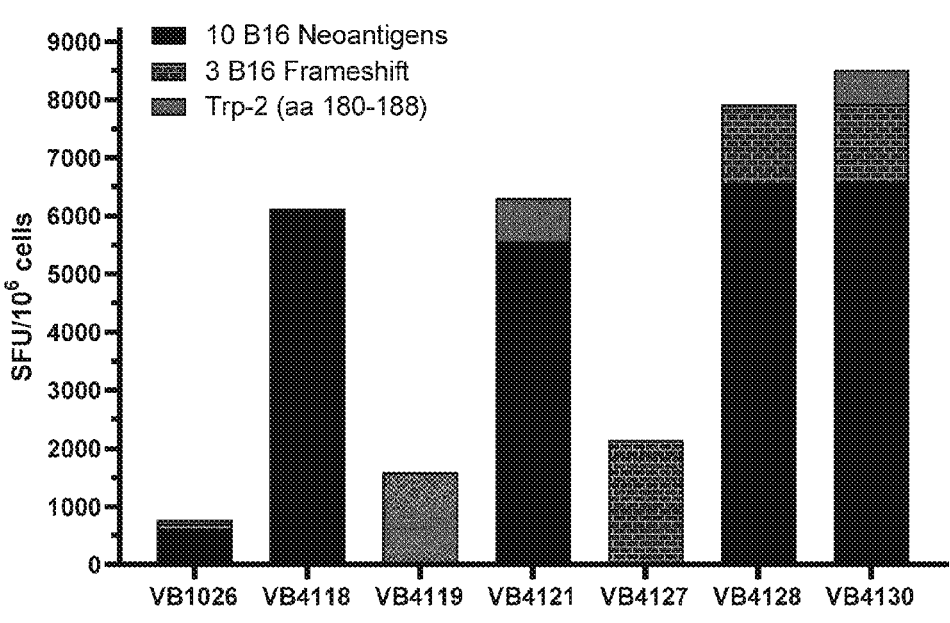
FIG. 12 shows the immunogenicity of DNA vaccines (constructs) VB4118, VB4119, VB4121, VB4127, VB4128 and VB4130 in mice vaccinated with these constructs by way of measuring the IFN-γ immune responses from T cells, compared to the negative control VB1026.

As shown in FIG. 12, mice vaccinated with the negative control VB1026 showed low basal immunogenicity against all the peptides tested.

Both the model construct of a vaccine comprising only patient-specific antigens (VB4118) and the model constructs of vaccines comprising only patient-present shared antigen(s) (VB4119 and VB4127) elicit an immune response in the vaccinated mice.

VB4118, VB4121, VB4128, and VB4130, all comprising the same 10 B16 neoepitopes, induce a similar total T cell response (INF-γ response) against the 10 neoepitopes (FIG. 12, black bars), independent of whether the antigenic unit only comprises the 10 neoepitopes (VB4118) or comprises in addition the TRP-2 epitope (VB4121), the 3 frameshift antigens (VB4128) or the TRP-2 epitope plus the 3 frameshift antigens (VB4130).

Further, FIG. 12 shows that adding the shared antigens to a neoepitope construct leads to a broader and increased total T cell response with the highest total T cell response observed for the construct encoding 10 neoepitopes, 3 frameshift antigens and the TRP-2 epitope (VB4130).

Also the results of this study indicate that a vaccine according to the invention comprising a patient-present shared antigen can elicit an immune response which is similar to that of a vaccine comprising patient-specific antigens (neoepitopes). Moreover, these results indicate that there is the benefit of an increased broader and total T cell response by including different types of shared antigens and patients-specific antigens (neoepitopes) into the antigenic unit.

SEQUENCES

SEQ ID NO: 1

C-C motif chemokine 3-like 1 precursor including signal peptide (aa 1-23) and mature peptide (hMIP1α/LD78-beta, aa 24-93):
MQVSTAALAVLLCTMALCNQVLSAPLAADTPTACCFSYTSRQIPQNFIADYFETSSQCSKPSVIF

LTKRGRQVCADPSEEWVQKYVSDLELSA

SEQ ID NO: 2

MQVSTAALAVLLCTMALCNQVLS | APLAADTPTACCFSYTSRQIPQNFIAD

YFETSSQCSKPSVIFLTKRGRQVCADPSEEWVQKYVSDLELSA | ELKTPLG

DTTHT | EPKSCDTPPPCPRCP | GGGSSGGGSG | GQPREPQVYTLPPSREEMTK

NQVSLTCLVKGFYPSDIAVEWESSGQPENNYNTTPPMLDSDGSFFLYSKL

TVDKSRWQQGNIFSCSVMHEALHNRFTQKSLSLSPGK | GLGGL |

SEQ ID NO: 3

Linker, amino acid sequence: GLSGL

SEQ ID NO: 4

Linker, amino acid sequence: GLGGL

-continued

SEQ ID NO: 5

Hinge region 1 (human IgG3 UH hinge), 12 amino acids: ELKTPLGDTTHT

SEQ ID NO: 6

Hinge region 4 (human IgG3, MH hinge, 15 amino acids): EPKSCDTPPPCPRCP

SEQ ID NO: 7

Gly-Ser Linker: GGGSSGGGSG

SEQ ID NO: 8 hCH3 IgG3, amino acid sequence:
GQPREPQVYTLPPSREEMTKNQVSLTCLVKGFYPSDIAVEWESSGQPENNYNTTPPMLDSDG

SFFLYSKL TVDKSRWQQG NIFSCSVM H EALH N RFTQKSLSLSPGK

SEQ ID NO: 9

Signal peptide
MNFGLRLIFLVLTLKGVQC

SEQ ID NO: 10

Signal peptide
MDAMKRGLCCVLLLCGAVFVSP

SEQ ID NO: 11: HPV16 E6

MFQDPQERPRKLPQLCTELQTTIHDIILECVYCKQQLLRREVYDFARRDLCIVYRDGNPYAVRD

KCLKFYSKISEYRHYCYSLYGTTLEQQYNKPLCDLLIRCINRQKPLCPEEKQRHLDKKQRFHNIR

GRWTGRCMSCCRSSRTRRETQL

SEQ ID NO: 12: HPV16 E7

MHGDTPTLHEYMLDLQPETTDLYGYGQLNDSSEEEDEIDGPAGQAEPDRAHYNIVTFCCKCDS

TLRLCVQSTHVDIRTLEDLLMGTLGIVCPICSQKP

SEQ ID NO: 13: NY-ESO-1

MQAEGRGTGGSTGDADGPGGPGIPDGPGGNAGGPGEAGATGGRGPRGAGAARASGPGGG

APRGPHGGAASGLNGCCRCGARGPESRLLEFYLAMPFATPMEAELARRSLAQDAPPLPVPGV

LLKEFTVSGNILTIRLTAADHRQLQLSISSCLQQLSLLMWITQCFLPVFLAQPPSGQRR

SEQ ID NO: 14 (302 amino acids)
Antigenic unit comprising antigen sequences in the following order: E7 | linker | NY-ESO-1 |
linker | E6.
VQSTHVDIRTLEDLLMGTLGIVCPICSQKPGGGGSGGGGSARGPESRLLEFYLAMPFATPMEA

ELARRSLAQDAPPLPVPGVLLKEFTVSGNILTIRLTAADHRQLQLSISSCLQQLSLLMWITQCFLP

VFLAQPPSGQRRSGGGGSGGGGMFQDPQERPRKLPQLCTELQTTIHDIILECVYCKQQLLRRE

VYDFARRDLCIVYRDGNPYAVRDKCLKFYSKISEYRHYCYSLYGTTLEQQYNKPLCDLLIRCINR

QKPLCPEEKQRHLDKKQRFHNIRGRWTGRCMSCCRSSRTRRETQL

SEQ ID NO: 15 (924 amino acids)
Antigenic unit comprising antigen sequences in the following order: T1D320 | linker | T1D814 |
linker | T1D182 | linker | T1D689 | linker | E7 | linker | T1D339 | linker | T1D428 | linker |NY-
ESO-1 | linker | T1D572 | linker | T1D359 | linker | T1D488 | linker | T1D554 | linker | T1D272 |
linker | T1D210 | linker | T1D849 | linker | T1D4 | linker | T1D77 | linker | T1D717 | linker |
T1D586 | linker | E6.

HNEGDDQQGSRYSLIPQIQKVCEVVDGGSSGGGSSGGSEQERMKSSLLKEHMLRKQAELES

AQCSGGGGSGGGGELRENLLTYLPDSVTQLRRLEELDLGNGGGGSGGGGSQEVFSSYKFNH

LVRRLVLQREKHFHYLSGGGGSGGGGVQSTHVDIRTLEDLLMGTLGIVCPICSQKPGGGGSG

GGGSIEKNADLCYLSTVHWSLILDAVSNNYIGGGGSGGGGSLATAGEPYHDIRFKLMAVVPDR

RIKYEGGGGSGGGGSARGPESRLLEFYLAMPFATPMEAELARRSLAQDAPPLPVPGVLLKEFT

VSGNILTIRLTAADHRQLQLSISSCLQQLSLLMWITQCFLPVFLAQPPSGQRRSGGGGSGGGG

MLRLPTVFRQIRPVSRVLAPHLTRSGGGGSGGGGIQIMENPFVQSMLWNPDLMRQLIMANPG

GGGSGGGGSLLRFLFLGLSALALPSRAQLQLHLPANGGGGSGGGGSMGKNPVRPPRAFPPV

-continued

PSIDDIPLSRGSGGGGSGGGGHVDFTIEVERALTVLDGAVLVLCAVGSSGGGGSSGGGEYKLMY

GMLFSIRLFVSKMSPLDMKDGGSSGGGSSGGSQGAGVESLDFRLYLRYEFLMLGIQPVGGGG

SGGGGSAAKTLVLCVSDIILLSANISETSSNKTSGGGGSGGGGCKDLQLYLSNLANHIDRETGI

GDVPLVGGGGSGGGGSQSKHTEARELMYSAALLFFSHGQQNSAGGGGSGGGGSMTLAESY

AQYVYNLCNSLSIKVEESSGGGGSGGGGMFQDPQERPRKLPQLCTELQTTIHDIILECVYCKQ

QLLRREVYDFARRDLCIVYRDGNPYAVRDKCLKFYSKISEYRHYCYSLYGTTLEQQYNKPLCDL

LIRCINRQKPLCPEEKQRHLDKKQRFHNIRGRWTGRCMSCCRSSRTRRETQL

SEQ ID NO: 16 (227 amino acids)
Antigenic unit comprising antigen sequences in the following order: E6 | linker | NY-ESO-1 |
linker | E7
VRDKCLKFYSKISEYRHYCYSLYGTTLEQQYNKPLCDLLIRCINRQKPLCPEEKQRHLDKKQRF

HNIRGRWTGRCMSCCRSSRTRRETQLSGGGGSGGGGGARGPESRLLEFYLAMPFATPMEAE

LARRSLAQDAPPLPVPGVLLKEFTVSGNILTIRLTAADHRQLQLSIGGGGSGGGGSAGQAEPDR

AHYNIVTFCCKCDSTLRLCVQSTHVDIRTLEDLLMGTL

SEQ ID NO: 17 (850 amino acids)
Antigenic unit comprising antigen sequences in the following order: E6 | linker | T1D323 | linker |
T1D506 | linker | T1D12 | linker | T1D315 | linker | T1D302 | linker | T1D700 | linker | NY-ESO-1
| linker | T1D535 | linker | T1D358 | linker | T1D670 | linker | T1D294 | linker | T1D336 | linker |
T1D499 | linker | T1D425 | linker T1D491 | linker | T1D314 | linker | T1D430 | linker | E7 | linker |
T1D582.
VRDKCLKFYSKISEYRHYCYSLYGTTLEQQYNKPLCDLLIRCINRQKPLCPEEKQRHLDKKQRF

HNIRGRWTGRCMSCCRSSRTRRETQLSGGGGSGGGGKKVSKTRHTRETVFRRAKRRWAPIP

CSSGGGGSGGGGNLKHENILQFLTAQERKTELGKQYWLIGGGGGGGGGSVQVFGLYFGEEF

HETFDCPIKGSGGGGSGGGGQAAASQAGGARGYARGAQLWPPGSDPGGGGSGGGGSSIM

QTWFTLFTPTDATSIVATTVMSNSSGGGGSGGGGQENVRFVLVRSEALLPNAGPRSAEARVG

GGGSGGGGSGARGPESRLLEFYLAMPFATPMEAELARRSLAQDAPPLPVPGVLLKEFTVSGNI

LTIRLTAADHRQLQLSIGGGGSGGGGSDAFPNLKDFISRFQVMPPSSFLFDAPCSGGGGSGGG

GPSSLQVKPETPASEAVAVAAAAAPTTTSGGGGSGGGGRFFHLADLFLSSSQLPAYLVAAFAK

RLSGGGGSGGGGLVFLWLHSLRRLFGCLYVSVFSNVMIHSGGGGSGGGGWENAIAALFRRHI

AVSWLIRATLSESEGGGGSGGGGSRYIFVKSAGSRIEEGVLQFLVLLVAGRSGGGGGGGGQ

EIEWLPFRCIKCLKLSFSTAELLCMHGGGGSGGGGSLVARCPPCLRLLRQARDFQAARYDRHD

GGGGSGGGGSALGTPEDLDSYIDLSLESLNQMILELDGGGGSGGGGSSQDMLSIMEKLEFLD

FSYDLNLCGLTEGGGGSGGGGSAGQAEPDRAHYNIVTFCCKCDSTLRLCVQSTHVDIRTLEDL

LMGTLGGGSGGGGSGRREQYIPNEEFLHFDLLEDSKYRKIYS

SEQ ID NO: 18 (221 amino acids):
Antigenic unit comprising antigen sequences in the following order: NY-ESO-1 | linker | E7 |
linker | E6.
GARGPESRLLEFYLAMPFATPMEAELARRSLAQDAPPLPVPGVLLKEFTVSGNILTIRLTAADHR

QLQLSISSCLQQLSLLMWITQCFLPVFGGGGSGGGGSAGQAEPDRAHYNIVTFCCKCDSTLRL

CVQSTHVDIRTLSGGGGSGGGGKFYSKISEYRHYCYSLYGTTLEQQYNKPLCDLLIRCINRQKP

LCPEEKQRHLDKKQRFHNIRGRWTGRCMS

SEQ ID NO: 19 (831 amino acids)
Antigenic unit comprising antigen sequences in the following order: T1D223 | linker | T1D164 |
linker | T1D56 | linker | T1D36 | linker | T1D129 | linker | T1D274 | linker | T1D62 | linker | T1D5 |
linker | T1D144 | linker | T1D441 | linker | T1D368 | linker | NY-ESO-1 | linker | T1D234 | linker |
T1D162 | linker | T1D39 | linker | T1D272 | linker | E7 | linker | T1D328 | linker | T1D188 | linker |
E6.
GPSYRSNSVSSLDLEGEGGGGSGGGGSLKEEKENLQGLVTHQTYIIQELEKQLNGGGGSGGGG

GSQRQKTAGKIFRAEVSTGQDAPRQAQARGGGSSGGGGSSILRPSTVNELESGEISYDEVGERI

```
KDFGGGGSGGGGSDTCINEDVESLRKMVQDLLAKLQEAKRSGGGGSGGGGLREEGTKYKSF

VQRARLVFREEGYLAFGGGGSGGGGSHEGARPMRAIFLANGNVFTTGFSRMSEGGGGSGG

GGSIPDAAFIQAARRKCELARAQDDYISLDGGGGSGGGGSMEIAKMRAGRRLWVHLIEKMFQP

KNSKGGGGSGGGGSMELVSFRDVAIEFSPEEWGGGGSGGGGSTCVHEIPFHFDLMELLPQC

QQLQMFFLGGGSGGGGSGGARGPESRLLEFYLAMPFATPMEAELARRSLAQDAPPLPVPGVL

LKEFTVSGNILTIRLTAADHRQLQLSISSCLQQLSLLMWITQCFLPVFGGGGSGGGGSVRRVFIT

DDFHDMIPKYLNFVKGVVDSSGGGGSGGGGNFHAHREKAPSLFCSRILNKAVYLFYGSSGGG

SSGGGDANKEGMFLFRAAHKLRQFLKMNSTGDGGGGSGGGGSLLSLGWSVDVGRHSGWTG

HVSTSWSINGGGGSGGGGSAGQAEPDRAHYNIVTFCCKCDSTLRLCVQSTHVDIRTLSGGGG

SGGGGNTIFSLRKDLRQGKARRLRCMEEKEMFGGGGSGGGGSNHFNDFEGDPAMTQFLEEF

EKNLEDTKGGGGSGGGGSKFYSKISEYRHYCYSLYGTTLEQQYNKPLCDLLIRCINRQKPLCP

EEKQRHLDKKQRFHNIRGRWTGRCMS
```

SEQ ID NO: 20

Amino acid sequence of VB4097

```
MQVSTAALAVLLCTMALCNQVLSAPLAADTPTACCFSYTSRQIPQNFIADYFETSSQCSKPSVIF

LTKRGRQVCADPSEEWVQKYVSDLELSAELKTPLGDTTHTEPKSCDTPPPCPRCPGGGSSGG

GSGGGQPREPQVYTLPPSREEMTKNQVSLTCLVKGFYPSDIAVEWESSGQPENNYNTTPPMLD

SDGSFFLYSKLTVDKSRWQQGNIFSCSVMHEALHNRFTQKSLSLSPGKGLGGLKIYEFDYHLY

GQNITMIMTSVSGHLLAGGGGSGGGGSAEYGDYQPEVHGVPYFRLEHYLPARVMGGGGSGG

GGSGSLFGSSRVQYVVNPAVKIVFLNIDPSGGGGSGGGGSLWVYLRPVPRPATIYLQILRLKPL

TGEGGGGSGGGGSTLAFLVLSTPAMFNRALKPFLKSCHFQGGGGSGGGGSFVSPMAHYVPG

IMAIESVVARFQFIVPGGGGSGGGGSVILPQAPSGPSYATYLQPAQAQMLTPPGGGGSGGGG

SEVIQTSKYYMRDVIAIESAWLLELAPHGGGGSGGGGSDTLSAMSNPRAMQVLLQIQQGLQTL

ATGGGGSGGGGSKSWIHCWKYLSVQSQLFRGSSLLFRRV
```

SEQ ID NO: 21

Amino acid sequence of VB4100

```
MQVSTAALAVLLCTMALCNQVLSAPLAADTPTACCFSYTSRQIPQNFIADYFETSSQCSKPSVIF

LTKRGRQVCADPSEEWVQKYVSDLELSAELKTPLGDTTHTEPKSCDTPPPCPRCPGGGSSGG

GSGGGQPREPQVYTLPPSREEMTKNQVSLTCLVKGFYPSDIAVEWESSGQPENNYNTTPPMLD

SDGSFFLYSKLTVDKSRWQQGNIFSCSVMHEALHNRFTQKSLSLSPGKGLGGLMQAEGRGTG

GSTGDADGPGGPGIPDGPGGNAGGPGEAGATGGRGPRGAGAARASGPGGGAPRGPHGGA

ASGLNGCCRCGARGPESRLLEFYLAMPFATPMEAELARRSLAQDAPPLPVPGVLLKEFTVSGN

ILTIRLTAADHRQLQLSISSCLQQLSLLMWITQCFLPVFLAQPPSGQRR
```

SEQ ID NO: 22

Amino acid sequence of VB4101

```
MQVSTAALAVLLCTMALCNQVLSAPLAADTPTACCFSYTSRQIPQNFIADYFETSSQCSKPSVIF

LTKRGRQVCADPSEEWVQKYVSDLELSAELKTPLGDTTHTEPKSCDTPPPCPRCPGGGSSGG

GSGGGQPREPQVYTLPPSREEMTKNQVSLTCLVKGFYPSDIAVEWESSGQPENNYNTTPPMLD

SDGSFFLYSKLTVDKSRWQQGNIFSCSVMHEALHNRFTQKSLSLSPGKGLGGLRGPESRLL
```

SEQ ID NO: 23

Amino acid sequence of VB4102

```
MQVSTAALAVLLCTMALCNQVLSAPLAADTPTACCFSYTSRQIPQNFIADYFETSSQCSKPSVIF

LTKRGRQVCADPSEEWVQKYVSDLELSAELKTPLGDTTHTEPKSCDTPPPCPRCPGGGSSGG
```

GSGGQPREPQVYTLPPSREEMTKNQVSLTCLVKGFYPSDIAVEWESSGQPENNYNTTPPMLD

SDGSFFLYSKLTVDKSRWQQGNIFSCSVMHEALHNRFTQKSLSLSPGKGLGGLRGPESRLLEF

YLAMPFATPMEAELARRSLAQDAPPLPVPGVLLKEF

SEQ ID NO: 24

Amino acid sequence of VB4105
MQVSTAALAVLLCTMALCNQVLSAPLAADTPTACCFSYTSRQIPQNFIADYFETSSQCSKPSVIF

LTKRGRQVCADPSEEWVQKYVSDLELSAELKTPLGDTTHTEPKSCDTPPPCPRCPGGGSSGG

GSGGQPREPQVYTLPPSREEMTKNQVSLTCLVKGFYPSDIAVEWESSGQPENNYNTTPPMLD

SDGSFFLYSKLTVDKSRWQQGNIFSCSVMHEALHNRFTQKSLSLSPGKGLGGLKIYEFDYHLY

GQNITMIMTSVSGHLLAGGGGSGGGGSAEYGDYQPEVHGVPYFRLEHYLPARVMGGGGSGG

GGSGSLFGSSRVQYVVNPAVKIVFLNIDPSGGGGGGGGGSLWVYLRPVPRPATIYLQILRLKPL

TGEGGGGSGGGGSTLAFLVLSTPAMFNRALKPFLKSCHFQGGGGSGGGGSFVSPMAHYVPG

IMAIESVVARFQFIVPGGGGSGGGGSVILPQAPSGPSYATYLQPAQAQMLTPPGGGGSGGGG

SEVIQTSKYYMRDVIAIESAWLLELAPHGGGGSGGGGSDTLSAMSNPRAMQVLLQIQQGLQTL

ATGGGGSGGGGSKSWIHCWKYLSVQSQLFRGSSLLFRRVGGGGSGGGGSMQAEGRGTGG

STGDADGPGGPGIPDGPGGNAGGPGEAGATGGRGPRGAGAARASGPGGGAPRGPHGGAA

SGLNGCCRCGARGPESRLLEFYLAMPFATPMEAELARRSLAQDAPPLPVPGVLLKEFTVSGNI

LTIRLTAADHRQLQLSISSCLQQLSLLMWITQCFLPVFLAQPPSGQRR

SEQ ID NO: 25

Amino acid sequence of VB1026
MQVSTAALAVLLCTMALCNQVLSAPLAADTPTACCFSYTSRQIPQNFIADYFETSSQCSKPSVIF

LTKRGRQVCADPSEEWVQKYVSDLELSAELKTPLGDTTHTEPKSCDTPPPCPRCPGGGSSGG

GSGGQPREPQVYTLPPSREEMTKNQVSLTCLVKGFYPSDIAVEWESSGQPENNYNTTPPMLD

SDGSFFLYSKLTVDKSRWQQGNIFSCSVMHEALHNRFTQKSLSLSPGK

SEQ ID NO: 26

Amino acid sequence of VB4118
MQVSTAALAVLLCTMALCNQVLSAPLAADTPTACCFSYTSRQIPQNFIADYFETSSQCSKPSVIF

LTKRGRQVCADPSEEWVQKYVSDLELSAELKTPLGDTTHTEPKSCDTPPPCPRCPGGGSSGG

GSGGQPREPQVYTLPPSREEMTKNQVSLTCLVKGFYPSDIAVEWESSGQPENNYNTTPPMLD

SDGSFFLYSKLTVDKSRWQQGNIFSCSVMHEALHNRFTQKSLSLSPGKGLGGLREGVELCPG

NKYEMRRHGTTHSLVIHDGGGGSGGGGSSSPDEVALVEGVQSLGFTYLRLKDNYMGGGGSG

GGGSLKDFFFSRGRFSSALKRTLILSSGFRLGGGGSGGGGSKNILAVSFAPLVQLSKNDNGTP

DSVGLGGGGSGGGGSLEAVLRYLETHPRLPKPDPVKSSSSVLGGGGSGGGGSPAADRWEP

RAPMRAPRVLHAMLGAAGRGGGGSGGGGSVLSADLVHYLRLSLEYLRAWHSEDVSLGGGGS

GGGGSYLPGGGAGHLDQNVFLRVRALCYVISGGGGGSGGGGSPATIEMAIETLQKFDGLSTH

RSSLLNSGGGGSGGGGSAGKDHKIKQWDADTFEHIQTLEGHHQE

SEQ ID NO: 27

Amino acid sequence of VB4119
MQVSTAALAVLLCTMALCNQVLSAPLAADTPTACCFSYTSRQIPQNFIADYFETSSQCSKPSVIF

LTKRGRQVCADPSEEWVQKYVSDLELSAELKTPLGDTTHTEPKSCDTPPPCPRCPGGGSSGG

GSGGQPREPQVYTLPPSREEMTKNQVSLTCLVKGFYPSDIAVEWESSGQPENNYNTTPPMLD

SDGSFFLYSKLTVDKSRWQQGNIFSCSVMHEALHNRFTQKSLSLSPGKGLGGLSVYDFFVWL

SEQ ID NO: 28

Amino acid sequence of VB4127
MQVSTAALAVLLCTMALCNQVLSAPLAADTPTACCFSYTSRQIPQNFIADYFETSSQCSKPSVIF

LTKRGRQVCADPSEEWVQKYVSDLELSAELKTPLGDTTHTEPKSCDTPPPCPRCPGGGSSGG

-continued

GSGGQPREPQVYTLPPSREEMTKNQVSLTCLVKGFYPSDIAVEWESSGQPENNYNTTPPMLD

SDGSFFLYSKLTVDKSRWQQGNIFSCSVMHEALHNRFTQKSLSLSPGKGLGGLYISDHMKVHS

PSPCLGGGGSGGGGSEGWQTCWGRSRKHWGSTWNGSARLSPGSTLWVMRICLRSLGIART

WLSCRSTSRKCSPAFPASSGGGGGSGGGGSLFRLLPSGPKVNDGHRSRRWHSLDLYPHLCS

HLDLPKQSQEVIRL

SEQ ID NO: 29

Amino acid sequence of VB4121
MQVSTAALAVLLCTMALCNQVLSAPLAADTPTACCFSYTSRQIPQNFIADYFETSSQCSKPSVIF

LTKRGRQVCADPSEEWVQKYVSDLELSAELKTPLGDTTHTEPKSCDTPPPCPRCPGGGSSGG

GSGGQPREPQVYTLPPSREEMTKNQVSLTCLVKGFYPSDIAVEWESSGQPENNYNTTPPMLD

SDGSFFLYSKLTVDKSRWQQGNIFSCSVMHEALHNRFTQKSLSLSPGKGLGGLREGVELCPG

NKYEMRRHGTTHSLVIHDGGGGSGGGGSSSPDEVALVEGVQSLGFTYLRLKDNYMGGGGSG

GGGSLKDFFFSRGRFSSALKRTLILSSGFRLGGGGSGGGGSKNILAVSFAPLVQLSKNDNGTP

DSVGLGGGGSGGGGSLEAVLRYLETHPRLPKPDPVKSSSSVLGGGGGGGGSPAADRWEP

RAPMRAPRVLHAMLGAAGRGGGGSGGGGSVLSADLVHYLRLSLEYLRAWHSEDVSLGGGGS

GGGGSYLPGGGAGHLDQNVFLRVRALCYVISGGGGGSGGGGSPATIEMAIETLQKFDGLSTH

RSSLLNSGGGGSGGGGSAGKDHKIKQWDADTFEHIQTLEGHHQEGGGGSGGGGSSVYDFFV

WL

SEQ ID NO: 30

Amino acid sequence of VB4128
MQVSTAALAVLLCTMALCNQVLSAPLAADTPTACCFSYTSRQIPQNFIADYFETSSQCSKPSVIF

LTKRGRQVCADPSEEWVQKYVSDLELSAELKTPLGDTTHTEPKSCDTPPPCPRCPGGGSSGG

GSGGQPREPQVYTLPPSREEMTKNQVSLTCLVKGFYPSDIAVEWESSGQPENNYNTTPPMLD

SDGSFFLYSKLTVDKSRWQQGNIFSCSVMHEALHNRFTQKSLSLSPGKGLGGLYISDHMKVHS

PSPCLGGGGSGGGGSEGWQTCWGRSRKHWGSTWNGSARLSPGSTLWVMRICLRSLGIART

WLSCRSTSRKCSPAFPASSGGGGGSGGGGSLFRLLPSGPKVNDGHRSRRWHSLDLYPHLCS

HLDLPKQSQEVIRLGGGGSGGGGSREGVELCPGNKYEMRRHGTTHSLVIHDGGGGGGGGS

SSPDEVALVEGVQSLGFTYLRLKDNYMGGGGSGGGGSLKDFFFSRGRFSSALKRTLILSSGFR

LGGGGSGGGGSKNILAVSFAPLVQLSKNDNGTPDSVGLGGGGSGGGGSLEAVLRYLETHPRL

PKPDPVKSSSSVLGGGGSGGGGSPAADRWEPRAPMRAPRVLHAMLGAAGRGGGGSGGGG

SVLSADLVHYLRLSLEYLRAWHSEDVSLGGGGSGGGGSYLPGGGAGHLDQNVFLRVRALCYV

ISGGGGGSGGGGSPATIEMAIETLQKFDGLSTHRSSLLNSGGGGSGGGGSAGKDHKIKQWDA

DTFEHIQTLEGHHQE

SEQ ID NO: 31

Amino acid sequence of VB4130
MQVSTAALAVLLCTMALCNQVLSAPLAADTPTACCFSYTSRQIPQNFIADYFETSSQCSKPSVIF

LTKRGRQVCADPSEEWVQKYVSDLELSAELKTPLGDTTHTEPKSCDTPPPCPRCPGGGSSGG

GSGGQPREPQVYTLPPSREEMTKNQVSLTCLVKGFYPSDIAVEWESSGQPENNYNTTPPMLD

SDGSFFLYSKLTVDKSRWQQGNIFSCSVMHEALHNRFTQKSLSLSPGKGLGGLYISDHMKVHS

PSPCLGGGGSGGGGSEGWQTCWGRSRKHWGSTWNGSARLSPGSTLWVMRICLRSLGIART

WLSCRSTSRKCSPAFPASSGGGGGSGGGGSLFRLLPSGPKVNDGHRSRRWHSLDLYPHLCS

HLDLPKQSQEVIRLGGGGSGGGGSREGVELCPGNKYEMRRHGTTHSLVIHDGGGGSGGGGS

SSPDEVALVEGVQSLGFTYLRLKDNYMGGGGGGGGGSLKDFFFSRGRFSSALKRTLILSSGFR

```
LGGGGSGGGGSKNILAVSFAPLVQLSKNDNGTPDSVGLGGGGSGGGGSLEAVLRYLETHPRL

PKPDPVKSSSSVLGGGGSGGGGSPAADRWEPRAPMRAPRVLHAMLGAAGRGGGGSGGGG

SVLSADLVHYLRLSLEYLRAWHSEDVSLGGGGSGGGGSYLPGGGAGHLDQNVFLRVRALCYV

ISGGGGGSGGGGSPATIEMAIETLQKFDGLSTHRSSLLNSGGGGSGGGGSAGKDHKIKQWDA

DTFEHIQTLEGHHQEGGGGSGGGGSSVYDFFVWLGGGGSGGGGS
```

SEQ ID NO: 32
Amino acids 6-15 of HPV E6
QERPRKLPQ

SEQ ID NO: 33
Amino acids 8-17 of HPV E6
RPRKLPQLC

SEQ ID NO: 34
Amino acids 23-32 of HPV E6
IHDIILECV

SEQ ID NO: 35
Amino acids 24-33 of HPV E6
HDIILECVY

SEQ ID NO: 36
Amino acids 26-35 of HPV E6
IILECVYCK

SEQ ID NO: 37
Amino acids 35-44 of HPV E6
QQLLRREVY

SEQ ID NO: 38
Amino acids 42-51 of HPV E6
VYDFARRDL

SEQ ID NO: 39
Amino acids 43-52 of HPV E6
YDFARRDLC

SEQ ID NO: 40
Amino acids 44-53 of HPV E6
DFARRDLCI

SEQ ID NO: 41
Amino acids 45-54 of HPV E6
FARRDLCIV

SEQ ID NO: 42
Amino acids 60-69 of HPV E6
YAVRDKCLK

SEQ ID NO: 43
Amino acids 62-71 of HPV E6
VRDKCLKFY

SEQ ID NO: 44
Amino acids 81-90 of HPV E6
YSLYGTTLE

SEQ ID NO: 45
Amino acids 125-134 of HPV E6
FHNIRGRWT

SEQ ID NO: 46
Amino acids 131-140 of HPV E6
RWTGRCMSC

SEQ ID NO: 47
Amino acids 143-152 of HPV E6
SRTRRETQL

SEQ ID NO: 48
Amino acids 16-31 of HPV E6
CTELQTTIHDIILEC

SEQ ID NO: 49
Amino acids 17-32 of HPV E6
TELQTTIHDIILECV

-continued

```
                                                          SEQ ID NO: 50
Amino acids 18-33 of HPV E6
ELQTTIHDIILECVY SEQ ID NO: 51
Amino acids 19-34 of HPV E6
LQTTIHDIILECVYC SEQ ID NO: 52
Amino acids 20-35 of HPV E6
QTTIHDIILECVYCK SEQ ID NO: 53
Amino acids 34-49 of HPV E6
KQQLLRREVYDFARR SEQ ID NO: 54
Amino acids 49-64 of HPV E6
DLCIVYRDGNPYAVR SEQ ID NO: 55
Amino acids 50-65 of HPV E6
LCIVYRDGNPYAVRD SEQ ID NO: 56
Amino acids 51-66 of HPV E6
CIVYRDGNPYAVRDK SEQ ID NO: 57
Amino acids 78-93 of HPV E6
HYCYSLYGTTLEQQY SEQ ID NO: 58
Amino acids 95-110 of HPV E6
PLCDLLIRCINRQKP SEQ ID NO: 59
Amino acids 96-111 of HPV E6
LCDLLIRCINRQKPL SEQ ID NO: 60
Amino acids 97-112 of HPV E6
CDLLIRCINRQKPLC SEQ ID NO: 61
Amino acids 98-113 of HPV E6
DLLIRCINRQKPLCP SEQ ID NO: 62
Amino acids 99-114 of HPV E6
LLIRCINRQKPLCPE SEQ ID NO: 63
Amino acids 121-136 of HPV E6
KKQRFHNIRGRWTGR SEQ ID NO: 64
Amino acids 7-16 of HPV E7
TLHEYMLDL SEQ ID NO: 65
Amino acids 22-31 of HPV E7
LYGYGQLND SEQ ID NO: 66
Amino acids 38-47 of HPV E7
IDGPAGQAE SEQ ID NO: 67
Amino acids 48-57 of HPV E7
DRAHYNIVT SEQ ID NO: 68
Amino acids 55-64 of HPV E7
VTFCCKCDS SEQ ID NO: 69
Amino acids 66-75 of HPV E7
RLCVQSTHV
```

-continued

```
                                               SEQ ID NO: 70
Amino acids 72-81 of HPV E7
THVDIRTLE SEQ ID NO: 71
Amino acids 73-82 of HPV E7
HVDIRTLED SEQ ID NO: 72
Amino acids 85-94 of HPV E7
GTLGIVCPI SEQ ID NO: 73
Amino acids 4-19 of HPV E7
DTPTLHEYMLDLQPE SEQ ID NO: 74
Amino acids 5-20 of HPV E7
TPTLHEYMLDLQPET SEQ ID NO: 75
Amino acids 6-21 of HPV E7
PTLHEYMLDLQPETT SEQ ID NO: 76
Amino acids 7-22 of HPV E7
TLHEYMLDLQPETTD SEQ ID NO: 77
Amino acids 8-23 of HPV E7
LHEYMLDLQPETTDL SEQ ID NO: 78
Amino acids 9-24 of HPV E7
HEYMLDLQPETTDLY SEQ ID NO: 79
Amino acids 10-25 of HPV E7
EYMLDLQPETTDLYG SEQ ID NO: 80
Amino acids 70-85 of HPV E7
QSTHVDIRTLEDLLM SEQ ID NO: 81
Amino acids 71-86 of HPV E7
STHVDIRTLEDLLMG SEQ ID NO: 82
Amino acids 72-87 of HPV E7
THVDIRTLEDLLMGT SEQ ID NO: 83
Amino acids 73-88 of HPV E7
HVDIRTLEDLLMGTL SEQ ID NO: 84
Amino acids 74-89 of HPV E7
VDIRTLEDLLMGTLG SEQ ID NO: 85
Amino acids 16-25 of HPV E6
CTELQTTIH SEQ ID NO: 86
Amino acids 42-51 of HPV E6
VYDFARRDL SEQ ID NO: 87
Amino acids 45-54 of HPV E6
FARRDLCIV SEQ ID NO: 88
Amino acids 52-61 of HPV E6
IVYRDGNPY SEQ ID NO: 89
Amino acids 54-63 of HPV E6
YRDGNPYAV
```

-continued

SEQ ID NO: 90
```
Amino acids 68-77 of HPV E6
KFYSKISEY
```

SEQ ID NO: 91
```
Amino acids 73-82 of HPV E6
ISEYRHYCY
```

SEQ ID NO: 92
```
Amino acids 75-84 of HPV E6
EYRHYCYSL
```

SEQ ID NO: 93
```
Amino acids 80-89 of HPV E6
CYSLYGTTL
```

SEQ ID NO: 94
```
Amino acids 84-93 of HPV E6
YGTTLEQQY
```

SEQ ID NO: 95
```
Amino acids 88-97 of HPV E6
LEQQYNKPL
```

SEQ ID NO: 96
```
Amino acids 91-100 of HPV E6
QYNKPLCDL
```

SEQ ID NO: 97
```
Amino acids 11-20 of HPV E6
RHLDKKQRF
```

SEQ ID NO: 98
```
Amino acids 12-21 of HPV E6
RFHNIRGRW
```

SEQ ID NO: 99
```
Amino acids 18-33 of HPV E6
ELQTTIHDIILECVY
```

SEQ ID NO: 100
```
Amino acids 49-64 of HPV E6
DLCIVYRDGNPYAVR
```

SEQ ID NO: 101
```
Amino acids 50-65 of HPV E6
LCIVYRDGNPYAVRD
```

SEQ ID NO: 102
```
Amino acids 51-66 of HPV E6
CIVYRDGNPYAVRDK
```

SEQ ID NO: 103
```
Amino acids 74-89 of HPV E6
SEYRHYCYSLYGTTL
```

SEQ ID NO: 104
```
Amino acids 75-90 of HPV E6
EYRHYCYSLYGTTLE
```

SEQ ID NO: 105
```
Amino acids 76-91 of HPV E6
YRHYCYSLYGTTLEQ
```

SEQ ID NO: 106
```
Amino acids 77-92 of HPV E6
RHYCYSLYGTTLEQQ
```

SEQ ID NO: 107
```
Amino acids 78-93 of HPV E6
HYCYSLYGTTLEQQY
```

SEQ ID NO: 108
```
Amino acids 96-111 of HPV E6
LCDLLIRCINRQKPL
```

SEQ ID NO: 109
```
Amino acids 97-112 of HPV E6
CDLLIRCINRQKPLC
```

-continued

SEQ ID NO: 110

Amino acids 98-113 of HPV E6
DLLIRCINRQKPLCP

SEQ ID NO: 111

Amino acids 99-114 of HPV E6
LLIRCINRQKPLCPE

SEQ ID NO: 112

Amino acids 121-136 of HPV E6
KKQRFHNIRGRWTGR

SEQ ID NO: 113

Amino acids 3-12 of HPV E7
GDTPTLHEY

SEQ ID NO: 114

Amino acids 7-16 of HPV E7
TLHEYMLDL

SEQ ID NO: 115

Amino acids 9-18 of HPV E6
HEYMLDLQP

SEQ ID NO: 116

Amino acids 15-24 of HPV E6
LQPETTDLY

SEQ ID NO: 117

Amino acids 19-28 of HPV E6
TTDLYGYGQ

SEQ ID NO: 118

Amino acids 20-29 of HPV E6
TDLYGYGQL

SEQ ID NO: 119

Amino acids 44-53 of HPV E6
QAEPDRAHY

SEQ ID NO: 120

Amino acids 49-58 of HPV E6
RAHYNIVTF

SEQ ID NO: 121

Amino acids 71-80 of HPV E6
STHVDIRTL

SEQ ID NO: 122

Amino acids 79-88 of HPV E6
LEDLLMGTL

SEQ ID NO: 123

Amino acids '03-18 of HPV E6
GDTPTLHEYMLDLQP

SEQ ID NO: 124

Amino acids 4-19 of HPV E6
DTPTLHEYMLDLQPE

SEQ ID NO: 125

Amino acids 5-20 of HPV E6
TPTLHEYMLDLQPET

SEQ ID NO: 126

Amino acids 6-21 of HPV E6
PTLHEYMLDLQPETT

SEQ ID NO: 127

Amino acids 7-22 of HPV E6
TLHEYMLDLQPETTD

SEQ ID NO: 128

Amino acids 8-23 of HPV E6
LHEYMLDLQPETTDL

SEQ ID NO: 129

Amino acids 70-85 of HPV E6
QSTHVDIRTLEDLLM

SEQ ID NO: 130

Amino acids 71-86 of HPV E6
STHVDIRTLEDLLMG

SEQ ID NO: 131

Amino acids 72-87 of HPV E6
THVDIRTLEDLLMGT

SEQ ID NO: 132

Amino acids 73-88 of HPV E6
HVDIRTLEDLLMGTL

SEQ ID NO: 133

Amino acids 74-89 of HPV E6
VDIRTLEDLLMGTLG

SEQ ID NO: 134

T1D320
HNEGDDQQGSRYSLIPQIQKVCEVVDG

SEQ ID NO: 135

T1D814
SEQERMKSSLLKEHMLRKQAELESAQC

SEQ ID NO: 136

T1D182
ELRENLLTYLPDSVTQLRRLEELDLGN

SEQ ID NO: 137

T1D689
QEVFSSYKFNHLVRRLVLQREKHFHYL

SEQ ID NO: 138

T1D339
IEKNADLCYLSTVHWSLILDAVSNNYI

SEQ ID NO: 139

T1D428
LATAGEPYHDIRFKLMAVVPDRRIKYE

SEQ ID NO: 140

T1D572
MLRLPTVFRQIRPVSRVLAPHLTR

SEQ ID NO: 141

T1D359
IQIMENPFVQSMLWNPDLMRQLIMANP

SEQ ID NO: 142

T1D488
LLRFLFLGLSALALPSRAQLQLHLPAN

SEQ ID NO: 143

T1D554
MGKNPVRPPRAFPPVPSIDDIPLSR

SEQ ID NO: 144

T1D272
GHVDFTIEVERALTVLDGAVLVLCAVG

SEQ ID NO: 145

T1D210
EYKLMYGMLFSIRLFVSKMSPLDMKDG

SEQ ID NO: 146

T1D849
SQGAGVESLDFRLYLRYEFLMLGIQPV

SEQ ID NO: 147

T1D4
AAKTLVLCVSDIILLSANISETSSNKT

SEQ ID NO: 148

T1D77
CKDLQLYLSNLANHIDRETGIGDVPLV

SEQ ID NO: 149

T1D717
QSKHTEARELMYSAALLFFSHGQQNSA

-continued

SEQ ID NO: 150
T1D586
MTLAESYAQYVYNLCNSLSIKVEES

SEQ ID NO: 151
T11D323
KKVSKTRHTRETVFRRAKRRWAPIPCS

SEQ ID NO: 152
T11D506
NLKHENILQFLTAQERKTELGKQYWLI

SEQ ID NO: 153
T11D12
VQVFGLYFGEEFHETFDCPIK

SEQ ID NO: 154
T11D315
GQAAASQAGGARGYARGAQLWPPGSDP

SEQ ID NO: 155
T11D302
SIMQTWFTLFTPTDATSIVATTVMSNS

SEQ ID NO: 156
T11D700
QENVRFVLVRSEALLPNAGPRSAEARV

SEQ ID NO: 157
T11D535
DAFPNLKDFISRFQVMPPSSFLFDAPC

SEQ ID NO: 158
T11D358
PSSLQVKPETPASEAVAVAAAAAPTTT

SEQ ID NO: 159
T11D670
RFFHLADLFLSSSQLPAYLVAAFAKRL

SEQ ID NO: 160
T11D294
LVFLWLHSLRRLFGCLYVSVFSNVMIH

SEQ ID NO: 161
T11D336
WENAIAALFRRHIAVSWLIRATLSESE

SEQ ID NO: 162
T11D499
RYIFVKSAGSRIEEGVLQFLVLLVAGR

SEQ ID NO: 163
T11D425
QEIEWLPFRCIKCLKLSFSTAELLCMH

SEQ ID NO: 164
T11D491
LVARCPPCLRLLRQARDFQAARYDRHD

SEQ ID NO: 165
T11D314
ALGTPEDLDSYIDLSLESLNQMILELD

SEQ ID NO: 166
T11D430
SQDMLSIMEKLEFLDFSYDLNLCGLTE

SEQ ID NO: 167
T11D582
RREQYIPNEEFLHFDLLEDSKYRKIYS

SEQ ID NO: 168
T1D223
GPSYRSNSVSSLDLEGE

SEQ ID NO: 169
T1D164
LKEEKENLQGLVTHQTYIIQELEKQLN

-continued

SEQ ID NO: 170

T1D56
QRQKTAGKIFRAEVSTGQDAPRQAQAR

SEQ ID NO: 171

T1D36
ILRPSTVNELESGEISYDEVGERIKDF

SEQ ID NO: 172

T1D129
DTCINEDVESLRKMVQDLLAKLQEAKR

SEQ ID NO: 173

T1D274
LREEGTKYKSFVQRARLVFREEGYLAF

SEQ ID NO: 174

T1D62
HEGARPMRAIFLANGNVFTTGFSRMSE

SEQ ID NO: 175

T1D5
IPDAAFIQAARRKCELARAQDDYISLD

SEQ ID NO: 176

T1D144
MEIAKMRAGRRLWVHLIEKMFQPKNSK

SEQ ID NO: 177

T1D441
MELVSFRDVAIEFSPEEW

SEQ ID NO: 178

T1D368
TCVHEIPFHFDLMELLPQCQQLQMFFL

SEQ ID NO: 179

T1D234
VRRVFITDDFHDMIPKYLNFVKGVVDS

SEQ ID NO: 180

T1D162
NFHAHREKAPSLFCSRILNKAVYLFYG

SEQ ID NO: 181

T1D39
DANKEGMFLFRAAHKLRQFLKMNSTGD

SEQ ID NO: 182

T1D272
LLSLGWSVDVGRHSGWTGHVSTSWSIN

SEQ ID NO: 183

T1D328
NTIFSLRKDLRQGKARRLRCMEEKEMF

SEQ ID NO: 184

T1D188
NHFNDFEGDPAMTQFLEEFEKNLEDTK

SEQ ID NO: 185

C-pepM1
VILPQAPSGPSYATYLQPAQAQMLTPP

SEQ ID NO: 186

C-pepM6
DTLSAMSNPRAMQVLLQIQQGLQTLAT

SEQ ID NO: 187

C-pepM8
EVIQTSKYYMRDVIAIESAWLLELAPH

SEQ ID NO: 188

C-pepM29
GSLFGSSRVQYVVNPAVKIVFLNIDPS

SEQ ID NO: 189

C-pepM31
AEYGDYQPEVHGVPYFRLEHYLPARVM

-continued

```
                                            SEQ ID NO: 190
C-pepM43
KSWIHCWKYLSVQSQLFRGSSLLFRRV SEQ ID NO: 191
C-pepM89
TLAFLVLSTPAMFNRALKPFLKSCHFQ SEQ ID NO: 192
C-pep149
FVSPMAHYVPGIMAIESVVARFQFIVP SEQ ID NO: 193
C-pepM171
LWVYLRPVPRPATIYLQILRLKPLTGE SEQ ID NO: 194
C-pepM173
KIYEFDYHLYGQNITMIMTSVSGHLLA SEQ ID NO: 195
VB 4101 Amino acids 81-88
RGPESRLL SEQ ID NO: 196
VB4102 Amino Acids 81-126
RGPESRLLEFYLAMPFATPMEAELARRSLAQDAPPLPVPGVLLKEF SEQ ID NO: 197
NY-ESO_Pep-1
MQAEGRGTGGSTGDA SEQ ID NO: 198
NY-ESO_Pep-2
TGGSTGDADGPGGPG SEQ ID NO: 199
NY-ESO_Pep-3
ADGPGGPGIPDGPGG SEQ ID NO: 200
NY-ESO_Pep-4
GIPDGPGGNAGGPGE SEQ ID NO: 201
NY-ESO_Pep-5
GNAGGPGEAGATGGR SEQ ID NO: 202
NY-ESO_Pep-6
EAGATGGRGPRGAGA SEQ ID NO: 203
NY-ESO_Pep-7
RGPRGAGAARASGPG SEQ ID NO: 204
NY-ESO_Pep-8
AARASGPGGGAPRGP SEQ ID NO: 205
NY-ESO_Pep-9
GGGAPRGPHGGAASG SEQ ID NO: 206
NY-ESO_Pep-10
PHGGAASGLNGCCRC SEQ ID NO: 207
NY-ESO_Pep-11
GLNGCCRCGARGPES SEQ ID NO: 208
NY-ESO_Pep-12
CGARGPESRLLEFYL SEQ ID NO: 209
NY-ESO_Pep-13
RGPESRLLEFYLAMP
```

-continued

SEQ ID NO: 210

NY-ESO_Pep-14
SRLLEFYLAMPFATP

SEQ ID NO: 211

NY-ESO_Pep-15
LAMPFATPMEAELAR

SEQ ID NO: 212

NY-ESO_Pep-16
PMEAELARRSLAQDA

SEQ ID NO: 213

NY-ESO_Pep-17
RRSLAQDAPPLPVPG

SEQ ID NO: 214

NY-ESO_Pep-18
DAPPLPVPGVLLKEF

SEQ ID NO: 215

NY-ESO_Pep-19
APPLPVPGVLLKEFT

SEQ ID NO: 216

NY-ESO_Pep-20
GVLLKEFTVSGNILT

SEQ ID NO: 217

NY-ESO_Pep-21
TVSGNILTIRLTAAD

SEQ ID NO: 218

NY-ESO_Pep-22
TIRLTAADHRQLQLS

SEQ ID NO: 219

NY-ESO_Pep-23
DHRQLQLSISSCLQQ

SEQ ID NO: 220

NY-ESO_Pep-24
SISSCLQQLSLLMWI

SEQ ID NO: 221

NY-ESO_Pep-25
QLSLLMWITQCFLPV

SEQ ID NO: 222

NY-ESO_Pep-26
ITQCFLPVFLAQPPS

SEQ ID NO: 223

NY-ESO_Pep-27
VFLAQPPSGQRR

SEQ ID NO: 224

NY-ESO_Pep-28
RGPESRLL

SEQ ID NO: 225

B-pepM2
REGVELCPGNKYEMRRHGTTHSLVIHD

SEQ ID NO: 226

B-pepM7
SSPDEVALVEGVQSLGFTYLRLKDNYM

SEQ ID NO: 227

B-pepM36
KNILAVSFAPLVQLSKNDNGTPDSVGL

SEQ ID NO: 228

B-pepM78
PAADRWEPRAPMRAPRVLHAMLGAAGR

SEQ ID NO: 229

B-pepM79
VLSADLVHYLRLSLEYLRAWHSEDVSL

-continued

```
                                                       SEQ ID NO: 230
B-pepM82
LEAVLRYLETHPRLPKPDPVKSSSSVL SEQ ID NO: 231
B-pepM83
LKDFFFSRGRFSSALKRTLILSSGFRL SEQ ID NO: 232
B-pepM84
AGKDHKIKQWDADTFEHIQTLEGHHQE SEQ ID NO: 233
B-pepM85
PATIEMAIETLQKFDGLSTHRSSLLNS SEQ ID NO: 234
B-pepM86
YLPGGGAGHLDQNVFLRVRALCYVISG SEQ ID NO: 235
VB4119 Amino acids 180-188
SVYDFFVWL SEQ ID NO: 236
B-pepM108
YISDHMKVHSPSPCL SEQ ID NO: 237
B-pepM115-M122
EGWQTCWGRSRKHWGSTWNGSARLSPGSTLWVMRICLRSLGIARTWLSCRSTSRKCSPAFP
ASS SEQ ID NO: 238
B-pepM141-M142
LFRLLPSGPKVNDGHRSRRWHSLDLYPHLCSHLDLPKQSQEVIRL SEQ ID NO: 239
B-pepM108
YISDHMKVHSPSPCL SEQ ID NO: 240
B-pepM115
EGWQTCWGRSRKHWG SEQ ID NO: 241
B-pepM116
GRSRKHWGSTWNGSA SEQ ID NO: 242
B-pepM117
GSTWNGSARLSPGST SEQ ID NO: 243
B-pepM118
ARLSPGSTLWVMRIC SEQ ID NO: 244
B-pepM119
TLWVMRICLRSLGIA SEQ ID NO: 245
B-pepM120
CLRSLGIARTWLSCR SEQ ID NO: 246
B-pepM121
ARTWLSCRSTSRKCS SEQ ID NO: 247
B-pepM122
RSTSRKCSPAFPASS SEQ ID NO: 248
B-pepM141
LFRLLPSGPKVNDGHRSRRWHSLDLYP SEQ ID NO: 249
B-pepM142
SRRWHSLDLYPHLCSHLDLPKQSQEVIRL
```

Embodiments A

1. An individualized therapeutic anticancer vaccine comprising an immunologically effective amount of:
   (i) a polynucleotide comprising a nucleotide sequence encoding a targeting unit, a dimerization unit and an antigenic unit, wherein said antigenic unit comprises at least one patient-present shared antigen sequence or one or more parts thereof, and optionally one or more patient-specific antigen sequences or one or more parts thereof; or
   (ii) a polypeptide encoded by the polynucleotide as defined in (i), or
   (iii) a dimeric protein consisting of two polypeptides encoded by the polynucleotide as defined in (i); and
   a pharmaceutically acceptable carrier.
2. The vaccine according to embodiment A1, wherein said at least one patient-present shared antigen sequence is a shared antigen selected from the group consisting of overexpressed cellular proteins, aberrantly expressed cellular proteins, cancer testis antigens, viral antigens, differentiation antigens, mutated oncogenes and mutated tumor suppressor genes, oncofetal antigens, shared fusion antigens, shared intron retention antigens, dark matter antigens and shared antigens caused by spliceosome mutations or frameshift mutations
3. The vaccine according to any of embodiments A1 or A2, wherein said at least one patient-present shared antigen sequence is a shared antigen that is a human cellular protein, preferably an overexpressed or aberrantly expressed human cellular protein or a differentiation antigen.
4. The vaccine according to any of embodiments A1 to A3, wherein said at least one patient-present shared antigen sequence is known to be immunogenic or wherein one or more parts thereof are known to be immunogenic or are predicted to bind to the patient's HLA class I or HLA class II alleles, preferably to the patient's HLA class I alleles.
5. The vaccine according to any of embodiments A1 to A4, wherein said at least one patient-present shared antigen sequence has a length suitable for presentation by the patient's HLA alleles, preferably a length of from 7 to 30 amino acids.
6. The vaccine according to any of embodiments A1 to A5, comprising more than one patient-present shared antigen sequence or one or more parts thereof.
7. The vaccine according to embodiment A6, comprising sequences of several patient-present shared antigens or one or more parts thereof, preferably several parts of sequences of several patient-present shared antigens, more preferably several epitopes of several patient-present shared antigen, which epitopes are known to be immunogenic or are predicted to bind to the particular patient's HLA class I and HLA class II alleles.
8. The vaccine according to any of embodiments A1 to A7, wherein the antigenic unit comprises one or more patient-present shared antigen sequences in full length, preferably 1 to 10 patient-present shared antigen sequences in full length.
9. The vaccine according to any of embodiments A1 to A7, wherein the antigenic unit comprises 1 to 30 parts of patient-present shared antigen sequences in the form of long peptide sequences, preferably peptide sequences of from about 28 to 100 amino acids.

10. The vaccine according to embodiment A9, wherein the long peptide sequences include multiple epitopes that are predicted to bind to the patient's HLA class I or HLA class II alleles.
11. The vaccine according to any of embodiments A1 to A7, wherein the antigenic unit comprises 1 to 50 parts of patient-present shared antigen sequences in the form of short peptide sequences/epitopes.
12. The vaccine according to embodiment A11, wherein the short peptide sequences/epitopes that are predicted to bind to the patient's HLA class I or HLA class II alleles.
13. The vaccine according to any of embodiments A11 to A12, wherein the short peptide sequences/epitopes have a length of from 7 to 30 amino acids, e.g. 7 to 10 or 13 to 30.
14. The vaccine according to any of the preceding embodiments A1 to A13, comprising one or more patient-specific antigen sequences or one or more parts thereof.
15. The vaccine according to embodiment A14, comprising several patient-specific antigen sequences or one or more parts thereof.
16. The vaccine according to embodiment A15, comprising one or more parts of said patient-specific antigen sequences, preferably one or more patient-specific epitope.
17. The vaccine according to embodiment A16, comprising one or more patient-specific epitopes having a length of from 7 to 30 amino acids, e.g. 7 to 10 or 13 to 30.
18. The vaccine according to any of embodiments A14 to A17, wherein antigenic unit comprises at least 10 patient-specific epitopes, preferably at least 15 patient-specific epitopes, such as at least 20 patient-specific epitopes.
19. The vaccine according to any of the preceding embodiments A1 to A18, wherein the antigenic unit comprises from 21 to 2000 amino acids, preferably from about 30 amino acids to about a 1500 amino acids, more preferably from about 50 to about 1000 amino acids, such as from about 100 to about 500 amino acids or from about 100 to about 400 amino acids or from about 100 to about 300 amino acids.
20. The vaccine according to any of the preceding embodiments A1 to A19, wherein the antigenic unit comprises one or more linkers, preferably one or more non-immunogenic and/or flexible linkers.
21. The vaccine according to embodiment A20, wherein the length of the one or more linkers is from 4 to 20 amino acids.
22. The vaccine according to any of embodiments A20 to A21, wherein the one or more linkers separate the antigen sequences from each other.
23. The vaccine according to any of the preceding embodiments A1 to A22, wherein the dimerization unit comprises a hinge region and optionally another domain that facilitates dimerization, optionally connected through a linker.
24. The vaccine according to embodiment A23, wherein the hinge region is Ig-derived.
25. The vaccine according to any one of embodiments A23 and A24, wherein the hinge region has the ability to form one or more covalent bonds, preferably a covalent bond in the form of a disulfide bridge.
26. The vaccine according to any one of embodiments A23 to A25, wherein the another domain that facilitates dimerization is an immunoglobulin domain, preferably a carboxyterminal C domain, or a sequence that is substantially identical to said C domain or a variant thereof.

27. The vaccine according to embodiment A26, wherein the carboxyterminal C domain is derived from IgG.

28. The vaccine according to any one of embodiments A26 and A37, wherein the immunoglobulin domain of the dimerization unit has the ability to homodimerize, preferably via noncovalent interactions and more preferably via noncovalent interactions that are hydrophobic interactions.

29. The vaccine according to any one of embodiments A23 to A28, wherein said dimerization unit does not comprise a CH2 domain.

30. The vaccine according to any one of embodiments A23 to A29, wherein the dimerization unit consist of hinge exons hi and h4 connected through said third linker to a $C_H3$ domain of human IgG3.

31. The vaccine according to any one of embodiments A23 to A30, wherein the dimerization unit comprises an amino acid sequence having at least 80% sequence identity to the amino acid sequence 94-237 of SEQ ID NO.: 3.

32. The vaccine according to any of the preceding embodiments A1 to A31, wherein the antigenic unit and the dimerization unit are connected through a linker, preferably a linker that comprises a restriction site.

33. The vaccine according to any of the preceding embodiments A1 to A32, wherein the targeting unit has affinity for a chemokine receptor selected from CCR1, CCR3 and CCR5.

34. The vaccine according to any of the preceding embodiments A1 to A33, wherein said targeting unit comprises antibody binding regions with specificity for CD14, CD40, or Toll-like receptor or ligands, such as soluble CD40 ligand, or chemokines, such as RANTES or MIP-1a or bacterial antigens, such as flagellin.

35. The vaccine according to any of embodiments A1 to A33, wherein said targeting unit has an affinity for MHC class II proteins, preferably MHC class II proteins, selected from the group consisting of anti-HLA-DP, anti-HLA-DR and anti-pan HLA class II 36. The vaccine according to any of embodiments A1 to A33, wherein said targeting unit has an amino acid sequence having at least 80% sequence identity to the amino acid sequence 24-93 of SEQ ID NO.: 1.

37. The vaccine according to any of the preceding embodiments A1 to A36, wherein said polynucleotide further encodes a signal peptide.

38. The vaccine according to any of the preceding embodiments A1 to A37, wherein said targeting unit, dimerization unit and antigenic unit in said peptide are in the N-terminal to C-terminal order of targeting unit, dimerization unit and antigenic unit.

39. The vaccine according to any of the preceding embodiments A1 to A38, wherein said polynucleotide sequence is human codon optimized.

40. The vaccine according to any of the preceding embodiments A1 to A39, wherein said polynucleotide sequence is a DNA nucleotide sequence or RNA nucleotide sequence.

41. A polynucleotide as defined in any of the embodiments A1 to A40.

42. A vector comprising the polynucleotide according to embodiment A41.

43. A host cell comprising the polynucleotide as defined in any of the embodiments A1 to A40 or comprising the vector according to embodiment A42.

44. The polynucleotide according to embodiment A41 formulated for administration to a patient to induce production of a dimeric protein in said patient.

45. A polypeptide encoded by the polynucleotide sequence as defined in any of the embodiments A1 to A40.

46. A dimeric protein consisting of two polypeptides according to embodiment A45.

47. The dimeric protein according to embodiment A46, being a homodimeric protein.

48. The polynucleotide according to embodiment A41 or the polypeptide according to embodiment A45 or the dimeric protein according to any of embodiments A46 to A47 for use as a medicament.

49. A method for preparing an individualized therapeutic anticancer vaccine comprising an immunologically effective amount of
   (i) a dimeric protein consisting of two polypeptides encoded by a polynucleotide comprising a nucleotide sequence encoding a targeting unit, a dimerization unit and an antigenic unit, wherein said antigenic unit comprises at least one patient-present shared antigen sequence or one or more parts thereof, and optionally one or more patient-specific antigen sequences or one or more parts thereof; or
   (ii) a polypeptide encoded by a polynucleotide comprising a nucleotide sequence encoding a targeting unit, a dimerization unit and an antigenic unit, wherein said antigenic unit comprises at least one patient-present shared antigen sequence or one or more parts thereof, and optionally one or more patient-specific antigen sequences or one or more parts thereof, the method comprises:
      a) transfecting cells with the polynucleotide;
      b) culturing the cells;
      c) collecting and purifying the dimeric protein or the polypeptide expressed from the cells, and
      d) mixing the dimeric protein or polypeptide obtained from step c) with a pharmaceutically acceptable carrier.

50. A method for preparing an individualized therapeutic anticancer vaccine comprising an immunologically effective amount of a polynucleotide comprising a nucleotide sequence encoding a targeting unit, a dimerization unit and an antigenic unit, wherein said antigenic unit comprises at least one patient-present shared antigen sequence or one or more parts thereof, and optionally one or more patient-specific antigen sequences or one or more parts thereof, the method comprises:
   a. preparing the polynucleotide;
   b. optionally cloning the polynucleotide into an expression vector and
   c. mixing the polynucleotide from step a) or the vector form step b) with a pharmaceutically acceptable carrier.

51. The method according to embodiments A49 or A50, including the steps of identifying patient-present shared antigens and patient-specific antigens, identifying the patient's HLA class I and HLA class II alleles, select patient-present shared antigen sequences and optionally patient-specific antigen sequences based on immunogenicity prior to preparing the polynucleotide.

52. A method of treating cancer in a patient, the method comprising administering to the said patient the vaccine according to any of embodiments A1 to A40.

53. The method according to embodiment A52, wherein the vaccine comprises a polynucleotide and is administered intradermally or intramuscularly.

54. The method according to embodiment A53 wherein the polynucleotide is a DNA.

55. The method according to embodiment A53 wherein the polynucleotide is an RNA.

56. The method according to any of claims A52 to A55, wherein administration is carried out with a jet injector.

57. The method according to any of claims A52 to A56, wherein administration is assisted by electroporation.

Embodiments B

1. An individualized therapeutic anticancer vaccine comprising an immunologically effective amount of:
   (i) a polynucleotide comprising a nucleotide sequence encoding a targeting unit, a dimerization unit and an antigenic unit, wherein said antigenic unit comprises at least one patient-present shared antigen sequence or one or more parts thereof; or
   (ii) a polypeptide encoded by the polynucleotide as defined in (i); or
   (iii) a dimeric protein consisting of two polypeptides encoded by the polynucleotide as defined in (i); and
a pharmaceutically acceptable carrier.

2. The vaccine according to embodiment B1, wherein said antigenic unit further comprises one or more patient-specific antigen sequences or one or more parts thereof.

3. The vaccine according to any of embodiments B1 or B2, wherein said at least one patient-present shared antigen sequence is a sequence of a shared antigen selected from the group consisting of overexpressed cellular proteins, aberrantly expressed cellular proteins, cancer testis antigens, viral antigens, differentiation antigens, mutated oncogenes, mutated tumor suppressor genes, oncofetal antigens, shared fusion antigens, shared intron retention antigens, dark matter antigens, shared antigens caused by spliceosome mutations and shared antigens caused by frameshift mutations.

4. The vaccine according to any of embodiments B1 to B3, wherein said at least one patient-present shared antigen sequence is a sequence of a shared antigen that is a human cellular protein.

5. The vaccine according to embodiment B4, wherein said human cellular protein is an overexpressed or aberrantly expressed human cellular protein or a differentiation antigen.

6. The vaccine according to any of embodiments B1 to B5, wherein said at least one patient-present shared antigen sequence or one or more parts thereof are known to be immunogenic or are predicted to bind to the patient's HLA class I and/or HLA class II alleles.

7. The vaccine according to embodiment B6, wherein said at least one patient-present shared antigen sequence or one or more parts thereof are predicted to bind to the patient's HLA class I alleles.

8. The vaccine according to any of embodiments B1 to B7, wherein said at least one patient-present shared antigen sequence or the one or more parts thereof have a length suitable for presentation by the patient's HLA alleles.

9. The vaccine according to embodiment B8, wherein said at least one patient-present shared antigen sequence or the one or more parts thereof have a length of from 7 to 30 amino acids.

10. The vaccine according to any of embodiments B1 to B9, wherein the antigenic unit comprises more than one patient-present shared antigen sequence or one or more parts thereof.

11. The vaccine according to embodiment B10, wherein the antigenic unit comprises sequences of several patient-present shared antigens or one or more parts thereof.

12. The vaccine according to embodiment B11, wherein the antigenic unit comprises several parts of sequences of several patient-present shared antigens.

13. The vaccine according to embodiment B12, wherein the antigenic unit comprises several epitopes of several patient-present shared antigens, which epitopes are known to be immunogenic or are predicted to bind to the patient's HLA class I and/or HLA class II alleles.

14. The vaccine according to any of embodiments B1 to B13, wherein the antigenic unit comprises one or more patient-present shared antigen sequences in full length.

15. The vaccine according to embodiment B14, wherein the antigenic unit comprises 1 to 10 patient-present shared antigen sequences in full length.

16. The vaccine according to any of embodiments B1 to B15, wherein the antigenic unit comprises 1 to 30 parts of at least one patient-present shared antigen sequence.

17. The vaccine according to embodiment B16, wherein said 1 to 30 parts have a length of from 28 to 100 amino acids.

18. The vaccine according to embodiment B17, wherein the parts include multiple epitopes that are predicted to bind to the patient's HLA class I and/or HLA class II alleles.

19. The vaccine according to any of embodiments B1 to B18, wherein the antigenic unit comprises 1 to 50 patient-present shared antigen sequences in the form of epitopes.

20. The vaccine according to embodiment B19, wherein the epitopes are predicted to bind to the patient's HLA class I and/or HLA class II alleles.

21. The vaccine according to any of embodiments B19 to B20, wherein the epitopes have a length of from 7 to 30 amino acids.

22. The vaccine according to any of embodiments B2 to B21, wherein the antigenic unit comprises several patient-specific antigen sequences or one or more parts thereof.

23. The vaccine according to embodiment B22, wherein the antigenic unit comprises one or more parts of said several patient-specific antigen sequences.

24. The vaccine according to any of embodiments B2 to B23, wherein the antigenic unit comprises one or more patient-specific epitopes.

25. The vaccine according to embodiment B24, wherein the one or more patient-specific epitopes have a length of from 7 to 30 amino acids.

26. The vaccine according to any of embodiments B24 to B25, wherein antigenic unit comprises at least 5 patient-specific epitopes.

27. The vaccine according to any of embodiments B24 to B25, wherein the antigenic unit comprises at least 10 patient-specific epitopes.

28. The vaccine according to any of embodiments B24 to B25, wherein the antigenic unit comprises at least 15 patient-specific epitopes.

29. The vaccine according to any of the preceding embodiments B1 to B28, wherein the antigenic unit comprises from 7 to 2000 amino acids.

30. The vaccine according to embodiment B29, wherein the antigenic unit comprises from 30 to 1500 amino acids.

31. The vaccine according to embodiment B29, wherein the antigenic unit comprises from 50 to 1000 amino acids.

32. The vaccine according to any of the preceding embodiments B1 to B31, wherein the antigenic unit comprises one or more linkers.

33. The vaccine according to embodiment B32, wherein the one or more linkers are non-immunogenic and/or flexible linkers.

34. The vaccine according to any of embodiments B32 or B33, wherein the length of the one or more linkers is from 4 to 20 amino acids.

35. The vaccine according to any of embodiments B32 to B34, wherein the one or more linkers separate the antigen sequences from each other.

36. The vaccine according to any of the preceding embodiments B1 to B35, wherein the dimerization unit comprises a hinge region.

37. The vaccine according to embodiment B36, wherein the hinge region has the ability to form one or more covalent bonds, preferably in the form of a disulfide bridge.

38. The vaccine according to any of embodiments B36 or 3B7, wherein the hinge region is Ig derived.

39. The vaccine according to any of embodiments B36 to B38, wherein the dimerization unit further comprises another domain that facilitates dimerization.

40. The vaccine according to embodiment B39, wherein the other domain is an immunoglobulin domain, preferably an immunoglobulin constant domain.

41. The vaccine according to any of embodiments B39 or B40, wherein the other domain is a carboxyterminal C domain derived from IgG, preferably derived from IgG3.

42. The vaccine according to any of embodiments B36 to B41, wherein the dimerization unit further comprises a linker, preferably a linker that connects the hinge region and the other domain that facilitates dimerization.

43. The vaccine according to any of embodiments B36 to B42, wherein the dimerization unit comprises hinge exons h1 and h4 connected through a linker to a CH3 domain of human IgG3.

44. The vaccine according to any of embodiments B36 to B43, wherein the dimerization unit comprises an amino acid sequence having at least 80% sequence identity to the amino acid sequence 94-237 of SEQ ID NO: 3.

45. The vaccine according to any of embodiments B36 to B44, wherein the dimerization unit consists of the amino acid sequence 94-237 of SEQ ID NO: 3.

46. The vaccine according to any of the preceding embodiments B1 to B45, wherein the antigenic unit and the dimerization unit are connected through a linker, preferably a linker that comprises a restriction site.

47. The vaccine according to any of the preceding embodiments B1 to B46, wherein the targeting unit targets antigen presenting cells.

48. The vaccine according to embodiment B47, wherein the targeting unit is or comprises a moiety that interacts with surface molecules on the antigen presenting cells.

49. The vaccine according to embodiment B48, wherein the surface molecule is selected from the group consisting of HLA, CD14, CD40, chemokine receptors and Toll-like receptors.

50. The vaccine according to any of embodiments B47 to B49, wherein the targeting unit comprises or consists of soluble CD40 ligand, RANTES, MIP-1a, XCL1, XCL2, flagellin, anti-HLA-DP, anti-HLA-DR, anti-pan HLA class II or an antibody variable domain with specificity for anti-CD40, anti-TLR-2, anti-TLR-4 or anti-TLR-5.

51. The vaccine according to embodiment B50, wherein the targeting unit comprises or consists of MIP-1a.

52. The vaccine according to embodiment B51, wherein the targeting unit comprises an amino acid sequence having at least 80% sequence identity to the amino acid sequence 24-93 of SEQ ID NO: 1.

53. The vaccine according to embodiment B52, wherein the targeting unit consists of an amino acid sequence having at least 80% sequence identity to the amino acid sequence 24-93 of SEQ ID NO: 1.

54. The vaccine according to embodiment B53, wherein the targeting unit consist of the amino acid sequence 24-93 of SEQ ID NO: 1.

55. The vaccine according to any of the preceding embodiments B1 to B54, wherein said vaccine comprises a polynucleotide, preferably an RNA or DNA.

56. The vaccine according to embodiment B55, wherein said polynucleotide is human codon optimized.

57. The vaccine according to any of embodiments B55 or B56, wherein the polynucleotide further comprises a nucleotide sequence encoding a signal peptide.

58. The vaccine according to embodiment B57, wherein the signal peptide is selected from the list consisting of Ig VH signal peptide, human TPA signal peptide and human MIP1-a signal peptide.

59. The vaccine according to any of embodiments B57 to B58, wherein the signal peptide comprises an amino acid sequence having at least 85% sequence identity to the amino acid sequence 1-23 of SEQ ID NO: 1.

60. The vaccine according to embodiment B59, wherein the signal peptide consists of an amino acid sequence having at least 85% sequence identity to the amino acid sequence 1-23 of SEQ ID NO: 1.

61. The vaccine according to embodiment B60, wherein the signal peptide consists of the amino acid sequence 1-23 of SEQ ID NO: 1.

62. The vaccine according to any of the preceding embodiments B1 to B61, wherein said targeting unit, dimerization unit and antigenic unit in said polypeptide are in the N-terminal to C-terminal order of targeting unit, dimerization unit and antigenic unit or wherein said targeting unit, dimerization unit and antigenic unit in said polynucleotide are in the 5' to 3' order of targeting unit, dimerization unit and antigenic unit.

63. The vaccine according to any of the preceding embodiments B1 to B62, wherein the pharmaceutically acceptable carrier is selected from the group consisting of saline, buffered saline, PBS, dextrose, water, glycerol, ethanol, sterile isotonic aqueous buffers, and combinations thereof.

64. A method for preparing the individualized therapeutic anticancer vaccine of embodiment B1, said method comprises the steps of:

a) identifying at least one patient-present shared antigen in the tumor tissue or body fluid of a patient b) determining the patient's HLA class I and/or class II alleles c) predicting the immunogenicity of the identified at least one antigen or one or more parts thereof by their predicted binding to the patient's HLA class I and/or II alleles d) selecting at least one antigen or one or more parts thereof based on their immunogenicity predicted in step c);

e) preparing a polynucleotide sequence comprising an antigenic unit comprising a nucleotide sequence encoding the at least one antigen or one or more parts thereof selected in step d);

f) cloning the polynucleotide sequence into an expression vector comprising nucleotide sequences encoding a targeting unit and a dimerization unit; and g) mixing the expression vector obtained in step f with a pharmaceutically acceptable carrier.

65. The method according to embodiment B64 for preparing the individualized anticancer vaccine of embodiment B2, wherein said method further comprises:

in step a) identifying one or more patient-specific antigens in the tumor tissue of the patient in step c) predicting the immunogenicity of the identified one or more patient-specific antigens or one or more parts thereof by their predicted binding to the patient's HLA class I and/or II alleles in step d) selecting one or more patient-specific antigens or one or more parts thereof based on their immunogenicity predicted in step c);

and wherein the polynucleotide sequence of step e) further comprises nucleotide sequences encoding the one or more patient-specific antigens or one or more parts thereof selected in step d).

66. A polynucleotide as defined in any of the embodiments B1 to B62.

67. A vector comprising the polynucleotide according to embodiment B66.

68. A host cell comprising the polynucleotide as defined in any of the embodiments B1 to B62 or comprising the vector according to embodiment B67.

69. The polynucleotide according to embodiment B66 formulated for administration to a patient to induce production of a dimeric protein in said patient.

70. A polypeptide encoded by the polynucleotide sequence as defined in any of the embodiments B1 to B62.

71. A dimeric protein consisting of two polypeptides as defined in embodiment B70.

72. The dimeric protein according to embodiment B71, being a homodimeric protein.

73. The polynucleotide according to embodiment B66 or the polypeptide according to embodiment B70 or the dimeric protein according to any of embodiments B71 or B72 for use as a medicament.

74. A method for preparing an individualized therapeutic anticancer vaccine comprising an immunologically effective amount of a dimeric protein as defined in any of embodiments B1 to B54 or a polypeptide as defined in any of embodiment B1 to B54, the method comprises:

a) transfecting cells with the polynucleotide as defined in any of embodiments B1 to B62;

b) culturing the cells;

c) collecting and purifying the dimeric protein or the polypeptide expressed from the cells; and d) mixing the dimeric protein or polypeptide obtained from step c) with a pharmaceutically acceptable carrier.

75. A method for preparing an individualized therapeutic anticancer vaccine comprising an immunologically effective amount of the polynucleotide as defined in any of embodiments B1 to B62, the method comprises a) preparing the polynucleotide;

b) optionally cloning the polynucleotide into an expression vector and c) mixing the polynucleotide from step a) or the vector form step b) with a pharmaceutically acceptable carrier.

76. A method of treating a patient having cancer, the method comprising administering to the patient the vaccine according to any of embodiments B1 to B63, which has been prepared specifically for the patient.

77. The method according to embodiment B76, wherein the vaccine comprises a polynucleotide and is administered intradermally or intramuscularly.

78. The method according to embodiment B77 wherein the polynucleotide is a DNA.

79. The method according to embodiment B78 wherein the polynucleotide is an RNA.

80. The method according to any of embodiments B76 to B79, wherein administration is carried out with a jet injector.

81. The method according to any of embodiments B76 to B80, wherein administration is assisted by electroporation.

82. The vaccine according to any of embodiments B1 to B63 for use in a method of treating cancer in a patient, wherein the vaccine has been specifically prepared for the patient.

83. Use of the polynucleotide according to embodiment B66 or the polypeptide according to embodiment 7B0 or the dimeric protein according to any of embodiments B71 or B72 for the manufacture of a medicament for the treatment of cancer in a patient, wherein the polynucleotide, polypeptide or dimeric protein has been specifically prepared for the patient.

84. A method for preparing the polynucleotide of embodiment B66, said method comprises the steps of:

a) identifying at least one patient-present shared antigen in the tumor tissue or body fluid of a patient b) determining the patient's HLA class I and/or class II alleles c) predicting the immunogenicity of the identified at least one antigen or one or more parts thereof by their predicted binding to the patient's HLA class I and/or II alleles d) selecting at least one antigen or one or more parts thereof based on their immunogenicity predicted in step c);

e) preparing a polynucleotide sequence comprising an antigenic unit comprising a nucleotide sequence encoding the at least one antigen or one or more parts thereof selected in step d); and f) cloning the polynucleotide sequence into an expression vector comprising nucleotide sequences encoding a targeting unit and a dimerization unit.

85. The method according to embodiment B84, wherein said method further comprises: in step a) identifying one or more patient-specific antigens in the tumor tissue of the patient in step c) predicting the immunogenicity of the identified one or more patient-specific antigens or one or more parts thereof by their predicted binding to the patient's HLA class I and/or II alleles in step d) selecting one or more patient-specific antigens or one or more parts thereof based on their immunogenicity predicted in step c);

and wherein the polynucleotide sequence of step e) further comprises nucleotide sequences encoding the one or more patient-specific antigens or one or more parts thereof selected in step d).

The invention claimed is:

1. An individualized therapeutic anticancer vaccine for a specific patient comprising an immunologically effective amount of:

(i) a polynucleotide comprising a nucleotide sequence encoding a targeting unit, a dimerization unit and an antigenic unit, wherein said antigenic unit comprises at least one patient-present shared antigen sequence or one or more parts thereof from said patient and wherein said antigenic unit further comprises one or more patient-specific antigen sequences or one or more parts thereof from said patient; or (ii) a polypeptide encoded by the polynucleotide as defined in (i); or (iii) a dimeric protein consisting of two polypeptides encoded by the polynucleotide as defined in (i); and a pharmaceutically acceptable carrier.

2. The vaccine according to claim 1, wherein said at least one patient-present shared antigen sequence is a sequence of a shared antigen selected from the group consisting of overexpressed cellular proteins, aberrantly expressed cellular proteins, cancer testis antigens, viral antigens, differentiation antigens, mutated oncogenes, mutated tumor suppressor genes, oncofetal antigens, shared fusion antigens, shared intron retention antigens, dark matter antigens, shared antigens caused by spliceosome mutations and shared antigens caused by frameshift mutations, and/or wherein said at least one patient-present shared antigen sequence is a sequence of a shared antigen that is a human cellular protein, and/or wherein said at least one patient-present shared antigen sequence or one or more parts thereof are known to be immunogenic or are predicted to bind to the patient's HLA class I and/or HLA class II alleles.

3. The vaccine according to claim 1, wherein the antigenic unit comprises sequences of several patient-present shared antigens or one or more parts thereof.

4. The vaccine according to claim 3, wherein the antigenic unit comprises several epitopes of several patient-present shared antigens, which epitopes are known to be immunogenic or are predicted to bind to the patient's HLA class I and/or HLA class II alleles.

5. The vaccine according to claim 1, wherein the antigenic unit comprises one or more patient-present shared antigen sequences in full length, and/or wherein the antigenic unit comprises 1 to 30 parts of at least one patient-present shared antigen sequence, wherein the parts include multiple epitopes that are known to be immunogenic or are predicted to bind to the patient's HLA class I and/or HLA class II alleles.

6. The vaccine according to claim 1, wherein the antigenic unit comprises 1 to 50 patient-present shared antigen sequences in the form of epitopes, wherein the epitopes are known to be immunogenic or predicted to bind to the patient's HLA class I and/or HLA class II alleles.

7. The vaccine according to claim 6, wherein the epitopes have a length of from 7 to 30 amino acids.

8. The vaccine according to claim 1, wherein the antigenic unit comprises several patient-specific antigen sequences or one or more parts thereof, and/or wherein the antigenic unit comprises one or more patient-specific epitopes.

9. The vaccine according to claim 8, wherein antigenic unit comprises at least 5 patient-specific epitopes.

10. The vaccine according to claim 1, wherein the dimerization unit comprises a hinge region and further comprises another domain that facilitates dimerization.

11. The vaccine according to claim 1, wherein the dimerization unit comprises hinge exons h1 and h4 connected through a linker to a CH3 domain of human IgG3.

12. The vaccine according to claim 1, wherein the targeting unit comprises or consists of soluble CD40 ligand, RANTES, MIP-1α, XCL1, XCL2, flagellin, anti-HLA-DP, anti-HLA-DR, anti-pan HLA class II or an antibody variable domain with specificity for anti-CD40, anti-TLR-2, anti-TLR-4 or anti-TLR-5.

13. The vaccine according to claim 1, wherein said vaccine comprises a polynucleotide which is an RNA or DNA and further comprises a nucleotide sequence encoding a signal peptide.

14. The vaccine according to claim 13, wherein the polynucleotide is a DNA.

15. The vaccine according to claim 1, wherein the pharmaceutically acceptable carrier is selected from the group consisting of saline, buffered saline, PBS, dextrose, water, glycerol, ethanol, sterile isotonic aqueous buffers, and combinations thereof.

16. A method for preparing the individualized therapeutic anticancer vaccine of claim 1, said method comprises the steps of:

a) identifying at least one patient-present shared antigen in the tumor tissue or body fluid of said patient b) determining the patient's HLA class I and/or class II alleles c) predicting the immunogenicity of the identified at least one antigen or one or more parts thereof by their predicted binding to the patient's HLA class I and/or II alleles d) selecting at least one antigen or one or more parts thereof based on their immunogenicity predicted in step c);

e) preparing a polynucleotide sequence comprising an antigenic unit comprising a nucleotide sequence encoding the at least one antigen or one or more parts thereof selected in step d);

f) cloning the polynucleotide sequence into an expression vector comprising nucleotide sequences encoding a targeting unit and a dimerization unit; and g) mixing the expression vector obtained in step f with a pharmaceutically acceptable carrier, and wherein said method further comprises:

in step a) identifying one or more patient-specific antigens in the tumor tissue of the patient in step c) predicting the immunogenicity of the identified one or more patient-specific antigens or one or more parts thereof by their predicted binding to the patient's HLA class I and/or II alleles in step d) selecting one or more patient-specific antigens or one or more parts thereof based on their immunogenicity predicted in step c);

and wherein the polynucleotide sequence of step e) further comprises nucleotide sequences encoding the one or more patient-specific antigens or one or more parts thereof selected in step d).

17. A polynucleotide as defined in claim 1.

18. The polynucleotide according to claim 17 wherein the polynucleotide is comprised in a vector.

19. The vaccine according to claim 1, wherein the targeting unit comprises or consists of MIP-1α.

* * * * *

SEQUENCE LISTING

```
<160> NUMBER OF SEQ ID NOS: 249

<210> SEQ ID NO 1
<211> LENGTH: 93
<212> TYPE: PRT
<213> ORGANISM: Homo sapiens

<400> SEQUENCE: 1

Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
            20                  25                  30

Ala Cys Cys Phe Ser Tyr Thr Ser Arg Gln Ile Pro Gln Asn Phe Ile
        35                  40                  45

Ala Asp Tyr Phe Glu Thr Ser Ser Gln Cys Ser Lys Pro Ser Val Ile
    50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala
                85                  90

<210> SEQ ID NO 2
<211> LENGTH: 242
<212> TYPE: PRT
<213> ORGANISM: Artificial
<220> FEATURE:
<223> OTHER INFORMATION: Assembly of protein
<220> FEATURE:
<221> NAME/KEY: MISC_FEATURE
<222> LOCATION: (1)..(242)
<223> OTHER INFORMATION: vaccibody sequence

<400> SEQUENCE: 2

Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
            20                  25                  30

Ala Cys Cys Phe Ser Tyr Thr Ser Arg Gln Ile Pro Gln Asn Phe Ile
        35                  40                  45

Ala Asp Tyr Phe Glu Thr Ser Ser Gln Cys Ser Lys Pro Ser Val Ile
    50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala Glu Leu Lys
                85                  90                  95

Thr Pro Leu Gly Asp Thr Thr His Thr Glu Pro Lys Ser Cys Asp Thr
            100                 105                 110

Pro Pro Pro Cys Pro Arg Cys Pro Gly Gly Gly Ser Ser Gly Gly Gly
        115                 120                 125

Ser Gly Gly Gln Pro Arg Glu Pro Gln Val Tyr Thr Leu Pro Pro Ser
    130                 135                 140
```

```
Arg Glu Glu Met Thr Lys Asn Gln Val Ser Leu Thr Cys Leu Val Lys
145                 150                 155                 160

Gly Phe Tyr Pro Ser Asp Ile Ala Val Glu Trp Glu Ser Ser Gly Gln
                165                 170                 175

Pro Glu Asn Asn Tyr Asn Thr Thr Pro Pro Met Leu Asp Ser Asp Gly
                180                 185                 190

Ser Phe Phe Leu Tyr Ser Lys Leu Thr Val Asp Lys Ser Arg Trp Gln
            195                 200                 205

Gln Gly Asn Ile Phe Ser Cys Ser Val Met His Glu Ala Leu His Asn
        210                 215                 220

Arg Phe Thr Gln Lys Ser Leu Ser Leu Ser Pro Gly Lys Gly Leu Gly
225                 230                 235                 240

Gly Leu
```

<210> SEQ ID NO 3
<211> LENGTH: 5
<212> TYPE: PRT
<213> ORGANISM: Artificial
<220> FEATURE:
<223> OTHER INFORMATION: Linker
<220> FEATURE:
<221> NAME/KEY: MISC_FEATURE
<222> LOCATION: (1)..(5)
<223> OTHER INFORMATION: Linker

<400> SEQUENCE: 3

```
Gly Leu Ser Gly Leu
1               5
```

<210> SEQ ID NO 4
<211> LENGTH: 5
<212> TYPE: PRT
<213> ORGANISM: Artificial
<220> FEATURE:
<223> OTHER INFORMATION: Linker
<220> FEATURE:
<221> NAME/KEY: MISC_FEATURE
<222> LOCATION: (1)..(5)
<223> OTHER INFORMATION: Linker

<400> SEQUENCE: 4

```
Gly Leu Gly Gly Leu
1               5
```

<210> SEQ ID NO 5
<211> LENGTH: 12
<212> TYPE: PRT
<213> ORGANISM: Homo sapiens

<400> SEQUENCE: 5

```
Glu Leu Lys Thr Pro Leu Gly Asp Thr Thr His Thr
1               5                   10
```

<210> SEQ ID NO 6
<211> LENGTH: 15
<212> TYPE: PRT
<213> ORGANISM: Homo sapiens

<400> SEQUENCE: 6

```
Glu Pro Lys Ser Cys Asp Thr Pro Pro Pro Cys Pro Arg Cys Pro
1               5                   10                  15
```

<210> SEQ ID NO 7
<211> LENGTH: 10

```
<212> TYPE: PRT
<213> ORGANISM: Artificial
<220> FEATURE:
<223> OTHER INFORMATION: Linker

<400> SEQUENCE: 7

Gly Gly Gly Ser Ser Gly Gly Gly Ser Gly
1               5                   10

<210> SEQ ID NO 8
<211> LENGTH: 107
<212> TYPE: PRT
<213> ORGANISM: Homo sapiens

<400> SEQUENCE: 8

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Ser Gly Gln Pro Glu
        35                  40                  45

Asn Asn Tyr Asn Thr Thr Pro Pro Met Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Ile Phe Ser Cys Ser Val Met His Glu Ala Leu His Asn Arg Phe
                85                  90                  95

Thr Gln Lys Ser Leu Ser Leu Ser Pro Gly Lys
            100                 105

<210> SEQ ID NO 9
<211> LENGTH: 19
<212> TYPE: PRT
<213> ORGANISM: Homo sapiens

<400> SEQUENCE: 9

Met Asn Phe Gly Leu Arg Leu Ile Phe Leu Val Leu Thr Leu Lys Gly
1               5                   10                  15

Val Gln Cys

<210> SEQ ID NO 10
<211> LENGTH: 22
<212> TYPE: PRT
<213> ORGANISM: Homo sapiens

<400> SEQUENCE: 10

Met Asp Ala Met Lys Arg Gly Leu Cys Cys Val Leu Leu Leu Cys Gly
1               5                   10                  15

Ala Val Phe Val Ser Pro
                20

<210> SEQ ID NO 11
<211> LENGTH: 151
<212> TYPE: PRT
<213> ORGANISM: Herpes simplex virus 16

<400> SEQUENCE: 11

Met Phe Gln Asp Pro Gln Glu Arg Pro Arg Lys Leu Pro Gln Leu Cys
1               5                   10                  15

Thr Glu Leu Gln Thr Thr Ile His Asp Ile Ile Leu Glu Cys Val Tyr
            20                  25                  30
```

```
Cys Lys Gln Gln Leu Leu Arg Arg Glu Val Tyr Asp Phe Ala Arg Arg
        35                  40                  45

Asp Leu Cys Ile Val Tyr Arg Asp Gly Asn Pro Tyr Ala Val Arg Asp
    50                  55                  60

Lys Cys Leu Lys Phe Tyr Ser Lys Ile Ser Glu Tyr Arg His Tyr Cys
65                  70                  75                  80

Tyr Ser Leu Tyr Gly Thr Thr Leu Glu Gln Gln Tyr Asn Lys Pro Leu
                85                  90                  95

Cys Asp Leu Leu Ile Arg Cys Ile Asn Arg Gln Lys Pro Leu Cys Pro
            100                 105                 110

Glu Glu Lys Gln Arg His Leu Asp Lys Lys Gln Arg Phe His Asn Ile
            115                 120                 125

Arg Gly Arg Trp Thr Gly Arg Cys Met Ser Cys Cys Arg Ser Ser Arg
    130                 135                 140

Thr Arg Arg Glu Thr Gln Leu
145                 150
```

<210> SEQ ID NO 12
<211> LENGTH: 98
<212> TYPE: PRT
<213> ORGANISM: Herpes simplex virus 16

<400> SEQUENCE: 12

```
Met His Gly Asp Thr Pro Thr Leu His Glu Tyr Met Leu Asp Leu Gln
1               5                   10                  15

Pro Glu Thr Thr Asp Leu Tyr Gly Tyr Gly Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro
```

<210> SEQ ID NO 13
<211> LENGTH: 180
<212> TYPE: PRT
<213> ORGANISM: Homo sapiens

<400> SEQUENCE: 13

```
Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
            20                  25                  30

Gly Pro Gly Glu Ala Gly Ala Thr Gly Gly Arg Gly Pro Arg Gly Ala
        35                  40                  45

Gly Ala Ala Arg Ala Ser Gly Pro Gly Gly Gly Ala Pro Arg Gly Pro
    50                  55                  60

His Gly Gly Ala Ala Ser Gly Leu Asn Gly Cys Cys Arg Cys Gly Ala
65                  70                  75                  80

Arg Gly Pro Glu Ser Arg Leu Leu Glu Phe Tyr Leu Ala Met Pro Phe
                85                  90                  95
```

-continued

```
Ala Thr Pro Met Glu Ala Glu Leu Ala Arg Arg Ser Leu Ala Gln Asp
            100                 105                 110

Ala Pro Pro Leu Pro Val Pro Gly Val Leu Leu Lys Glu Phe Thr Val
            115             120                 125

Ser Gly Asn Ile Leu Thr Ile Arg Leu Thr Ala Ala Asp His Arg Gln
        130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Pro Pro Ser
                165                 170                 175

Gly Gln Arg Arg
            180

<210> SEQ ID NO 14
<211> LENGTH: 302
<212> TYPE: PRT
<213> ORGANISM: Artificial
<220> FEATURE:
<223> OTHER INFORMATION: Antigenic unit
<220> FEATURE:
<221> NAME/KEY: MISC_FEATURE
<222> LOCATION: (1)..(302)
<223> OTHER INFORMATION: Antigenic unit

<400> SEQUENCE: 14

Val Gln Ser Thr His Val Asp Ile Arg Thr Leu Glu Asp Leu Leu Met
1               5                   10                  15

Gly Thr Leu Gly Ile Val Cys Pro Ile Cys Ser Gln Lys Pro Gly Gly
            20                  25                  30

Gly Gly Ser Gly Gly Gly Gly Ser Ala Arg Gly Pro Glu Ser Arg Leu
            35                  40                  45

Leu Glu Phe Tyr Leu Ala Met Pro Phe Ala Thr Pro Met Glu Ala Glu
        50                  55                  60

Leu Ala Arg Arg Ser Leu Ala Gln Asp Ala Pro Pro Leu Pro Val Pro
65                  70                  75                  80

Gly Val Leu Leu Lys Glu Phe Thr Val Ser Gly Asn Ile Leu Thr Ile
                85                  90                  95

Arg Leu Thr Ala Ala Asp His Arg Gln Leu Gln Leu Ser Ile Ser Ser
            100                 105                 110

Cys Leu Gln Gln Leu Ser Leu Leu Met Trp Ile Thr Gln Cys Phe Leu
            115                 120                 125

Pro Val Phe Leu Ala Gln Pro Pro Ser Gly Gln Arg Arg Ser Gly Gly
        130                 135                 140

Gly Gly Ser Gly Gly Gly Gly Met Phe Gln Asp Pro Gln Glu Arg Pro
145                 150                 155                 160

Arg Lys Leu Pro Gln Leu Cys Thr Glu Leu Gln Thr Thr Ile His Asp
                165                 170                 175

Ile Ile Leu Glu Cys Val Tyr Cys Lys Gln Gln Leu Leu Arg Arg Glu
            180                 185                 190

Val Tyr Asp Phe Ala Arg Arg Asp Leu Cys Ile Val Tyr Arg Asp Gly
        195                 200                 205

Asn Pro Tyr Ala Val Arg Asp Lys Cys Leu Lys Phe Tyr Ser Lys Ile
        210                 215                 220

Ser Glu Tyr Arg His Tyr Cys Tyr Ser Leu Tyr Gly Thr Thr Leu Glu
225                 230                 235                 240

Gln Gln Tyr Asn Lys Pro Leu Cys Asp Leu Leu Ile Arg Cys Ile Asn
                245                 250                 255
```

```
Arg Gln Lys Pro Leu Cys Pro Glu Glu Lys Gln Arg His Leu Asp Lys
          260                 265                 270

Lys Gln Arg Phe His Asn Ile Arg Gly Arg Trp Thr Gly Arg Cys Met
          275                 280                 285

Ser Cys Cys Arg Ser Ser Arg Thr Arg Arg Glu Thr Gln Leu
    290                 295                 300

<210> SEQ ID NO 15
<211> LENGTH: 924
<212> TYPE: PRT
<213> ORGANISM: Artificial
<220> FEATURE:
<223> OTHER INFORMATION: Antigenic unit
<220> FEATURE:
<221> NAME/KEY: MISC_FEATURE
<222> LOCATION: (1)..(924)
<223> OTHER INFORMATION: antigenic unit

<400> SEQUENCE: 15

His Asn Glu Gly Asp Asp Gln Gln Gly Ser Arg Tyr Ser Leu Ile Pro
1               5                   10                  15

Gln Ile Gln Lys Val Cys Glu Val Val Asp Gly Gly Ser Ser Gly Gly
          20                  25                  30

Gly Ser Ser Gly Gly Ser Glu Gln Glu Arg Met Lys Ser Ser Leu Leu
          35                  40                  45

Lys Glu His Met Leu Arg Lys Gln Ala Glu Leu Glu Ser Ala Gln Cys
          50                  55                  60

Ser Gly Gly Gly Gly Ser Gly Gly Gly Glu Leu Arg Glu Asn Leu
65                  70                  75                  80

Leu Thr Tyr Leu Pro Asp Ser Val Thr Gln Leu Arg Arg Leu Glu Glu
              85                  90                  95

Leu Asp Leu Gly Asn Gly Gly Gly Ser Gly Gly Gly Gly Ser Gln
          100                 105                 110

Glu Val Phe Ser Ser Tyr Lys Phe Asn His Leu Val Arg Arg Leu Val
          115                 120                 125

Leu Gln Arg Glu Lys His Phe His Tyr Leu Ser Gly Gly Gly Gly Ser
          130                 135                 140

Gly Gly Gly Gly Val Gln Ser Thr His Val Asp Ile Arg Thr Leu Glu
145                 150                 155                 160

Asp Leu Leu Met Gly Thr Leu Gly Ile Val Cys Pro Ile Cys Ser Gln
              165                 170                 175

Lys Pro Gly Gly Gly Gly Ser Gly Gly Gly Gly Ser Ile Glu Lys Asn
          180                 185                 190

Ala Asp Leu Cys Tyr Leu Ser Thr Val His Trp Ser Leu Ile Leu Asp
          195                 200                 205

Ala Val Ser Asn Asn Tyr Ile Gly Gly Gly Ser Gly Gly Gly Gly
          210                 215                 220

Ser Leu Ala Thr Ala Gly Glu Pro Tyr His Asp Ile Arg Phe Lys Leu
225                 230                 235                 240

Met Ala Val Val Pro Asp Arg Arg Ile Lys Tyr Glu Gly Gly Gly Gly
              245                 250                 255

Ser Gly Gly Gly Gly Ser Ala Arg Gly Pro Glu Ser Arg Leu Leu Glu
          260                 265                 270

Phe Tyr Leu Ala Met Pro Phe Ala Thr Pro Met Glu Ala Glu Leu Ala
          275                 280                 285

Arg Arg Ser Leu Ala Gln Asp Ala Pro Pro Leu Pro Val Pro Gly Val
```

-continued

```
           290                 295                 300

Leu Leu Lys Glu Phe Thr Val Ser Gly Asn Ile Leu Thr Ile Arg Leu
305                 310                 315                 320

Thr Ala Ala Asp His Arg Gln Leu Gln Leu Ser Ile Ser Ser Cys Leu
                325                 330                 335

Gln Gln Leu Ser Leu Leu Met Trp Ile Thr Gln Cys Phe Leu Pro Val
                340                 345                 350

Phe Leu Ala Gln Pro Pro Ser Gly Gln Arg Arg Ser Gly Gly Gly Gly
                355                 360                 365

Ser Gly Gly Gly Gly Met Leu Arg Leu Pro Thr Val Phe Arg Gln Ile
                370                 375                 380

Arg Pro Val Ser Arg Val Leu Ala Pro His Leu Thr Arg Ser Gly Gly
385                 390                 395                 400

Gly Gly Ser Gly Gly Gly Gly Ile Gln Ile Met Glu Asn Pro Phe Val
                405                 410                 415

Gln Ser Met Leu Trp Asn Pro Asp Leu Met Arg Gln Leu Ile Met Ala
                420                 425                 430

Asn Pro Gly Gly Gly Gly Ser Gly Gly Gly Gly Ser Leu Leu Arg Phe
                435                 440                 445

Leu Phe Leu Gly Leu Ser Ala Leu Ala Leu Pro Ser Arg Ala Gln Leu
                450                 455                 460

Gln Leu His Leu Pro Ala Asn Gly Gly Gly Gly Ser Gly Gly Gly Gly
465                 470                 475                 480

Ser Met Gly Lys Asn Pro Val Arg Pro Pro Arg Ala Phe Pro Pro Val
                485                 490                 495

Pro Ser Ile Asp Asp Ile Pro Leu Ser Arg Gly Ser Gly Gly Gly Gly
                500                 505                 510

Ser Gly Gly Gly Gly His Val Asp Phe Thr Ile Glu Val Glu Arg Ala
                515                 520                 525

Leu Thr Val Leu Asp Gly Ala Val Leu Val Leu Cys Ala Val Gly Ser
                530                 535                 540

Ser Gly Gly Gly Ser Ser Gly Gly Gly Glu Tyr Lys Leu Met Tyr Gly
545                 550                 555                 560

Met Leu Phe Ser Ile Arg Leu Phe Val Ser Lys Met Ser Pro Leu Asp
                565                 570                 575

Met Lys Asp Gly Gly Ser Ser Gly Gly Gly Ser Ser Gly Gly Ser Gln
                580                 585                 590

Gly Ala Gly Val Glu Ser Leu Asp Phe Arg Leu Tyr Leu Arg Tyr Glu
                595                 600                 605

Phe Leu Met Leu Gly Ile Gln Pro Val Gly Gly Gly Ser Gly Gly
                610                 615                 620

Gly Gly Ser Ala Ala Lys Thr Leu Val Leu Cys Val Ser Asp Ile Ile
625                 630                 635                 640

Leu Leu Ser Ala Asn Ile Ser Glu Thr Ser Ser Asn Lys Thr Ser Gly
                645                 650                 655

Gly Gly Gly Ser Gly Gly Gly Gly Cys Lys Asp Leu Gln Leu Tyr Leu
                660                 665                 670

Ser Asn Leu Ala Asn His Ile Asp Arg Glu Thr Gly Ile Gly Asp Val
                675                 680                 685

Pro Leu Val Gly Gly Gly Gly Ser Gly Gly Gly Gly Ser Gln Ser Lys
                690                 695                 700

His Thr Glu Ala Arg Glu Leu Met Tyr Ser Ala Ala Leu Leu Phe Phe
705                 710                 715                 720
```

-continued

```
Ser His Gly Gln Gln Asn Ser Ala Gly Gly Gly Gly Ser Gly Gly Gly
                725             730             735

Gly Ser Met Thr Leu Ala Glu Ser Tyr Ala Gln Tyr Val Tyr Asn Leu
            740             745             750

Cys Asn Ser Leu Ser Ile Lys Val Glu Glu Ser Ser Gly Gly Gly Gly
            755             760             765

Ser Gly Gly Gly Gly Met Phe Gln Asp Pro Gln Glu Arg Pro Arg Lys
        770             775             780

Leu Pro Gln Leu Cys Thr Glu Leu Gln Thr Thr Ile His Asp Ile Ile
785             790             795             800

Leu Glu Cys Val Tyr Cys Lys Gln Gln Leu Leu Arg Arg Glu Val Tyr
            805             810             815

Asp Phe Ala Arg Arg Asp Leu Cys Ile Val Tyr Arg Asp Gly Asn Pro
            820             825             830

Tyr Ala Val Arg Asp Lys Cys Leu Lys Phe Tyr Ser Lys Ile Ser Glu
            835             840             845

Tyr Arg His Tyr Cys Tyr Ser Leu Tyr Gly Thr Thr Leu Glu Gln Gln
        850             855             860

Tyr Asn Lys Pro Leu Cys Asp Leu Leu Ile Arg Cys Ile Asn Arg Gln
865             870             875             880

Lys Pro Leu Cys Pro Glu Glu Lys Gln Arg His Leu Asp Lys Lys Gln
            885             890             895

Arg Phe His Asn Ile Arg Gly Arg Trp Thr Gly Arg Cys Met Ser Cys
            900             905             910

Cys Arg Ser Ser Arg Thr Arg Arg Glu Thr Gln Leu
        915             920
```

```
<210> SEQ ID NO 16
<211> LENGTH: 227
<212> TYPE: PRT
<213> ORGANISM: Artificial
<220> FEATURE:
<223> OTHER INFORMATION: Antigenic unit
<220> FEATURE:
<221> NAME/KEY: MISC_FEATURE
<222> LOCATION: (1)..(227)
<223> OTHER INFORMATION: Antigenic unit

<400> SEQUENCE: 16

Val Arg Asp Lys Cys Leu Lys Phe Tyr Ser Lys Ile Ser Glu Tyr Arg
1               5               10              15

His Tyr Cys Tyr Ser Leu Tyr Gly Thr Thr Leu Glu Gln Gln Tyr Asn
            20              25              30

Lys Pro Leu Cys Asp Leu Leu Ile Arg Cys Ile Asn Arg Gln Lys Pro
        35              40              45

Leu Cys Pro Glu Glu Lys Gln Arg His Leu Asp Lys Lys Gln Arg Phe
    50              55              60

His Asn Ile Arg Gly Arg Trp Thr Gly Arg Cys Met Ser Cys Cys Arg
65              70              75              80

Ser Ser Arg Thr Arg Arg Glu Thr Gln Leu Ser Gly Gly Gly Gly Ser
            85              90              95

Gly Gly Gly Gly Gly Ala Arg Gly Pro Glu Ser Arg Leu Leu Glu Phe
            100             105             110

Tyr Leu Ala Met Pro Phe Ala Thr Pro Met Glu Ala Glu Leu Ala Arg
            115             120             125

Arg Ser Leu Ala Gln Asp Ala Pro Pro Leu Pro Val Pro Gly Val Leu
```

```
            130             135             140

Leu Lys Glu Phe Thr Val Ser Gly Asn Ile Leu Thr Ile Arg Leu Thr
145                 150                 155                 160

Ala Ala Asp His Arg Gln Leu Gln Leu Ser Ile Gly Gly Gly Gly Ser
                165                 170                 175

Gly Gly Gly Gly Ser Ala Gly Gln Ala Glu Pro Asp Arg Ala His Tyr
            180                 185                 190

Asn Ile Val Thr Phe Cys Cys Lys Cys Asp Ser Thr Leu Arg Leu Cys
            195                 200                 205

Val Gln Ser Thr His Val Asp Ile Arg Thr Leu Glu Asp Leu Leu Met
    210                 215                 220

Gly Thr Leu
225
```

<210> SEQ ID NO 17
<211> LENGTH: 850
<212> TYPE: PRT
<213> ORGANISM: Artificial
<220> FEATURE:
<223> OTHER INFORMATION: Antigenic unit
<220> FEATURE:
<221> NAME/KEY: MISC_FEATURE
<222> LOCATION: (1)..(850)
<223> OTHER INFORMATION: Antigenic unit

<400> SEQUENCE: 17

```
Val Arg Asp Lys Cys Leu Lys Phe Tyr Ser Lys Ile Ser Glu Tyr Arg
1               5                   10                  15

His Tyr Cys Tyr Ser Leu Tyr Gly Thr Thr Leu Glu Gln Gln Tyr Asn
            20                  25                  30

Lys Pro Leu Cys Asp Leu Leu Ile Arg Cys Ile Asn Arg Gln Lys Pro
        35                  40                  45

Leu Cys Pro Glu Glu Lys Gln Arg His Leu Asp Lys Lys Gln Arg Phe
    50                  55                  60

His Asn Ile Arg Gly Arg Trp Thr Gly Arg Cys Met Ser Cys Cys Arg
65                  70                  75                  80

Ser Ser Arg Thr Arg Arg Glu Thr Gln Leu Ser Gly Gly Gly Gly Ser
                85                  90                  95

Gly Gly Gly Gly Lys Lys Val Ser Lys Thr Arg His Thr Arg Glu Thr
            100                 105                 110

Val Phe Arg Arg Ala Lys Arg Arg Trp Ala Pro Ile Pro Cys Ser Ser
            115                 120                 125

Gly Gly Gly Gly Ser Gly Gly Gly Gly Asn Leu Lys His Glu Asn Ile
    130                 135                 140

Leu Gln Phe Leu Thr Ala Gln Glu Arg Lys Thr Glu Leu Gly Lys Gln
145                 150                 155                 160

Tyr Trp Leu Ile Gly Gly Gly Gly Ser Gly Gly Gly Gly Ser Val Gln
                165                 170                 175

Val Phe Gly Leu Tyr Phe Gly Glu Glu Phe His Glu Thr Phe Asp Cys
            180                 185                 190

Pro Ile Lys Gly Ser Gly Gly Gly Gly Ser Gly Gly Gly Gly Gln Ala
        195                 200                 205

Ala Ala Ser Gln Ala Gly Gly Ala Arg Gly Tyr Ala Arg Gly Ala Gln
    210                 215                 220

Leu Trp Pro Pro Gly Ser Asp Pro Gly Gly Gly Gly Ser Gly Gly Gly
225                 230                 235                 240
```

```
Gly Ser Ser Ile Met Gln Thr Trp Phe Thr Leu Phe Thr Pro Thr Asp
            245                 250                 255

Ala Thr Ser Ile Val Ala Thr Thr Val Met Ser Asn Ser Ser Gly Gly
            260                 265                 270

Gly Gly Ser Gly Gly Gly Gly Gln Glu Asn Val Arg Phe Val Leu Val
            275                 280                 285

Arg Ser Glu Ala Leu Leu Pro Asn Ala Gly Pro Arg Ser Ala Glu Ala
        290                 295                 300

Arg Val Gly Gly Gly Gly Ser Gly Gly Gly Ser Gly Ala Arg Gly
        305                 310                 315                 320

Pro Glu Ser Arg Leu Leu Glu Phe Tyr Leu Ala Met Pro Phe Ala Thr
                325                 330                 335

Pro Met Glu Ala Glu Leu Ala Arg Arg Ser Leu Ala Gln Asp Ala Pro
            340                 345                 350

Pro Leu Pro Val Pro Gly Val Leu Leu Lys Glu Phe Thr Val Ser Gly
            355                 360                 365

Asn Ile Leu Thr Ile Arg Leu Thr Ala Ala Asp His Arg Gln Leu Gln
        370                 375                 380

Leu Ser Ile Gly Gly Gly Gly Ser Gly Gly Gly Ser Asp Ala Phe
        385                 390                 395                 400

Pro Asn Leu Lys Asp Phe Ile Ser Arg Phe Gln Val Met Pro Pro Ser
                405                 410                 415

Ser Phe Leu Phe Asp Ala Pro Cys Ser Gly Gly Gly Gly Ser Gly Gly
                420                 425                 430

Gly Gly Pro Ser Ser Leu Gln Val Lys Pro Glu Thr Pro Ala Ser Glu
            435                 440                 445

Ala Val Ala Val Ala Ala Ala Ala Pro Thr Thr Thr Ser Gly Gly
        450                 455                 460

Gly Gly Ser Gly Gly Gly Gly Arg Phe Phe His Leu Ala Asp Leu Phe
        465                 470                 475                 480

Leu Ser Ser Ser Gln Leu Pro Ala Tyr Leu Val Ala Ala Phe Ala Lys
                485                 490                 495

Arg Leu Ser Gly Gly Gly Gly Ser Gly Gly Gly Gly Leu Val Phe Leu
                500                 505                 510

Trp Leu His Ser Leu Arg Arg Leu Phe Gly Cys Leu Tyr Val Ser Val
            515                 520                 525

Phe Ser Asn Val Met Ile His Ser Gly Gly Gly Gly Ser Gly Gly Gly
        530                 535                 540

Gly Trp Glu Asn Ala Ile Ala Ala Leu Phe Arg Arg His Ile Ala Val
        545                 550                 555                 560

Ser Trp Leu Ile Arg Ala Thr Leu Ser Glu Ser Glu Gly Gly Gly Gly
                565                 570                 575

Ser Gly Gly Gly Gly Ser Arg Tyr Ile Phe Val Lys Ser Ala Gly Ser
                580                 585                 590

Arg Ile Glu Glu Gly Val Leu Gln Phe Leu Val Leu Leu Val Ala Gly
            595                 600                 605

Arg Ser Gly Gly Gly Gly Ser Gly Gly Gly Gly Gln Glu Ile Glu Trp
            610                 615                 620

Leu Pro Phe Arg Cys Ile Lys Cys Leu Lys Leu Ser Phe Ser Thr Ala
        625                 630                 635                 640

Glu Leu Leu Cys Met His Gly Gly Gly Gly Ser Gly Gly Gly Gly Ser
                645                 650                 655

Leu Val Ala Arg Cys Pro Pro Cys Leu Arg Leu Leu Arg Gln Ala Arg
```

```
                 660                    665                      670

Asp Phe Gln Ala Ala Arg Tyr Asp Arg His Asp Gly Gly Gly Gly Ser
            675              680               685

Gly Gly Gly Gly Ser Ala Leu Gly Thr Pro Glu Asp Leu Asp Ser Tyr
        690              695              700

Ile Asp Leu Ser Leu Glu Ser Leu Asn Gln Met Ile Leu Glu Leu Asp
705                  710              715                  720

Gly Gly Gly Gly Ser Gly Gly Gly Ser Ser Gln Asp Met Leu Ser
            725              730              735

Ile Met Glu Lys Leu Glu Phe Leu Asp Phe Ser Tyr Asp Leu Asn Leu
            740              745              750

Cys Gly Leu Thr Glu Gly Gly Gly Ser Gly Gly Gly Ser Ala
        755              760              765

Gly Gln Ala Glu Pro Asp Arg Ala His Tyr Asn Ile Val Thr Phe Cys
        770              775              780

Cys Lys Cys Asp Ser Thr Leu Arg Leu Cys Val Gln Ser Thr His Val
785                  790              795                  800

Asp Ile Arg Thr Leu Glu Asp Leu Leu Met Gly Thr Leu Gly Gly Gly
            805              810              815

Ser Gly Gly Gly Gly Ser Gly Arg Arg Glu Gln Tyr Ile Pro Asn Glu
            820              825              830

Glu Phe Leu His Phe Asp Leu Leu Glu Asp Ser Lys Tyr Arg Lys Ile
            835              840              845

Tyr Ser
    850

<210> SEQ ID NO 18
<211> LENGTH: 221
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(221)
<223> OTHER INFORMATION: Antigenic unit

<400> SEQUENCE: 18

Gly Ala Arg Gly Pro Glu Ser Arg Leu Leu Glu Phe Tyr Leu Ala Met
1               5               10               15

Pro Phe Ala Thr Pro Met Glu Ala Glu Leu Ala Arg Arg Ser Leu Ala
            20              25              30

Gln Asp Ala Pro Pro Leu Pro Val Pro Gly Val Leu Leu Lys Glu Phe
        35              40              45

Thr Val Ser Gly Asn Ile Leu Thr Ile Arg Leu Thr Ala Ala Asp His
        50              55              60

Arg Gln Leu Gln Leu Ser Ile Ser Ser Cys Leu Gln Gln Leu Ser Leu
65              70              75              80

Leu Met Trp Ile Thr Gln Cys Phe Leu Pro Val Phe Gly Gly Gly Gly
            85              90              95

Ser Gly Gly Gly Gly Ser Ala Gly Gln Ala Glu Pro Asp Arg Ala His
            100              105              110

Tyr Asn Ile Val Thr Phe Cys Cys Lys Cys Asp Ser Thr Leu Arg Leu
            115              120              125

Cys Val Gln Ser Thr His Val Asp Ile Arg Thr Leu Ser Gly Gly Gly
            130              135              140
```

```
Gly Ser Gly Gly Gly Gly Lys Phe Tyr Ser Lys Ile Ser Glu Tyr Arg
145                 150                 155                 160

His Tyr Cys Tyr Ser Leu Tyr Gly Thr Thr Leu Glu Gln Gln Tyr Asn
                165                 170                 175

Lys Pro Leu Cys Asp Leu Leu Ile Arg Cys Ile Asn Arg Gln Lys Pro
            180                 185                 190

Leu Cys Pro Glu Glu Lys Gln Arg His Leu Asp Lys Lys Gln Arg Phe
        195                 200                 205

His Asn Ile Arg Gly Arg Trp Thr Gly Arg Cys Met Ser
    210                 215                 220
```

```
<210> SEQ ID NO 19
<211> LENGTH: 831
<212> TYPE: PRT
<213> ORGANISM: Artificial
<220> FEATURE:
<223> OTHER INFORMATION: Antigenic unit
<220> FEATURE:
<221> NAME/KEY: MISC_FEATURE
<222> LOCATION: (1)..(831)
<223> OTHER INFORMATION: Antigenic unit

<400> SEQUENCE: 19
```

```
Gly Pro Ser Tyr Arg Ser Asn Ser Val Ser Ser Leu Asp Leu Glu Gly
1               5                   10                  15

Glu Gly Gly Gly Gly Ser Gly Gly Gly Ser Leu Lys Glu Glu Lys
            20                  25                  30

Glu Asn Leu Gln Gly Leu Val Thr His Gln Thr Tyr Ile Ile Gln Glu
        35                  40                  45

Leu Glu Lys Gln Leu Asn Gly Gly Gly Gly Ser Gly Gly Gly Gly Ser
    50                  55                  60

Gln Arg Gln Lys Thr Ala Gly Lys Ile Phe Arg Ala Glu Val Ser Thr
65                  70                  75                  80

Gly Gln Asp Ala Pro Arg Gln Ala Gln Ala Arg Gly Gly Gly Ser Ser
                85                  90                  95

Gly Gly Gly Ser Ser Ile Leu Arg Pro Ser Thr Val Asn Glu Leu Glu
            100                 105                 110

Ser Gly Glu Ile Ser Tyr Asp Glu Val Gly Glu Arg Ile Lys Asp Phe
            115                 120                 125

Gly Gly Gly Gly Ser Gly Gly Gly Gly Ser Asp Thr Cys Ile Asn Glu
    130                 135                 140

Asp Val Glu Ser Leu Arg Lys Met Val Gln Asp Leu Leu Ala Lys Leu
145                 150                 155                 160

Gln Glu Ala Lys Arg Ser Gly Gly Gly Ser Gly Gly Gly Gly Leu
            165                 170                 175

Arg Glu Glu Gly Thr Lys Tyr Lys Ser Phe Val Gln Arg Ala Arg Leu
            180                 185                 190

Val Phe Arg Glu Glu Gly Tyr Leu Ala Phe Gly Gly Gly Gly Ser Gly
        195                 200                 205

Gly Gly Gly Ser His Glu Gly Ala Arg Pro Met Arg Ala Ile Phe Leu
    210                 215                 220

Ala Asn Gly Asn Val Phe Thr Thr Gly Phe Ser Arg Met Ser Glu Gly
225                 230                 235                 240

Gly Gly Gly Ser Gly Gly Gly Gly Ser Ile Pro Asp Ala Ala Phe Ile
            245                 250                 255

Gln Ala Ala Arg Arg Lys Cys Glu Leu Ala Arg Ala Gln Asp Asp Tyr
            260                 265                 270
```

```
Ile Ser Leu Asp Gly Gly Gly Gly Ser Gly Gly Gly Gly Ser Met Glu
        275             280             285

Ile Ala Lys Met Arg Ala Gly Arg Arg Leu Trp Val His Leu Ile Glu
    290             295             300

Lys Met Phe Gln Pro Lys Asn Ser Lys Gly Gly Gly Ser Gly Gly
305             310             315             320

Gly Gly Ser Met Glu Leu Val Ser Phe Arg Asp Val Ala Ile Glu Phe
            325             330             335

Ser Pro Glu Glu Trp Gly Gly Gly Ser Gly Gly Gly Gly Ser Thr
            340             345             350

Cys Val His Glu Ile Pro Phe His Phe Asp Leu Met Glu Leu Leu Pro
            355             360             365

Gln Cys Gln Gln Leu Gln Met Phe Phe Leu Gly Gly Gly Ser Gly Gly
        370             375             380

Gly Gly Ser Gly Gly Ala Arg Gly Pro Glu Ser Arg Leu Leu Glu Phe
385             390             395             400

Tyr Leu Ala Met Pro Phe Ala Thr Pro Met Glu Ala Glu Leu Ala Arg
            405             410             415

Arg Ser Leu Ala Gln Asp Ala Pro Pro Leu Pro Val Pro Gly Val Leu
            420             425             430

Leu Lys Glu Phe Thr Val Ser Gly Asn Ile Leu Thr Ile Arg Leu Thr
            435             440             445

Ala Ala Asp His Arg Gln Leu Gln Leu Ser Ile Ser Ser Cys Leu Gln
        450             455             460

Gln Leu Ser Leu Leu Met Trp Ile Thr Gln Cys Phe Leu Pro Val Phe
465             470             475             480

Gly Gly Gly Gly Ser Gly Gly Gly Gly Ser Val Arg Arg Val Phe Ile
            485             490             495

Thr Asp Asp Phe His Asp Met Ile Pro Lys Tyr Leu Asn Phe Val Lys
            500             505             510

Gly Val Val Asp Ser Ser Gly Gly Gly Gly Ser Gly Gly Gly Gly Asn
            515             520             525

Phe His Ala His Arg Glu Lys Ala Pro Ser Leu Phe Cys Ser Arg Ile
        530             535             540

Leu Asn Lys Ala Val Tyr Leu Phe Tyr Gly Ser Ser Gly Gly Gly Ser
545             550             555             560

Ser Gly Gly Gly Asp Ala Asn Lys Glu Gly Met Phe Leu Phe Arg Ala
            565             570             575

Ala His Lys Leu Arg Gln Phe Leu Lys Met Asn Ser Thr Gly Asp Gly
            580             585             590

Gly Gly Gly Ser Gly Gly Gly Gly Ser Leu Leu Ser Leu Gly Trp Ser
            595             600             605

Val Asp Val Gly Arg His Ser Gly Trp Thr Gly His Val Ser Thr Ser
    610             615             620

Trp Ser Ile Asn Gly Gly Gly Gly Ser Gly Gly Gly Gly Ser Ala Gly
625             630             635             640

Gln Ala Glu Pro Asp Arg Ala His Tyr Asn Ile Val Thr Phe Cys Cys
            645             650             655

Lys Cys Asp Ser Thr Leu Arg Leu Cys Val Gln Ser Thr His Val Asp
            660             665             670

Ile Arg Thr Leu Ser Gly Gly Gly Gly Ser Gly Gly Gly Gly Asn Thr
            675             680             685
```

```
Ile Phe Ser Leu Arg Lys Asp Leu Arg Gln Gly Lys Ala Arg Arg Leu
    690             695             700

Arg Cys Met Glu Glu Lys Glu Met Phe Gly Gly Gly Gly Ser Gly Gly
705             710             715             720

Gly Gly Ser Asn His Phe Asn Asp Phe Glu Gly Asp Pro Ala Met Thr
            725             730             735

Gln Phe Leu Glu Glu Phe Glu Lys Asn Leu Glu Asp Thr Lys Gly Gly
            740             745             750

Gly Gly Ser Gly Gly Gly Gly Ser Lys Phe Tyr Ser Lys Ile Ser Glu
            755             760             765

Tyr Arg His Tyr Cys Tyr Ser Leu Tyr Gly Thr Thr Leu Glu Gln Gln
    770             775             780

Tyr Asn Lys Pro Leu Cys Asp Leu Leu Ile Arg Cys Ile Asn Arg Gln
785             790             795             800

Lys Pro Leu Cys Pro Glu Glu Lys Gln Arg His Leu Asp Lys Lys Gln
            805             810             815

Arg Phe His Asn Ile Arg Gly Arg Trp Thr Gly Arg Cys Met Ser
            820             825             830

<210> SEQ ID NO 20
<211> LENGTH: 602
<212> TYPE: PRT
<213> ORGANISM: Artificial
<220> FEATURE:
<223> OTHER INFORMATION: Assembly of protein
<220> FEATURE:
<221> NAME/KEY: MISC_FEATURE
<222> LOCATION: (1)..(602)
<223> OTHER INFORMATION: Amino acid sequence of VB4097

<400> SEQUENCE: 20

Met Gln Val Ser Thr Ala Ala Leu Ala Val Leu Leu Cys Thr Met Ala
1               5               10              15

Leu Cys Asn Gln Val Leu Ser Ala Pro Leu Ala Ala Asp Thr Pro Thr
            20              25              30

Ala Cys Cys Phe Ser Tyr Thr Ser Arg Gln Ile Pro Gln Asn Phe Ile
            35              40              45

Ala Asp Tyr Phe Glu Thr Ser Ser Gln Cys Ser Lys Pro Ser Val Ile
    50              55              60

Phe Leu Thr Lys Arg Gly Arg Gln Val Cys Ala Asp Pro Ser Glu Glu
65              70              75              80

Trp Val Gln Lys Tyr Val Ser Asp Leu Glu Leu Ser Ala Glu Leu Lys
            85              90              95

Thr Pro Leu Gly Asp Thr Thr His Thr Glu Pro Lys Ser Cys Asp Thr
            100             105             110

Pro Pro Pro Cys Pro Arg Cys Pro Gly Gly Gly Ser Ser Gly Gly Gly
            115             120             125

Ser Gly Gly Gln Pro Arg Glu Pro Gln Val Tyr Thr Leu Pro Pro Ser
    130             135             140

Arg Glu Glu Met Thr Lys Asn Gln Val Ser Leu Thr Cys Leu Val Lys
145             150             155             160

Gly Phe Tyr Pro Ser Asp Ile Ala Val Glu Trp Glu Ser Ser Gly Gln
            165             170             175

Pro Glu Asn Asn Tyr Asn Thr Thr Pro Pro Met Leu Asp Ser Asp Gly
            180             185             190

Ser Phe Phe Leu Tyr Ser Lys Leu Thr Val Asp Lys Ser Arg Trp Gln
    195             200             205
```

-continued

```
Gln Gly Asn Ile Phe Ser Cys Ser Val Met His Glu Ala Leu His Asn
    210                 215                 220

Arg Phe Thr Gln Lys Ser Leu Ser Leu Ser Pro Gly Lys Gly Leu Gly
225                 230                 235                 240

Gly Leu Lys Ile Tyr Glu Phe Asp Tyr His Leu Tyr Gly Gln Asn Ile
            245                 250                 255

Thr Met Ile Met Thr Ser Val Ser Gly His Leu Leu Ala Gly Gly Gly
            260                 265                 270

Gly Ser Gly Gly Gly Gly Ser Ala Glu Tyr Gly Asp Tyr Gln Pro Glu
    275                 280                 285

Val His Gly Val Pro Tyr Phe Arg Leu Glu His Tyr Leu Pro Ala Arg
    290                 295                 300

Val Met Gly Gly Gly Gly Ser Gly Gly Gly Ser Gly Ser Leu Phe
305                 310                 315                 320

Gly Ser Ser Arg Val Gln Tyr Val Val Asn Pro Ala Val Lys Ile Val
            325                 330                 335

Phe Leu Asn Ile Asp Pro Ser Gly Gly Gly Gly Ser Gly Gly Gly Gly
            340                 345                 350

Ser Leu Trp Val Tyr Leu Arg Pro Val Pro Arg Pro Ala Thr Ile Tyr
    355                 360                 365

Leu Gln Ile Leu Arg Leu Lys Pro Leu Thr Gly Glu Gly Gly Gly Gly
    370                 375                 380

Ser Gly Gly Gly Gly Ser Thr Leu Ala Phe Leu Val Leu Ser Thr Pro
385                 390                 395                 400

Ala Met Phe Asn Arg Ala Leu Lys Pro Phe Leu Lys Ser Cys His Phe
                405                 410                 415

Gln Gly Gly Gly Gly Ser Gly Gly Gly Gly Ser Phe Val Ser Pro Met
            420                 425                 430

Ala His Tyr Val Pro Gly Ile Met Ala Ile Glu Ser Val Val Ala Arg
            435                 440                 445

Phe Gln Phe Ile Val Pro Gly Gly Gly Gly Ser Gly Gly Gly Gly Ser
    450                 455                 460

Val Ile Leu Pro Gln Ala Pro Ser Gly Pro Ser Tyr Ala Thr Tyr Leu
465                 470                 475                 480

Gln Pro Ala Gln Ala Gln Met Leu Thr Pro Pro Gly Gly Gly Gly Ser
            485                 490                 495

Gly Gly Gly Gly Ser Glu Val Ile Gln Thr Ser Lys Tyr Tyr Met Arg
            500                 505                 510

Asp Val Ile Ala Ile Glu Ser Ala Trp Leu Leu Glu Leu Ala Pro His
            515                 520                 525

Gly Gly Gly Gly Ser Gly Gly Gly Gly Ser Asp Thr Leu Ser Ala Met
    530                 535                 540

Ser Asn Pro Arg Ala Met Gln Val Leu Leu Gln Ile Gln Gln Gly Leu
545                 550                 555                 560

Gln Thr Leu Ala Thr Gly Gly Gly Gly Ser Gly Gly Gly Gly Ser Lys
            565                 570                 575

Ser Trp Ile His Cys Trp Lys Tyr Leu Ser Val Gln Ser Gln Leu Phe
            580                 585                 590

Arg Gly Ser Ser Leu Leu Phe Arg Arg Val
            595                 600
```

<210> SEQ ID NO 21
<211> LENGTH: 422

```
<212> TYPE: PRT
<213> ORGANISM: Artificial
<220> FEATURE:
<223> OTHER INFORMATION: Assembly of protein
<220> FEATURE:
<221> NAME/KEY: MISC_FEATURE
<222> LOCATION: (1)..(422)
<223> OTHER INFORMATION: Amino acid sequence of VB4100

<400> SEQUENCE: 21

Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
            20                  25                  30

Ala Cys Cys Phe Ser Tyr Thr Ser Arg Gln Ile Pro Gln Asn Phe Ile
            35                  40                  45

Ala Asp Tyr Phe Glu Thr Ser Ser Gln Cys Ser Lys Pro Ser Val Ile
        50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala Glu Leu Lys
                85                  90                  95

Thr Pro Leu Gly Asp Thr Thr His Thr Glu Pro Lys Ser Cys Asp Thr
            100                 105                 110

Pro Pro Pro Cys Pro Arg Cys Pro Gly Gly Gly Ser Ser Gly Gly Gly
            115                 120                 125

Ser Gly Gly Gln Pro Arg Glu Pro Gln Val Tyr Thr Leu Pro Pro Ser
        130                 135                 140

Arg Glu Glu Met Thr Lys Asn Gln Val Ser Leu Thr Cys Leu Val Lys
145                 150                 155                 160

Gly Phe Tyr Pro Ser Asp Ile Ala Val Glu Trp Glu Ser Ser Gly Gln
                165                 170                 175

Pro Glu Asn Asn Tyr Asn Thr Thr Pro Pro Met Leu Asp Ser Asp Gly
            180                 185                 190

Ser Phe Phe Leu Tyr Ser Lys Leu Thr Val Asp Lys Ser Arg Trp Gln
            195                 200                 205

Gln Gly Asn Ile Phe Ser Cys Ser Val Met His Glu Ala Leu His Asn
        210                 215                 220

Arg Phe Thr Gln Lys Ser Leu Ser Leu Ser Pro Gly Lys Gly Leu Gly
225                 230                 235                 240

Gly Leu Met Gln Ala Glu Gly Arg Gly Thr Gly Gly Ser Thr Gly Asp
                245                 250                 255

Ala Asp Gly Pro Gly Gly Pro Gly Ile Pro Asp Gly Pro Gly Gly Asn
            260                 265                 270

Ala Gly Gly Pro Gly Glu Ala Gly Ala Thr Gly Gly Arg Gly Pro Arg
            275                 280                 285

Gly Ala Gly Ala Ala Arg Ala Ser Gly Pro Gly Gly Gly Ala Pro Arg
        290                 295                 300

Gly Pro His Gly Gly Ala Ala Ser Gly Leu Asn Gly Cys Cys Arg Cys
305                 310                 315                 320

Gly Ala Arg Gly Pro Glu Ser Arg Leu Leu Glu Phe Tyr Leu Ala Met
                325                 330                 335

Pro Phe Ala Thr Pro Met Glu Ala Glu Leu Ala Arg Arg Ser Leu Ala
            340                 345                 350

Gln Asp Ala Pro Pro Leu Pro Val Pro Gly Val Leu Leu Lys Glu Phe
            355                 360                 365
```

-continued

```
Thr Val Ser Gly Asn Ile Leu Thr Ile Arg Leu Thr Ala Ala Asp His
    370             375             380

Arg Gln Leu Gln Leu Ser Ile Ser Ser Cys Leu Gln Gln Leu Ser Leu
385             390             395             400

Leu Met Trp Ile Thr Gln Cys Phe Leu Pro Val Phe Leu Ala Gln Pro
            405             410             415

Pro Ser Gly Gln Arg Arg
            420

<210> SEQ ID NO 22
<211> LENGTH: 250
<212> TYPE: PRT
<213> ORGANISM: Artificial
<220> FEATURE:
<223> OTHER INFORMATION: Assembly of protein
<220> FEATURE:
<221> NAME/KEY: MISC_FEATURE
<222> LOCATION: (1)..(250)
<223> OTHER INFORMATION: Amino acid sequence of VB4101

<400> SEQUENCE: 22

Met Gln Val Ser Thr Ala Ala Leu Ala Val Leu Leu Cys Thr Met Ala
1               5               10              15

Leu Cys Asn Gln Val Leu Ser Ala Pro Leu Ala Ala Asp Thr Pro Thr
            20              25              30

Ala Cys Cys Phe Ser Tyr Thr Ser Arg Gln Ile Pro Gln Asn Phe Ile
            35              40              45

Ala Asp Tyr Phe Glu Thr Ser Ser Gln Cys Ser Lys Pro Ser Val Ile
    50              55              60

Phe Leu Thr Lys Arg Gly Arg Gln Val Cys Ala Asp Pro Ser Glu Glu
65              70              75              80

Trp Val Gln Lys Tyr Val Ser Asp Leu Glu Leu Ser Ala Glu Leu Lys
            85              90              95

Thr Pro Leu Gly Asp Thr Thr His Thr Glu Pro Lys Ser Cys Asp Thr
            100             105             110

Pro Pro Pro Cys Pro Arg Cys Pro Gly Gly Gly Ser Ser Gly Gly Gly
            115             120             125

Ser Gly Gly Gln Pro Arg Glu Pro Gln Val Tyr Thr Leu Pro Pro Ser
    130             135             140

Arg Glu Glu Met Thr Lys Asn Gln Val Ser Leu Thr Cys Leu Val Lys
145             150             155             160

Gly Phe Tyr Pro Ser Asp Ile Ala Val Glu Trp Glu Ser Ser Gly Gln
            165             170             175

Pro Glu Asn Asn Tyr Asn Thr Thr Pro Pro Met Leu Asp Ser Asp Gly
            180             185             190

Ser Phe Phe Leu Tyr Ser Lys Leu Thr Val Asp Lys Ser Arg Trp Gln
            195             200             205

Gln Gly Asn Ile Phe Ser Cys Ser Val Met His Glu Ala Leu His Asn
    210             215             220

Arg Phe Thr Gln Lys Ser Leu Ser Leu Ser Pro Gly Lys Gly Leu Gly
225             230             235             240

Gly Leu Arg Gly Pro Glu Ser Arg Leu Leu
            245             250

<210> SEQ ID NO 23
<211> LENGTH: 288
<212> TYPE: PRT
```

<213> ORGANISM: Artificial
<220> FEATURE:
<223> OTHER INFORMATION: Assembly of protein
<220> FEATURE:
<221> NAME/KEY: MISC_FEATURE
<222> LOCATION: (1)..(288)
<223> OTHER INFORMATION: Amino acid sequence of VB4102

<400> SEQUENCE: 23

```
Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
                20                  25                  30

Ala Cys Cys Phe Ser Tyr Thr Ser Arg Gln Ile Pro Gln Asn Phe Ile
                35                  40                  45

Ala Asp Tyr Phe Glu Thr Ser Ser Gln Cys Ser Lys Pro Ser Val Ile
        50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala Glu Leu Lys
                85                  90                  95

Thr Pro Leu Gly Asp Thr Thr His Thr Glu Pro Lys Ser Cys Asp Thr
                100                 105                 110

Pro Pro Pro Cys Pro Arg Cys Pro Gly Gly Gly Ser Ser Gly Gly Gly
                115                 120                 125

Ser Gly Gly Gln Pro Arg Glu Pro Gln Val Tyr Thr Leu Pro Pro Ser
        130                 135                 140

Arg Glu Glu Met Thr Lys Asn Gln Val Ser Leu Thr Cys Leu Val Lys
145                 150                 155                 160

Gly Phe Tyr Pro Ser Asp Ile Ala Val Glu Trp Glu Ser Ser Gly Gln
                165                 170                 175

Pro Glu Asn Asn Tyr Asn Thr Thr Pro Pro Met Leu Asp Ser Asp Gly
                180                 185                 190

Ser Phe Phe Leu Tyr Ser Lys Leu Thr Val Asp Lys Ser Arg Trp Gln
                195                 200                 205

Gln Gly Asn Ile Phe Ser Cys Ser Val Met His Glu Ala Leu His Asn
        210                 215                 220

Arg Phe Thr Gln Lys Ser Leu Ser Leu Ser Pro Gly Lys Gly Leu Gly
225                 230                 235                 240

Gly Leu Arg Gly Pro Glu Ser Arg Leu Leu Glu Phe Tyr Leu Ala Met
                245                 250                 255

Pro Phe Ala Thr Pro Met Glu Ala Glu Leu Ala Arg Arg Ser Leu Ala
                260                 265                 270

Gln Asp Ala Pro Pro Leu Pro Val Pro Gly Val Leu Leu Lys Glu Phe
        275                 280                 285
```

<210> SEQ ID NO 24
<211> LENGTH: 792
<212> TYPE: PRT
<213> ORGANISM: Artificial
<220> FEATURE:
<223> OTHER INFORMATION: Assembly of protein
<220> FEATURE:
<221> NAME/KEY: MISC_FEATURE
<222> LOCATION: (1)..(792)
<223> OTHER INFORMATION: Amino acid sequence of VB4105

<400> SEQUENCE: 24

```
Met Gln Val Ser Thr Ala Ala Leu Ala Val Leu Leu Cys Thr Met Ala
```

```
1                5                        10                       15

Leu Cys Asn Gln Val Leu Ser Ala Pro Leu Ala Ala Asp Thr Pro Thr
             20                  25                  30

Ala Cys Cys Phe Ser Tyr Thr Ser Arg Gln Ile Pro Gln Asn Phe Ile
         35                  40                  45

Ala Asp Tyr Phe Glu Thr Ser Ser Gln Cys Ser Lys Pro Ser Val Ile
     50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala Glu Leu Lys
                 85                  90                  95

Thr Pro Leu Gly Asp Thr Thr His Thr Glu Pro Lys Ser Cys Asp Thr
             100                 105                 110

Pro Pro Pro Cys Pro Arg Cys Pro Gly Gly Gly Ser Ser Gly Gly Gly
             115                 120                 125

Ser Gly Gly Gln Pro Arg Glu Pro Gln Val Tyr Thr Leu Pro Pro Ser
     130                 135                 140

Arg Glu Glu Met Thr Lys Asn Gln Val Ser Leu Thr Cys Leu Val Lys
145                 150                 155                 160

Gly Phe Tyr Pro Ser Asp Ile Ala Val Glu Trp Glu Ser Ser Gly Gln
                 165                 170                 175

Pro Glu Asn Asn Tyr Asn Thr Thr Pro Pro Met Leu Asp Ser Asp Gly
             180                 185                 190

Ser Phe Phe Leu Tyr Ser Lys Leu Thr Val Asp Lys Ser Arg Trp Gln
             195                 200                 205

Gln Gly Asn Ile Phe Ser Cys Ser Val Met His Glu Ala Leu His Asn
     210                 215                 220

Arg Phe Thr Gln Lys Ser Leu Ser Leu Ser Pro Gly Lys Gly Leu Gly
225                 230                 235                 240

Gly Leu Lys Ile Tyr Glu Phe Asp Tyr His Leu Tyr Gly Gln Asn Ile
             245                 250                 255

Thr Met Ile Met Thr Ser Val Ser Gly His Leu Leu Ala Gly Gly Gly
             260                 265                 270

Gly Ser Gly Gly Gly Gly Ser Ala Glu Tyr Gly Asp Tyr Gln Pro Glu
         275                 280                 285

Val His Gly Val Pro Tyr Phe Arg Leu Glu His Tyr Leu Pro Ala Arg
     290                 295                 300

Val Met Gly Gly Gly Gly Ser Gly Gly Gly Gly Ser Gly Ser Leu Phe
305                 310                 315                 320

Gly Ser Ser Arg Val Gln Tyr Val Val Asn Pro Ala Val Lys Ile Val
             325                 330                 335

Phe Leu Asn Ile Asp Pro Ser Gly Gly Gly Ser Gly Gly Gly Gly
             340                 345                 350

Ser Leu Trp Val Tyr Leu Arg Pro Val Pro Arg Pro Ala Thr Ile Tyr
             355                 360                 365

Leu Gln Ile Leu Arg Leu Lys Pro Leu Thr Gly Glu Gly Gly Gly Gly
     370                 375                 380

Ser Gly Gly Gly Gly Ser Thr Leu Ala Phe Leu Val Leu Ser Thr Pro
385                 390                 395                 400

Ala Met Phe Asn Arg Ala Leu Lys Pro Phe Leu Lys Ser Cys His Phe
             405                 410                 415

Gln Gly Gly Gly Gly Ser Gly Gly Gly Gly Ser Phe Val Ser Pro Met
             420                 425                 430
```

```
Ala His Tyr Val Pro Gly Ile Met Ala Ile Glu Ser Val Val Ala Arg
        435                 440                 445

Phe Gln Phe Ile Val Pro Gly Gly Gly Ser Gly Gly Gly Gly Ser
    450                 455                 460

Val Ile Leu Pro Gln Ala Pro Ser Gly Pro Ser Tyr Ala Thr Tyr Leu
465                 470                 475                 480

Gln Pro Ala Gln Ala Gln Met Leu Thr Pro Pro Gly Gly Gly Gly Ser
                485                 490                 495

Gly Gly Gly Gly Ser Glu Val Ile Gln Thr Ser Lys Tyr Tyr Met Arg
                500                 505                 510

Asp Val Ile Ala Ile Glu Ser Ala Trp Leu Leu Glu Leu Ala Pro His
        515                 520                 525

Gly Gly Gly Gly Ser Gly Gly Gly Gly Ser Asp Thr Leu Ser Ala Met
        530                 535                 540

Ser Asn Pro Arg Ala Met Gln Val Leu Leu Gln Ile Gln Gln Gly Leu
545                 550                 555                 560

Gln Thr Leu Ala Thr Gly Gly Gly Gly Ser Gly Gly Gly Gly Ser Lys
                565                 570                 575

Ser Trp Ile His Cys Trp Lys Tyr Leu Ser Val Gln Ser Gln Leu Phe
        580                 585                 590

Arg Gly Ser Ser Leu Leu Phe Arg Arg Val Gly Gly Gly Gly Ser Gly
        595                 600                 605

Gly Gly Gly Ser Met Gln Ala Glu Gly Arg Gly Thr Gly Gly Ser Thr
        610                 615                 620

Gly Asp Ala Asp Gly Pro Gly Gly Pro Gly Ile Pro Asp Gly Pro Gly
625                 630                 635                 640

Gly Asn Ala Gly Gly Pro Gly Glu Ala Gly Ala Thr Gly Gly Arg Gly
                645                 650                 655

Pro Arg Gly Ala Gly Ala Ala Arg Ala Ser Gly Pro Gly Gly Gly Ala
                660                 665                 670

Pro Arg Gly Pro His Gly Gly Ala Ala Ser Gly Leu Asn Gly Cys Cys
        675                 680                 685

Arg Cys Gly Ala Arg Gly Pro Glu Ser Arg Leu Leu Glu Phe Tyr Leu
        690                 695                 700

Ala Met Pro Phe Ala Thr Pro Met Glu Ala Glu Leu Ala Arg Arg Ser
705                 710                 715                 720

Leu Ala Gln Asp Ala Pro Pro Leu Pro Val Pro Gly Val Leu Leu Lys
                725                 730                 735

Glu Phe Thr Val Ser Gly Asn Ile Leu Thr Ile Arg Leu Thr Ala Ala
                740                 745                 750

Asp His Arg Gln Leu Gln Leu Ser Ile Ser Ser Cys Leu Gln Gln Leu
        755                 760                 765

Ser Leu Leu Met Trp Ile Thr Gln Cys Phe Leu Pro Val Phe Leu Ala
    770                 775                 780

Gln Pro Pro Ser Gly Gln Arg Arg
785                 790
```

<210> SEQ ID NO 25
<211> LENGTH: 237
<212> TYPE: PRT
<213> ORGANISM: Artificial
<220> FEATURE:
<223> OTHER INFORMATION: Assembly of protein
<220> FEATURE:
<221> NAME/KEY: MISC_FEATURE
<222> LOCATION: (1)..(237)
<223> OTHER INFORMATION: Amino acid sequence of VB1026

<400> SEQUENCE: 25

Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
                20                  25                  30

Ala Cys Cys Phe Ser Tyr Thr Ser Arg Gln Ile Pro Gln Asn Phe Ile
            35                  40                  45

Ala Asp Tyr Phe Glu Thr Ser Ser Gln Cys Ser Lys Pro Ser Val Ile
        50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala Glu Leu Lys
                85                  90                  95

Thr Pro Leu Gly Asp Thr Thr His Thr Glu Pro Lys Ser Cys Asp Thr
                100                 105                 110

Pro Pro Pro Cys Pro Arg Cys Pro Gly Gly Gly Ser Ser Gly Gly Gly
            115                 120                 125

Ser Gly Gly Gln Pro Arg Glu Pro Gln Val Tyr Thr Leu Pro Pro Ser
        130                 135                 140

Arg Glu Glu Met Thr Lys Asn Gln Val Ser Leu Thr Cys Leu Val Lys
145                 150                 155                 160

Gly Phe Tyr Pro Ser Asp Ile Ala Val Glu Trp Glu Ser Ser Gly Gln
                165                 170                 175

Pro Glu Asn Asn Tyr Asn Thr Thr Pro Pro Met Leu Asp Ser Asp Gly
                180                 185                 190

Ser Phe Phe Leu Tyr Ser Lys Leu Thr Val Asp Lys Ser Arg Trp Gln
                195                 200                 205

Gln Gly Asn Ile Phe Ser Cys Ser Val Met His Glu Ala Leu His Asn
        210                 215                 220

Arg Phe Thr Gln Lys Ser Leu Ser Leu Ser Pro Gly Lys
225                 230                 235

<210> SEQ ID NO 26
<211> LENGTH: 602
<212> TYPE: PRT
<213> ORGANISM: Artificial
<220> FEATURE:
<223> OTHER INFORMATION: Assembly of protein
<220> FEATURE:
<221> NAME/KEY: MISC_FEATURE
<222> LOCATION: (1)..(602)
<223> OTHER INFORMATION: Amino acid sequence of VB4118

<400> SEQUENCE: 26

Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
                20                  25                  30

Ala Cys Cys Phe Ser Tyr Thr Ser Arg Gln Ile Pro Gln Asn Phe Ile
            35                  40                  45

Ala Asp Tyr Phe Glu Thr Ser Ser Gln Cys Ser Lys Pro Ser Val Ile
        50                  55                  60

Phe Leu Thr Lys Arg Gly Arg Gln Val Cys Ala Asp Pro Ser Glu Glu
65                  70                  75                  80

```
Trp Val Gln Lys Tyr Val Ser Asp Leu Glu Leu Ser Ala Glu Leu Lys
            85                  90                  95

Thr Pro Leu Gly Asp Thr Thr His Thr Glu Pro Lys Ser Cys Asp Thr
            100                 105                 110

Pro Pro Pro Cys Pro Arg Cys Pro Gly Gly Gly Ser Ser Gly Gly Gly
            115                 120                 125

Ser Gly Gly Gln Pro Arg Glu Pro Gln Val Tyr Thr Leu Pro Pro Ser
    130                 135                 140

Arg Glu Glu Met Thr Lys Asn Gln Val Ser Leu Thr Cys Leu Val Lys
145                 150                 155                 160

Gly Phe Tyr Pro Ser Asp Ile Ala Val Glu Trp Glu Ser Ser Gly Gln
                165                 170                 175

Pro Glu Asn Asn Tyr Asn Thr Thr Pro Pro Met Leu Asp Ser Asp Gly
            180                 185                 190

Ser Phe Phe Leu Tyr Ser Lys Leu Thr Val Asp Lys Ser Arg Trp Gln
            195                 200                 205

Gln Gly Asn Ile Phe Ser Cys Ser Val Met His Glu Ala Leu His Asn
    210                 215                 220

Arg Phe Thr Gln Lys Ser Leu Ser Leu Ser Pro Gly Lys Gly Leu Gly
225                 230                 235                 240

Gly Leu Arg Glu Gly Val Glu Leu Cys Pro Gly Asn Lys Tyr Glu Met
                245                 250                 255

Arg Arg His Gly Thr Thr His Ser Leu Val Ile His Asp Gly Gly Gly
                260                 265                 270

Gly Ser Gly Gly Gly Gly Ser Ser Ser Pro Asp Glu Val Ala Leu Val
            275                 280                 285

Glu Gly Val Gln Ser Leu Gly Phe Thr Tyr Leu Arg Leu Lys Asp Asn
    290                 295                 300

Tyr Met Gly Gly Gly Gly Ser Gly Gly Gly Gly Ser Leu Lys Asp Phe
305                 310                 315                 320

Phe Phe Ser Arg Gly Arg Phe Ser Ser Ala Leu Lys Arg Thr Leu Ile
                325                 330                 335

Leu Ser Ser Gly Phe Arg Leu Gly Gly Gly Gly Ser Gly Gly Gly Gly
            340                 345                 350

Ser Lys Asn Ile Leu Ala Val Ser Phe Ala Pro Leu Val Gln Leu Ser
            355                 360                 365

Lys Asn Asp Asn Gly Thr Pro Asp Ser Val Gly Leu Gly Gly Gly Gly
    370                 375                 380

Ser Gly Gly Gly Gly Ser Leu Glu Ala Val Leu Arg Tyr Leu Glu Thr
385                 390                 395                 400

His Pro Arg Leu Pro Lys Pro Asp Pro Val Lys Ser Ser Ser Ser Val
                405                 410                 415

Leu Gly Gly Gly Gly Ser Gly Gly Gly Gly Ser Pro Ala Ala Asp Arg
            420                 425                 430

Trp Glu Pro Arg Ala Pro Met Arg Ala Pro Arg Val Leu His Ala Met
            435                 440                 445

Leu Gly Ala Ala Gly Arg Gly Gly Gly Gly Ser Gly Gly Gly Gly Ser
    450                 455                 460

Val Leu Ser Ala Asp Leu Val His Tyr Leu Arg Leu Ser Leu Glu Tyr
465                 470                 475                 480

Leu Arg Ala Trp His Ser Glu Asp Val Ser Leu Gly Gly Gly Gly Ser
                485                 490                 495

Gly Gly Gly Gly Ser Tyr Leu Pro Gly Gly Gly Ala Gly His Leu Asp
```

-continued

```
               500                 505                 510

Gln Asn Val Phe Leu Arg Val Arg Ala Leu Cys Tyr Val Ile Ser Gly
        515                 520                 525

Gly Gly Gly Gly Ser Gly Gly Gly Gly Ser Pro Ala Thr Ile Glu Met
        530                 535                 540

Ala Ile Glu Thr Leu Gln Lys Phe Asp Gly Leu Ser Thr His Arg Ser
545                 550                 555                 560

Ser Leu Leu Asn Ser Gly Gly Gly Gly Ser Gly Gly Gly Gly Ser Ala
                565                 570                 575

Gly Lys Asp His Lys Ile Lys Gln Trp Asp Ala Asp Thr Phe Glu His
                580                 585                 590

Ile Gln Thr Leu Glu Gly His His Gln Glu
        595                 600

<210> SEQ ID NO 27
<211> LENGTH: 251
<212> TYPE: PRT
<213> ORGANISM: Artificial
<220> FEATURE:
<223> OTHER INFORMATION: Assembly of protein
<220> FEATURE:
<221> NAME/KEY: MISC_FEATURE
<222> LOCATION: (1)..(251)
<223> OTHER INFORMATION: Amino acid sequence of VB4119

<400> SEQUENCE: 27

Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
                20                  25                  30

Ala Cys Cys Phe Ser Tyr Thr Ser Arg Gln Ile Pro Gln Asn Phe Ile
                35                  40                  45

Ala Asp Tyr Phe Glu Thr Ser Ser Gln Cys Ser Lys Pro Ser Val Ile
        50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala Glu Leu Lys
                85                  90                  95

Thr Pro Leu Gly Asp Thr Thr His Thr Glu Pro Lys Ser Cys Asp Thr
                100                 105                 110

Pro Pro Pro Cys Pro Arg Cys Pro Gly Gly Gly Ser Ser Gly Gly Gly
        115                 120                 125

Ser Gly Gly Gln Pro Arg Glu Pro Gln Val Tyr Thr Leu Pro Pro Ser
        130                 135                 140

Arg Glu Glu Met Thr Lys Asn Gln Val Ser Leu Thr Cys Leu Val Lys
145                 150                 155                 160

Gly Phe Tyr Pro Ser Asp Ile Ala Val Glu Trp Glu Ser Ser Gly Gln
                165                 170                 175

Pro Glu Asn Asn Tyr Asn Thr Thr Pro Pro Met Leu Asp Ser Asp Gly
                180                 185                 190

Ser Phe Phe Leu Tyr Ser Lys Leu Thr Val Asp Lys Ser Arg Trp Gln
        195                 200                 205

Gln Gly Asn Ile Phe Ser Cys Ser Val Met His Glu Ala Leu His Asn
        210                 215                 220

Arg Phe Thr Gln Lys Ser Leu Ser Leu Ser Pro Gly Lys Gly Leu Gly
225                 230                 235                 240
```

-continued

```
Gly Leu Ser Val Tyr Asp Phe Phe Val Trp Leu
            245                 250

<210> SEQ ID NO 28
<211> LENGTH: 387
<212> TYPE: PRT
<213> ORGANISM: Artificial
<220> FEATURE:
<223> OTHER INFORMATION: Assembly of protein
<220> FEATURE:
<221> NAME/KEY: MISC_FEATURE
<222> LOCATION: (1)..(387)
<223> OTHER INFORMATION: Amino acid sequence of VB4127

<400> SEQUENCE: 28

Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
            20                  25                  30

Ala Cys Cys Phe Ser Tyr Thr Ser Arg Gln Ile Pro Gln Asn Phe Ile
            35                  40                  45

Ala Asp Tyr Phe Glu Thr Ser Ser Gln Cys Ser Lys Pro Ser Val Ile
        50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala Glu Leu Lys
                85                  90                  95

Thr Pro Leu Gly Asp Thr Thr His Thr Glu Pro Lys Ser Cys Asp Thr
            100                 105                 110

Pro Pro Pro Cys Pro Arg Cys Pro Gly Gly Ser Ser Gly Gly Gly
            115                 120                 125

Ser Gly Gly Gln Pro Arg Glu Pro Gln Val Tyr Thr Leu Pro Pro Ser
        130                 135                 140

Arg Glu Glu Met Thr Lys Asn Gln Val Ser Leu Thr Cys Leu Val Lys
145                 150                 155                 160

Gly Phe Tyr Pro Ser Asp Ile Ala Val Glu Trp Glu Ser Ser Gly Gln
                165                 170                 175

Pro Glu Asn Asn Tyr Asn Thr Thr Pro Pro Met Leu Asp Ser Asp Gly
            180                 185                 190

Ser Phe Phe Leu Tyr Ser Lys Leu Thr Val Asp Lys Ser Arg Trp Gln
            195                 200                 205

Gln Gly Asn Ile Phe Ser Cys Ser Val Met His Glu Ala Leu His Asn
        210                 215                 220

Arg Phe Thr Gln Lys Ser Leu Ser Leu Ser Pro Gly Lys Gly Leu Gly
225                 230                 235                 240

Gly Leu Tyr Ile Ser Asp His Met Lys Val His Ser Pro Ser Pro Cys
                245                 250                 255

Leu Gly Gly Gly Gly Ser Gly Gly Gly Ser Glu Gly Trp Gln Thr
            260                 265                 270

Cys Trp Gly Arg Ser Arg Lys His Trp Gly Ser Thr Trp Asn Gly Ser
        275                 280                 285

Ala Arg Leu Ser Pro Gly Ser Thr Leu Trp Val Met Arg Ile Cys Leu
        290                 295                 300

Arg Ser Leu Gly Ile Ala Arg Thr Trp Leu Ser Cys Arg Ser Thr Ser
305                 310                 315                 320

Arg Lys Cys Ser Pro Ala Phe Pro Ala Ser Ser Gly Gly Gly Gly Gly
                325                 330                 335
```

-continued

```
Ser Gly Gly Gly Gly Ser Leu Phe Arg Leu Leu Pro Ser Gly Pro Lys
        340                 345                 350

Val Asn Asp Gly His Arg Ser Arg Arg Trp His Ser Leu Asp Leu Tyr
        355                 360                 365

Pro His Leu Cys Ser His Leu Asp Leu Pro Lys Gln Ser Gln Glu Val
        370                 375                 380

Ile Arg Leu
385

<210> SEQ ID NO 29
<211> LENGTH: 621
<212> TYPE: PRT
<213> ORGANISM: Artificial
<220> FEATURE:
<223> OTHER INFORMATION: Assembly of protein
<220> FEATURE:
<221> NAME/KEY: MISC_FEATURE
<222> LOCATION: (1)..(621)
<223> OTHER INFORMATION: Amino acid sequence of VB4121

<400> SEQUENCE: 29

Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
                20                  25                  30

Ala Cys Cys Phe Ser Tyr Thr Ser Arg Gln Ile Pro Gln Asn Phe Ile
        35                  40                  45

Ala Asp Tyr Phe Glu Thr Ser Ser Gln Cys Ser Lys Pro Ser Val Ile
        50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala Glu Leu Lys
                85                  90                  95

Thr Pro Leu Gly Asp Thr Thr His Thr Glu Pro Lys Ser Cys Asp Thr
                100                 105                 110

Pro Pro Pro Cys Pro Arg Cys Pro Gly Gly Gly Ser Ser Gly Gly Gly
            115                 120                 125

Ser Gly Gly Gln Pro Arg Glu Pro Gln Val Tyr Thr Leu Pro Pro Ser
        130                 135                 140

Arg Glu Glu Met Thr Lys Asn Gln Val Ser Leu Thr Cys Leu Val Lys
145                 150                 155                 160

Gly Phe Tyr Pro Ser Asp Ile Ala Val Glu Trp Glu Ser Ser Gly Gln
                165                 170                 175

Pro Glu Asn Asn Tyr Asn Thr Thr Pro Pro Met Leu Asp Ser Asp Gly
            180                 185                 190

Ser Phe Phe Leu Tyr Ser Lys Leu Thr Val Asp Lys Ser Arg Trp Gln
        195                 200                 205

Gln Gly Asn Ile Phe Ser Cys Ser Val Met His Glu Ala Leu His Asn
        210                 215                 220

Arg Phe Thr Gln Lys Ser Leu Ser Leu Ser Pro Gly Lys Gly Leu Gly
225                 230                 235                 240

Gly Leu Arg Glu Gly Val Glu Leu Cys Pro Gly Asn Lys Tyr Glu Met
                245                 250                 255

Arg Arg His Gly Thr Thr His Ser Leu Val Ile His Asp Gly Gly Gly
                260                 265                 270

Gly Ser Gly Gly Gly Gly Ser Ser Ser Pro Asp Glu Val Ala Leu Val
```

```
              275                 280                 285
Glu Gly Val Gln Ser Leu Gly Phe Thr Tyr Leu Arg Leu Lys Asp Asn
    290                 295                 300

Tyr Met Gly Gly Gly Gly Ser Gly Gly Gly Ser Leu Lys Asp Phe
305                 310                 315                 320

Phe Phe Ser Arg Gly Arg Phe Ser Ser Ala Leu Lys Arg Thr Leu Ile
                325                 330                 335

Leu Ser Ser Gly Phe Arg Leu Gly Gly Gly Ser Gly Gly Gly Gly
                340                 345                 350

Ser Lys Asn Ile Leu Ala Val Ser Phe Ala Pro Leu Val Gln Leu Ser
                355                 360                 365

Lys Asn Asp Asn Gly Thr Pro Asp Ser Val Gly Leu Gly Gly Gly Gly
    370                 375                 380

Ser Gly Gly Gly Gly Ser Leu Glu Ala Val Leu Arg Tyr Leu Glu Thr
385                 390                 395                 400

His Pro Arg Leu Pro Lys Pro Asp Pro Val Lys Ser Ser Ser Ser Val
                405                 410                 415

Leu Gly Gly Gly Gly Ser Gly Gly Gly Gly Ser Pro Ala Ala Asp Arg
                420                 425                 430

Trp Glu Pro Arg Ala Pro Met Arg Ala Pro Arg Val Leu His Ala Met
                435                 440                 445

Leu Gly Ala Ala Gly Arg Gly Gly Gly Gly Ser Gly Gly Gly Gly Ser
    450                 455                 460

Val Leu Ser Ala Asp Leu Val His Tyr Leu Arg Leu Ser Leu Glu Tyr
465                 470                 475                 480

Leu Arg Ala Trp His Ser Glu Asp Val Ser Leu Gly Gly Gly Gly Ser
                485                 490                 495

Gly Gly Gly Gly Ser Tyr Leu Pro Gly Gly Gly Ala Gly His Leu Asp
                500                 505                 510

Gln Asn Val Phe Leu Arg Val Arg Ala Leu Cys Tyr Val Ile Ser Gly
                515                 520                 525

Gly Gly Gly Gly Ser Gly Gly Gly Gly Ser Pro Ala Thr Ile Glu Met
    530                 535                 540

Ala Ile Glu Thr Leu Gln Lys Phe Asp Gly Leu Ser Thr His Arg Ser
545                 550                 555                 560

Ser Leu Leu Asn Ser Gly Gly Gly Gly Ser Gly Gly Gly Gly Ser Ala
                565                 570                 575

Gly Lys Asp His Lys Ile Lys Gln Trp Asp Ala Asp Thr Phe Glu His
                580                 585                 590

Ile Gln Thr Leu Glu Gly His His Gln Glu Gly Gly Gly Gly Ser Gly
                595                 600                 605

Gly Gly Gly Ser Ser Val Tyr Asp Phe Phe Val Trp Leu
    610                 615                 620
```

<210> SEQ ID NO 30
<211> LENGTH: 757
<212> TYPE: PRT
<213> ORGANISM: Artificial
<220> FEATURE:
<223> OTHER INFORMATION: Assembly of protein
<220> FEATURE:
<221> NAME/KEY: MISC_FEATURE
<222> LOCATION: (1)..(757)
<223> OTHER INFORMATION: Amino acid sequence of VB4128

<400> SEQUENCE: 30

-continued

```
Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
            20                  25                  30

Ala Cys Cys Phe Ser Tyr Thr Ser Arg Gln Ile Pro Gln Asn Phe Ile
            35                  40                  45

Ala Asp Tyr Phe Glu Thr Ser Ser Gln Cys Ser Lys Pro Ser Val Ile
    50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala Glu Leu Lys
                85                  90                  95

Thr Pro Leu Gly Asp Thr Thr His Thr Glu Pro Lys Ser Cys Asp Thr
            100                 105                 110

Pro Pro Pro Cys Pro Arg Cys Pro Gly Gly Gly Ser Ser Gly Gly Gly
        115                 120                 125

Ser Gly Gly Gln Pro Arg Glu Pro Gln Val Tyr Thr Leu Pro Pro Ser
    130                 135                 140

Arg Glu Glu Met Thr Lys Asn Gln Val Ser Leu Thr Cys Leu Val Lys
145                 150                 155                 160

Gly Phe Tyr Pro Ser Asp Ile Ala Val Glu Trp Glu Ser Ser Gly Gln
                165                 170                 175

Pro Glu Asn Asn Tyr Asn Thr Thr Pro Pro Met Leu Asp Ser Asp Gly
            180                 185                 190

Ser Phe Phe Leu Tyr Ser Lys Leu Thr Val Asp Lys Ser Arg Trp Gln
            195                 200                 205

Gln Gly Asn Ile Phe Ser Cys Ser Val Met His Glu Ala Leu His Asn
    210                 215                 220

Arg Phe Thr Gln Lys Ser Leu Ser Leu Ser Pro Gly Lys Gly Leu Gly
225                 230                 235                 240

Gly Leu Tyr Ile Ser Asp His Met Lys Val His Ser Pro Ser Pro Cys
                245                 250                 255

Leu Gly Gly Gly Gly Ser Gly Gly Gly Ser Glu Gly Trp Gln Thr
            260                 265                 270

Cys Trp Gly Arg Ser Arg Lys His Trp Gly Ser Thr Trp Asn Gly Ser
        275                 280                 285

Ala Arg Leu Ser Pro Gly Ser Thr Leu Trp Val Met Arg Ile Cys Leu
    290                 295                 300

Arg Ser Leu Gly Ile Ala Arg Thr Trp Leu Ser Cys Arg Ser Thr Ser
305                 310                 315                 320

Arg Lys Cys Ser Pro Ala Phe Pro Ala Ser Ser Gly Gly Gly Gly Gly
            325                 330                 335

Ser Gly Gly Gly Gly Ser Leu Phe Arg Leu Leu Pro Ser Gly Pro Lys
            340                 345                 350

Val Asn Asp Gly His Arg Ser Arg Arg Trp His Ser Leu Asp Leu Tyr
            355                 360                 365

Pro His Leu Cys Ser His Leu Asp Leu Pro Lys Gln Ser Gln Glu Val
        370                 375                 380

Ile Arg Leu Gly Gly Gly Gly Ser Gly Gly Gly Gly Ser Arg Glu Gly
385                 390                 395                 400

Val Glu Leu Cys Pro Gly Asn Lys Tyr Glu Met Arg Arg His Gly Thr
                405                 410                 415

Thr His Ser Leu Val Ile His Asp Gly Gly Gly Gly Ser Gly Gly Gly
```

-continued

```
                    420                 425                 430
Gly Ser Ser Ser Pro Asp Glu Val Ala Leu Val Glu Gly Val Gln Ser
        435                 440                 445

Leu Gly Phe Thr Tyr Leu Arg Leu Lys Asp Asn Tyr Met Gly Gly Gly
        450                 455                 460

Gly Ser Gly Gly Gly Gly Ser Leu Lys Asp Phe Phe Phe Ser Arg Gly
465                 470                 475                 480

Arg Phe Ser Ser Ala Leu Lys Arg Thr Leu Ile Leu Ser Ser Gly Phe
                485                 490                 495

Arg Leu Gly Gly Gly Gly Ser Gly Gly Gly Gly Ser Lys Asn Ile Leu
                500                 505                 510

Ala Val Ser Phe Ala Pro Leu Val Gln Leu Ser Lys Asn Asp Asn Gly
                515                 520                 525

Thr Pro Asp Ser Val Gly Leu Gly Gly Gly Gly Ser Gly Gly Gly Gly
        530                 535                 540

Ser Leu Glu Ala Val Leu Arg Tyr Leu Glu Thr His Pro Arg Leu Pro
545                 550                 555                 560

Lys Pro Asp Pro Val Lys Ser Ser Ser Val Leu Gly Gly Gly Gly
                565                 570                 575

Ser Gly Gly Gly Gly Ser Pro Ala Ala Asp Arg Trp Glu Pro Arg Ala
                580                 585                 590

Pro Met Arg Ala Pro Arg Val Leu His Ala Met Leu Gly Ala Ala Gly
                595                 600                 605

Arg Gly Gly Gly Gly Ser Gly Gly Gly Gly Ser Val Leu Ser Ala Asp
        610                 615                 620

Leu Val His Tyr Leu Arg Leu Ser Leu Glu Tyr Leu Arg Ala Trp His
625                 630                 635                 640

Ser Glu Asp Val Ser Leu Gly Gly Gly Gly Ser Gly Gly Gly Gly Ser
                645                 650                 655

Tyr Leu Pro Gly Gly Gly Ala Gly His Leu Asp Gln Asn Val Phe Leu
                660                 665                 670

Arg Val Arg Ala Leu Cys Tyr Val Ile Ser Gly Gly Gly Gly Gly Ser
                675                 680                 685

Gly Gly Gly Gly Ser Pro Ala Thr Ile Glu Met Ala Ile Glu Thr Leu
        690                 695                 700

Gln Lys Phe Asp Gly Leu Ser Thr His Arg Ser Ser Leu Leu Asn Ser
705                 710                 715                 720

Gly Gly Gly Gly Ser Gly Gly Gly Gly Ser Ala Gly Lys Asp His Lys
                725                 730                 735

Ile Lys Gln Trp Asp Ala Asp Thr Phe Glu His Ile Gln Thr Leu Glu
                740                 745                 750

Gly His His Gln Glu
        755
```

<210> SEQ ID NO 31
<211> LENGTH: 786
<212> TYPE: PRT
<213> ORGANISM: Artificial
<220> FEATURE:
<223> OTHER INFORMATION: Assembly of protein
<220> FEATURE:
<221> NAME/KEY: MISC_FEATURE
<222> LOCATION: (1)..(786)
<223> OTHER INFORMATION: Amino acid sequence of VB4130

<400> SEQUENCE: 31

```
Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
            20                  25                  30

Ala Cys Cys Phe Ser Tyr Thr Ser Arg Gln Ile Pro Gln Asn Phe Ile
        35                  40                  45

Ala Asp Tyr Phe Glu Thr Ser Ser Gln Cys Ser Lys Pro Ser Val Ile
    50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala Glu Leu Lys
                85                  90                  95

Thr Pro Leu Gly Asp Thr Thr His Thr Glu Pro Lys Ser Cys Asp Thr
            100                 105                 110

Pro Pro Pro Cys Pro Arg Cys Pro Gly Gly Gly Ser Ser Gly Gly Gly
        115                 120                 125

Ser Gly Gly Gln Pro Arg Glu Pro Gln Val Tyr Thr Leu Pro Pro Ser
    130                 135                 140

Arg Glu Glu Met Thr Lys Asn Gln Val Ser Leu Thr Cys Leu Val Lys
145                 150                 155                 160

Gly Phe Tyr Pro Ser Asp Ile Ala Val Glu Trp Glu Ser Ser Gly Gln
                165                 170                 175

Pro Glu Asn Asn Tyr Asn Thr Thr Pro Pro Met Leu Asp Ser Asp Gly
            180                 185                 190

Ser Phe Phe Leu Tyr Ser Lys Leu Thr Val Asp Lys Ser Arg Trp Gln
            195                 200                 205

Gln Gly Asn Ile Phe Ser Cys Ser Val Met His Glu Ala Leu His Asn
    210                 215                 220

Arg Phe Thr Gln Lys Ser Leu Ser Leu Ser Pro Gly Lys Gly Leu Gly
225                 230                 235                 240

Gly Leu Tyr Ile Ser Asp His Met Lys Val His Ser Pro Ser Pro Cys
            245                 250                 255

Leu Gly Gly Gly Gly Ser Gly Gly Gly Ser Glu Gly Trp Gln Thr
            260                 265                 270

Cys Trp Gly Arg Ser Arg Lys His Trp Gly Ser Thr Trp Asn Gly Ser
            275                 280                 285

Ala Arg Leu Ser Pro Gly Ser Thr Leu Trp Val Met Arg Ile Cys Leu
    290                 295                 300

Arg Ser Leu Gly Ile Ala Arg Thr Trp Leu Ser Cys Arg Ser Thr Ser
305                 310                 315                 320

Arg Lys Cys Ser Pro Ala Phe Pro Ala Ser Ser Gly Gly Gly Gly Gly
            325                 330                 335

Ser Gly Gly Gly Gly Ser Leu Phe Arg Leu Leu Pro Ser Gly Pro Lys
            340                 345                 350

Val Asn Asp Gly His Arg Ser Arg Arg Trp His Ser Leu Asp Leu Tyr
            355                 360                 365

Pro His Leu Cys Ser His Leu Asp Leu Pro Lys Gln Ser Gln Glu Val
    370                 375                 380

Ile Arg Leu Gly Gly Gly Gly Ser Gly Gly Gly Gly Ser Arg Glu Gly
385                 390                 395                 400

Val Glu Leu Cys Pro Gly Asn Lys Tyr Glu Met Arg Arg His Gly Thr
            405                 410                 415

Thr His Ser Leu Val Ile His Asp Gly Gly Gly Gly Ser Gly Gly Gly
```

-continued

```
            420              425              430
Gly Ser Ser Ser Pro Asp Glu Val Ala Leu Val Glu Gly Val Gln Ser
        435              440              445

Leu Gly Phe Thr Tyr Leu Arg Leu Lys Asp Asn Tyr Met Gly Gly Gly
        450              455              460

Gly Ser Gly Gly Gly Gly Ser Leu Lys Asp Phe Phe Phe Ser Arg Gly
465              470              475              480

Arg Phe Ser Ser Ala Leu Lys Arg Thr Leu Ile Leu Ser Ser Gly Phe
                485              490              495

Arg Leu Gly Gly Gly Gly Ser Gly Gly Gly Gly Ser Lys Asn Ile Leu
                500              505              510

Ala Val Ser Phe Ala Pro Leu Val Gln Leu Ser Lys Asn Asp Asn Gly
                515              520              525

Thr Pro Asp Ser Val Gly Leu Gly Gly Gly Gly Ser Gly Gly Gly Gly
        530              535              540

Ser Leu Glu Ala Val Leu Arg Tyr Leu Glu Thr His Pro Arg Leu Pro
545              550              555              560

Lys Pro Asp Pro Val Lys Ser Ser Ser Val Leu Gly Gly Gly Gly
                565              570              575

Ser Gly Gly Gly Gly Ser Pro Ala Ala Asp Arg Trp Glu Pro Arg Ala
                580              585              590

Pro Met Arg Ala Pro Arg Val Leu His Ala Met Leu Gly Ala Ala Gly
                595              600              605

Arg Gly Gly Gly Gly Ser Gly Gly Gly Gly Ser Val Leu Ser Ala Asp
        610              615              620

Leu Val His Tyr Leu Arg Leu Ser Leu Glu Tyr Leu Arg Ala Trp His
625              630              635              640

Ser Glu Asp Val Ser Leu Gly Gly Gly Gly Ser Gly Gly Gly Gly Ser
                645              650              655

Tyr Leu Pro Gly Gly Gly Ala Gly His Leu Asp Gln Asn Val Phe Leu
                660              665              670

Arg Val Arg Ala Leu Cys Tyr Val Ile Ser Gly Gly Gly Gly Gly Ser
                675              680              685

Gly Gly Gly Gly Ser Pro Ala Thr Ile Glu Met Ala Ile Glu Thr Leu
        690              695              700

Gln Lys Phe Asp Gly Leu Ser Thr His Arg Ser Ser Leu Leu Asn Ser
705              710              715              720

Gly Gly Gly Gly Ser Gly Gly Gly Gly Ser Ala Gly Lys Asp His Lys
                725              730              735

Ile Lys Gln Trp Asp Ala Asp Thr Phe Glu His Ile Gln Thr Leu Glu
                740              745              750

Gly His His Gln Glu Gly Gly Gly Gly Ser Gly Gly Gly Gly Ser Ser
        755              760              765

Val Tyr Asp Phe Phe Val Trp Leu Gly Gly Gly Gly Ser Gly Gly Gly
        770              775              780

Gly Ser
785
```

```
<210> SEQ ID NO 32
<211> LENGTH: 9
<212> TYPE: PRT
<213> ORGANISM: Artificial
<220> FEATURE:
<223> OTHER INFORMATION: Epitope for binding
<220> FEATURE:
```

```
<221> NAME/KEY: MISC_FEATURE
<222> LOCATION: (1)..(9)
<223> OTHER INFORMATION: Epitope

<400> SEQUENCE: 32

Gln Glu Arg Pro Arg Lys Leu Pro Gln
1               5

<210> SEQ ID NO 33
<211> LENGTH: 9
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(9)
<223> OTHER INFORMATION: Epitope

<400> SEQUENCE: 33

Arg Pro Arg Lys Leu Pro Gln Leu Cys
1               5

<210> SEQ ID NO 34
<211> LENGTH: 9
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(9)
<223> OTHER INFORMATION: Epitope

<400> SEQUENCE: 34

Ile His Asp Ile Ile Leu Glu Cys Val
1               5

<210> SEQ ID NO 35
<211> LENGTH: 9
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(9)
<223> OTHER INFORMATION: Epitope

<400> SEQUENCE: 35

His Asp Ile Ile Leu Glu Cys Val Tyr
1               5

<210> SEQ ID NO 36
<211> LENGTH: 9
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(9)
<223> OTHER INFORMATION: Epitope

<400> SEQUENCE: 36

Ile Ile Leu Glu Cys Val Tyr Cys Lys
1               5

<210> SEQ ID NO 37
```

```
<211> LENGTH: 9
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(9)
<223> OTHER INFORMATION: Epitope

<400> SEQUENCE: 37

Gln Gln Leu Leu Arg Arg Glu Val Tyr
1               5

<210> SEQ ID NO 38
<211> LENGTH: 9
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(9)
<223> OTHER INFORMATION: Epitope

<400> SEQUENCE: 38

Val Tyr Asp Phe Ala Arg Arg Asp Leu
1               5

<210> SEQ ID NO 39
<211> LENGTH: 9
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(9)
<223> OTHER INFORMATION: Epitope

<400> SEQUENCE: 39

Tyr Asp Phe Ala Arg Arg Asp Leu Cys
1               5

<210> SEQ ID NO 40
<211> LENGTH: 9
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(9)
<223> OTHER INFORMATION: Epitope

<400> SEQUENCE: 40

Asp Phe Ala Arg Arg Asp Leu Cys Ile
1               5

<210> SEQ ID NO 41
<211> LENGTH: 9
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(9)
<223> OTHER INFORMATION: Epitope

<400> SEQUENCE: 41
```

Phe Ala Arg Arg Asp Leu Cys Ile Val
1               5

<210> SEQ ID NO 42
<211> LENGTH: 9
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(9)
<223> OTHER INFORMATION: Epitope

<400> SEQUENCE: 42

Tyr Ala Val Arg Asp Lys Cys Leu Lys
1               5

<210> SEQ ID NO 43
<211> LENGTH: 9
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(9)
<223> OTHER INFORMATION: Epitope

<400> SEQUENCE: 43

Val Arg Asp Lys Cys Leu Lys Phe Tyr
1               5

<210> SEQ ID NO 44
<211> LENGTH: 9
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(9)
<223> OTHER INFORMATION: Epitope

<400> SEQUENCE: 44

Tyr Ser Leu Tyr Gly Thr Thr Leu Glu
1               5

<210> SEQ ID NO 45
<211> LENGTH: 9
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(9)
<223> OTHER INFORMATION: Epitope

<400> SEQUENCE: 45

Phe His Asn Ile Arg Gly Arg Trp Thr
1               5

<210> SEQ ID NO 46
<211> LENGTH: 9
<212> TYPE: PRT
<213> ORGANISM: Artificial
<220> FEATURE:
<223> OTHER INFORMATION: Epitope for binding

```
<220> FEATURE:
<221> NAME/KEY: MISC_FEATURE
<222> LOCATION: (1)..(9)
<223> OTHER INFORMATION: Epitope

<400> SEQUENCE: 46

Arg Trp Thr Gly Arg Cys Met Ser Cys
1               5

<210> SEQ ID NO 47
<211> LENGTH: 9
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(9)
<223> OTHER INFORMATION: Epitope

<400> SEQUENCE: 47

Ser Arg Thr Arg Arg Glu Thr Gln Leu
1               5

<210> SEQ ID NO 48
<211> LENGTH: 15
<212> TYPE: PRT
<213> ORGANISM: Artificial
<220> FEATURE:
<223> OTHER INFORMATION: Epitope for binding

<400> SEQUENCE: 48

Cys Thr Glu Leu Gln Thr Thr Ile His Asp Ile Ile Leu Glu Cys
1               5                   10                  15

<210> SEQ ID NO 49
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 49

Thr Glu Leu Gln Thr Thr Ile His Asp Ile Ile Leu Glu Cys Val
1               5                   10                  15

<210> SEQ ID NO 50
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 50

Glu Leu Gln Thr Thr Ile His Asp Ile Ile Leu Glu Cys Val Tyr
1               5                   10                  15

<210> SEQ ID NO 51
<211> LENGTH: 15
<212> TYPE: PRT
<213> ORGANISM: Artificial
```

-continued

```
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 51

Leu Gln Thr Thr Ile His Asp Ile Ile Leu Glu Cys Val Tyr Cys
1               5                   10                  15

<210> SEQ ID NO 52
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 52

Gln Thr Thr Ile His Asp Ile Ile Leu Glu Cys Val Tyr Cys Lys
1               5                   10                  15

<210> SEQ ID NO 53
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 53

Lys Gln Gln Leu Leu Arg Arg Glu Val Tyr Asp Phe Ala Arg Arg
1               5                   10                  15

<210> SEQ ID NO 54
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 54

Asp Leu Cys Ile Val Tyr Arg Asp Gly Asn Pro Tyr Ala Val Arg
1               5                   10                  15

<210> SEQ ID NO 55
<211> LENGTH: 15
<212> TYPE: PRT
<213> ORGANISM: Artificial
<220> FEATURE:
<223> OTHER INFORMATION: Epitope for binding

<400> SEQUENCE: 55

Leu Cys Ile Val Tyr Arg Asp Gly Asn Pro Tyr Ala Val Arg Asp
1               5                   10                  15

<210> SEQ ID NO 56
<211> LENGTH: 15
```

```
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<220> FEATURE:
<221> NAME/KEY: MISC_FEATURE
<222> LOCATION: (1)..(15)
<223> OTHER INFORMATION: Epitope

<400> SEQUENCE: 56

Cys Ile Val Tyr Arg Asp Gly Asn Pro Tyr Ala Val Arg Asp Lys
1               5                   10                  15

<210> SEQ ID NO 57
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 57

His Tyr Cys Tyr Ser Leu Tyr Gly Thr Thr Leu Glu Gln Gln Tyr
1               5                   10                  15

<210> SEQ ID NO 58
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 58

Pro Leu Cys Asp Leu Leu Ile Arg Cys Ile Asn Arg Gln Lys Pro
1               5                   10                  15

<210> SEQ ID NO 59
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 59

Leu Cys Asp Leu Leu Ile Arg Cys Ile Asn Arg Gln Lys Pro Leu
1               5                   10                  15

<210> SEQ ID NO 60
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope
```

<400> SEQUENCE: 60

Cys Asp Leu Leu Ile Arg Cys Ile Asn Arg Gln Lys Pro Leu Cys
1               5                   10                  15

<210> SEQ ID NO 61
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 61

Asp Leu Leu Ile Arg Cys Ile Asn Arg Gln Lys Pro Leu Cys Pro
1               5                   10                  15

<210> SEQ ID NO 62
<211> LENGTH: 15
<212> TYPE: PRT
<213> ORGANISM: Artificial
<220> FEATURE:
<223> OTHER INFORMATION: Epitope for binding

<400> SEQUENCE: 62

Leu Leu Ile Arg Cys Ile Asn Arg Gln Lys Pro Leu Cys Pro Glu
1               5                   10                  15

<210> SEQ ID NO 63
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 63

Lys Lys Gln Arg Phe His Asn Ile Arg Gly Arg Trp Thr Gly Arg
1               5                   10                  15

<210> SEQ ID NO 64
<211> LENGTH: 9
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(9)
<223> OTHER INFORMATION: Epitope

<400> SEQUENCE: 64

Thr Leu His Glu Tyr Met Leu Asp Leu
1               5

<210> SEQ ID NO 65
<211> LENGTH: 9
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE -continued

```
<222> LOCATION: (1)..(9)
<223> OTHER INFORMATION: Epitope

<400> SEQUENCE: 65

Leu Tyr Gly Tyr Gly Gln Leu Asn Asp
1               5

<210> SEQ ID NO 66
<211> LENGTH: 9
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(9)
<223> OTHER INFORMATION: Epitope

<400> SEQUENCE: 66

Ile Asp Gly Pro Ala Gly Gln Ala Glu
1               5

<210> SEQ ID NO 67
<211> LENGTH: 9
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(9)
<223> OTHER INFORMATION: Epitope

<400> SEQUENCE: 67

Asp Arg Ala His Tyr Asn Ile Val Thr
1               5

<210> SEQ ID NO 68
<211> LENGTH: 9
<212> TYPE: PRT
<213> ORGANISM: Artificial
<220> FEATURE:
<223> OTHER INFORMATION: Epitope for binding

<400> SEQUENCE: 68

Val Thr Phe Cys Cys Lys Cys Asp Ser
1               5

<210> SEQ ID NO 69
<211> LENGTH: 9
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(9)
<223> OTHER INFORMATION: Epitope

<400> SEQUENCE: 69

Arg Leu Cys Val Gln Ser Thr His Val
1               5

<210> SEQ ID NO 70
<211> LENGTH: 9
<212> TYPE: PRT
<213> ORGANISM: Artificial
<220> FEATURE:
<223> OTHER INFORMATION: Epitope for binding
```

```
<220> FEATURE:
<221> NAME/KEY: MISC_FEATURE
<222> LOCATION: (1)..(9)
<223> OTHER INFORMATION: Epitope

<400> SEQUENCE: 70

Thr His Val Asp Ile Arg Thr Leu Glu
1               5

<210> SEQ ID NO 71
<211> LENGTH: 9
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(9)
<223> OTHER INFORMATION: Epitope

<400> SEQUENCE: 71

His Val Asp Ile Arg Thr Leu Glu Asp
1               5

<210> SEQ ID NO 72
<211> LENGTH: 9
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(9)
<223> OTHER INFORMATION: Epitope

<400> SEQUENCE: 72

Gly Thr Leu Gly Ile Val Cys Pro Ile
1               5

<210> SEQ ID NO 73
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 73

Asp Thr Pro Thr Leu His Glu Tyr Met Leu Asp Leu Gln Pro Glu
1               5                   10                  15

<210> SEQ ID NO 74
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 74

Thr Pro Thr Leu His Glu Tyr Met Leu Asp Leu Gln Pro Glu Thr
1               5                   10                  15
```

```
<210> SEQ ID NO 75
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 75

Pro Thr Leu His Glu Tyr Met Leu Asp Leu Gln Pro Glu Thr Thr
1               5                   10                  15

<210> SEQ ID NO 76
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 76

Thr Leu His Glu Tyr Met Leu Asp Leu Gln Pro Glu Thr Thr Asp
1               5                   10                  15

<210> SEQ ID NO 77
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 77

Leu His Glu Tyr Met Leu Asp Leu Gln Pro Glu Thr Thr Asp Leu
1               5                   10                  15

<210> SEQ ID NO 78
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 78

His Glu Tyr Met Leu Asp Leu Gln Pro Glu Thr Thr Asp Leu Tyr
1               5                   10                  15

<210> SEQ ID NO 79
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope
```

-continued

```
<400> SEQUENCE: 79

Glu Tyr Met Leu Asp Leu Gln Pro Glu Thr Thr Asp Leu Tyr Gly
1               5                   10                  15

<210> SEQ ID NO 80
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 80

Gln Ser Thr His Val Asp Ile Arg Thr Leu Glu Asp Leu Leu Met
1               5                   10                  15

<210> SEQ ID NO 81
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 81

Ser Thr His Val Asp Ile Arg Thr Leu Glu Asp Leu Leu Met Gly
1               5                   10                  15

<210> SEQ ID NO 82
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 82

Thr His Val Asp Ile Arg Thr Leu Glu Asp Leu Leu Met Gly Thr
1               5                   10                  15

<210> SEQ ID NO 83
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 83

His Val Asp Ile Arg Thr Leu Glu Asp Leu Leu Met Gly Thr Leu
1               5                   10                  15

<210> SEQ ID NO 84
<211> LENGTH: 15
<212> TYPE: PRT
<213> ORGANISM: Artificial
<220> FEATURE:
```

```
<223> OTHER INFORMATION: Epitope for binding
<220> FEATURE:
<221> NAME/KEY: MISC_FEATURE
<222> LOCATION: (1)..(15)
<220> FEATURE:
<221> NAME/KEY: MISC_FEATURE
<222> LOCATION: (1)..(15)
<223> OTHER INFORMATION: Epitope

<400> SEQUENCE: 84

Val Asp Ile Arg Thr Leu Glu Asp Leu Leu Met Gly Thr Leu Gly
1               5                   10                  15

<210> SEQ ID NO 85
<211> LENGTH: 9
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(9)
<223> OTHER INFORMATION: Epitope

<400> SEQUENCE: 85

Cys Thr Glu Leu Gln Thr Thr Ile His
1               5

<210> SEQ ID NO 86
<211> LENGTH: 9
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(9)
<223> OTHER INFORMATION: Epitope

<400> SEQUENCE: 86

Val Tyr Asp Phe Ala Arg Arg Asp Leu
1               5

<210> SEQ ID NO 87
<211> LENGTH: 9
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(9)
<223> OTHER INFORMATION: Epitope

<400> SEQUENCE: 87

Phe Ala Arg Arg Asp Leu Cys Ile Val
1               5

<210> SEQ ID NO 88
<211> LENGTH: 9
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(9)
<223> OTHER INFORMATION: Epitope

<400> SEQUENCE: 88
```

-continued

```
Ile Val Tyr Arg Asp Gly Asn Pro Tyr
1               5

<210> SEQ ID NO 89
<211> LENGTH: 9
<212> TYPE: PRT
<213> ORGANISM: Artificial
<220> FEATURE:
<223> OTHER INFORMATION: Epitope for binding

<400> SEQUENCE: 89

Tyr Arg Asp Gly Asn Pro Tyr Ala Val
1               5

<210> SEQ ID NO 90
<211> LENGTH: 9
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(9)
<223> OTHER INFORMATION: Epitope

<400> SEQUENCE: 90

Lys Phe Tyr Ser Lys Ile Ser Glu Tyr
1               5

<210> SEQ ID NO 91
<211> LENGTH: 9
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(9)
<223> OTHER INFORMATION: Epitope

<400> SEQUENCE: 91

Ile Ser Glu Tyr Arg His Tyr Cys Tyr
1               5

<210> SEQ ID NO 92
<211> LENGTH: 9
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(9)
<223> OTHER INFORMATION: Epitope

<400> SEQUENCE: 92

Glu Tyr Arg His Tyr Cys Tyr Ser Leu
1               5

<210> SEQ ID NO 93
<211> LENGTH: 9
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(9)
<223> OTHER INFORMATION: Epitope
```

-continued

```
<400> SEQUENCE: 93

Cys Tyr Ser Leu Tyr Gly Thr Thr Leu
1               5

<210> SEQ ID NO 94
<211> LENGTH: 9
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(9)
<223> OTHER INFORMATION: Epitope

<400> SEQUENCE: 94

Tyr Gly Thr Thr Leu Glu Gln Gln Tyr
1               5

<210> SEQ ID NO 95
<211> LENGTH: 9
<212> TYPE: PRT
<213> ORGANISM: Artificial
<220> FEATURE:
<223> OTHER INFORMATION: Epitope for binding

<400> SEQUENCE: 95

Leu Glu Gln Gln Tyr Asn Lys Pro Leu
1               5

<210> SEQ ID NO 96
<211> LENGTH: 9
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(9)
<223> OTHER INFORMATION: Epitope

<400> SEQUENCE: 96

Gln Tyr Asn Lys Pro Leu Cys Asp Leu
1               5

<210> SEQ ID NO 97
<211> LENGTH: 9
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(9)
<223> OTHER INFORMATION: Epitope

<400> SEQUENCE: 97

Arg His Leu Asp Lys Lys Gln Arg Phe
1               5

<210> SEQ ID NO 98
<211> LENGTH: 9
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(9)
```

-continued

```
<223> OTHER INFORMATION: Epitope

<400> SEQUENCE: 98

Arg Phe His Asn Ile Arg Gly Arg Trp
1               5

<210> SEQ ID NO 99
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 99

Glu Leu Gln Thr Thr Ile His Asp Ile Ile Leu Glu Cys Val Tyr
1               5                   10                  15

<210> SEQ ID NO 100
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 100

Asp Leu Cys Ile Val Tyr Arg Asp Gly Asn Pro Tyr Ala Val Arg
1               5                   10                  15

<210> SEQ ID NO 101
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 101

Leu Cys Ile Val Tyr Arg Asp Gly Asn Pro Tyr Ala Val Arg Asp
1               5                   10                  15

<210> SEQ ID NO 102
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 102

Cys Ile Val Tyr Arg Asp Gly Asn Pro Tyr Ala Val Arg Asp Lys
1               5                   10                  15

<210> SEQ ID NO 103
<211> LENGTH: 15
<212> TYPE: PRT
```

<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 103

Ser Glu Tyr Arg His Tyr Cys Tyr Ser Leu Tyr Gly Thr Thr Leu
1               5                   10                  15

<210> SEQ ID NO 104
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 104

Glu Tyr Arg His Tyr Cys Tyr Ser Leu Tyr Gly Thr Thr Leu Glu
1               5                   10                  15

<210> SEQ ID NO 105
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 105

Tyr Arg His Tyr Cys Tyr Ser Leu Tyr Gly Thr Thr Leu Glu Gln
1               5                   10                  15

<210> SEQ ID NO 106
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 106

Arg His Tyr Cys Tyr Ser Leu Tyr Gly Thr Thr Leu Glu Gln Gln
1               5                   10                  15

<210> SEQ ID NO 107
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 107

His Tyr Cys Tyr Ser Leu Tyr Gly Thr Thr Leu Glu Gln Gln Tyr

-continued

```
1               5                       10                      15
```

<210> SEQ ID NO 108
<211> LENGTH: 15
<212> TYPE: PRT
<213> ORGANISM: Artificial
<220> FEATURE:
<223> OTHER INFORMATION: Epitope for binding

<400> SEQUENCE: 108

Leu Cys Asp Leu Leu Ile Arg Cys Ile Asn Arg Gln Lys Pro Leu
1               5                       10                      15

<210> SEQ ID NO 109
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 109

Cys Asp Leu Leu Ile Arg Cys Ile Asn Arg Gln Lys Pro Leu Cys
1               5                       10                      15

<210> SEQ ID NO 110
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 110

Asp Leu Leu Ile Arg Cys Ile Asn Arg Gln Lys Pro Leu Cys Pro
1               5                       10                      15

<210> SEQ ID NO 111
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 111

Leu Leu Ile Arg Cys Ile Asn Arg Gln Lys Pro Leu Cys Pro Glu
1               5                       10                      15

<210> SEQ ID NO 112
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 112

```
Lys Lys Gln Arg Phe His Asn Ile Arg Gly Arg Trp Thr Gly Arg
1               5                   10                  15
```

<210> SEQ ID NO 113
<211> LENGTH: 9
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(9)
<223> OTHER INFORMATION: Epitope

<400> SEQUENCE: 113

```
Gly Asp Thr Pro Thr Leu His Glu Tyr
1               5
```

<210> SEQ ID NO 114
<211> LENGTH: 9
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(9)
<223> OTHER INFORMATION: Epitope

<400> SEQUENCE: 114

```
Thr Leu His Glu Tyr Met Leu Asp Leu
1               5
```

<210> SEQ ID NO 115
<211> LENGTH: 9
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(9)
<223> OTHER INFORMATION: Epitope

<400> SEQUENCE: 115

```
His Glu Tyr Met Leu Asp Leu Gln Pro
1               5
```

<210> SEQ ID NO 116
<211> LENGTH: 9
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(9)
<223> OTHER INFORMATION: Epitope

<400> SEQUENCE: 116

```
Leu Gln Pro Glu Thr Thr Asp Leu Tyr
1               5
```

<210> SEQ ID NO 117
<211> LENGTH: 9
<212> TYPE: PRT
<213> ORGANISM: Artificial
<220> FEATURE:
<223> OTHER INFORMATION: Epitope for binding

```
<220> FEATURE:
<221> NAME/KEY: MISC_FEATURE
<222> LOCATION: (1)..(9)
<223> OTHER INFORMATION: Epitope

<400> SEQUENCE: 117

Thr Thr Asp Leu Tyr Gly Tyr Gly Gln
1               5

<210> SEQ ID NO 118
<211> LENGTH: 9
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(9)
<223> OTHER INFORMATION: Epitope

<400> SEQUENCE: 118

Thr Asp Leu Tyr Gly Tyr Gly Gln Leu
1               5

<210> SEQ ID NO 119
<211> LENGTH: 9
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(9)
<223> OTHER INFORMATION: Epitope

<400> SEQUENCE: 119

Gln Ala Glu Pro Asp Arg Ala His Tyr
1               5

<210> SEQ ID NO 120
<211> LENGTH: 9
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(9)
<223> OTHER INFORMATION: Epitope

<400> SEQUENCE: 120

Arg Ala His Tyr Asn Ile Val Thr Phe
1               5

<210> SEQ ID NO 121
<211> LENGTH: 9
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(9)
<223> OTHER INFORMATION: Epitope

<400> SEQUENCE: 121

Ser Thr His Val Asp Ile Arg Thr Leu
1               5
```

```
<210> SEQ ID NO 122
<211> LENGTH: 9
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(9)
<223> OTHER INFORMATION: Epitope

<400> SEQUENCE: 122

Leu Glu Asp Leu Leu Met Gly Thr Leu
1               5

<210> SEQ ID NO 123
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 123

Gly Asp Thr Pro Thr Leu His Glu Tyr Met Leu Asp Leu Gln Pro
1               5                   10                  15

<210> SEQ ID NO 124
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 124

Asp Thr Pro Thr Leu His Glu Tyr Met Leu Asp Leu Gln Pro Glu
1               5                   10                  15

<210> SEQ ID NO 125
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 125

Thr Pro Thr Leu His Glu Tyr Met Leu Asp Leu Gln Pro Glu Thr
1               5                   10                  15

<210> SEQ ID NO 126
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope
```

-continued

<400> SEQUENCE: 126

Pro Thr Leu His Glu Tyr Met Leu Asp Leu Gln Pro Glu Thr Thr
1               5                   10                  15

<210> SEQ ID NO 127
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 127

Thr Leu His Glu Tyr Met Leu Asp Leu Gln Pro Glu Thr Thr Asp
1               5                   10                  15

<210> SEQ ID NO 128
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 128

Leu His Glu Tyr Met Leu Asp Leu Gln Pro Glu Thr Thr Asp Leu
1               5                   10                  15

<210> SEQ ID NO 129
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 129

Gln Ser Thr His Val Asp Ile Arg Thr Leu Glu Asp Leu Leu Met
1               5                   10                  15

<210> SEQ ID NO 130
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 130

Ser Thr His Val Asp Ile Arg Thr Leu Glu Asp Leu Leu Met Gly
1               5                   10                  15

<210> SEQ ID NO 131
<211> LENGTH: 15
<212> TYPE: PRT
<213> ORGANISM: Artificial
<220> FEATURE:

<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 131

Thr His Val Asp Ile Arg Thr Leu Glu Asp Leu Leu Met Gly Thr
1               5                   10                  15

<210> SEQ ID NO 132
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 132

His Val Asp Ile Arg Thr Leu Glu Asp Leu Leu Met Gly Thr Leu
1               5                   10                  15

<210> SEQ ID NO 133
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 133

Val Asp Ile Arg Thr Leu Glu Asp Leu Leu Met Gly Thr Leu Gly
1               5                   10                  15

<210> SEQ ID NO 134
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 134

His Asn Glu Gly Asp Asp Gln Gln Gly Ser Arg Tyr Ser Leu Ile Pro
1               5                   10                  15

Gln Ile Gln Lys Val Cys Glu Val Val Asp Gly
            20                  25

<210> SEQ ID NO 135
<211> LENGTH: 27
<212> TYPE: PRT
<213> ORGANISM: Artificial
<220> FEATURE:
<223> OTHER INFORMATION: Epitope for binding

<400> SEQUENCE: 135

Ser Glu Gln Glu Arg Met Lys Ser Ser Leu Leu Lys Glu His Met Leu
1               5                   10                  15

Arg Lys Gln Ala Glu Leu Glu Ser Ala Gln Cys

-continued

```
                20                  25

<210> SEQ ID NO 136
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 136

Glu Leu Arg Glu Asn Leu Leu Thr Tyr Leu Pro Asp Ser Val Thr Gln
1               5                  10                  15

Leu Arg Arg Leu Glu Glu Leu Asp Leu Gly Asn
            20                  25

<210> SEQ ID NO 137
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 137

Gln Glu Val Phe Ser Ser Tyr Lys Phe Asn His Leu Val Arg Arg Leu
1               5                  10                  15

Val Leu Gln Arg Glu Lys His Phe His Tyr Leu
            20                  25

<210> SEQ ID NO 138
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 138

Ile Glu Lys Asn Ala Asp Leu Cys Tyr Leu Ser Thr Val His Trp Ser
1               5                  10                  15

Leu Ile Leu Asp Ala Val Ser Asn Asn Tyr Ile
            20                  25

<210> SEQ ID NO 139
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 139

Leu Ala Thr Ala Gly Glu Pro Tyr His Asp Ile Arg Phe Lys Leu Met
1               5                  10                  15
```

Ala Val Val Pro Asp Arg Arg Ile Lys Tyr Glu
            20                    25

<210> SEQ ID NO 140
<211> LENGTH: 24
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(24)
<223> OTHER INFORMATION: Epitope

<400> SEQUENCE: 140

Met Leu Arg Leu Pro Thr Val Phe Arg Gln Ile Arg Pro Val Ser Arg
1               5                    10                   15

Val Leu Ala Pro His Leu Thr Arg
            20

<210> SEQ ID NO 141
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 141

Ile Gln Ile Met Glu Asn Pro Phe Val Gln Ser Met Leu Trp Asn Pro
1               5                    10                   15

Asp Leu Met Arg Gln Leu Ile Met Ala Asn Pro
            20                    25

<210> SEQ ID NO 142
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 142

Leu Leu Arg Phe Leu Phe Leu Gly Leu Ser Ala Leu Ala Leu Pro Ser
1               5                    10                   15

Arg Ala Gln Leu Gln Leu His Leu Pro Ala Asn
            20                    25

<210> SEQ ID NO 143
<211> LENGTH: 25
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(25)
<223> OTHER INFORMATION: Epitope

<400> SEQUENCE: 143

Met Gly Lys Asn Pro Val Arg Pro Pro Arg Ala Phe Pro Pro Val Pro
1               5                    10                   15

Ser Ile Asp Asp Ile Pro Leu Ser Arg
            20                  25

<210> SEQ ID NO 144
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 144

Gly His Val Asp Phe Thr Ile Glu Val Glu Arg Ala Leu Thr Val Leu
1               5                   10                  15

Asp Gly Ala Val Leu Val Leu Cys Ala Val Gly
            20                  25

<210> SEQ ID NO 145
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 145

Glu Tyr Lys Leu Met Tyr Gly Met Leu Phe Ser Ile Arg Leu Phe Val
1               5                   10                  15

Ser Lys Met Ser Pro Leu Asp Met Lys Asp Gly
            20                  25

<210> SEQ ID NO 146
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 146

Ser Gln Gly Ala Gly Val Glu Ser Leu Asp Phe Arg Leu Tyr Leu Arg
1               5                   10                  15

Tyr Glu Phe Leu Met Leu Gly Ile Gln Pro Val
            20                  25

<210> SEQ ID NO 147
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 147

Ala Ala Lys Thr Leu Val Leu Cys Val Ser Asp Ile Ile Leu Leu Ser

-continued

```
1              5                    10                   15

Ala Asn Ile Ser Glu Thr Ser Ser Asn Lys Thr
               20                   25
```

<210> SEQ ID NO 148
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 148

```
Cys Lys Asp Leu Gln Leu Tyr Leu Ser Asn Leu Ala Asn His Ile Asp
1              5                    10                   15

Arg Glu Thr Gly Ile Gly Asp Val Pro Leu Val
               20                   25
```

<210> SEQ ID NO 149
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 149

```
Gln Ser Lys His Thr Glu Ala Arg Glu Leu Met Tyr Ser Ala Ala Leu
1              5                    10                   15

Leu Phe Phe Ser His Gly Gln Gln Asn Ser Ala
               20                   25
```

<210> SEQ ID NO 150
<211> LENGTH: 25
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(25)
<223> OTHER INFORMATION: Epitope

<400> SEQUENCE: 150

```
Met Thr Leu Ala Glu Ser Tyr Ala Gln Tyr Val Tyr Asn Leu Cys Asn
1              5                    10                   15

Ser Leu Ser Ile Lys Val Glu Glu Ser
               20                   25
```

<210> SEQ ID NO 151
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 151

Lys Lys Val Ser Lys Thr Arg His Thr Arg Glu Thr Val Phe Arg Arg
1               5                   10                  15

Ala Lys Arg Arg Trp Ala Pro Ile Pro Cys Ser
            20                  25

<210> SEQ ID NO 152
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 152

Asn Leu Lys His Glu Asn Ile Leu Gln Phe Leu Thr Ala Gln Glu Arg
1               5                   10                  15

Lys Thr Glu Leu Gly Lys Gln Tyr Trp Leu Ile
            20                  25

<210> SEQ ID NO 153
<211> LENGTH: 21
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(21)
<223> OTHER INFORMATION: Epitope

<400> SEQUENCE: 153

Val Gln Val Phe Gly Leu Tyr Phe Gly Glu Glu Phe His Glu Thr Phe
1               5                   10                  15

Asp Cys Pro Ile Lys
            20

<210> SEQ ID NO 154
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 154

Gly Gln Ala Ala Ala Ser Gln Ala Gly Gly Ala Arg Gly Tyr Ala Arg
1               5                   10                  15

Gly Ala Gln Leu Trp Pro Pro Gly Ser Asp Pro
            20                  25

<210> SEQ ID NO 155
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 155

Ser Ile Met Gln Thr Trp Phe Thr Leu Phe Thr Pro Thr Asp Ala Thr
1               5                   10                  15

Ser Ile Val Ala Thr Thr Val Met Ser Asn Ser
            20                  25

<210> SEQ ID NO 156
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 156

Gln Glu Asn Val Arg Phe Val Leu Val Arg Ser Glu Ala Leu Leu Pro
1               5                   10                  15

Asn Ala Gly Pro Arg Ser Ala Glu Ala Arg Val
            20                  25

<210> SEQ ID NO 157
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 157

Asp Ala Phe Pro Asn Leu Lys Asp Phe Ile Ser Arg Phe Gln Val Met
1               5                   10                  15

Pro Pro Ser Ser Phe Leu Phe Asp Ala Pro Cys
            20                  25

<210> SEQ ID NO 158
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 158

Pro Ser Ser Leu Gln Val Lys Pro Glu Thr Pro Ala Ser Glu Ala Val
1               5                   10                  15

Ala Val Ala Ala Ala Ala Ala Pro Thr Thr Thr
            20                  25

<210> SEQ ID NO 159
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 159

Arg Phe Phe His Leu Ala Asp Leu Phe Leu Ser Ser Ser Gln Leu Pro
1               5                   10                  15

Ala Tyr Leu Val Ala Ala Phe Ala Lys Arg Leu
            20                  25

<210> SEQ ID NO 160
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 160

Leu Val Phe Leu Trp Leu His Ser Leu Arg Arg Leu Phe Gly Cys Leu
1               5                   10                  15

Tyr Val Ser Val Phe Ser Asn Val Met Ile His
            20                  25

<210> SEQ ID NO 161
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 161

Trp Glu Asn Ala Ile Ala Ala Leu Phe Arg Arg His Ile Ala Val Ser
1               5                   10                  15

Trp Leu Ile Arg Ala Thr Leu Ser Glu Ser Glu
            20                  25

<210> SEQ ID NO 162
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 162

Arg Tyr Ile Phe Val Lys Ser Ala Gly Ser Arg Ile Glu Glu Gly Val
1               5                   10                  15

Leu Gln Phe Leu Val Leu Leu Val Ala Gly Arg
            20                  25

<210> SEQ ID NO 163
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 163

Gln Glu Ile Glu Trp Leu Pro Phe Arg Cys Ile Lys Cys Leu Lys Leu
1               5                   10                  15

Ser Phe Ser Thr Ala Glu Leu Leu Cys Met His
            20                  25

<210> SEQ ID NO 164
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 164

Leu Val Ala Arg Cys Pro Pro Cys Leu Arg Leu Leu Arg Gln Ala Arg
1               5                   10                  15

Asp Phe Gln Ala Ala Arg Tyr Asp Arg His Asp
            20                  25

<210> SEQ ID NO 165
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 165

Ala Leu Gly Thr Pro Glu Asp Leu Asp Ser Tyr Ile Asp Leu Ser Leu
1               5                   10                  15

Glu Ser Leu Asn Gln Met Ile Leu Glu Leu Asp
            20                  25

<210> SEQ ID NO 166
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 166

Ser Gln Asp Met Leu Ser Ile Met Glu Lys Leu Glu Phe Leu Asp Phe
1               5                   10                  15

Ser Tyr Asp Leu Asn Leu Cys Gly Leu Thr Glu
            20                  25

<210> SEQ ID NO 167
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)

```
<223> OTHER INFORMATION: Epitope

<400> SEQUENCE: 167

Arg Arg Glu Gln Tyr Ile Pro Asn Glu Glu Phe Leu His Phe Asp Leu
1               5                   10                  15

Leu Glu Asp Ser Lys Tyr Arg Lys Ile Tyr Ser
            20                  25

<210> SEQ ID NO 168
<211> LENGTH: 17
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(17)
<223> OTHER INFORMATION: Epitope

<400> SEQUENCE: 168

Gly Pro Ser Tyr Arg Ser Asn Ser Val Ser Ser Leu Asp Leu Glu Gly
1               5                   10                  15

Glu

<210> SEQ ID NO 169
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 169

Leu Lys Glu Glu Lys Glu Asn Leu Gln Gly Leu Val Thr His Gln Thr
1               5                   10                  15

Tyr Ile Ile Gln Glu Leu Glu Lys Gln Leu Asn
            20                  25

<210> SEQ ID NO 170
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 170

Gln Arg Gln Lys Thr Ala Gly Lys Ile Phe Arg Ala Glu Val Ser Thr
1               5                   10                  15

Gly Gln Asp Ala Pro Arg Gln Ala Gln Ala Arg
            20                  25

<210> SEQ ID NO 171
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
```

```
<223> OTHER INFORMATION: Epitope

<400> SEQUENCE: 171

Ile Leu Arg Pro Ser Thr Val Asn Glu Leu Glu Ser Gly Glu Ile Ser
1               5                   10                  15

Tyr Asp Glu Val Gly Glu Arg Ile Lys Asp Phe
            20                  25

<210> SEQ ID NO 172
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 172

Asp Thr Cys Ile Asn Glu Asp Val Glu Ser Leu Arg Lys Met Val Gln
1               5                   10                  15

Asp Leu Leu Ala Lys Leu Gln Glu Ala Lys Arg
            20                  25

<210> SEQ ID NO 173
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 173

Leu Arg Glu Glu Gly Thr Lys Tyr Lys Ser Phe Val Gln Arg Ala Arg
1               5                   10                  15

Leu Val Phe Arg Glu Glu Gly Tyr Leu Ala Phe
            20                  25

<210> SEQ ID NO 174
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 174

His Glu Gly Ala Arg Pro Met Arg Ala Ile Phe Leu Ala Asn Gly Asn
1               5                   10                  15

Val Phe Thr Thr Gly Phe Ser Arg Met Ser Glu
            20                  25

<210> SEQ ID NO 175
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
```

<222> LOCATION: (1)..(27)
<223> OTHER INFORMATION: Epitope

<400> SEQUENCE: 175

Ile Pro Asp Ala Ala Phe Ile Gln Ala Ala Arg Arg Lys Cys Glu Leu
1               5                   10                  15

Ala Arg Ala Gln Asp Asp Tyr Ile Ser Leu Asp
            20                  25

<210> SEQ ID NO 176
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 176

Met Glu Ile Ala Lys Met Arg Ala Gly Arg Arg Leu Trp Val His Leu
1               5                   10                  15

Ile Glu Lys Met Phe Gln Pro Lys Asn Ser Lys
            20                  25

<210> SEQ ID NO 177
<211> LENGTH: 18
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(18)
<223> OTHER INFORMATION: Epitope

<400> SEQUENCE: 177

Met Glu Leu Val Ser Phe Arg Asp Val Ala Ile Glu Phe Ser Pro Glu
1               5                   10                  15

Glu Trp

<210> SEQ ID NO 178
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 178

Thr Cys Val His Glu Ile Pro Phe His Phe Asp Leu Met Glu Leu Leu
1               5                   10                  15

Pro Gln Cys Gln Gln Leu Gln Met Phe Phe Leu
            20                  25

<210> SEQ ID NO 179
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE -continued

```
<222> LOCATION: (1)..(27)
<223> OTHER INFORMATION: Epitope

<400> SEQUENCE: 179

Val Arg Arg Val Phe Ile Thr Asp Asp Phe His Asp Met Ile Pro Lys
1               5                   10                  15

Tyr Leu Asn Phe Val Lys Gly Val Val Asp Ser
            20                  25

<210> SEQ ID NO 180
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 180

Asn Phe His Ala His Arg Glu Lys Ala Pro Ser Leu Phe Cys Ser Arg
1               5                   10                  15

Ile Leu Asn Lys Ala Val Tyr Leu Phe Tyr Gly
            20                  25

<210> SEQ ID NO 181
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 181

Asp Ala Asn Lys Glu Gly Met Phe Leu Phe Arg Ala Ala His Lys Leu
1               5                   10                  15

Arg Gln Phe Leu Lys Met Asn Ser Thr Gly Asp
            20                  25

<210> SEQ ID NO 182
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 182

Leu Leu Ser Leu Gly Trp Ser Val Asp Val Gly Arg His Ser Gly Trp
1               5                   10                  15

Thr Gly His Val Ser Thr Ser Trp Ser Ile Asn
            20                  25

<210> SEQ ID NO 183
<211> LENGTH: 27
<212> TYPE: PRT
<213> ORGANISM: Artificial
<220> FEATURE:
<223> OTHER INFORMATION: Epitope for binding
<220> FEATURE:
```

<221> NAME/KEY: MISC_FEATURE
<222> LOCATION: (1)..(27)
<223> OTHER INFORMATION: Epitope

<400> SEQUENCE: 183

Asn Thr Ile Phe Ser Leu Arg Lys Asp Leu Arg Gln Gly Lys Ala Arg
1               5                   10                  15

Arg Leu Arg Cys Met Glu Glu Lys Glu Met Phe
            20                  25

<210> SEQ ID NO 184
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 184

Asn His Phe Asn Asp Phe Glu Gly Asp Pro Ala Met Thr Gln Phe Leu
1               5                   10                  15

Glu Glu Phe Glu Lys Asn Leu Glu Asp Thr Lys
            20                  25

<210> SEQ ID NO 185
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 185

Val Ile Leu Pro Gln Ala Pro Ser Gly Pro Ser Tyr Ala Thr Tyr Leu
1               5                   10                  15

Gln Pro Ala Gln Ala Gln Met Leu Thr Pro Pro
            20                  25

<210> SEQ ID NO 186
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 186

Asp Thr Leu Ser Ala Met Ser Asn Pro Arg Ala Met Gln Val Leu Leu
1               5                   10                  15

Gln Ile Gln Gln Gly Leu Gln Thr Leu Ala Thr
            20                  25

<210> SEQ ID NO 187
<211> LENGTH: 27
<212> TYPE: PRT
<213> ORGANISM: Artificial
<220> FEATURE:
<223> OTHER INFORMATION: Epitope for binding

```
<220> FEATURE:
<221> NAME/KEY: MISC_FEATURE
<222> LOCATION: (1)..(27)
<223> OTHER INFORMATION: Epitope

<400> SEQUENCE: 187

Glu Val Ile Gln Thr Ser Lys Tyr Tyr Met Arg Asp Val Ile Ala Ile
1               5                   10                  15

Glu Ser Ala Trp Leu Leu Glu Leu Ala Pro His
            20                  25

<210> SEQ ID NO 188
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 188

Gly Ser Leu Phe Gly Ser Ser Arg Val Gln Tyr Val Val Asn Pro Ala
1               5                   10                  15

Val Lys Ile Val Phe Leu Asn Ile Asp Pro Ser
            20                  25

<210> SEQ ID NO 189
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 189

Ala Glu Tyr Gly Asp Tyr Gln Pro Glu Val His Gly Val Pro Tyr Phe
1               5                   10                  15

Arg Leu Glu His Tyr Leu Pro Ala Arg Val Met
            20                  25

<210> SEQ ID NO 190
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 190

Lys Ser Trp Ile His Cys Trp Lys Tyr Leu Ser Val Gln Ser Gln Leu
1               5                   10                  15

Phe Arg Gly Ser Ser Leu Leu Phe Arg Arg Val
            20                  25

<210> SEQ ID NO 191
<211> LENGTH: 27
<212> TYPE: PRT
<213> ORGANISM: Artificial
<220> FEATURE:
```

```
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 191

Thr Leu Ala Phe Leu Val Leu Ser Thr Pro Ala Met Phe Asn Arg Ala
1               5                   10                  15

Leu Lys Pro Phe Leu Lys Ser Cys His Phe Gln
            20                  25

<210> SEQ ID NO 192
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 192

Phe Val Ser Pro Met Ala His Tyr Val Pro Gly Ile Met Ala Ile Glu
1               5                   10                  15

Ser Val Val Ala Arg Phe Gln Phe Ile Val Pro
            20                  25

<210> SEQ ID NO 193
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 193

Leu Trp Val Tyr Leu Arg Pro Val Pro Arg Pro Ala Thr Ile Tyr Leu
1               5                   10                  15

Gln Ile Leu Arg Leu Lys Pro Leu Thr Gly Glu
            20                  25

<210> SEQ ID NO 194
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 194

Lys Ile Tyr Glu Phe Asp Tyr His Leu Tyr Gly Gln Asn Ile Thr Met
1               5                   10                  15

Ile Met Thr Ser Val Ser Gly His Leu Leu Ala
            20                  25

<210> SEQ ID NO 195
<211> LENGTH: 8
<212> TYPE: PRT
<213> ORGANISM: Artificial
```

```
<220> FEATURE:
<223> OTHER INFORMATION: Epitope for binding
<220> FEATURE:
<221> NAME/KEY: MISC_FEATURE
<222> LOCATION: (1)..(8)
<223> OTHER INFORMATION: VB 4101 Amino acids 81-88

<400> SEQUENCE: 195

Arg Gly Pro Glu Ser Arg Leu Leu
1               5

<210> SEQ ID NO 196
<211> LENGTH: 46
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(46)
<223> OTHER INFORMATION: VB4102 Amino Acids 81-126

<400> SEQUENCE: 196

Arg Gly Pro Glu Ser Arg Leu Leu Glu Phe Tyr Leu Ala Met Pro Phe
1               5                   10                  15

Ala Thr Pro Met Glu Ala Glu Leu Ala Arg Arg Ser Leu Ala Gln Asp
            20                  25                  30

Ala Pro Pro Leu Pro Val Pro Gly Val Leu Leu Lys Glu Phe
        35                  40                  45

<210> SEQ ID NO 197
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 197

Met Gln Ala Glu Gly Arg Gly Thr Gly Gly Ser Thr Gly Asp Ala
1               5                   10                  15

<210> SEQ ID NO 198
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 198

Thr Gly Gly Ser Thr Gly Asp Ala Asp Gly Pro Gly Gly Pro Gly
1               5                   10                  15

<210> SEQ ID NO 199
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
```

-continued

```
<223> OTHER INFORMATION: Epitope

<400> SEQUENCE: 199

Ala Asp Gly Pro Gly Gly Pro Gly Ile Pro Asp Gly Pro Gly Gly
1               5                   10                  15

<210> SEQ ID NO 200
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 200

Gly Ile Pro Asp Gly Pro Gly Gly Asn Ala Gly Gly Pro Gly Glu
1               5                   10                  15

<210> SEQ ID NO 201
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 201

Gly Asn Ala Gly Gly Pro Gly Glu Ala Gly Ala Thr Gly Gly Arg
1               5                   10                  15

<210> SEQ ID NO 202
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 202

Glu Ala Gly Ala Thr Gly Gly Arg Gly Pro Arg Gly Ala Gly Ala
1               5                   10                  15

<210> SEQ ID NO 203
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 203

Arg Gly Pro Arg Gly Ala Gly Ala Ala Arg Ala Ser Gly Pro Gly
1               5                   10                  15

<210> SEQ ID NO 204
<211> LENGTH: 15
<212> TYPE: PRT
```

```
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 204

Ala Ala Arg Ala Ser Gly Pro Gly Gly Gly Ala Pro Arg Gly Pro
1               5                   10                  15

<210> SEQ ID NO 205
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 205

Gly Gly Gly Ala Pro Arg Gly Pro His Gly Gly Ala Ala Ser Gly
1               5                   10                  15

<210> SEQ ID NO 206
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 206

Pro His Gly Gly Ala Ala Ser Gly Leu Asn Gly Cys Cys Arg Cys
1               5                   10                  15

<210> SEQ ID NO 207
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 207

Gly Leu Asn Gly Cys Cys Arg Cys Gly Ala Arg Gly Pro Glu Ser
1               5                   10                  15

<210> SEQ ID NO 208
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 208

Cys Gly Ala Arg Gly Pro Glu Ser Arg Leu Leu Glu Phe Tyr Leu
```

-continued

```
1               5               10              15

<210> SEQ ID NO 209
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 209

Arg Gly Pro Glu Ser Arg Leu Leu Glu Phe Tyr Leu Ala Met Pro
1               5               10              15

<210> SEQ ID NO 210
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 210

Ser Arg Leu Leu Glu Phe Tyr Leu Ala Met Pro Phe Ala Thr Pro
1               5               10              15

<210> SEQ ID NO 211
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 211

Leu Ala Met Pro Phe Ala Thr Pro Met Glu Ala Glu Leu Ala Arg
1               5               10              15

<210> SEQ ID NO 212
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 212

Pro Met Glu Ala Glu Leu Ala Arg Arg Ser Leu Ala Gln Asp Ala
1               5               10              15

<210> SEQ ID NO 213
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
```

```
<222> LOCATION: (1)..(15)
<223> OTHER INFORMATION: Epitope

<400> SEQUENCE: 213

Arg Arg Ser Leu Ala Gln Asp Ala Pro Pro Leu Pro Val Pro Gly
1               5                   10                  15

<210> SEQ ID NO 214
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 214

Asp Ala Pro Pro Leu Pro Val Pro Gly Val Leu Leu Lys Glu Phe
1               5                   10                  15

<210> SEQ ID NO 215
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 215

Ala Pro Pro Leu Pro Val Pro Gly Val Leu Leu Lys Glu Phe Thr
1               5                   10                  15

<210> SEQ ID NO 216
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 216

Gly Val Leu Leu Lys Glu Phe Thr Val Ser Gly Asn Ile Leu Thr
1               5                   10                  15

<210> SEQ ID NO 217
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 217

Thr Val Ser Gly Asn Ile Leu Thr Ile Arg Leu Thr Ala Ala Asp
1               5                   10                  15

<210> SEQ ID NO 218
<211> LENGTH: 15
```

```
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 218

Thr Ile Arg Leu Thr Ala Ala Asp His Arg Gln Leu Gln Leu Ser
1               5                   10                  15

<210> SEQ ID NO 219
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 219

Asp His Arg Gln Leu Gln Leu Ser Ile Ser Ser Cys Leu Gln Gln
1               5                   10                  15

<210> SEQ ID NO 220
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 220

Ser Ile Ser Ser Cys Leu Gln Gln Leu Ser Leu Leu Met Trp Ile
1               5                   10                  15

<210> SEQ ID NO 221
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 221

Gln Leu Ser Leu Leu Met Trp Ile Thr Gln Cys Phe Leu Pro Val
1               5                   10                  15

<210> SEQ ID NO 222
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 222
```

-continued

```
Ile Thr Gln Cys Phe Leu Pro Val Phe Leu Ala Gln Pro Pro Ser
1               5                   10                  15
```

<210> SEQ ID NO 223
<211> LENGTH: 12
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(12)
<223> OTHER INFORMATION: Epitope

<400> SEQUENCE: 223

```
Val Phe Leu Ala Gln Pro Pro Ser Gly Gln Arg Arg
1               5                   10
```

<210> SEQ ID NO 224
<211> LENGTH: 8
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(8)
<223> OTHER INFORMATION: Epitope

<400> SEQUENCE: 224

```
Arg Gly Pro Glu Ser Arg Leu Leu
1               5
```

<210> SEQ ID NO 225
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 225

```
Arg Glu Gly Val Glu Leu Cys Pro Gly Asn Lys Tyr Glu Met Arg Arg
1               5                   10                  15

His Gly Thr Thr His Ser Leu Val Ile His Asp
            20                  25
```

<210> SEQ ID NO 226
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 226

```
Ser Ser Pro Asp Glu Val Ala Leu Val Glu Gly Val Gln Ser Leu Gly
1               5                   10                  15

Phe Thr Tyr Leu Arg Leu Lys Asp Asn Tyr Met
            20                  25
```

<210> SEQ ID NO 227

```
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 227

Lys Asn Ile Leu Ala Val Ser Phe Ala Pro Leu Val Gln Leu Ser Lys
1               5                   10                  15

Asn Asp Asn Gly Thr Pro Asp Ser Val Gly Leu
            20                  25

<210> SEQ ID NO 228
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 228

Pro Ala Ala Asp Arg Trp Glu Pro Arg Ala Pro Met Arg Ala Pro Arg
1               5                   10                  15

Val Leu His Ala Met Leu Gly Ala Ala Gly Arg
            20                  25

<210> SEQ ID NO 229
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 229

Val Leu Ser Ala Asp Leu Val His Tyr Leu Arg Leu Ser Leu Glu Tyr
1               5                   10                  15

Leu Arg Ala Trp His Ser Glu Asp Val Ser Leu
            20                  25

<210> SEQ ID NO 230
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 230

Leu Glu Ala Val Leu Arg Tyr Leu Glu Thr His Pro Arg Leu Pro Lys
1               5                   10                  15

Pro Asp Pro Val Lys Ser Ser Ser Ser Val Leu
            20                  25
```

-continued

```
<210> SEQ ID NO 231
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 231

Leu Lys Asp Phe Phe Phe Ser Arg Gly Arg Phe Ser Ser Ala Leu Lys
1               5                   10                  15

Arg Thr Leu Ile Leu Ser Ser Gly Phe Arg Leu
            20                  25

<210> SEQ ID NO 232
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 232

Ala Gly Lys Asp His Lys Ile Lys Gln Trp Asp Ala Asp Thr Phe Glu
1               5                   10                  15

His Ile Gln Thr Leu Glu Gly His His Gln Glu
            20                  25

<210> SEQ ID NO 233
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 233

Pro Ala Thr Ile Glu Met Ala Ile Glu Thr Leu Gln Lys Phe Asp Gly
1               5                   10                  15

Leu Ser Thr His Arg Ser Ser Leu Leu Asn Ser
            20                  25

<210> SEQ ID NO 234
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 234

Tyr Leu Pro Gly Gly Gly Ala Gly His Leu Asp Gln Asn Val Phe Leu
1               5                   10                  15

Arg Val Arg Ala Leu Cys Tyr Val Ile Ser Gly
            20                  25
```

```
<210> SEQ ID NO 235
<211> LENGTH: 9
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(9)
<223> OTHER INFORMATION: Epitope

<400> SEQUENCE: 235

Ser Val Tyr Asp Phe Phe Val Trp Leu
1               5

<210> SEQ ID NO 236
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 236

Tyr Ile Ser Asp His Met Lys Val His Ser Pro Ser Pro Cys Leu
1               5                   10                  15

<210> SEQ ID NO 237
<211> LENGTH: 64
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(64)
<223> OTHER INFORMATION: B-pepM115-M122

<400> SEQUENCE: 237

Glu Gly Trp Gln Thr Cys Trp Gly Arg Ser Arg Lys His Trp Gly Ser
1               5                   10                  15

Thr Trp Asn Gly Ser Ala Arg Leu Ser Pro Gly Ser Thr Leu Trp Val
            20                  25                  30

Met Arg Ile Cys Leu Arg Ser Leu Gly Ile Ala Arg Thr Trp Leu Ser
        35                  40                  45

Cys Arg Ser Thr Ser Arg Lys Cys Ser Pro Ala Phe Pro Ala Ser Ser
    50                  55                  60

<210> SEQ ID NO 238
<211> LENGTH: 45
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(45)
<223> OTHER INFORMATION: B-pepM141-M142

<400> SEQUENCE: 238

Leu Phe Arg Leu Leu Pro Ser Gly Pro Lys Val Asn Asp Gly His Arg
1               5                   10                  15

Ser Arg Arg Trp His Ser Leu Asp Leu Tyr Pro His Leu Cys Ser His
            20                  25                  30
```

```
Leu Asp Leu Pro Lys Gln Ser Gln Glu Val Ile Arg Leu
      35                  40                  45

<210> SEQ ID NO 239
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 239

Tyr Ile Ser Asp His Met Lys Val His Ser Pro Ser Pro Cys Leu
1               5                   10                  15

<210> SEQ ID NO 240
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 240

Glu Gly Trp Gln Thr Cys Trp Gly Arg Ser Arg Lys His Trp Gly
1               5                   10                  15

<210> SEQ ID NO 241
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 241

Gly Arg Ser Arg Lys His Trp Gly Ser Thr Trp Asn Gly Ser Ala
1               5                   10                  15

<210> SEQ ID NO 242
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 242

Gly Ser Thr Trp Asn Gly Ser Ala Arg Leu Ser Pro Gly Ser Thr
1               5                   10                  15

<210> SEQ ID NO 243
<211> LENGTH: 15
<212> TYPE: PRT
<213> ORGANISM: Artificial
<220> FEATURE:
<223> OTHER INFORMATION: Epitope for binding
```

```
<220> FEATURE:
<221> NAME/KEY: MISC_FEATURE
<222> LOCATION: (1)..(15)
<223> OTHER INFORMATION: Epitope

<400> SEQUENCE: 243

Ala Arg Leu Ser Pro Gly Ser Thr Leu Trp Val Met Arg Ile Cys
1               5                   10                  15

<210> SEQ ID NO 244
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 244

Thr Leu Trp Val Met Arg Ile Cys Leu Arg Ser Leu Gly Ile Ala
1               5                   10                  15

<210> SEQ ID NO 245
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 245

Cys Leu Arg Ser Leu Gly Ile Ala Arg Thr Trp Leu Ser Cys Arg
1               5                   10                  15

<210> SEQ ID NO 246
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 246

Ala Arg Thr Trp Leu Ser Cys Arg Ser Thr Ser Arg Lys Cys Ser
1               5                   10                  15

<210> SEQ ID NO 247
<211> LENGTH: 15
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(15)
<223> OTHER INFORMATION: Epitope

<400> SEQUENCE: 247

Arg Ser Thr Ser Arg Lys Cys Ser Pro Ala Phe Pro Ala Ser Ser
1               5                   10                  15
```

-continued

```
<210> SEQ ID NO 248
<211> LENGTH: 27
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(27)
<223> OTHER INFORMATION: Epitope

<400> SEQUENCE: 248

Leu Phe Arg Leu Leu Pro Ser Gly Pro Lys Val Asn Asp Gly His Arg
1               5                   10                  15

Ser Arg Arg Trp His Ser Leu Asp Leu Tyr Pro
            20                  25

<210> SEQ ID NO 249
<211> LENGTH: 29
<212> TYPE: PRT
<213> ORGANISM: Artificial
<220> FEATURE:
<223> OTHER INFORMATION: Epitope for binding
<220> FEATURE:
<221> NAME/KEY: MISC_FEATURE
<222> LOCATION: (1)..(29)
<223> OTHER INFORMATION: Epitope

<400> SEQUENCE: 249

Ser Arg Arg Trp His Ser Leu Asp Leu Tyr Pro His Leu Cys Ser His
1               5                   10                  15

Leu Asp Leu Pro Lys Gln Ser Gln Glu Val Ile Arg Leu
            20                  25
```